(12) United States Patent
Chen et al.

(10) Patent No.: US 10,053,431 B2
(45) Date of Patent: Aug. 21, 2018

(54) TETRAHYDRO-BENZODIAZEPINONES

(71) Applicant: Hoffmann-La Roche Inc., Nutley, NJ (US)

(72) Inventors: Shaoqing Chen, Bridgewater, NJ (US); Andrew F. Donnell, West Windsor, NJ (US); Robert Francis Kester, West Orange, NJ (US); Kang Le, Sugar Land, TX (US); Yan Lou, Pleasanton, CA (US); Christophe Michoud, New York, NY (US); Stacy Remiszewski, Washington, NJ (US); Kenneth C. Rupert, Bedminster, NJ (US); Martin Weisel, Mannheim (DE)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 15/037,240

(22) PCT Filed: Nov. 14, 2014

(86) PCT No.: PCT/EP2014/074564
§ 371 (c)(1),
(2) Date: May 17, 2016

(87) PCT Pub. No.: WO2015/071393
PCT Pub. Date: May 21, 2015

(65) Prior Publication Data
US 2016/0272596 A1    Sep. 22, 2016

Related U.S. Application Data

(60) Provisional application No. 61/905,448, filed on Nov. 18, 2013.

(51) Int. Cl.
| | | |
|---|---|---|
| *C07D 243/12* | (2006.01) | |
| *C07D 243/14* | (2006.01) | |
| *C07D 401/06* | (2006.01) | |
| *C07D 401/14* | (2006.01) | |
| *C07D 403/06* | (2006.01) | |
| *C07D 403/12* | (2006.01) | |
| *C07D 405/06* | (2006.01) | |
| *C07D 405/14* | (2006.01) | |
| *C07D 413/06* | (2006.01) | |
| *C07D 417/12* | (2006.01) | |
| *C07D 487/08* | (2006.01) | |

(52) U.S. Cl.
CPC ......... *C07D 243/14* (2013.01); *C07D 243/12* (2013.01); *C07D 401/06* (2013.01); *C07D 401/14* (2013.01); *C07D 403/06* (2013.01); *C07D 403/12* (2013.01); *C07D 405/06* (2013.01); *C07D 405/14* (2013.01); *C07D 413/06* (2013.01); *C07D 417/12* (2013.01); *C07D 487/08* (2013.01)

(58) Field of Classification Search
CPC .. C07D 243/12; C07D 243/14; C07D 401/06; C07D 401/14; C07D 403/06; C07D 403/12; C07D 405/06; C07D 405/14; C07D 413/06; C07D 417/12
See application file for complete search history.

(56) References Cited

U.S. PATENT DOCUMENTS 9,422,331 B2 * 8/2016 Donnell ................. A61K 38/05

FOREIGN PATENT DOCUMENTS

| WO | 2006017295 A2 | 2/2006 |
| WO | 2007101347 A1 | 9/2007 |
| WO | 2014044622 A1 | 3/2014 |
| WO | 2014090709 A1 | 6/2014 |

OTHER PUBLICATIONS

The International Search Report and Written Opinion, dated Mar. 19, 2015, in the related PCT Application No. PCT/EP2014/074564.
Kester et al., "'Optimization of Benzodiazepinones as Selective Inhibitors of the X-Linked Inhibitor of Apoptosis Protein (XIAP) Second Baculovirus IAP Repeat (BIR2) Domain'" Journal of Medicinal Chemistry 56(20):7788-7803 (Oct. 24, 2013).
Donnell et al., "'Benzazepinones and Benzoxazepinones as Antagonists of Inhibitor of Apoptosis Proteins (IAPs) Selective for the Second Baculovirus IAP Repeat (BIR2) Domain'" Journal of Medicinal Chemistry 56(20):7772-7787 (Oct. 24, 2013).

* cited by examiner

*Primary Examiner* — Kendra D Carter

(57) ABSTRACT

Disclosed are compounds of Formula I, or pharmaceutically acceptable salts thereof, wherein W, X, Y, Z, $R^1$, $R^2$, $R^3$, $R^4$ and $R^5$ are as described in this application, and methods of using said compounds in the treatment of cancer.

4 Claims, No Drawings

SEQUENCE LISTING

<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: TR-FRET peptide

<400> SEQUENCE: 1

Ala Val Pro Ile Ala Gln Lys Ser Glu Lys
1               5                   10

<210> SEQ ID NO 2
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 2

Met Arg His His His His His His Arg Asp His Phe Ala Leu Asp Arg
1               5                   10                  15

Pro Ser Glu Thr His Ala Asp Tyr Leu Leu Arg Thr Gly Gln Val Val
                20                  25                  30

Asp Ile Ser Asp Thr Ile Tyr Pro Arg Asn Pro Ala Met Tyr Ser Glu
            35                  40                  45

Glu Ala Arg Leu Lys Ser Phe Gln Asn Trp Pro Asp Tyr Ala His Leu

Thr Pro Arg Glu Leu Ala Ser Ala Gly Leu Tyr Tyr Thr Gly Ile Gly
65                  70                  75                  80

Asp Gln Val Gln Cys Phe Ala Cys Gly Gly Lys Leu Lys Asn Trp Glu
                85                  90                  95

Pro Gly Asp Arg Ala Trp Ser Glu His Arg Arg His Phe Pro Asn Cys
            100                 105                 110

Phe Phe Val Leu Gly Arg Asn Leu Asn Ile Arg Ser Glu
            115                 120             125

<210> SEQ ID NO 3
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 3

Met Arg His His His His His His Arg Ser Asp Ala Val Ser Ser Asp
1               5                   10                  15

Arg Asn Phe Pro Asn Ser Thr Asn Leu Pro Arg Asn Pro Ser Met Ala
                20                  25                  30

Asp Tyr Glu Ala Arg Ile Phe Thr Phe Gly Thr Trp Ile Tyr Ser Val
            35                  40                  45

Asn Lys Glu Gln Leu Ala Arg Ala Gly Phe Tyr Ala Leu Gly Glu Gly
        50                  55                  60

Asp Lys Val Lys Cys Phe His Cys Gly Gly Gly Leu Thr Asp Trp Lys
65                  70                  75                  80

Pro Ser Glu Asp Pro Trp Glu Gln His Ala Lys Trp Tyr Pro Gly Cys
                85                  90                  95

Lys Tyr Leu Leu Glu Gln Lys Gly Gln Glu Tyr Ile Asn Asn Ile His
            100                 105                 110

Leu Thr His Ser Leu Glu Glu Cys Leu Val Arg Thr Thr
            115                 120                 125

TETRAHYDRO-BENZODIAZEPINONES

CROSS-REFERENCE TO RELATED APPLICATIONS

This application is a National Stage Application of PCT/EP2014/074564 filed Nov. 14, 2014, which claims priority from U.S. Provisional Patent Application No. 61/905,448, filed on Nov. 18, 2013. Each of the prior mentioned applications is hereby incorporated by reference herein in its entirety.

FIELD OF THE INVENTION

The present invention relates to substituted 1,5-disubstituted, (S)-3-amino-substituted 2,3,4,5-tetrahydro-benzo[b][1,4]diazepin-2-ones which act as inhibitors of SMAC protein binding to Inhibitor of Apoptosis Proteins (IAPs), and/or inhibitors of activated caspase proteins binding to IAPs. These molecules are useful in the amelioration, treatment or control of cancer, especially solid tumors.

These compounds bind to the BIR2 and/or BIR3 regions of IAP proteins, including XIAP and cIAP, resulting in activation or reactivation of the caspase cascade and, as such, are useful for the treatment of proliferative diseases, including cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer. See, e.g., E. Dean et al., "X-linked inhibitor of apoptosis protein as a therapeutic target," Expert Opin. Ther. Targets (2007) 11(11):1459-1471

The two basic pathways for apoptotic cell death are the intrinsic pathway and the extrinsic pathway. The intrinsic apoptotic pathway can be initiated by various mechanisms including cellular stress and drug-induced DNA damage. The extrinsic pathway can be initiated by activation of the death receptors by a chemokine. Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis. See, e.g., Dean, supra at 1460.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can block the BIR2 and BIR3 domains of IAPs competing with activated caspases resulting in release of the activated caspases from the IAPs and completion of the apoptotic program. See, e.g., S. Wang, "Design of Small-Molecule Smac Mimetics as IAP Antagonists," Current Topics in Microbiology and Immunology 348, DOI 10.1007/82_2010_111, pp. 89-113.

Peptides and small molecules have been reported to bind to the BIR3 region of XIAP and cIAP, mimicking the action of Smac protein and releasing activated caspases. See, e.g., Dean, supra; and M. Gyrd-Hanse et al., "IAPB: From caspase inhibitors to modulators of NF-κB, inflammation and cancer," Nature Review/Cancer, August 2010, Vol 10:561-574.

Certain Azepinone derivatives have been reported as Antagonists of Inhibitor of Apoptosis Proteins (Donnell et al., J. Med. Chem. 2013, 56, 7772-7787 and Kester et al., J. Med. Chem. 2013, 56, 7788-7803).

SUMMARY OF THE INVENTION

One aspect of the present invention is a compound of Formula I

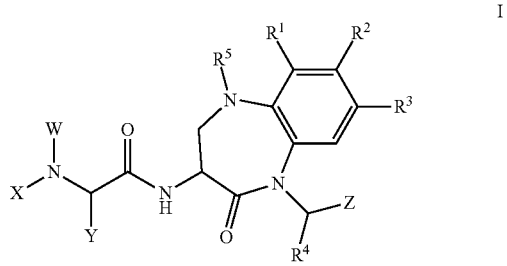

or pharmaceutically acceptable salts thereof, wherein W, X, Y, Z, $R^1$, $R^2$, $R^3$, $R^4$ and $R^5$ are described in this application.

The present invention also relates to pharmaceutical compositions comprising one or more compounds of the invention, or a pharmaceutically acceptable salt thereof, and a pharmaceutically acceptable carrier or excipient.

The present invention further relates to a method of ameliorating, controlling or treating cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

DETAILED DESCRIPTION OF THE INVENTION

Unless otherwise defined, all technical and scientific terms used herein have the same meaning as commonly understood by one of ordinary skill in the art to which this invention belongs.

As used herein, the following terms shall have the following definitions.

"Alkyl", alone or in combination with other groups, means a monovalent linear or branched saturated hydrocarbon of 1 to 12 carbon atoms. In particular embodiments, alkyl has 1 to 6 carbon atoms, and in more particular embodiments 1 to 4 carbon atoms. As used herein, "lower alkyl" denotes an alkyl group having from 1-6 carbon atoms ($C_{1-6}$-alkyl). Examples of alkyl include methyl, ethyl, propyl, isopropyl, butyl (also known as n-butyl), iso-butyl, sec-butyl, tert-butyl, pentyl, hexyl, and the like. The alkyl group can be optionally enriched in deuterium, e.g., —$CD_3$, —$CD_2CD_3$ and the like.

"Acyl", alone or in combination with other groups, means a group of the formula C(O)$R^{20}$ where, unless otherwise specified for a particular substituent, $R^{20}$ can be, for example H, alkyl, aryl, arylalkyl, heterocyclyl, for example methyl, ethyl, isoxazolyl, pyrazinyl and the like.

"Alkenyl", alone or in combination with other groups, means a monovalent linear or branched hydrocarbon group of 2 to 6 carbon atoms with at least one double bond ($C_{2-6}$-alkenyl). In particular embodiments, alkenyl has 2 to 4 carbon atoms with at least one double bond ($C_{2-4}$-alkenyl). Examples of alkenyl include ethenyl, propenyl, prop-2-enyl, isopropenyl, n-butenyl, iso-butenyl, and tert-butenyl.

"Alkynyl", alone or in combination with other groups, means a monovalent linear or branched saturated hydrocarbon group of 2 to 6 carbon atoms comprising one, two or three triple bonds ($C_{2-6}$-alkynyl). In particular embodiments alkynyl has from 2 to 4 carbon atoms comprising one or two triple bonds ($C_{2-4}$-alkynyl). Examples of alkynyl include ethynyl, propynyl, prop-2-ynyl, isopropynyl, n-butynyl, and iso-butynyl.

"Alkoxy, alkoxyl or lower alkoxy", alone or in combination with other groups, means any one of the above alkyl groups which is attached to the remainder of the molecule by an oxygen atom (RO—). $C_{1-6}$-alkoxy means $C_{1-6}$-alkyl-O—. Typical alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxyphosphoryl methoxy and the like.

"Aryl", alone or in combination with other groups, means a monovalent aromatic carbocyclic mono-, bi- or tricyclic ring system comprising 6 to 19 carbon ring atoms. Examples of aryl moieties include, but are not limited to, phenyl, naphthyl (or naphthalenyl), tolyl, xylyl, pyridinyl, quinolinyl, pyrimidinyl, imidazolyl, thiazolyl, tetrazolyl, and fluorenyl. Specific aryl are phenyl and naphthyl.

"Aryloxy" means ($R^{30}$O—), wherein $R^{30}$ is aryl. Examples of aryloxy moieties include benzyloxy.

"Cyano" means C≡N.

"Cycloalkyl", alone or in combination with other groups, means a substituted on unsubstituted stable monovalent saturated monocyclic, bicyclic or tricyclic system which consists of 3 to 10 ring carbon atoms ($C_{3-10}$-cycloalkyl). In particular embodiments cycloalkyl denotes a monovalent saturated monocyclic hydrocarbon group of 3 to 7 ring carbon atoms ($C_{3-7}$-cycloalkyl). Particular cycloalkyl groups are monocyclic. Examples for monocyclic cycloalkyl are cyclopropyl, cyclobutnyl, cyclopentyl, cyclohexyl or cycloheptyl. Bicyclic means consisting of two saturated carbocycles having one or more carbon atoms in common. Examples for bicyclic cycloalkyl are bicyclo[2.2.1]heptanyl, or bicyclo[2.2.2]octanyl. Tricyclic means consisting of three saturated carbocycles having two or more carbon atoms in common. Examples of tricyclic cycloalkyl include adamantyl.

"Halo", alone or in combination with other groups, or means at atom selected from F, Cl, Br or I. In particular embodiments Halo means F and Cl.

"Halo-$C_{1-6}$-alkoxy" means a "halo" as defined herein linked to an "$C_{1-6}$-alkoxy" as defined herein.

"Halo-$C_{1-6}$-alkyl" means a "halo" as defined herein linked to an "$C_{1-6}$-alkyl" as defined herein.

"Heteroatom" means at atom selected from N, O or S.

"Heteroaryl", alone or in combination with other groups, means a substituted or unsubstituted aromatic heterocyclic ring system containing up to two rings, at least one ring of which includes 1, 2, or 3 heteroatoms, the remaining ring atoms being carbon. Examples of heteroaryl groups include, but are not limited to, thienyl (or thiophenyl), furyl, indolyl, pyrrolyl, pyridinyl, pyrazinyl, oxazolyl, thiazolyl, quinolinyl, pyrimidinyl, imidazolyl, triazolyl, tetrazolyl, benzo[d]isoxazolyl, chromenyl (or benzopyran).

In the case of a heteroaryl that is bicyclic it should be understood that one ring may be aryl while the other is heteroaryl and both may be independently substituted or unsubstituted.

"Heterocyclyl," "heterocycle" or "heterocyclic ring", alone or in combination with other groups, means a substituted or unsubstituted monovalent saturated or partly unsaturated mono- or bicyclic ring, non-aromatic hydrocarbon system of 3 to 9 ring atoms ($C_{3-9}$-heterocycle), comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, tetrahydrofuranyl, piperazinyl, morpholinyl, thiomorpholinyl, 1,1-dioxo-thiomorpholin-4-yl, azepanyl, diazepanyl, homopiperazinyl, or oxazepanyl. Examples of partly unsaturated heterocycloalkyl are dihydrofuryl, imidazolinyl, dihydro-oxazolyl, tetrahydro-pyridinyl, or dihydropyranyl.

In the case of a heterocycle that is bicyclic it should be understood that one ring may be heterocycle while the other is cycloalkyl, and either or both may be independently substituted. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl.

"$IC_{50}$" refers to the concentration of a particular compound required to inhibit 50% of a specific measured activity. $IC_{50}$ can be measured, inter alia, as is described subsequently in Example 103.

"Oxo" means =O.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

"Substituted," as in substituted alkyl, aryl or heteroaryl means that the substitution (i.e. replacement of one hydrogen atom) can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent.

"Sulfonyl" means a group of formula $-SO_2R^{20}$ where, unless otherwise specified for a specific substituent, $R^{20}$ may be as is previously defined in the definition of acyl.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

As used in this application, if a formula or group appears to be missing a substituent, that is it appears the valence is not complete, it is presumed the missing substituent is an H.

In the structural formulae presented herein a broken bond (a) denotes that the substituent is below the plane of the paper and a wedged bond (b) denotes that the substituent is above the plane of the paper.

The invention relates to a compound of formula I':

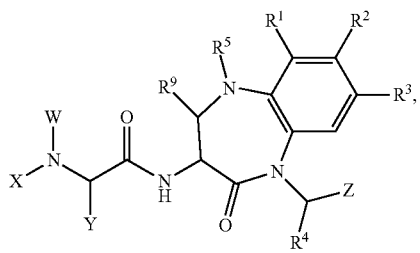

I' wherein

W and X are the same or different and each is independently selected from the group constituting of
H,
hydroxyl-$C_{1-6}$-alkyl, and
$C_{1-6}$-alkyl that optionally includes 1-3 deuterium atoms,
or alternatively, W together with the nitrogen to which it is bound and Y together with the carbon to which it is bound can form a $C_{3-9}$-heterocycle;
Y is $C_{1-6}$-alkyl
Z is selected from the group constituting of
$C_{1-6}$-alkyl that optionally may be substituted with aryl,
aryl that optionally may be substituted with cyano, $C_{1-6}$-alkyl, $C_{1-6}$-alkoxy, $C_{3-7}$-cycloalkyl, $OCD_3$, halo-$C_{1-6}$-alkoxy, halo, COO—$C_{1-6}$-alkyl, COOH or CON(H, $C_{1-6}$-alkyl), and
heteroaryl that optionally may be substituted with $C_{1-6}$-alkyl, $C_{1-6}$-alkoxy, $C_{3-7}$-cycloalkyl, halo-$C_{1-6}$-alkoxy, halo, $COOR^9$, $CONR^6R^7$, oxo or phenyl that optionally may be substituted with cyano,
$CONR^{10}R^{11}$;
$R^1$, $R^2$ and $R^3$ are selected from the group constituting of
H,
CN,
halo, and
halo-$C_{1-6}$-alkyl;
$R^4$ is selected from the group constituting of
H,
$C_{1-6}$-alkyl, and
aryl;
$R^5$ is selected from the group constituting of
H,
benzyl, that optionally may be substituted with acetyl, amido, amino, cyano, $C_{1-6}$-alkyl, $C_{1-6}$-alkoxy, hydroxy-$C_{1-6}$-alkyl, halo and nitro,
aryl that optionally may be substituted with acetyl, amido, amino, cyano, $C_{1-6}$-alkyl, $C_{1-6}$-alkoxy, hydroxy-$C_{1-6}$-alkyl, halo and nitro,
heteroaryl,
$C_{1-6}$-alkyl that optionally may be substituted with aryl that optionally may be substituted with cyano or $C_{1-6}$-alkoxy,
$C(O)R^6$,
$SO_2—CH_2—SO_2—C_{1-6}$ alkyl,
$SO_2—N(C_{1-6}-alkyl)_2$,
$SO_2—NH_2$,
$SO_2—N(H,C_{1-6}-alkyl)$,
$SO_2$-aryl that optionally may be substituted with $C_{1-6}$-alkoxy, nitro, amino, N(H, C(O)—$C_{1-6}$-alkyl) or C(O)—$C_{1-6}$-alkyl,
$SO_2—C_{1-6}$-alkyl, and
COO—$C_{1-6}$-alkyl,
and $R^5$ optionally may be linked with Z to form
—C(=O)—$(CH_2)_a$—$NR^{12}$—C(=O)-aryl-$CH_2$—,
whereby
a is 1, 2, 3 or 4, and
the aryl moiety can optionally be substituted by $C_{1-6}$-alkoxy;
$R^6$ is selected from the group constituting of
$C_{1-6}$-alkyl that optionally may be substituted with amino, N(H, $C_{1-6}$ alkyl), COOH, nitro or $C_{1-6}$-alkoxy,
$(CH_2)_i$-aryl that optionally may be substituted with amino, cyano, nitro, halo, $SO_2—C_{1-6}$-alkyl, C(O)—$C_{1-6}$-alkyl, C(O)—O—$C_{1-6}$-alkyl, C(O)—OH, $C_{1-6}$-alkoxy, C(O)—$NH_2$, C(O)—NH—$(CH_2)_j$—$C_{3-7}$-cycloalkyl, N(H, C(O)—$C_{1-6}$-alkyl), N(H, C(O)—O—

$C_{1-6}$-alkyl-aryl) or $C_{1-6}$-alkyl that optionally may be substituted with halo and hydroxy, i=0 or 1 and j=0 or 1, $(CH_2)_k$-heterocycle that optionally may be substituted with $C_{1-6}$-alkyl, k=0, 1 or 2, $(CH_2)_l$-heteroaryl that optionally may be substituted with $C_{1-6}$-alkyl, $C_{3-7}$-cycloalkyl, phenyl or halo, l=0, 1 or 2 and the aryl moiety may optionally be substituted by CN, $(CH_2)_m$—O—$(CH_2)_n$—O—$C_{1-6}$-alkyl, m=1 or 2, n=1, 2 or 3, $(CH_2)_o$—(C=O)—$NR^7R^8$, o=0, 1 or 2, $(CH_2)_p$—O—$(CH_2)_q$—O—$(CH_2)_r$—O—$C_{1-6}$-alkyl, p=1 or 2, q=1, 2 or 3, r=1, 2 or 3, $(CH_2)_s$—(C=O)—$C_{1-6}$-alkyl, s=1, 2 or 3, $(CH_2)_t$—(C=O)—O—$C_{1-6}$-alkyl, t=1, 2, 3 or 4, $(CH_2)_u$—$C_{3-7}$-cycloalkyl, u=1 or 2, $(CH_2)_v$—NH—(C=O)—O—$(CH_2)w$-aryl, v=1, 2 or 3, w=1 or 2, and $(CH_2)x$-$SO_2$—$C_{1-6}$-alkyl, x=1 or 2, N(H, $C_{1-6}$-alkyl);

$R^7$ or $R^8$ each individually selected from the group constituting of

H, and $C_{1-6}$-alkyl;

$R^9$ is selected from the group constituting of

H, $R^{10}$ is selected from the group constituting of

H, $R^{11}$ is selected from the group constituting of aryl, and heteroaryl;

$R^{12}$ is selected from the group constituting of

H, and $C_{1-6}$-alkyl;

or a pharmaceutically acceptable salt thereof.

The invention further relates to a compound of formula I:

I wherein

W and X are the same or different and each is independently selected from the group H, and $C_{1-6}$-alkyl that optionally includes 1-3 deuterium atoms, or alternatively, W together with the nitrogen to which it is bound and Y together with the carbon to which it is bound can form a $C_{3-9}$-heterocycle;

Y is $C_{1-6}$-alkyl

Z is selected from the group $C_{1-6}$-alkyl that optionally may be substituted with aryl, aryl that optionally may be substituted with $C_{1-6}$-alkyl, $C_{1-6}$-alkoxy, $OCD_3$, halo-$C_{1-6}$-alkoxy, halo, COO—$C_{1-6}$-alkyl, COOH or CON(H, $C_{1-6}$-alkyl), and heteroaryl that optionally may be substituted with $C_{1-6}$-alkyl, $C_{1-6}$-alkoxy, halo-$C_{1-6}$-alkoxy, halo, $COOR^9$, $CONR^6R^7$ or oxo, $R^1$, $R^2$ and $R^3$ are H;

$R^4$ is selected from the group

H, and $C_{1-6}$-alkyl;

$R^5$ is selected from the group

H $C_{1-6}$-alkyl that optionally may be substituted with aryl that optionally may be substituted with cyano, $C(O)R^6$, $SO_2$—$CH_2$—$SO_2$—$C_{1-6}$-alkyl, $SO_2$—$N(C_{1-6}$-alkyl$)_2$, $SO_2$—$NH_2$, $SO_2$—N(H,$C_{1-6}$-alkyl), $SO_2$-aryl that optionally may be substituted with $C_{1-6}$-alkoxy, nitro, N(H, C(O)—$C_{1-6}$-alkyl) or C(O)—$C_{1-6}$-alkyl, $SO_2$—$C_{1-6}$-alkyl, and COO—$C_{1-6}$-alkyl, and $R^5$ optionally may be linked with Z to form a cyclic group;

$R^6$ is selected from the group $C_{1-6}$-alkyl that optionally may be substituted with amino, nitro or $C_{1-6}$-alkoxy, $(CH_2)_i$-aryl that optionally may be substituted with amino, cyano, nitro, halo, $SO_2$—$C_{1-6}$-alkyl, C(O)—$C_{1-6}$-alkyl, $C_{1-6}$-alkoxy, C(O)—$NH_2$, C(O)—NH$(CH_2)j$-$C_{3-7}$-cycloalkyl, N(H, C(O)—$C_{1-6}$-alkyl) or $C_{1-6}$-alkyl that optionally may be substituted with halo and hydroxy, i=0, 1 or 1 and j=0 or 1, $(CH_2)_k$-heterocycle that optionally may be substituted with $C_{1-6}$-alkyl, k=0, 1 or 2, $(CH_2)_l$-heteroaryl that optionally may be substituted with $C_{1-6}$-alkyl or halo, l=0, or 2, $(CH_2)_m$—O—$(CH_2)_n$—O—$C_{1-6}$-alkyl, m=1 or 2, n=1, 2 or 3, $(CH_2)_o$—(C=O)—$NR^7R^8$, o=0, 1 or 2, $(CH_2)_p$—O—$(CH_2)_q$—O—$(CH_2)_r$—O—$C_{1-6}$-alkyl, p=1 or 2, q=1, 2 or 3, r=1, 2 or 3, $(CH_2)_s$—(C=O)—$C_{1-6}$-alkyl, s=1, 2 or 3, $(CH_2)_t$—(C=O)—O—$C_{1-6}$-alkyl, t=1, 2, 3 or 4, $(CH_2)_u$—$C_{3-7}$-cycloalkyl, u=1 or 2, $(CH_2)_v$—NH—(C=O)—O—$(CH_2)w$-heteroaryl, v=1, 2 or 3, w=1 or 2, and $(CH_2)_x$—$SO_2$—$C_{1-6}$-alkyl, x=1

$R^7$ or $R^8$ each individually selected from the group

H, and $C_{1-6}$-alkyl.

or a pharmaceutically acceptable salt thereof.

A certain embodiment of the invention relates to a compound of formula I as described herein wherein W and X are the same or different and each is independently selected from the group H, and $C_{1-6}$-alkyl, or alternatively, W together with the nitrogen to which it is bound and Y together with the carbon to which it is bound can form a $C_{3-9}$-heterocycle;

Y is $C_{1-6}$-alkyl

Z is selected from the group $C_{1-6}$-alkyl that optionally may be substituted with aryl, aryl that optionally may be substituted with $C_{1-6}$-alkyl, $C_{1-6}$-alkoxy, $OCD_3$, halo-$C_{1-6}$-alkoxy, halo, COO—$C_{1-6}$-alkyl, COOH or CON(H, $C_{1-6}$-alkyl), and heteroaryl that optionally may be substituted with $C_{1-6}$-alkyl, $C_{1-6}$-alkoxy, halo-$C_{1-6}$-alkoxy, halo, COOR$^9$, CONR$^6$R$^7$ or oxo, R$^1$, R$^2$ and R$^3$ are H;

R$^4$ is selected from the group

H, and $C_{1-6}$-alkyl;

R$^5$ is selected from the group

H $C_{1-6}$-alkyl that optionally may be substituted with aryl that optionally may be substituted with cyano,

C(O)R$^6$,

SO$_2$—CH$_2$—SO$_2$—$C_{1-6}$-alkyl,

SO$_2$—N($C_{1-6}$-alkyl)$_2$,

SO$_2$—NH$_2$,

SO$_2$—N(H,$C_{1-6}$-alkyl),

SO$_2$-aryl that optionally may be substituted with $C_{1-6}$-alkoxy, nitro, N(H, C(O)—$C_{1-6}$-alkyl) or C(O)—$C_{1-6}$-alkyl, SO$_2$—$C_{1-6}$-alkyl, and COO—$C_{1-6}$-alkyl, and R$^5$ optionally may be linked with Z to form a cyclic group;

R$^6$ is selected from the group $C_{1-6}$-alkyl that optionally may be substituted with amino, nitro or $C_{1-6}$-alkoxy, (CH$_2$)$_i$-aryl that optionally may be substituted with amino, cyano, nitro, halo, SO$_2$—$C_{1-6}$-alkyl, C(O)—$C_{1-6}$-alkyl, $C_{1-6}$-alkoxy, C(O)—NH$_2$, C(O)—NH(CH$_2$)j-$C_{3-7}$-cycloalkyl, N(H, C(O)—$C_{1-6}$-alkyl) or $C_{1-6}$-alkyl that optionally may be substituted with halo and hydroxy, i=0, 1 or 1 and j=0 or 1, (CH$_2$)$_k$-heterocycle that optionally may be substituted with $C_{1-6}$-alkyl, k=0, 1 or 2, (CH$_2$)$_l$-heteroaryl that optionally may be substituted with $C_{1-6}$-alkyl or halo, l=0, or 2, (CH$_2$)$_m$—O—(CH$_2$)$_n$—O—$C_{1-6}$-alkyl, m=1 or 2, n=1, 2 or 3, (CH$_2$)$_o$—(C=O)—NR$^7$R$^8$, o=0, 1 or 2, (CH$_2$)$_p$—O—(CH$_2$)$_q$—O—(CH$_2$)$_r$—O—$C_{1-6}$-alkyl, p=1 or 2, q=1, 2 or 3, r=1, 2 or 3, (CH$_2$)$_s$—(C=O)—$C_{1-6}$-alkyl, s=1, 2 or 3, (CH$_2$)$_t$—(C=O)—O—$C_{1-6}$-alkyl, t=1, 2, 3 or 4, (CH$_2$)$_u$—$C_{3-7}$-cycloalkyl, u=1 or 2, (CH$_2$)$_v$—NH—(C=O)—O—(CH$_2$)w-heteroaryl, v=1, 2 or 3, w=1 or 2, and (CH$_2$)$_x$—SO$_2$—$C_{1-6}$-alkyl, x=1, R$^7$ or R$^8$ each individually selected from the group H, and $C_{1-6}$-alkyl.

or a pharmaceutically acceptable salt thereof.

A certain embodiment of the invention relates to a compound of formula I as described herein wherein W and X are the same or different and each is independently selected from the group H, and $C_{1-6}$-alkyl, or alternatively, W together with the nitrogen to which it is bound and Y together with the carbon to which it is bound can form a $C_{3-9}$-heterocycle;

Y is $C_{1-6}$-alkyl

Z is selected from the group $C_{1-6}$-alkyl that optionally may be substituted with naphthyl naphthyl that optionally may be substituted with $C_{1-6}$-alkyl, $C_{1-6}$-alkoxy, OCD$_3$, halo-$C_{1-6}$-alkoxy, halo, COO—$C_{1-6}$-alkyl, COOH or CON(H, $C_{1-6}$-alkyl), and heteroaryl that optionally may be substituted with $C_{1-6}$-alkyl, $C_{1-6}$-alkoxy, halo-$C_{1-6}$-alkoxy, halo or oxo, and R$^1$, R$^2$ and R$^3$ are H, R$^4$ is selected from the group H, and $C_{1-6}$-alkyl;

R$^5$ is selected from the group

H $C_{1-6}$-alkyl that optionally may be substituted with aryl that optionally may be substituted with cyano,

C(O)R$^6$,

SO$_2$—CH$_2$—SO$_2$—$C_{1-6}$-alkyl,

SO$_2$—N($C_{1-6}$-alkyl)$_2$,

SO$_2$—NH$_2$,

SO$_2$—N(H,$C_{1-6}$-alkyl),

SO$_2$-aryl that optionally may be substituted with $C_{1-6}$-alkoxy, nitro, N(H, C(O)—$C_{1-6}$-alkyl) or C(O)—$C_{1-6}$-alkyl, SO$_2$—$C_{1-6}$-alkyl, and COO—$C_{1-6}$-alkyl, and R$^5$ optionally may be linked with Z to form a cyclic group;

R$^6$ is selected from the group $C_{1-6}$-alkyl that optionally may be substituted with amino, nitro, $C_{1-6}$-alkoxy or COOH (CH$_2$)$_i$-aryl that optionally may be substituted with amino, cyano, nitro, halo, SO$_2$—$C_{1-6}$-alkyl, C(O)—$C_{1-6}$-alkyl, $C_{1-6}$-alkoxy, C(O)—NH$_2$, C(O)—NH(CH$_2$)j-$C_{3-7}$-cycloalkyl, N(H, C(O)—$C_{1-6}$-alkyl) or $C_{1-6}$-alkyl that optionally may be substituted with halo and hydroxy, i=0, 1, j=1

(CH$_2$)$_k$-heterocycle that optionally may be substituted with $C_{1-6}$-alkyl, k=0, 1, (CH$_2$)$_l$-heteroaryl that optionally may be substituted with $C_{1-6}$-alkyl or halo, l=0, 1, (CH$_2$)$_m$—O—(CH$_2$)$_n$—O—$C_{1-6}$-alkyl, m=1, n=2, (CH$_2$)$_o$—(C=O)—NR$^7$R$^8$, o=0, 1, (CH$_2$)$_p$—O—(CH$_2$)$_q$—O—(CH$_2$)$_r$—O—$C_{1-6}$-alkyl, p=1, q=2, r=2, (CH$_2$)$_s$—(C=O)—$C_{1-6}$-alkyl, s=3, (CH$_2$)$_t$—(C=O)—O—$C_{1-6}$-alkyl, t=4, (CH$_2$)$_u$—$C_{3-7}$-cycloalkyl, u=1, (CH$_2$)$_v$—NH—(C=O)—O—(CH$_2$)w-heteroaryl, v=2, 3, w=1, and (CH$_2$)$_x$—SO$_2$—$C_{1-6}$-alkyl, x=1

R$^7$ or R$^8$ each individually selected from the group

H, and $C_{1-6}$-alkyl.

or a pharmaceutically acceptable salt thereof.

A certain embodiment of the invention relates to a compound of formula I as described herein wherein X is H or CH$_3$.

A certain embodiment of the invention relates to a compound of formula I as described herein wherein X is H.

A certain embodiment of the invention relates to a compound of formula I as described herein wherein X is CH$_3$.

A certain embodiment of the invention relates to a compound of formula I as described herein wherein W is H, CH$_3$ or —CH$_2$—CH$_3$.

A certain embodiment of the invention relates to a compound of formula I as described herein wherein W is H.

A certain embodiment of the invention relates to a compound of formula I as described herein wherein W is CH$_3$.

A certain embodiment of the invention relates to a compound of formula I as described herein wherein W together with the nitrogen to which it is bound and Y together with the carbon to which it is bound can form a $C_{3-9}$-heterocycle, in particular azetidinyl.

A certain embodiment of the invention relates to a compound of formula I as described herein wherein —$CH_2$—$CH_3$.

A certain embodiment of the invention relates to a compound of formula I as described herein wherein Y is $CH_3$ or —$CH_2$—$CH_3$.

A certain embodiment of the invention relates to a compound of formula I as described herein wherein Y is $CH_3$.

A certain embodiment of the invention relates to a compound of formula I as described herein wherein Y is —$CH_2$—$CH_3$.

A certain embodiment of the invention relates to a compound of formula I as described herein wherein $R^4$ is H or $CH_3$.

A certain embodiment of the invention relates to a compound of formula I as described herein wherein $R^4$ is H.

A certain embodiment of the invention relates to a compound of formula I as described herein wherein $R^4$ is $CH_3$.

A certain embodiment of the invention relates to a compound of formula I as described herein wherein X is H, W is $CH_3$, Y is $CH_3$, $R^1$ is H, $R^2$ is H, $R^3$ is H and $R^4$ is H.

A certain embodiment of the invention relates to a compound of formula I as described herein wherein $R^5$ is H, $C(O)R^6$, $C_{1-6}$-alkyl, $C_{1-6}$-alkyl that optionally may be substituted with phenyl that optionally may be substituted with cyano, COO $C_{1-6}$-alkyl, $SO_2$-phenyl that optionally may be substituted with $C_{1-6}$-alkoxy, nitro, N(H, C(O)—$C_{1-6}$-alkyl) and C(O)—$C_{1-6}$-alkyl, $SO_2$—N($C_{1-6}$-alkyl)$_2$, $SO_2$—N(H, $C_{1-6}$-alkyl), $SO_2$—$C_{1-6}$-alkyl or $SO_2$—$C_{1-6}$-alkyl-$SO_2$—$C_{1-6}$-alkyl.

A certain embodiment of the invention relates to a compound of formula I as described herein wherein $R^5$ is —$(CH_2)_2$-Ph, $_3$-methyl-butyl, —$C(O)R6$, —$CH_2$-Ph, —$CH_2$-Ph-CN, —$CH_3$, COO—$CH_3$, —H, —, $SO_2$—$CH_2$—$SO_2$—$CH_3$, $SO_2$—$CH_3$, $SO_2$—N($CH_3$)$_2$, $SO_2$—N(H,$CH_3$), $SO_2$-Ph, $SO_2$-Ph-CO—$CH_3$, $SO_2$-Ph-NH—CO—$CH_3$, $SO_2$-Ph-$NO_2$ or $SO_2$-Ph-$OCH_3$.

A certain embodiment of the invention relates to a compound of formula I as described herein wherein $R^5$ is $R^5$ is $C_{1-6}$-alkyl that is substituted with phenyl that optionally may be substituted with cyano or COO—$C_{1-6}$-alkyl, $SO_2$-phenyl that optionally may be substituted with $C_{1-6}$-alkoxy, nitro, N(H, C(O)—$C_{1-6}$-alkyl) and C(O)—$C_{1-6}$-alkyl, $SO_2$—N($C_{1-6}$-alkyl)$_2$, $SO_2$—N(H,$C_{1-6}$-alkyl), $SO_2$—$C_{1-6}$-alkyl or $SO_2$—$C_{1-6}$-alkyl-$SO_2$—$C_{1-6}$-alkyl.

A certain embodiment of the invention relates to a compound of formula I as described herein wherein $R^5$ is $C(O)R^6$.

A certain embodiment of the invention relates to a compound of formula I as described herein wherein X is H, W is $CH_3$, Y is $CH_3$, $R^1$ is H, $R^2$ is H, $R^3$ is H, $R^4$ is H and $R^5$ is $C(O)R^6$.

A certain embodiment of the invention relates to a compound of formula I as described herein wherein $R^6$ is selected from $C_{1-6}$-alkyl that optionally may be substituted with amino, nitro and $C_{1-6}$-alkoxy, $(CH_2)_i$-aryl that optionally may be substituted with amino, cyano, nitro, halo, $SO_2$—$C_{1-6}$-alkyl, C(O)—$C_{1-6}$-alkyl, $C_{1-6}$-alkoxy, C(O)—$NH_2$, C(O)—NH$(CH_2)j$-$C_{3-7}$-cycloalkyl, N(H, C(O)—$C_{1-6}$-alkyl), $C_{1-6}$-alkyl that optionally may be substituted with halo and hydroxy, i=0, 1, j=1

$(CH_2)_k$-heterocycle that optionally may be substituted with $C_{1-6}$-alkyl, k=0, 1, $(CH_2)_l$-heteroaryl that optionally may be substituted with $C_{1-6}$-alkyl, halo, l=0, 1, $(CH_2)_m$—O—$(CH_2)_n$—O—$C_{1-6}$-alkyl, m=1, n=2, $(CH_2)_o$—(C=O)—$NR^7R^8$, o=0, 1, $(CH_2)_p$—O—$(CH_2)_q$—O—$(CH_2)_r$—O—$C_{1-6}$-alkyl, p=1, q=2, r=2, $(CH_2)_s$—(C=O)—$C_{1-6}$-alkyl, s=3, $(CH_2)_t$—(C=O)—O—$C_{1-6}$-alkyl, t=4, $(CH_2)_u$—$C_{3-7}$-cycloalkyl, u=1, $(CH_2)_v$—NH—(C=O)—O—$(CH_2)w$-heteroaryl, v=2, 3, w=1, and $(CH_2)_x$—$SO_2$—$C_{1-6}$-alkyl, x=1.

A certain embodiment of the invention relates to a compound of formula I as described herein wherein $R^6$ is selected from $(CH_2)_m$—O—$(CH_2)_n$—O—$C_{1-6}$-alkyl, m=1, n=2, $(CH_2)_o$—(C=O)—$NR^7R^8$, o=0, 1, $(CH_2)_p$—O—$(CH_2)_q$—O—$(CH_2)_r$—O—$C_{1-6}$-alkyl, p=1, q=2, r=2, $(CH_2)_s$—(C=O)—$C_{1-6}$-alkyl, s=3, $(CH_2)_t$—(C=O)—O—$C_{1-6}$-alkyl, t=4, $(CH_2)_u$—$C_{3-7}$-cycloalkyl, u=1, and $(CH_2)_v$—NH—(C=O)—O—$(CH_2)w$-heteroaryl, v=2, 3, w=1.

A certain embodiment of the invention relates to a compound of formula I as described herein wherein $R^6$ is $CH_2)_2COOH$, —$(CH_2)_2$—$NH_2$, —$(CH_2)_2$—$OCH_3$, —$(CH_2)_3$—CO—$CH_3$, —$(CH_2)_3COOH$, —$(CH_2)_3$—$NH_2$, —$(CH_2)_3$—$NO_2$, —$(CH_2)_4$—COO—$CH_3$, —$(CH_2)_4$—COOH, —$(CH_2)_4$—$NH_2$, 1H-pyrazolyl-$CH_3$, 1H-pyrazolyl-$CH_3$, 3-methyl-butyl-, 4-methyl-piperazin-1-yl, adamantyl, —$CH_2$-1H-tetrazolyl, —$CH_2$-adamantyl, —$CH_2$—C(O)—$NH_2$, —$CH_2$-cyclohexyl, —$CH_2$—O—$(CH_2)_2$—O—$(CH_2)_2$—O—$CH_3$, —$CH_2$—O—$(CH_2)_2$—O—$CH_3$, —$CH_2$-Ph, —$CH_2$-Ph-$CH_2OH$, —$CH_2$-Ph-CO—$CH_3$, —$CH_2$-Ph-CO—$NH_2$, —$CH_2$-pyridinyl, —$CH_2$—$SO_2$—$CH_3$, —$CH_2$-tetrahydro-pyranyl, $CH_3$, -furanyl-$CH_3$, H, isoxazolyl, N(H,$CH_3$), -Ph, -Ph-$(OCH_3)_3$, -Ph-C(H,OH)—$CF_3$, -Ph-C(H,OH)—$CH_3$, -Ph-$C(OH)_2$—$CF_3$, -Ph-$CF_3$, -Ph-$CH_2OH$, -Ph-$CH_3$, -Ph-Cl, -Ph-CN, -Ph-$CNO_2$, -Ph-CO—$(CH_3)_3$, -Ph-CO—$CH_3$, -Ph-CO—$NH_2$, -Ph-CO—NH—$CH_2$-cyclohexyl, -Ph-CO—$NO_2$, -Ph-CO—$OCH_3$, -Ph-COOH, -Ph-cyano, -Ph-F, -Ph-$NH_2$, -Ph-NH—CO—$CH_3$, -Ph-NH—CO—O—$CH_2$-9H-fluorenyl, -Ph-$OCH_3$, -Ph-$SO_2CH_3$, pyrazinyl, pyridinyl, pyridinyl, pyridinyl, or tetrahydro-2H-pyranyl.

A certain embodiment of the invention relates to a compound of formula I as described herein wherein $R^6$ is $(CH_2)_i$-phenyl that optionally may be substituted with amino, cyano, nitro, halo, $SO_2$—$C_{1-6}$-alkyl, C(O)—$C_{1-6}$-alkyl, $C_{1-6}$-alkoxy, C(O)—$NH_2$, C(O)—NH$(CH_2)_j$—$C_{3-7}$-cycloalkyl, N(H, C(O)—$C_{1-6}$-alkyl), $C_{1-6}$-alkyl that optionally may be substituted with halo and hydroxy, i=0, 1, j=1.

A certain embodiment of the invention relates to a compound of formula I as described herein wherein $R^6$ is phenyl or $(CH_2)$-phenyl, each phenyl may optionally be substituted by amino, cyano, $C_{1-6}$-alkyl, halo, $C_{1-6}$-alkoxy or C(O)—$C_{1-6}$-alkyl.

A certain embodiment of the invention relates to a compound of formula I as described herein wherein X is H, W is $CH_3$, Y is $CH_3$, $R^1$ is H, $R^2$ is H, $R^3$ is H, $R^4$ is H, $R^5$ is $C(O)R^6$ and $R^6$ is $R^6$ is $(CH_2)_i$-phenyl that optionally may be substituted with amino, cyano, nitro, halo, $SO_2$—$C_{1-6}$-alkyl, C(O)—$C_{1-6}$-alkyl, $C_{1-6}$-alkoxy, C(O)—$NH_2$, C(O)—NH ($CH_2$)$_j$—$C_{3-7}$-cycloalkyl, N(H, C(O)—$C_{1-6}$-alkyl), $C_{1-6}$-alkyl that optionally may be substituted with halo and hydroxy, i=0, 1, j=1.

A certain embodiment of the invention relates to a compound of formula I as described herein wherein X is H, W is $CH_3$, Y is $CH_3$, $R^1$ is H, $R^2$ is H, $R^3$ is H, $R^4$ is H, $R^5$ is C(O)$R^6$ and $R^6$ is phenyl or ($CH_2$)-phenyl, each phenyl may optionally be substituted by amino, cyano, $C_{1-6}$-alkyl, halo, $C_{1-6}$-alkoxy or C(O)—$C_{1-6}$-alkyl.

A certain embodiment of the invention relates to a compound of formula I as described herein wherein Z is
- $C_{1-6}$-alkyl that optionally may be substituted with naphthyl
- naphthyl that optionally may be substituted with $C_{1-6}$-alkyl, $C_{1-6}$-alkoxy, $OCD_3$, halo-$C_{1-6}$-alkoxy, COO—$C_{1-6}$-alkyl, COOH and CON(H, $C_{1-6}$-alkyl), and
- heteroaryl that optionally may be substituted with $C_{1-6}$-alkyl, $C_{1-6}$-alkoxy, halo-$C_{1-6}$-alkoxy, halo, and oxo.

A certain embodiment of the invention relates to a compound of formula I as described herein wherein Z is naphthyl that optionally may be substituted with $C_{1-6}$-alkyl, halo and $C_{1-6}$-alkoxy.

A certain embodiment of the invention relates to a compound of formula I as described herein wherein X is H, W is $CH_3$, Y is $CH_3$, $R^1$ is H, $R^2$ is H, $R^3$ is H, $R^4$ is H, $R^5$ is C(O)$R^6$, $R^6$ is phenyl or ($CH_2$)-phenyl, each phenyl may optionally be substituted by amino, cyano, $C_{1-6}$-alkyl, halo, $C_{1-6}$-alkoxy or C(O)—$C_{1-6}$-alkyl and Z is naphthyl that optionally may be substituted with $C_{1-6}$-alkyl, halo and $C_{1-6}$-alkoxy.

A certain embodiment of the invention relates to a compound of formula I as described herein wherein $R^5$ optionally may be linked with Z to form a cyclic group.

A certain embodiment of the invention relates to a compound of formula I as described herein wherein $R^5$ optionally may be linked with Z to form a cyclic group, selected from the group consisting of
- Cyclic-5-[(S)-5-(2-Amino-ethyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride,
- Cyclic-5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride,
- Cyclic-5-[(S)-5-(3-amino-propyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride,
- Cyclic-5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, and
- Cyclic-5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride.

A certain embodiment of the invention relates to a compound of formula I as described herein that is selected from the group consisting of
- (S)-2-Methylamino-N—((S)-1-naphthalen-1-ylmethyl-2-oxo-2,3,4,5-tetrahydro-1H-benzo[b][1,4]diazepin-3-yl)-propionamide hydrochloride,
- (S)—N—((S)-5-Acetyl-1-naphthalen-1-ylmethyl-2-oxo-2,3,4,5-tetrahydro-1H-benzo[b][1,4]diazepin-3-yl)-2-methylamino-propionamide hydrochloride,
- (S)-2-Methylamino-N—[(S)-5-(3-methyl-butyryl)-1-naphthalen-1-ylmethyl-2-oxo-2,3,4,5-tetrahydro-1H-benzo[b][1,4]diazepin-3-yl]-propionamide hydrochloride,
- (S)-2-Methylamino-N—((S)-1-naphthalen-1-ylmethyl-2-oxo-5-phenylacetyl-2,3,4,5-tetrahydro-1H-benzo[b][1,4]diazepin-3-yl)-propionamide hydrochloride,
- (S)-2-Methylamino-N—((S)-5-methyl-1-naphthalen-1-ylmethyl-2-oxo-2,3,4,5-tetrahydro-1H-benzo[b][1,4]diazepin-3-yl)-propionamide hydrochloride,
- (S)-2-Methylamino-N—[(S)-5-(3-methyl-butyl)-1-naphthalen-1-ylmethyl-2-oxo-2,3,4,5-tetrahydro-1H-benzo[b][1,4]diazepin-3-yl]-propionamide hydrochloride,
- (S)-2-Methylamino-N—((S)-1-naphthalen-1-ylmethyl-2-oxo-5-phenethyl-2,3,4,5-tetrahydro-1H-benzo[b][1,4]diazepin-3-yl)-propionamide trifluoroacetate,
- (S)-2-Methylamino-N—[(S)-5-(3-methyl-butyryl)-1-(2-methyl-naphthalen-1-ylmethyl)-2oxo-2,3,4,5-tetrahydro-1H-benzo[b][1,4]diazepin-3-yl]-propionamide hydrochloride,
- (S)-2-Methylamino-N—[(S)-1-(2-methyl-naphthalen-1-naphthalen-1ylmethyl)-2-oxo-5-(pyridine-4-carbonyl)-2,3,4,5-tetrahydro-1H-benzo[b][1,4]diazepin-3-yl]-propionamide hydrochloride,
- (S)—N—[(S)-5-[2-(2-methoxy-ethoxy)-acetyl]-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
- (S)—N—[(S)-5-(2-Carbamoyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
- (S)-2-methylamino-N—{(S)-1(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-yl}-propionamide hydrochloride,
- (S)—N—[(S)-5-{2-[2-(2-Methoxy-ethoxy)-ethoxy]-acetyl}-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride,
- (S)-2-Methylamino-N—[(S)-1-(2-methyl-naphthalen-1-ylmethyl)-2-oxo-5-(2-pyridin-4-yl-acetyl)-2,3,4,5-tetrahydro-1H-benzo[b][1,4]diazepin-3-yl]-propionamide dihydrochloride,
- (S)—N—[(S)-5-(4-Methanesulfonyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
- (S)-2-Methylamino-N—[(S)-1-(2-methyl-naphthalen-1-ylmethyl)-2-oxo-5-(5-oxo-hexanoyl)-2,3,4,5-tetrahydro-1H-benzo[b][1,4]diazepin-3-yl]-propionamide hydrochloride,
- methyl 6-((S)-3-((S)-2-(methylamino)propanamido)-5-((2-methylnaphthalen-1-yl)methyl)-4-oxo-2,3,4,5-tetrahydro-1H-benzo[b][1,4]diazepin-1-yl)-6-oxohexanoate hydrochloride,
- (S)—N—[(S)-5-(4-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
- (S)-2-Methylamino-N—[(S)-1-(2-methyl-naphthalen-1-yl-methyl)-2-oxo-5-(3,4,5-trimethoxy-benzoyl)-2,3,4,5-tetrahydro-1H-benzo[b][1,4]diazepin-3-yl]-propionamide hydrochloride,
- (S)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino) propanamide hydrochloride, (S)—N—((S)-1-((6-bromo-2-methoxynaphthalen-1-yl) methyl)-5-(2-cyclohexylacetyl)-2-oxo-2,3,4,5-tetrahydro-1H-benzo[b][1,4]diazepin-3-yl)-2-(methylamino)propanamide hydrochloride, (S)—N—{(S)-1-(6-Bromo-2-methoxy-naphthalen-1-ylmethyl)-5-[4-(2,2-dimethyl-propionyl)-benzoyl]-2-oxo-2,3,4,5-tetrahydro-1H-benzo[b][1,4]diazepin-3-yl}-2-methylamino-propionamide hydrochloride, (S)—N—{(S)-1-(6-Bromo-2-methoxy-naphthalen-1-ylmethyl)-2-oxo-5-[4-(2,2,2-trifluoro-1,1-dihydroxy-ethyl)-benzoyl]-2,3,4,5-tetrahydro-1H-benzo[b][1,4]diazepin-3-yl}-2-methylamino-propionamide trifluoroacetate, (S)—N—[(S)-5-(3-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(4-nitro-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(4-nitro-butyryl)-2-oxo-2,3,4,5-tetrahydro-1H-benzo[b][1,4]diazepin-3-yl]-2-methylamino-propionamide hydrochloride, (S)—N—[(S)-5-[2-(4-Acetyl-phenyl)-acetyl]-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—((S)-1-((6-bromo-2-methoxynaphthalen-1-yl) methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—[(S)-5-(2-Adamantan-1-yl-acetyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, methyl 5-[[(3S)-1-[3-(9H-fluoren-9-ylmethoxycarbonylamino)propanoyl]-3-[[(2S)-2-(methylamino)propanoyl]amino]-4-oxo-2,3-dihydro-1,5-benzodiazepin-5-yl]methyl]-6-methoxy-naphthalene-2-carboxylate hydrochloride, (S)—N—[(S)-5-acetyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, 5-[(S)-3-((S)-2-methylamino-propionylamino)-5-(2-methyl-naphthalen-1-ymethyl)-4-oxo-2,3,4,5-tetrahydrobenzo[b][1,4]diazepin-1yl]-5-oxo-pentanoic acid hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-yl]-4-oxo-butyric acid hydrochloride, (S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methylamide hydrochloride, (S)—N—[(S)-5-methanesulfonylmethanesulfonyl-1-(2-methyl-naphthalen-1-ylmethyl)-2-oxo-2,3,4,5-tetrahydro-1H-benzo[b][1,4]diazepin-3-yl]-2-methylamino-propionamide trifluoroacetate, (S)—N—[(S)-5-methanesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methyl ester hydrochloride, (S)—N—[(S)-1-benzyl-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-1-(2-methoxy-benzyl)-5-(3-methyl-butyryl)-2-oxo-2,3,4,5-tetrahydro-1H-benzo[b][1,4]diazepin-3-yl]-2-methylamino-propionamide hydrochloride, (S)-2-Methylamino-N—[(S)-5-(3-methyl-butyryl)-2-oxo-1-phenethyl-2,3,4,5-tetrahydro-1H-benzo[b][1,4]diazepin-3-yl]-propionamide hydrochloride, (S)—N—[(S)-1-(2-Methoxy-naphthalen-1-ylmethyl)-5-(3-methyl-butyryl)-2-oxo-2,3,4,5-tetrahydro-1H-benzo[b[1,4]diazepin-3-yl]-2-methylamino-propionamide hydrochloride, (S)-2-Methylamino-N—[(S)-5-(3-methyl-butyryl)-1-(1-naphthalen-1-yl-ethyl)-2-oxo-2,3,4,5-tetrahydro-1H-benzo[b][1,4]diazepin-3-yl]-propionamide hydrochloride, (S)—N—[(S)-1-(6-bromo-2-methoxy-naphthalen-1-ylmethyl)-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-1-(6-bromo-2-methoxy-naphthalen-1-ylmethyl)-2-oxo-5-(5-oxo-hexanoyl)-2,3,4,5-tetrahydro-1H-benzo[b][1,4]diazepin-3-yl]-2-methylamino-propionamide hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid methyl ester hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzamide hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-N-cyclohexylmethyl-benzamide hydrochloride, (S)—N—{(S)-1-(6-bromo-2-methoxy-naphthalen-1-ylmethyl)-2-oxo-5-[4-(2,2,2-trifluoro-1-hydroxy-ethyl)-benzoyl]-2,3,4,5-tetrahydro-1H-benzo[b][1,4]diazepin-3-yl}-2-methylamino-propionamide hydrochloride, (S)—N—{(S)-1-(6-bromo-2-methoxy-naphthalen-1-ylmethyl)-5-(4-(1-hydroxy-ethyl)-benzoyl)-2-oxo-2,3,4,5-tetrahydro-1H-benzo[b][1,4]diazepin-3-yl}-2-methylamino-propionamide hydrochloride, (S)—N—[(S)-5-(Adamantan-1-carbonyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Amino-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)-Azetidine-2-carbonxylic acid[(S)-5-(4-acetyl-benzoyl)-1-(6-bromo-2-methoxy-naphthalen-1-ylmethyl)-2-oxo-2,3,4,5-tetrahydro-1H-benzo[[b][1,4]diazepin-3-yl]-amide hydrochloride, (R)—N—[(S)-5-(4-acetyl-benzoyl)-1-(6-bromo-2-methoxyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-dimethylamino-propionamide, (S)—N—[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-amino-propionamide, (S)—N—[(S)-5-(4-Acetyl-benzoyl)-1-(2-naphthalen-1-ylethyl)-2-oxo-2,3,4,5-tetrahydro-1H-benzo[b][1,4]diazepin-3-yl]-2-methylamino-propionamide hydrochloride, (S)—N—[(S)-5-(4-amino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-acetylamino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, 5-[(S)-5-(4-Acetyl-benzoyl)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid methyl ester hydrochloride, 5-[(S)-5-(4-acetyl-benzoyl)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid hydrochloride, 5-[(S)-5-(4-acetyl-benzoy)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid hydroxyamide trifluoroacetate, 6-Methoxy-5-[(S)-3 ((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid methyl ester hydrochloride, 6-Methoxy-5-[(S)-3 ((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid hydrochloride, 5-[(S)-5-[4-(9H-Fluoren-9-ylmethoxycarbonylamino)-butyryl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, Cyclic-5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, 5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, Cyclic-5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, 5-[(S)-5-[4-(9H-Fluoren-9-ylmethoxycarbonylamino)-benzoyl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(4-Amino-benzoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(4-Amino-benzoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, Cyclic-5-[(S)-5-(3-amino-propyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, Cyclic-5-[(S)-5-(2-Amino-ethyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, 6-[(S)-3-((S)-2-Methylamino-propionylamino)-5-(2-methyl-naphthalen-1-ylmethyl)-4-oxo-2,3,4,5-tetrahydro-benzo[b][1,4]diazepin-1-yl]-6-oxo-hexanoic acid hydrochloride, 5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, Cyclic-5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, (S)—N—((S)-5-(4-Acetylbenzoyl)-1-((2-methylnaphthalen-1-yl)methyl)-2-oxo-2,3,4,5-tetrahydro-1H-benzo[b][1,4]diazepin-3-yl)-2-aminopropanamide hydrochloride, (S)-2-Amino-N—((S)-5-(4-aminobenzoyl)-1-((2-methoxynaphthalen-1-yl)methyl)-2-oxo-2,3,4,5-tetrahydro-1H-benzo[b][1,4]diazepin-3-yl)propanamide hydrochloride, (S)-2-(Methylamino)-N—((S)-1-((2-methylnaphthalen-1-yl)methyl)-5-(4-nitrobenzoyl)-2-oxo-2,3,4,5-tetrahydro-1H-benzo[b][1,4]diazepin-3-yl)propanamide hydrochloride, (S)—N—((S)-5-(4-Aminobenzoyl)-1-((2-methylnaphthalen-1-yl)methyl)-2-oxo-2,3,4,5-tetrahydro-1H-benzo[b][1,4]diazepin-3-yl)-N-methyl-2-(methylamino)propanamide hydrochloride, (R)—N—((S)-5-(4-Acetylbenzoyl)-1-((2-methylnaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-Acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((7-methoxy-2-oxo-2H-chromen-4-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((6-bromobenzo[d]isoxazol-3-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-aminopropanamide hydrochloride, (S)—N—((S)-5-(4-acetylbenzoyl)-1-((2-(difluoromethoxy)naphthalen-1-yl)methyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-((7-methoxy-2-oxo-2H-chromen-4-yl)methyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-(benzo[d]isoxazol-3-ylmethyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, 4-(((S)-5-(4-Acetylbenzoyl)-3-((S)-2-(methylamino)propanamido)-2-oxo-2,3,4,5-tetrahydro-1H-benzo[b][1,4]diazepin-1-yl)methyl)-3-(2,2,2-trifluoroethoxy)quinoline 1-oxide hydrochloride, (S)—N—((S)-5-(4-Aminobenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, Methyl 4-((S)-5-(benzo[d]isoxazol-3-ylmethyl)-3-((S)-2-(methylamino)propanamido)-4-oxo-2,3,4,5-tetrahydro-1H-benzo[b][1,4]diazepine-1-carbonyl)benzoate hydrochloride, (S)—N—((S)-1-((5-Bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-5-(4-Cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide, (S)—N—((S)-1-((6-Bromo-2-methoxynaphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-methylbenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(isoxazole-5-carbonyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride, (S)—N—((S)-1-((6-Bromo-2-methoxynaphthalen-1-yl)methyl)-2-oxo-5-(2-(pyridin-3-yl)acetyl)-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(pyrazine-2-carbonyl)-2,3,4,5-tetrahydro-1H-benzo[b][1,4]diazepin-3-yl)-2-(methylamino)propanamide hydrochloride, (S)—N—((S)-5-(4-acetamidobenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—((S)-1-((6-bromo-2-methoxynaphthalen-1-yl)methyl)-5-(1-methyl-1H-pyrazole-3-carbonyl)-2-oxo-2,3,4,5-tetrahydro-1H-benzo[b][1,4]diazepin-3-yl)-2-(methylamino)propanamide trifluoroacetate, (S)—N—((S)-5-Benzyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—((S)-1-((6-Bromo-2-methoxynaphthalen-1-yl)methyl)-5-(4-cyanobenzyl)-2-oxo-2,3,4,5-tetrahydro-1H-benzo[b][1,4]diazepin-3-yl)-2-(methylamino)propanamide trifluoroacetate, (S)—N—((S)-5-(4-Acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)butanamide hydrochloride, (S)—N—((S)-5-(4-Acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(ethylamino)propanamide hydrochloride, (S)—N—((S)-1-((5-Bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((2-Methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((2-(Difluoromethoxy)naphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—[(S)-1-(6-Bromo-2-(d3-methoxy)-naphthalen-1-ylmethyl)-5-(4-cyano-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-(d3-methoxy)-naphthalen-1-ylmethyl)-2-oxo-5-(2-pyridin-3-yl-acetyl)-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-2-oxo-5-(2-pyridin-3-yl-acetyl)-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-2-oxo-5-(pyridine-2-carbonyl)-2,3,4,5-tetrahydro-1H-benzo[b][1,4]diazepin-3-yl]-2-methylamino-propionamide hydrochloride, (S)—N—((S)-1-((6-bromo-2-methoxynaphthalen-1-yl)methyl)-5-nicotinoyl-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(2-(pyridin-2-yl)acetyl)-2,3,4,5-tetrahydro-1H-benzo[b][1,4]diazepin-3-yl)-2-(methylamino)propanamide hydrochloride, (S)—N—((S)-5-benzoyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(1-methyl-1H-pyrazole-4-carbonyl)-2-oxo-2,3,4,5-tetrahydro-1H-benzo[b][1,4]diazepin-3-yl)-2-(methylamino)propanamide hydrochloride, (S)—N—[(S)-1-(6-Bromo-2-methoxy-naphthalen-1-ylmethyl)-5-(2-fluoro-benzoyl)-2-oxo-2,3,4,5-tetrahydro-1H-benzo[b][1,4]diazepin-3-yl]-2-methylamino-propionamide hydrochloride, (S)—N—((S)-1-((6-bromo-2-methoxynaphthalen-1-yl)methyl)-5-(3-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-(methylsulfonyl)benzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-methoxypropanoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-cyanobenzoyl)-2-oxo-2,3,4,5-tetrahydro-1H-benzo[b][1,4]diazepin-3-yl)-2-(methylamino)propanamide hydrochloride, (S)—N—[(S)-5-Benzoyl-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—((S)-5-acetyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(5-methylfuran-2-carbonyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(4-(trifluoromethyl)benzoyl)-2,3,4,5-tetrahydro-1H-benzo[b][1,4]diazepin-3-yl)-2-(methylamino)propanamide hydrochloride, (S)—N—[(S)-1-(5-Bromo-2-methoxy-naphthalen-1-ylmethyl)-5-(4-fluoro-benzoyl)-2-oxo-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-5-(4-methyl-benzoyl)-2-oxo-2,3,4,5-tetrahydro-1H-benzo[b][1,4]diazepin-3-yl]-2-methylamino-propionamide hydrochloride, (S)—N—{(S)-1-(5-Bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-yl}-2-methylamino-propionamide, (S)—N—{(S)-1-(6-Bromo-2-methoxy-naphthalen-1-ylmethyl)-5-[4-(1-hydroxy-1-methyl-ethyl)-benzoyl]-2-oxo-2,3,4,5-tetrahydro-1H-benzo[b][1,4]diazepin-3-yl}-2-methylamino-propionamide trifluoroacetate, 4-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzoic acid methyl ester hydrochloride, (S)-2-Methylamino-N—[(S)-1-(2-methyl-naphthalen-1-ylmethyl)-2-oxo-5-(2-1H-tetrazol-5-yl-acetyl)-2,3,4,5-tetrahydro-1H-benzo[b][1,4]diazepin-3-yl]-propionamide hydrochloride, (S)-2-Methylamino-N—[(S)-1-(2-methyl-naphthalen-1-ylmethyl)-2-oxo-5-(2-tetrahydro-pyran-4-yl-acetyl)-2,3,4,5-tetrahydro-1H-benzo[b][1,4]diazepin-3-yl]-propionamide hydrochloride, (S)—N—[(S)-5-(4-Cyano-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(2-Cyclohexyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Chloro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)-2-Methylamino-N—[(S)-1-(2-methyl-naphthalen-1-ylmethyl)-2-oxo-5-(2-pyridin-3-yl-acetyl)-2,3,4,5-tetrahydro-1H-benzo[b][1,4]diazepin-3-yl]-propionamide, (S)—N—[(S)-5-(4-Fluoro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Amino-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)-2-Methylamino-N—[(S)-5-(4-methyl-benzoyl)-1-(2-methyl-naphthalen-1-ylmethyl)-2-oxo-2,3,4,5-tetrahydro-1H-benzo[b][1,4]diazepin-3-yl]-propionamide hydrochloride, (S)—N—[(S)-5-(4-Methoxy-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochoride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-carbonyl]-benzoic acid hydrochloride, (S)—N—[(S)-5-(4-Acetylamino-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)-2-Methylamino-N—[(S)-1-(2-methyl-naphthalen-1-ylmethyl)-5-methylsulfamoyl-2-oxo-2,3,4,5-tetrahydro-1H-benzo[b][1,4]diazepin-3-yl]-propionamide hydrochloride, (S)—N—[(S)-5-(4-Acetyl-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)-2-Methylamino-N—[(S)-1-(2-methyl-naphthalen-1-ylmethyl)-5-(4-nitro-benzenesulfonyl)-2-oxo-2,3,4,5-tetrahydro-1H-benzo[b][1,4]diazepin-3-yl]-propionamide hydrochloride, (S)—N—[(S)-5-Benzenesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methoxy-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, 3-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzamide hydrochloride, (S)—N—[(S)-5-Dimethylsulfamoyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(2-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Hydroxymethyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (2S)—N-((3S)-1-((6-bromo-2-methoxynaphthalen-1-yl)methyl)-5-(4-(1-hydroxyethyl)benzoyl)-2-oxo-2,3,4,5-tetrahydro-1H-benzo[b][1,4]diazepin-3-yl)-2-(methylamino)propanamide, (2S)—N-((3S)-1-((6-bromo-2-methoxynaphthalen-1-yl)methyl)-5-(4-(1-hydroxyethyl)benzoyl)-2-oxo-2,3,4,5-tetrahydro-1H-benzo[b][1,4]diazepin-3-yl)-2-(methylamino)propanamide, (2S)—N-[(3S)-1-(4-acetylbenzoyl)-5-[2-(naphthalen-1-ylamino)-2-oxoethyl]-4-oxo-2,3-dihydro-1,5-benzodiazepin-3-yl]-2-(methylamino)propanamide; 2,2,2-trifluoroacetic acid, (2S)—N-[(3S)-1-(4-acetylbenzoyl)-4-oxo-5-[2-oxo-2-(1,3-thiazol-2-ylamino)ethyl]-2,3-dihydro-1,5-benzodiazepin-3-yl]-(methylamino)propanamide; 2,2,2-trifluoroacetic acid, (S)—N—((S)-1-((6-bromo-2-methoxynaphthalen-1-yl)methyl)-5-(4-nitrobenzoyl)-2-oxo-2,3,4,5-tetrahydro-1H-benzo[b][1,4]diazepin-3-yl)-N-methyl-2-(methylamino)propanamide hydrochloride, (2S)—N-[(3S)-1-(4-acetylbenzoyl)-5-[2-(1,3-benzothiazol-2-ylamino)-2-oxoethyl]-4-oxo-2,3-dihydro-1,5-benzodiazepin-3-yl]-2-(methylamino)propanamide; 2,2,2-trifluoroacetic acid, (2S)—N-[5-(1-adamantylmethyl)-1-[(2-methoxynaphthalen-1-yl)methyl]-2,4-dioxo-1,5-benzodiazepin-3-yl]-2-(methylamino)propanamide, (2S)—N-[5-(1-adamantylmethyl)-1-[(2-methoxynaphthalen-1-yl)methyl]-2,4-dioxo-1,5-benzodiazepin-3-yl]-2-aminopropanamide, (2S)—N-[5-(1-adamantylmethyl)-1-[(2-methoxynaphthalen-1-yl)methyl]-2,4-dioxo-1,5-benzodiazepin-3-yl]-2-(methylamino)butanamide, (2S)—N-(1-methyl-5-((2-methylnaphthalen-1-yl)methyl)-2,4-dioxo-2,3,4,5-tetrahydro-1H-benzo[b][1,4]diazepin-3-yl)-2-(methylamino)butanamide, (2S)-2-(methylamino)-N-(1-((2-methylnaphthalen-1-yl)methyl)-2,4-dioxo-5-phenyl-2,3,4,5-tetrahydro-1H-benzo[b][1,4]diazepin-3-yl)butanamide, (2S)-2-(methylamino)-N-(1-((2-methylnaphthalen-1-yl)methyl)-2,4-dioxo-5-phenyl-2,3,4,5-tetrahydro-1H-benzo[b][1,4]diazepin-3-yl)propanamide, (2S)—N-[(3S)-1-(4-aminophenyl)sulfonyl-5-[(2-methyl-naphthalen-1-yl)methyl]-4-oxo-2,3-dihydro-1,5-benzodiazepin-3-yl]-2-(methylamino)propanamide; hydrochloride, (2S)—N-[(3S)-1-[3-(1-hydroxyethyl)benzoyl]-5-[(2-methylnaphthalen-1-yl)methyl]-4-oxo-2,3-dihydro-1,5-benzodiazepin-3-yl]-2-(methylamino)propanamide; hydrochloride, (2S)—N-[(3S)-1-[3-(1-hydroxyethyl)benzoyl]-5-[(2-methylnaphthalen-1-yl)methyl]-4-oxo-2,3-dihydro-1,5-benzodiazepin-3-yl]-2-(methylamino)propanamide; hydrochloride, (S)—N—((S)-5-(4-acetylbenzoyl)-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide 2,2,2-trifluoroacetate, (S)—N—((S)-5-(4-aminobenzoyl)-7-chloro-1-((2-methylnaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-aminobenzoyl)-7-chloro-1-((2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-aminobenzoyl)-1-((5-bromo-2-methoxynaphthalen-1-yl)methyl)-7-chloro-2-oxo-2,3,4,5-tetrahydro-1H-benzo[b][1,4]diazepin-3-yl)-2-(methylamino)propanamide hydrochloride, (S)—N—((S)-5-(4-aminobenzoyl)-1-((6-bromo-2-methoxynaphthalen-1-yl)methyl)-7-chloro-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-7-chloro-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-7-chloro-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-7-chloro-5-(4-cyanobenzoyl)-2-oxo-2,3,4,5-tetrahydro-1H-benzo[b][1,4]diazepin-3-yl)-2-(methylamino)propanamide hydrochloride, (2S)—N-(1-((6-bromo-2-methoxynaphthalen-1-yl)methyl)-2,4-dioxo-5-phenyl-2,3,4,5-tetrahydro-1H-benzo[b][1,4]diazepin-3-yl)-2-(methylamino)propanamide, (2S)—N-(1-((5-bromo-2-methoxynaphthalen-1-yl)methyl)-2,4-dioxo-5-phenyl-2,3,4,5-tetrahydro-1H-benzo[b][1,4]diazepin-3-yl)-2-(methylamino)propanamide, (S)—N—((S)-1-((6-bromo-2-methoxynaphthalen-1-yl)methyl)-7-chloro-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-7-chloro-5-(4-cyanobenzoyl)-2-oxo-2,3,4,5-tetrahydro-1H-benzo[b][1,4]diazepin-3-yl)-2-(methylamino)propanamide hydrochloride, (2S)—N-(1-((6-bromo-2-methoxynaphthalen-1-yl)methyl)-2,4-dioxo-5-phenyl-2,3,4,5-tetrahydro-1H-benzo[b][1,4]diazepin-3-yl)-2-(ethylamino)butanamide, (2S)-2-amino-N-(1-((6-bromo-2-methoxynaphthalen-1-yl)methyl)-2,4-dioxo-5-phenyl-2,3,4,5-tetrahydro-1H-benzo[b][1,4]diazepin-3-yl)butanamide, (2S)—N-(1-((5-bromo-2-methoxynaphthalen-1-yl)methyl)-2,4-dioxo-5-phenyl-2,3,4,5-tetrahydro-1H-benzo[b][1,4]diazepin-3-yl)-2-(ethylamino)butanamide, (S)—N—((S)-1-((6-bromo-2-(2,2,2-trifluoroethoxy)naphthalen-1-yl)methyl)-7-chloro-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-(2,2,2-trifluoroethoxy)naphthalen-1-yl)methyl)-7-chloro-5-(4-fluorobenzoyl)-2-oxo-2,3,4,5-tetrahydro-1H-benzo[b][1,4]diazepin-3-yl)-2-(methylamino)propanamide hydrochloride, (2S)-2-amino-N-(1-((5-bromo-2-methoxynaphthalen-1-yl)methyl)-2,4-dioxo-5-phenyl-2,3,4,5-tetrahydro-1H-benzo[b][1,4]diazepin-3-yl)butanamide, (2S)—N-(1-((5-bromo-2-methoxynaphthalen-1-yl)methyl)-2,4-dioxo-5-phenyl-2,3,4,5-tetrahydro-1H-benzo[b][1,4]diazepin-3-yl)-2-(2-hydroxyethylamino)butanamide, (S)—N—((S)-7-chloro-5-(4-cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, (S)—N—((S)-7-chloro-1-((2-(difluoromethoxy)naphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (2S)—N-[(3S)-1-(1H-indazole-5-carbonyl)-5-[(2-methylnaphthalen-1-yl)methyl]-4-oxo-2,3-dihydro-1,5-benzodiazepin-3-yl]-2-(methylamino)propanamide, (S)—N—((S)-7-cyano-5-(4-cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-7-cyano-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-7-cyano-5-(4-cyanobenzoyl)-2-oxo-2,3,4,5-tetrahydro-1H-benzo[b][1,4]diazepin-3-yl)-2-(methylamino)propanamide hydrochloride, (2S)—N-[(3S)-1-(1H-indole-5-carbonyl)-5-[(2-methylnaphthalen-1-yl)methyl]-4-oxo-2,3-dihydro-1,5-benzodiazepin-3-yl]-2-(methylamino)propanamide, (2S)—N-[(3S)-1-(1H-indole-4-carbonyl)-5-[(2-methylnaphthalen-1-yl)methyl]-4-oxo-2,3-dihydro-1,5-benzodiazepin-3-yl]-2-(methylamino)propanamide, (2S)—N-[(3S)-1-(1H-indazole-4-carbonyl)-5-[(2-methylnaphthalen-1-yl)methyl]-4-oxo-2,3-dihydro-1,5-benzodiazepin-3-yl]-2-(methylamino)propanamide, (2S)—N-[(3S)-1-[2-[(1S)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide;

(2S)—N-[(3S)-1-[2-[(1R)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide, (S)—N—((S)-1-((6-bromo-2-methoxynaphthalen-1-yl)methy)-5-(2-(methylsulfonyl)acetyl)-2-oxo-2,3,4,5-tetrahydro-1H-benzo[b][1,4]diazepin-3-yl)-2-(ethylamino)propanamide, (S)—N—((S)-1-((5-bromo-2-methoxynaphthalen-1-yl)methyl)-7-cyano-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-7-cyano-1-((2-(difluoromethoxy)naphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (2S)—N-[(3S)-1-(1H-indole-6-carbonyl)-5-[(2-methylnaphthalen-1-yl)methyl]-4-oxo-2,3-dihydro-1,5-benzodiazepin-3-yl]-2-(methylamino)propanamide, (2S)—N-[(3S)-1-[2-[(1S)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide;

(2S)—N-[(3S)-1-[2-[(1R)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide, (S)—N—((S)-1-((6-bromo-2-methoxynaphthalen-1-yl)methyl)-7-cyano-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride, (S)—N—((S)-1-((5-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)propanamide hydrochloride, (S)—N—((S)-1-((6-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride, (2S)—N-[(3S)-1-(1H-indazole-6-carbonyl)-5-[(2-methylnaphthalen-1-yl)methyl]-4-oxo-2,3-dihydro-1,5-benzodiazepin-3-yl]-2-(methylamino)propanamide, (S)—N—((S)-1-((1-(2-cyanophenyl)-1H-indazol-3-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-7-cyano-5-(2-(methylsulfonyl)acetyl)-2-oxo-2,3,4,5-tetrahydro-1H-benzo[b][1,4]diazepin-3-yl)-2-(methylamino)propanamide hydrochloride, (2S)—N-[(3S)-7-cyano-1-[[1-(2-cyanophenyl)indazol-3-yl]methyl]-5-(2-methylsulfonylacetyl)-2-oxo-3,4-dihydro-1,5-benzodiazepin-3-yl]-2-(methylamino)propanamide; 2,2,2-trifluoroacetic acid, (S)—N—((S)-5-(4-acetylbenzoyl)-7-cyano-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-7-cyano-1-((1-methyl-1H-indazol-3-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-7-cyano-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-7-cyano-1-((2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-8-cyano-1-((1-(2-cyanophenyl)-1H-indazol-3-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide dihydrochloride, (S)—N—((S)-5-acetyl-7-cyano-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride, (S)—N—((S)-8-cyano-1-((2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-8-cyano-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-5-(3-methoxypropanoyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-5-isonicotinoyl-2-oxo-2,3,4,5-tetrahydro-1H-benzo[b][1,4]diazepin-3-yl)-2-(methylamino)propanamide dihydrochloride, (S)—N—((S)-1-((5-bromo-2-methoxynaphthalen-1-yl)methyl)-8-cyano-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-5-acetyl-7-cyano-1-((5-cyano-2-cyclopropylnaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-acetyl-1-((1-(2-cyanophenyl)-1H-indazol-3-yl)methyl)-2-oxo-7-(trifluoromethyl)-2,3,4,5-tetrahydro-1H-benzo[b][1,4]diazepin-3-yl)-2-(methylamino)propanamide hydrochloride, (2S)—N-[(3S)-1-(4-aminobenzoyl)-5-[[2-(2-fluoroethoxy)naphthalen-1-yl]methyl]-4-oxo-2,3-dihydro-1,5-benzodiazepin-3-yl]-2-(methylamino)propanamide; hydrochloride, (S)—N—((S)-5-acetyl-1-((5-bromo-2-methoxynaphthalen-1-yl)methyl)-7-cyano-2-oxo-2,3,4,5-tetrahydro-1H-benzo[b][1,4]diazepin-3-yl)-2-(methylamino)propanamide, (S)—N—((S)-7-cyano-1-((3-cyclopropylquinolin-4-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide, (S)—N—((S)-7-cyano-1-((3-cyclopropylquinolin-4-yl)methyl)-5-isonicotinoyl-2-oxo-2,3,4,5-tetrahydro-1H-benzo[b][1,4]diazepin-3-yl)-2-(methylamino)propanamide, (S)—N—((S)-5-acetyl-7-cyano-1-((5-cyano-2-methoxynaphthalen-1-yl)methyl)-2-oxo-2,3,4,5-tetrahydro-1H-benzo[b][1,4]diazepin-3-yl)-2-(methylamino)propanamide, (S)—N—((S)-5-acetyl-1-((3-cyclopropylquinolin-4-yl)methyl)-2-oxo-7-(trifluoromethyl)-2,3,4,5-tetrahydro-1H-benzo[b][1,4]diazepin-3-yl)-2-(methylamino)propanamide, (S)—N—((S)-1-((3-cyclopropylquinolin-4-yl)methyl)-2-oxo-5-(tetrahydro-2H-pyran-4-carbonyl)-7-(trifluoromethyl)-2,3,4,5-tetrahydro-1H-benzo[b][1,4]diazepin-3-yl)-2-(methylamino)propanamide, (S)—N—((S)-1-((3-cyclopropylquinolin-4-yl)methyl)-5-(3-methoxypropanoyl)-2-oxo-7-(trifluoromethyl)-2,3,4,5-tetrahydro-1H-benzo[b][1,4]diazepin-3-yl)-2-(methylamino)propanamide, (S)—N—((S)-1-((3-cyclopropylquinolin-4-yl)methyl)-5-isonicotinoyl-2-oxo-7-(trifluoromethyl)-2,3,4,5-tetrahydro-1H-benzo[b][1,4]diazepin-3-yl)-2-(methylamino)propanamide, (S)—N—((S)-1-((3-cyclopropylquinolin-4-yl)methyl)-5-(2-(methylsulfonyl)acetyl)-2-oxo-7-(trifluoromethyl)-2,3,4,5-tetrahydro-1H-benzo[b][1,4]diazepin-3-yl)-2-(methylamino)propanamide, (S)—N—((S)-1-((3-cyclopropylquinolin-4-yl)methyl)-5-(3-(methylsulfonyl)propanoyl)-2-oxo-7-(trifluoromethyl)-2,3,4,5-tetrahydro-1H-benzo[b][1,4]diazepin-3-yl)-2-(methylamino)propanamide, (S)—N—((S)-5-acetyl-1-((5-cyano-2-cyclopropylnaphthalen-1-yl)methyl)-2-oxo-7-(trifluoromethyl)-2,3,4,5-tetrahydro-1H-benzo[b][1,4]diazepin-3-yl)-2-(methylamino)propanamide, (S)—N-((2S,3S)-1-acetyl-5-(2-(2,6-difluorophenylamino)-2-oxoethyl)-2-methyl-4-oxo-2,3,4,5-tetrahydro-1H-benzo[b][1,4]diazepin-3-yl)-2-(methylamino)propanamide hydrochloride, (S)—N-((2S,3S)-1-acetyl-2-methyl-4-oxo-5-(2-oxo-2-(phenylamino)ethyl)-2,3,4,5-tetrahydro-1H-benzo[b][1,4]diazepin-3-yl)-2-(methylamino)propanamide hydrochloride, Cyclic-5-[(S)-5-(3-Amino-acetyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide, Cyclic-5-[(S)-5-(3-Amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride and (2S)—N-((2S,3S)-1-acetyl-5-(2-(2,6-difluorophenylamino)-2-oxo-1-phenylethyl)-2-methyl-4-oxo-2,3,4, 5-tetrahydro-1H-benzo[b][1,4]diazepin-3-yl)-2-(methylamino)propanamide hydrochloride.

A certain embodiment of the invention relates to a compound of formula I as described herein that is selected from the group consisting of (R)—N—((S)-5-(4-Acetylbenzoyl)-1-((2-methylnaphthalen-1-yl)methyl)-2-oxo-2,3,4,5-tetrahydro-1H-benzo[b][1,4]diazepin-3-yl)-2-(methylamino)propanamide hydrochloride, (R)—N—[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-methylaminopropionamide hydrochloride, (S)-2-(Methylamino)-N—((S)-1-((2-methylnaphthalen-1-yl)methyl)-5-(4-nitrobenzoyl)-2-oxo-2,3,4,5-tetrahydro-1H-benzo[b][1,4]diazepin-3-yl)propanamide hydrochloride, (S)-2-Amino-N—((S)-5-(4-aminobenzoyl)-1-((2-methoxynaphthalen-1-yl)methyl)-2-oxo-2,3,4,5-tetrahydro-1H-benzo[b][1,4]diazepin-3-yl)propanamide hydrochloride, (S)-2-Methylamino-N—((S)-1-naphthalen-1-ylmethyl-2-oxo-2,3,4,5-tetrahydro-1H-benzo[b][1,4]diazepin-3-yl)-propionamide hydrochloride, (S)-2-Methylamino-N—((S)-1-naphthalen-1-ylmethyl-2-oxo-5-phenethyl-2,3,4,5-tetrahydro-1H-benzo[b][1,4]diazepin-3-yl)-propionamide trifluoroacetate, (S)-2-Methylamino-N—((S)-1-naphthalen-1-ylmethyl-2-oxo-5-phenylacetyl-2,3,4,5-tetrahydro-1H-benzo[b][1,4]diazepin-3-yl)-propionamide hydrochloride, (S)-2-Methylamino-N—((S)-5-methyl-1-naphthalen-1-ylmethyl-2-oxo-2,3,4,5-tetrahydro-1H-benzo[b][1,4]diazepin-3-yl)-propionamide hydrochloride, (S)-2-Methylamino-N—[(S)-1-(2-methyl-naphthalen-1-naphthalen-1 ylmethyl)-2-oxo-5-(pyridine-4-carbonyl)-2,3,4,5-tetrahydro-1H-benzo[b][1,4]diazepin-3-yl]-propionamide hydrochloride, (S)-2-Methylamino-N—[(S)-1-(2-methyl-naphthalen-1-yl-methyl)-2-oxo-5-(2-pyridin-4-yl-acetyl)-2,3,4,5-tetrahydro-1H-benzo[b][1,4]diazepin-3-yl]-propionamide dihydrochloride, (S)-2-Methylamino-N—[(S)-1-(2-methyl-naphthalen-1-yl-methyl)-2-oxo-5-(5-oxo-hexanoyl)-2,3,4,5-tetrahydro-1H-benzo[b][1,4]diazepin-3-yl]-propionamide hydrochloride, (S)-2-Methylamino-N—[(S)-1-(2-methyl-naphthalen-1-yl-methyl)-2-oxo-5-(3,4,5-trimethoxy-benzoyl)-2,3,4,5-tetrahydro-1H-benzo[b][1,4]diazepin-3-yl]-propionamide hydrochloride, (S)-2-Methylamino-N—[(S)-1-(2-methyl-naphthalen-1-yl-methyl)-2-oxo-5-(2-1H-tetrazol-5-yl-acetyl)-2,3,4,5-tetrahydro-1H-benzo[b][1,4]diazepin-3-yl]-propionamide hydrochloride, (S)-2-Methylamino-N—[(S)-1-(2-methyl-naphthalen-1-yl-methyl)-2-oxo-5-(2-tetrahydro-pyran-4-yl-acetyl)-2,3,4,5-tetrahydro-1H-benzo[b][1,4]diazepin-3-yl]-propionamide hydrochloride, (S)-2-Methylamino-N—[(S)-1-(2-methyl-naphthalen-1-yl-methyl)-2-oxo-5-(2-pyridin-3-yl-acetyl)-2,3,4,5-tetrahydro-1H-benzo[b][1,4]diazepin-3-yl]-propionamide, (S)-2-Methylamino-N—[(S)-1-(2-methyl-naphthalen-1-yl-methyl)-5-(4-nitro-benzenesulfonyl)-2-oxo-2,3,4,5-tetrahydro-1H-benzo[b][1,4]diazepin-3-yl]-propionamide hydrochloride, (S)-2-Methylamino-N—[(S)-1-(2-methyl-naphthalen-1-yl-methyl)-5-methylsulfamoyl-2-oxo-2,3,4,5-tetrahydro-1H-benzo[b][1,4]diazepin-3-yl]-propionamide hydrochloride, (S)-2-Methylamino-N—[(S)-5-(3-methyl-butyl)-1-naphthalen-1-ylmethyl-2-oxo-2,3,4,5-tetrahydro-1H-benzo[b][1,4]diazepin-3-yl]-propionamide hydrochloride, (S)-2-Methylamino-N—[(S)-5-(3-methyl-butyryl)-1-(1-naphthalen-1-yl-ethyl)-2-oxo-2,3,4,5-tetrahydro-1H-benzo[b][1,4]diazepin-3-yl]-propionamide hydrochloride, (S)-2-Methylamino-N—[(S)-5-(3-methyl-butyryl)-1-(2-methyl-naphthalen-1-ylmethyl)-2oxo-2,3,4,5-tetrahydro-1H-benzo[b][1,4]diazepin-3-yl]-propionamide hydrochloride, (S)-2-Methylamino-N—[(S)-5-(3-methyl-butyryl)-1-naphthalen-1-ylmethyl-2-oxo-2,3,4,5-tetrahydro-1H-benzo[b][1,4]diazepin-3-yl]-propionamide hydrochloride, (S)-2-Methylamino-N—[(S)-5-(3-methyl-butyryl)-2-oxo-1-phenethyl-2,3,4,5-tetrahydro-1H-benzo[b][1,4]diazepin-3-yl]-propionamide hydrochloride, (S)-2-Methylamino-N—[(S)-5-(4-methyl-benzoyl)-1-(2-methyl-naphthalen-1-ylmethyl)-2-oxo-2,3,4,5-tetrahydro-1H-benzo[b][1,4]diazepin-3-yl]-propionamide hydrochloride, (S)-2-methylamino-N—{(S)-1(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-yl}-propionamide hydrochloride, (S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methylamide hydrochloride, (S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methyl ester hydrochloride, (S)-Azetidine-2-carbonxylic acid[(S)-5-(4-acetyl-benzoyl)-1-(6-bromo-2-methoxy-naphthalen-1-ylmethyl)-2-oxo-2,3,4,5-tetrahydro-1H-benzo[[b][1,4]diazepin-3-yl]-amide hydrochloride, (S)—N—((S)-1-((2-(Difluoromethoxy)naphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((2-Methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((5-Bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((5-Bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride, (S)—N—((S)-1-((6-Bromo-2-methoxynaphthalen-1-yl)methyl)-2-oxo-5-(2-(pyridin-3-yl)acetyl)-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)
methyl)-2-oxo-5-(pyrazine-2-carbonyl)-2,3,4,5-tetra-
hydro-1H-benzo[b][1,4]diazepin-3-yl)-2-(methylamino)
propanamide hydrochloride, (S)—N—((S)-1-((6-bromo-2-methoxynaphthalen-1-yl)
methyl)-2-oxo-5-(2-(pyridin-2-yl)acetyl)-2,3,4,5-tetra-
hydro-1H-benzo[b][1,4]diazepin-3-yl)-2-(methylamino)
propanamide hydrochloride, (S)—N—((S)-1-((6-bromo-2-methoxynaphthalen-1-yl)
methyl)-2-oxo-5-(4-(trifluoromethyl)benzoyl)-2,3,4,5-
tetrahydro-1H-benzo[b][1,4]diazepin-3-yl)-2-(methyl-
amino)propanamide hydrochloride, (S)—N—((S)-1-((6-bromo-2-methoxynaphthalen-1-yl)
methyl)-5-(isoxazole-5-carbonyl)-2-oxo-2,3,4,5-tetra-
hydro-1H-benzo[b][1,4]diazepin-3-yl)-2-(methylamino)
propanamide hydrochloride, (S)—N—((S)-1-((6-bromo-2-methoxynaphthalen-1-yl)
methyl)-5-(1-methyl-1H-pyrazole-3-carbonyl)-2-oxo-2,
3,4,5-tetrahydro-1H-benzo[b][1,4]diazepin-3-yl)-2-
(methylamino)propanamide trifluoroacetate, (S)—N—((S)-1-((6-bromo-2-methoxynaphthalen-1-yl)
methyl)-5-(1-methyl-1H-pyrazole-4-carbonyl)-2-oxo-2,
3,4,5-tetrahydro-1H-benzo[b][1,4]diazepin-3-yl)-2-
(methylamino)propanamide hydrochloride, (S)—N—((S)-1-((6-bromo-2-methoxynaphthalen-1-yl)
methyl)-5-(2-(methylsulfonyl)acetyl)-2-oxo-2,3,4,5-tet-
rahydro-1H-benzo[b][1,4]diazepin-3-yl)-2-(methyl-
amino)propanamide hydrochloride, (S)—N—((S)-1-((6-bromo-2-methoxynaphthalen-1-yl)
methyl)-5-(2-cyanobenzoyl)-2-oxo-2,3,4,5-tetrahydro-
1H-benzo[b][1,4]diazepin-3-yl)-2-(methylamino)pro-
panamide hydrochloride, (S)—N—((S)-1-((6-bromo-2-methoxynaphthalen-1-yl)
methyl)-5-(2-cyclohexylacetyl)-2-oxo-2,3,4,5-tetra-
hydro-1H-benzo[b][1,4]diazepin-3-yl)-2-(methylamino)
propanamide hydrochloride, (S)—N—((S)-1-((6-bromo-2-methoxynaphthalen-1-yl)
methyl)-5-(3-cyanobenzoyl)-2-oxo-2,3,4,5-tetrahydro-
1H-benzo[b][1,4]diazepin-3-yl)-2-(methylamino)pro-
panamide hydrochloride, (S)—N—((S)-1-((6-bromo-2-methoxynaphthalen-1-yl)
methyl)-5-(3-fluorobenzoyl)-2-oxo-2,3,4,5-tetrahydro-
1H-benzo[b][1,4]diazepin-3-yl)-2-(methylamino)pro-
panamide hydrochloride, (S)—N—((S)-1-((6-bromo-2-methoxynaphthalen-1-yl)
methyl)-5-(3-methoxypropanoyl)-2-oxo-2,3,4,5-tetra-
hydro-1H-benzo[b][1,4]diazepin-3-yl)-2-(methylamino)
propanamide hydrochloride, (S)—N—((S)-1-((6-bromo-2-methoxynaphthalen-1-yl)
methyl)-5-(4-(methylsulfonyl)benzoyl)-2-oxo-2,3,4,5-
tetrahydro-1H-benzo[b][1,4]diazepin-3-yl)-2-(methyl-
amino)propanamide hydrochloride, (S)—N—((S)-1-((6-bromo-2-methoxynaphthalen-1-yl)
methyl)-5-(4-cyanobenzoyl)-2-oxo-2,3,4,5-tetrahydro-
1H-benzo[b][1,4]diazepin-3-yl)-2-(methylamino)pro-
panamide hydrochloride, (S)—N—((S)-1-((6-Bromo-2-methoxynaphthalen-1-yl)
methyl)-5-(4-cyanobenzyl)-2-oxo-2,3,4,5-tetrahydro-1H-
benzo[b][1,4]diazepin-3-yl)-2-(methylamino)propana-
mide trifluoroacetate, (S)—N—((S)-1-((6-Bromo-2-methoxynaphthalen-1-yl)
methyl)-5-(4-fluorobenzoyl)-2-oxo-2,3,4,5-tetrahydro-
1H-benzo[b][1,4]diazepin-3-yl)-2-(methylamino)pro-
panamide hydrochloride, (S)—N—((S)-1-((6-bromo-2-methoxynaphthalen-1-yl)
methyl)-5-(4-methylbenzoyl)-2-oxo-2,3,4,5-tetrahydro-
1H-benzo[b][1,4]diazepin-3-yl)-2-(methylamino)pro-
panamide hydrochloride, (S)—N—((S)-1-((6-bromo-2-methoxynaphthalen-1-yl)
methyl)-5-(5-methylfuran-2-carbonyl)-2-oxo-2,3,4,5-tet-
rahydro-1H-benzo[b][1,4]diazepin-3-yl)-2-(methyl-
amino)propanamide hydrochloride, (S)—N—((S)-1-((6-bromo-2-methoxynaphthalen-1-yl)
methyl)-5-nicotinoyl-2-oxo-2,3,4,5-tetrahydro-1H-benzo
[b][1,4]diazepin-3-yl)-2-(methylamino)propanamide
hydrochloride, (S)—N—((S)-5-(4-acetamidobenzoyl)-1-((6-bromo-2-
methoxynaphthalen-1-yl)methyl)-2-oxo-2,3,4,5-tetra-
hydro-1H-benzo[b][1,4]diazepin-3-yl)-2-(methylamino)
propanamide trifluoroacetate, (S)—N—((S)-5-(4-acetylbenzoyl)-1-((2-(difluoromethoxy)
naphthalen-1-yl)methyl)-2-oxo-2,3,4,5-tetrahydro-1H-
benzo[b][1,4]diazepin-3-yl)-2-(methylamino)propana-
mide hydrochloride, (S)—N—((S)-5-(4-acetylbenzoyl)-1-((2-(difluoromethoxy)
naphthalen-1-yl)methyl)-2-oxo-2,3,4,5-tetrahydro-1H-
benzo[b][1,4]diazepin-3-yl)-2-aminopropanamide hydro-
chloride, (S)—N—((S)-5-(4-acetylbenzoyl)-1-((2-(difluoromethoxy)
naphthalen-1-yl)methyl)-2-oxo-2,3,4,5-tetrahydro-1H-
benzo[b][1,4]diazepin-3-yl)-2-(methylamino)propana-
mide hydrochloride, (S)—N—((S)-5-(4-acetylbenzoyl)-1-((2-methoxynaphtha-
len-1-yl)methyl)-2-oxo-2,3,4,5-tetrahydro-1H-benzo[b]
[1,4]diazepin-3-yl)-2-(methylamino)propanamide hydro-
chloride, (S)—N—((S)-5-(4-Acetylbenzoyl)-1-((2-methylnaphtha-
len-1-yl)methyl)-2-oxo-2,3,4,5-tetrahydro-1H-benzo[b]
[1,4]diazepin-3-yl)-2-aminopropanamide hydrochloride, (S)—N—((S)-5-(4-acetylbenzoyl)-1-((5-bromo-2-
methoxynaphthalen-1-yl)methyl)-2-oxo-2,3,4,5-tetra-
hydro-1H-benzo[b][1,4]diazepin-3-yl)-2-(methylamino)
propanamide hydrochloride, (S)—N—((S)-5-(4-acetylbenzoyl)-1-((5-bromo-2-
methoxynaphthalen-1-yl)methyl)-2-oxo-2,3,4,5-tetra-
hydro-1H-benzo[b][1,4]diazepin-3-yl)-2-(methylamino)
propanamide hydrochloride, (S)—N—((S)-5-(4-acetylbenzoyl)-1-((5-bromo-2-
methoxynaphthalen-1-yl)methyl)-2-oxo-2,3,4,5-tetra-
hydro-1H-benzo[b][1,4]diazepin-3-yl)-2-(methylamino)
propanamide hydrochloride, (S)—N—((S)-5-(4-acetylbenzoyl)-1-((6-bromo-2-
methoxynaphthalen-1-yl)methyl)-2-oxo-2,3,4,5-tetra-
hydro-1H-benzo[b][1,4]diazepin-3-yl)-2-(methylamino)
propanamide hydrochloride, (S)—N—((S)-5-(4-Acetylbenzoyl)-1-((6-bromo-2-
methoxynaphthalen-1-yl)methyl)-2-oxo-2,3,4,5-tetra-
hydro-1H-benzo[b][1,4]diazepin-3-yl)-2-(methylamino)
butanamide hydrochloride, (S)—N—((S)-5-(4-Acetylbenzoyl)-1-((6-bromo-2-
methoxynaphthalen-1-yl)methyl)-2-oxo-2,3,4,5-tetra-
hydro-1H-benzo[b][1,4]diazepin-3-yl)-2-(ethylamino)
propanamide hydrochloride, (S)—N—((S)-5-(4-acetylbenzoyl)-1-((6-bromobenzo[d]
isoxazol-3-yl)methyl)-2-oxo-2,3,4,5-tetrahydro-1H-
benzo[b][1,4]diazepin-3-yl)-2-(methylamino)propana-
mide hydrochloride, (S)—N—((S)-5-(4-acetylbenzoyl)-1-((7-methoxy-2-oxo-
2H-chromen-4-yl)methyl)-2-oxo-2,3,4,5-tetrahydro-1H-
benzo[b][1,4]diazepin-3-yl)-2-(methylamino)propana-
mide hydrochloride, (S)—N—((S)-5-(4-acetylbenzoyl)-1-((7-methoxy-2-oxo-2H-chromen-4-yl)methyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-(benzo[d]isoxazol-3-ylmethyl)-2-oxo-2,3,4,5-tetrahydro-1H-benzo[b][1,4]diazepin-3-yl)-2-aminopropanamide hydrochloride, (S)—N—((S)-5-(4-Acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-(methylamino)propanamide hydrochloride, (S)—N—((S)-5-(4-acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-aminopropanamide hydrochloride, (S)—N—((S)-5-(4-Aminobenzoyl)-1-((2-methylnaphthalen-1-yl)methyl)-2-oxo-2,3,4,5-tetrahydro-1H-benzo[b][1,4]diazepin-3-yl)-N-methyl-2-(methylamino)propanamide hydrochloride, (S)—N—((S)-5-(4-Aminobenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, (S)—N—((S)-5-(4-Cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide, (S)—N—((S)-5-acetyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-Acetyl-1-naphthalen-1-ylmethyl-2-oxo-2,3,4,5-tetrahydro-1H-benzo[b][1,4]diazepin-3-yl)-2-methylamino-propionamide hydrochloride, (S)—N—((S)-5-benzoyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-Benzyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—[(S)-1-(2-methoxy-benzyl)-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-1-(2-Methoxy-naphthalen-1-ylmethyl)-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-2-oxo-5-(2-pyridin-3-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-5-(4-fluoro-benzoyl)-2-oxo-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-5-(4-methyl-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-(d3-methoxy)-naphthalen-1-ylmethyl)-2-oxo-5-(2-pyridin-3-yl-acetyl)-2,3,4,5-tetrahydro-1H-benzo[b][1,4]diazepin-3-yl]-2-methylamino-propionamide hydrochloride, (S)—N—[(S)-1-(6-Bromo-2-(d3-methoxy)-naphthalen-1-ylmethyl)-5-(4-cyano-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(6-bromo-2-methoxy-naphthalen-1-ylmethyl)-2-oxo-5-(5-oxo-hexanoyl)-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-2-oxo-5-(pyridine-2-carbonyl)-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(2-fluoro-benzoyl)-2-oxo-2,3,4,5-tetrahydro-1H-benzo[b][1,4]diazepin-3-yl]-2-methylamino-propionamide hydrochloride, (S)—N—[(S)-1-(6-bromo-2-methoxy-naphthalen-1-ylmethyl)-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(4-nitro-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(4-nitro-butyryl)-2-oxo-2,3,4,5-tetrahydro-1H-benzo[b][1,4]diazepin-3-yl]-2-methylamino-propionamide hydrochloride, (S)—N—[(S)-1-benzyl-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-5-(2-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(2-Adamantan-1-yl-acetyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(2-Carbamoyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(2-Cyclohexyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(3-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(3-Amino-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Acetylamino-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-acetylamino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(2-naphthalen-1-ylethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-dimethylamino-propionamide, (S)—N—[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-amino-propionamide, (S)—N—[(S)-5-(4-amino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Amino-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Chloro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Cyano-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Fluoro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Hydroxymethyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methanesulfonyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methoxy-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methoxy-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochoride, (S)—N—[(S)-5-(Adamantan-1-carbonyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-[2-(2-methoxy-ethoxy)-acetyl]-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-[2-(4-Acetyl-phenyl)-acetyl]-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-{2-[2-(2-Methoxy-ethoxy)-ethoxy]-acetyl}-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-acetyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Benzenesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Benzoyl-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Dimethylsulfamoyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-methanesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-methanesulfonylmethanesulfonyl-1-(2-methyl-naphthalen-1-ylmethyl)-2-oxo-2,3,4,5-tetrahydro-1H-benzo[b][1,4]diazepin-3-yl]-2-methylamino-propionamide trifluoroacetate, (S)—N—{(S)-1-(5-Bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-yl}-2-methylamino-propionamide, (S)—N—{(S)-1-(6-Bromo-2-methoxy-naphthalen-1-ylmethyl)-2-oxo-5-[4-(2,2,2-trifluoro-1,1-dihydroxy-ethyl)-benzoyl]-2,3,4,5-tetrahydro-1H-benzo[b][1,4]diazepin-3-yl}-2-methylamino-propionamide trifluoroacetate, (S)—N—{(S)-1-(6-bromo-2-methoxy-naphthalen-1-ylmethyl)-2-oxo-5-[4-(2,2,2-trifluoro-1-hydroxy-ethyl)-benzoyl]-2,3,4,5-tetrahydro-1H-benzo[b][1,4]diazepin-3-yl}-2-methylamino-propionamide hydrochloride, (S)—N—{(S)-1-(6-bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-yl}-2-methylamino-propionamide hydrochloride, (S)—N—{(S)-1-(6-Bromo-2-methoxy-naphthalen-1-ylmethyl)-5-[4-(1-hydroxy-1-methyl-ethyl)-benzoyl]-2-oxo-2,3,4,5-tetrahydro-1H-benzo[b][1,4]diazepin-3-yl}-2-methylamino-propionamide trifluoroacetate, (S)—N—{(S)-1-(6-Bromo-2-methoxy-naphthalen-1-ylmethyl)-5-[4-(2,2-dimethyl-propionyl)-benzoyl]-2-oxo-2,3,4,5-tetrahydro-1H-benzo[b][1,4]diazepin-3-yl}-2-methylamino-propionamide hydrochloride, 3-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzamide hydrochloride, 4-(((S)-5-(4-Acetylbenzoyl)-3-((S)-2-(methylamino)propanamido)-2-oxo-2,3,4,5-tetrahydro-1H-benzo[b][1,4]diazepin-1-yl)methyl)-3-(2,2,2-trifluoroethoxy)quinoline 1-oxide hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-yl]-4-oxo-butyric acid hydrochloride, 4-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzoic acid methyl ester hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid methyl ester hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzamide hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-N-cyclohexylmethyl-benzamide hydrochloride, 5-[(S)-3-((S)-2-methylamino-propionylamino)-5-(2-methyl-naphthalen-1-ymethyl)-4-oxo-2,3,4,5-tetrahydrobenzo[b][1,4]diazepin-1yl]-5-oxo-pentanoic acid hydrochloride, 5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, 5-[(S)-5-(4-acetyl-benzoy)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid hydrochloride, 5-[(S)-5-(4-acetyl-benzoy)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid hydroxyamide trifluoroacetate, 5-[(S)-5-(4-Acetyl-benzoyl)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid methyl ester hydrochloride, 5-[(S)-5-(4-Amino-benzoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(4-Amino-benzoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, 5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, 5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, 5-[(S)-5-[4-(9H-Fluoren-9-ylmethoxycarbonylamino)-benzoyl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-[4-(9H-Fluoren-9-ylmethoxycarbonylamino)-butyryl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 6-[(S)-3-((S)-2-Methylamino-propionylamino)-5-(2-methyl-naphthalen-1-ylmethyl)-4-oxo-2,3,4,5-tetrahydro-benzo[b][1,4]diazepin-1-yl]-6-oxo-hexanoic acid hydrochloride, 6-Methoxy-5-[(S)-3 ((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid methyl ester hydrochloride, 6-Methoxy-5-[(S)-3 ((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid hydrochloride, Cyclic-5-[(S)-5-(2-Amino-ethyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, Cyclic-5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, Cyclic-5-[(S)-5-(3-amino-propyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, Cyclic-5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, Cyclic-5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, Methyl 4-((S)-5-(benzo[d]isoxazol-3-ylmethyl)-3-((S)-2-(methylamino)propanamido)-4-oxo-2,3,4,5-tetrahydro-1H-benzo[b][1,4]diazepine-1-carbonyl)benzoate hydrochloride, methyl 5-(((S)-5-(3-(((9H-fluoren-9-yl)methoxy)carbonylamino)propanoyl)-3-((S)-2-(methylamino)propanamido)-2-oxo-2,3,4,5-tetrahydro-1H-benzo[b][1,4]diazepin-1-yl)methyl)-6-methoxy-2-naphthoate hydrochloride, and methyl 6-((S)-3-((S)-2-(methylamino)propanamido)-5-((2-methylnaphthalen-1-yl)methyl)-4-oxo-2,3,4,5-tetrahydro-1H-benzo[b][1,4]diazepin-1-yl)-6-oxohexanoate hydrochloride.

A certain embodiment of the invention relates to a compound of formula I as described herein that is selected from the group consisting of
- (R)—N—((S)-5-(4-Acetylbenzoyl)-1-((2-methylnaphthalen-1-yl)methyl)-2-oxo-2,3,4,5-tetrahydro-1H-benzo[b][1,4]diazepin-3-yl)-2-(methylamino)propanamide hydrochloride,
- (R)—N—[(S)-5-(4-acetyl-benzoyl)-1-(6-bromo-2-methoxyl-naphthalen-1-ylmethyl)-2-oxo-2,3,4,5-tetrahydro-1H-benzo[b][1,4]diazepin-3-yl]-2-methylamino-propionamide hydrochloride,
- (S)-2-(Methylamino)-N—((S)-1-((2-methylnaphthalen-1-yl)methyl)-5-(4-nitrobenzoyl)-2-oxo-2,3,4,5-tetrahydro-1H-benzo[b][1,4]diazepin-3-yl)propanamide hydrochloride,
- (S)-2-Methylamino-N—((S)-1-naphthalen-1-ylmethyl-2-oxo-5-phenylacetyl-2,3,4,5-tetrahydro-1H-benzo[b][1,4]diazepin-3-yl)-propionamide hydrochloride,
- (S)-2-Methylamino-N—[(S)-1-(2-methyl-naphthalen-1-naphthalen-1 ylmethyl)-2-oxo-5-(pyridine-4-carbonyl)-2,3,4,5-tetrahydro-1H-benzo[b][1,4]diazepin-3-yl]-propionamide hydrochloride,
- (S)-2-Methylamino-N—[(S)-1-(2-methyl-naphthalen-1-ylmethyl)-2-oxo-5-(2-pyridin-4-yl-acetyl)-2,3,4,5-tetrahydro-1H-benzo[b][1,4]diazepin-3-yl]-propionamide dihydrochloride,
- (S)-2-Methylamino-N—[(S)-1-(2-methyl-naphthalen-1-ylmethyl)-2-oxo-5-(5-oxo-hexanoyl)-2,3,4,5-tetrahydro-1H-benzo[b][1,4]diazepin-3-yl]-propionamide hydrochloride,
- (S)-2-Methylamino-N—[(S)-1-(2-methyl-naphthalen-1-ylmethyl)-2-oxo-5-(3,4,5-trimethoxy-benzoyl)-2,3,4,5-tetrahydro-1H-benzo[b][1,4]diazepin-3-yl]-propionamide hydrochloride,
- (S)-2-Methylamino-N—[(S)-1-(2-methyl-naphthalen-1-ylmethyl)-2-oxo-5-(2-1H-tetrazol-5-yl-acetyl)-2,3,4,5-tetrahydro-1H-benzo[b][1,4]diazepin-3-yl]-propionamide hydrochloride,
- (S)-2-Methylamino-N—[(S)-1-(2-methyl-naphthalen-1-ylmethyl)-2-oxo-5-(2-tetrahydro-pyran-4-yl-acetyl)-2,3,4,5-tetrahydro-1H-benzo[b][1,4]diazepin-3-yl]-propionamide hydrochloride,
- (S)-2-Methylamino-N—[(S)-1-(2-methyl-naphthalen-1-ylmethyl)-2-oxo-5-(2-pyridin-3-yl-acetyl)-2,3,4,5-tetrahydro-1H-benzo[b][1,4]diazepin-3-yl]-propionamide,
- (S)-2-Methylamino-N—[(S)-5-(3-methyl-butyryl)-1-(2-methyl-naphthalen-1-ylmethyl)-2oxo-2,3,4,5-tetrahydro-1H-benzo[b][1,4]diazepin-3-yl]-propionamide hydrochloride,
- (S)-2-Methylamino-N—[(S)-5-(3-methyl-butyryl)-1-naphthalen-1-ylmethyl-2-oxo-2,3,4,5-tetrahydro-1H-benzo[b][1,4]diazepin-3-yl]-propionamide hydrochloride,
- (S)-2-Methylamino-N—[(S)-5-(3-methyl-butyryl)-2-oxo-1-phenethyl-2,3,4,5-tetrahydro-1H-benzo[b[1,4]diazepin-3-yl]-propionamide hydrochloride,
- (S)-2-Methylamino-N—[(S)-5-(4-methyl-benzoyl)-1-(2-methyl-naphthalen-1-ylmethyl)-2-oxo-2,3,4,5-tetrahydro-1H-benzo[b][1,4]diazepin-3-yl]-propionamide hydrochloride,
- (S)-2-methylamino-N—{(S)-1(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-yl}-propionamide hydrochloride,
- (S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methylamide hydrochloride,
- (S)—N—((S)-1-((2-(Difluoromethoxy)naphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride,
- (S)—N—((S)-1-((2-Methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride,
- (S)—N—((S)-1-((5-Bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride,
- (S)—N—((S)-1-((5-Bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride,
- (S)—N—((S)-1-((6-Bromo-2-methoxynaphthalen-1-yl)methyl)-2-oxo-5-(2-(pyridin-3-yl)acetyl)-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-2-oxo-5-(pyrazine-2-carbonyl)-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-2-oxo-5-(2-(pyridin-2-yl)acetyl)-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-2-oxo-5-(4-(trifluoromethyl)benzoyl)-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-5-(isoxazole-5-carbonyl)-2-oxo-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-5-(1-methyl-1H-pyrazole-3-carbonyl)-2-oxo-2,3,4,5-tetrahydro-1H-benzo[b][1,4]diazepin-3-yl)-2-(methylamino)propanamide trifluoroacetate,
- (S)—N—((S)-1-((6-bromo-2-methoxynaphthalen-1-yl)methyl)-5-(1-methyl-1H-pyrazole-4-carbonyl)-2-oxo-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-5-(2-cyanobenzoyl)-2-oxo-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-5-(2-cyclohexylacetyl)-2-oxo-2,3,4,5-tetrahydro-1H-benzo[b][1,4]diazepin-3-yl)-2-(methylamino)propanamide hydrochloride,
- (S)—N—((S)-1-((6-bromo-2-methoxynaphthalen-1-yl)methyl)-5-(3-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-methoxypropanoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-(methylsulfonyl)benzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-Bromo-2-methoxynaphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-methylbenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(5-methylfuran-2-carbonyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-nicotinoyl-2-oxo-2,3,4,5-tetrahydro-1H-benzo[b][1,4]diazepin-3-yl)-2-(methylamino)propanamide hydrochloride, (S)—N—((S)-5-(4-acetamidobenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—((S)-5-(4-acetylbenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((6-bromobenzo[d]isoxazol-3-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((7-methoxy-2-oxo-2H-chromen-4-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, (S)—N—((S)-5-(4-Acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-(methylamino)propanamide hydrochloride, (S)—N—((S)-5-(4-Aminobenzoyl)-1-((2-methylnaphthalen-1-yl)methyl)-2-oxo-2,3,4,5-tetrahydro-1H-benzo[b][1,4]diazepin-3-yl)-N-methyl-2-(methylamino)propanamide hydrochloride, (S)—N—((S)-5-(4-Aminobenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, (S)—N—((S)-5-(4-Cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide, (S)—N—((S)-5-acetyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-Acetyl-1-naphthalen-1-ylmethyl-2-oxo-2,3,4,5-tetrahydro-1H-benzo[b][1,4]diazepin-3-yl)-2-methylamino-propionamide hydrochloride, (S)—N—((S)-5-benzoyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—[(S)-1-(2-methoxy-benzyl)-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-1-(2-Methoxy-naphthalen-1-ylmethyl)-5-(3-methyl-butyryl)-2-oxo-2,3,4,5-tetrahydro-1H-benzo[b[1,4]diazepin-3-yl]-2-methylamino-propionamide hydrochloride, (S)—N—[(S)-1-(5-Bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-2-oxo-5-(2-pyridin-3-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-5-(4-fluoro-benzoyl)-2-oxo-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-5-(4-methyl-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-(d3-methoxy)-naphthalen-1-ylmethyl)-2-oxo-5-(2-pyridin-3-yl-acetyl)-2,3,4,5-tetrahydro-1H-benzo[b][1,4]diazepin-3-yl]-2-methylamino-propionamide hydrochloride, (S)—N—[(S)-1-(6-Bromo-2-(d3-methoxy)-naphthalen-1-ylmethyl)-5-(4-cyano-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(6-bromo-2-methoxy-naphthalen-1-ylmethyl)-2-oxo-5-(5-oxo-hexanoyl)-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylm-ethyl)-2-oxo-5-(pyridine-2-carbonyl)-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylm-ethyl)-5-(2-fluoro-benzoyl)-2-oxo-2,3,4,5-tetrahydro-1H-benzo[b][1,4]diazepin-3-yl]-2-methylamino-propionamide hydrochloride, (S)—N—[(S)-1-(6-bromo-2-methoxy-naphthalen-1-ylm-ethyl)-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylm-ethyl)-5-(4-nitro-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylm-ethyl)-5-(4-nitro-butyryl)-2-oxo-2,3,4,5-tetrahydro-1H-benzo[b][1,4]diazepin-3-yl]-2-methylamino-propionamide hydrochloride, (S)—N—[(S)-1-benzyl-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-5-(2-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(2-Adamantan-1-yl-acetyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(2-Carbamoyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(2-Cyclohexyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(3-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(3-Amino-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-acetylamino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(2-naphthalen-1-ylethyl)-2-oxo-2,3,4,5-tetrahydro-1H-benzo[b][1,4]diazepin-3-yl]-2-methylamino-propionamide hydrochloride, (S)—N—[(S)-5-(4-amino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Amino-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Chloro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Cyano-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Fluoro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Hydroxymethyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methanesulfonyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methoxy-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochoride, (S)—N—[(S)-5-(Adamantan-1-carbonyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-[2-(2-methoxy-ethoxy)-acetyl]-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-[2-(4-Acetyl-phenyl)-acetyl]-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-{2-[2-(2-Methoxy-ethoxy)-ethoxy]-acetyl}-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-acetyl-1-(2-methyl-naphthalen-1-ylm-ethyl)-2-oxo-2,3,4,5-tetrahydro-1H-benzo[b][1,4]diazepin-3-yl]-2-methylamino-propionamide hydrochloride, (S)—N—[(S)-5-Benzoyl-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—{(S)-1-(5-Bromo-2-methoxy-naphthalen-1-ylm-ethyl)-5-[4-(1-hydroxy-ethyl)-benzoyl]-2-oxo-2,3,4,5-tetrahydro-1H-benzo[b][1,4]diazepin-3-yl}-2-methylamino-propionamide, (S)—N—{(S)-1-(6-Bromo-2-methoxy-naphthalen-1-ylm-ethyl)-2-oxo-5-[4-(2,2,2-trifluoro-1,1-dihydroxy-ethyl)-benzoyl]-2,3,4,5-tetrahydro-1H-benzo[b][1,4]diazepin-3-yl}-2-methylamino-propionamide trifluoroacetate, (S)—N—{(S)-1-(6-bromo-2-methoxy-naphthalen-1-ylm-ethyl)-2-oxo-5-[4-(2,2,2-trifluoro-1-hydroxy-ethyl)-benzoyl]-2,3,4,5-tetrahydro-1H-benzo[b][1,4]diazepin-3-yl}-2-methylamino-propionamide hydrochloride, (S)—N—{(S)-1-(6-bromo-2-methoxy-naphthalen-1-ylm-ethyl)-5-(4-(1-hydroxy-ethyl)-benzoyl)-2-oxo-2,3,4,5-tetrahydro-1H-benzo[b][1,4]diazepin-3-yl}-2-methylamino-propionamide hydrochloride, (S)—N—{(S)-1-(6-Bromo-2-methoxy-naphthalen-1-ylm-ethyl)-5-[4-(1-hydroxy-1-methyl-ethyl)-benzoyl]-2-oxo-2,3,4,5-tetrahydro-1H-benzo[b][1,4]diazepin-3-yl}-2-methylamino-propionamide trifluoroacetate, (S)—N—{(S)-1-(6-Bromo-2-methoxy-naphthalen-1-ylm-ethyl)-5-[4-(2,2-dimethyl-propionyl)-benzoyl]-2-oxo-2, 3,4,5-tetrahydro-1H-benzo[b][1,4]diazepin-3-yl}-2-methylamino-propionamide hydrochloride, 3-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzamide hydrochloride, 4-(((S)-5-(4-Acetylbenzoyl)-3-((S)-2-(methylamino)propanamido)-2-oxo-2,3,4,5-tetrahydro-1H-benzo[b][1,4]diazepin-1-yl)methyl)-3-(2,2,2-trifluoroethoxy)quinoline 1-oxide hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-yl]-4-oxo-butyric acid hydrochloride, 4-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzoic acid methyl ester hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid methyl ester hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzamide hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-N-cyclohexylmethyl-benzamide hydrochloride, 5-[(S)-3-((S)-2-methylamino-propionylamino)-5-(2-methyl-naphthalen-1-ymethyl)-4-oxo-2,3,4,5-tetrahydro-benzo[b][1,4]diazepin-1yl]-5-oxo-pentanoic acid hydrochloride, 5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, 5-[(S)-5-(4-acetyl-benzoy)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid hydrochloride, 5-[(S)-5-(4-acetyl-benzoy)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid hydroxyamide trifluoroacetate, 5-[(S)-5-(4-Acetyl-benzoyl)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid methyl ester hydrochloride, 5-[(S)-5-(4-Amino-benzoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(4-Amino-benzoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, 5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, 5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, 5-[(S)-5-[4-(9H-Fluoren-9-ylmethoxycarbonylamino)-benzoyl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-[4-(9H-Fluoren-9-ylmethoxycarbonylamino)-butyryl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 6-[(S)-3-((S)-2-Methylamino-propionylamino)-5-(2-methyl-naphthalen-1-ylmethyl)-4-oxo-2,3,4,5-tetrahydro-benzo[b][1,4]diazepin-1-yl]-6-oxo-hexanoic acid hydrochloride, 6-Methoxy-5-[(S)-3 ((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid methyl ester hydrochloride, 6-Methoxy-5-[(S)-3 ((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid hydrochloride, Methyl 4-((S)-5-(benzo[d]isoxazol-3-ylmethyl)-3-((S)-2-(methylamino)propanamido)-4-oxo-2,3,4,5-tetrahydro-1H-benzo[b][1,4]diazepine-1-carbonyl)benzoate hydrochloride, methyl 5-(((S)-5-(3-(((9H-fluoren-9-yl)methoxy)carbonylamino)propanoyl)-3-((S)-2-(methylamino)propanamido)-2-oxo-2,3,4,5-tetrahydro-1H-benzo[b][1,4]diazepin-1-yl)methyl)-6-methoxy-2-naphthoate hydrochloride, and methyl 6-((S)-3-((S)-2-(methylamino)propanamido)-5-((2-methylnaphthalen-1-yl)methyl)-4-oxo-2,3,4,5-tetrahydro-1H-benzo[b][1,4]diazepin-1-yl)-6-oxohexanoate hydrochloride.

A certain embodiment of the invention relates to a compound of formula I as described herein that is selected from the group consisting of (R)—N—((S)-5-(4-Acetylbenzoyl)-1-((2-methylnaphthalen-1-yl)methyl)-2-oxo-2,3,4,5-tetrahydro-1H-benzo[b][1,4]diazepin-3-yl)-2-(methylamino)propanamide hydrochloride, (R)—N—[(S)-5-(4-acetyl-benzoyl)-1-(6-bromo-2-methoxyl-naphthalen-1-ylmethyl)-2-oxo-2,3,4,5-tetrahydro-1H-benzo[b][1,4]diazepin-3-yl]-2-methylamino-propionamide hydrochloride, (S)-2-(Methylamino)-N—((S)-1-((2-methylnaphthalen-1-yl)methyl)-5-(4-nitrobenzoyl)-2-oxo-2,3,4,5-tetrahydro-1H-benzo[b][1,4]diazepin-3-yl)propanamide hydrochloride, (S)-2-Methylamino-N—((S)-1-naphthalen-1-ylmethyl-2-oxo-5-phenylacetyl-2,3,4,5-tetrahydro-1H-benzo[b][1,4]diazepin-3-yl)-propionamide hydrochloride, (S)-2-Methylamino-N—[(S)-1-(2-methyl-naphthalen-1-ylmethyl)-2-oxo-5-(3,4,5-trimethoxy-benzoyl)-2,3,4,5-tetrahydro-1H-benzo[b][1,4]diazepin-3-yl]-propionamide hydrochloride, (S)-2-Methylamino-N—[(S)-5-(4-methyl-benzoyl)-1-(2-methyl-naphthalen-1-ylmethyl)-2-oxo-2,3,4,5-tetrahydro-1H-benzo[b][1,4]diazepin-3-yl]-propionamide hydrochloride, (S)—N—((S)-1-((5-Bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(4-(trifluoromethyl)benzoyl)-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-(methylsulfonyl)benzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-Bromo-2-methoxynaphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-methylbenzoyl)-2-oxo-2,3,4,5-tetrahydro-1H-benzo[b][1,4]diazepin-3-yl)-2-(methylamino)propanamide hydrochloride, (S)—N—((S)-5-(4-acetamidobenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—((S)-5-(4-acetylbenzoyl)-1-((2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-Acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-(methylamino)propanamide hydrochloride, (S)—N—((S)-5-(4-Aminobenzoyl)-1-((2-methylnaphthalen-1-yl)methyl)-2-oxo-2,3,4,5-tetrahydro-1H-benzo[b][1,4]diazepin-3-yl)-N-methyl-2-(methylamino)propanamide hydrochloride, (S)—N—[(S)-1-(5-Bromo-2-methoxy-naphthalen-1-ylmethyl)-5-(4-fluoro-benzoyl)-2-oxo-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-5-(4-methyl-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(2-fluoro-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(4-nitro-benzoyl)-2-oxo-2,3,4,5-tetrahydro-1H-benzo[b][1,4]diazepin-3-yl]-2-methylamino-propionamide hydrochloride, (S)—N—[(S)-5-(2-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(3-Amino-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-acetylamino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(2-naphthalen-1-ylethyl)-2-oxo-2,3,4,5-tetrahydro-1H-benzo[b][1,4]diazepin-3-yl]-2-methylamino-propionamide hydrochloride, (S)—N—[(S)-5-(4-amino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Amino-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Chloro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Cyano-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Fluoro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Hydroxymethyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methanesulfonyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methoxy-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochoride, (S)—N—[(S)-5-[2-(4-Acetyl-phenyl)-acetyl]-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Benzoyl-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—{(S)-1-(5-Bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-yl}-2-methylamino-propionamide, (S)—N—{(S)-1-(6-Bromo-2-methoxy-naphthalen-1-ylmethyl)-2-oxo-5-[4-(2,2,2-trifluoro-1,1-dihydroxy-ethyl)-benzoyl]-2,3,4,5-tetrahydro-1H-benzo[b][1,4]diazepin-3-yl}-2-methylamino-propionamide trifluoroacetate, (S)—N—{(S)-1-(6-bromo-2-methoxy-naphthalen-1-ylmethyl)-2-oxo-5-[4-(2,2,2-trifluoro-1-hydroxy-ethyl)-benzoyl]-2,3,4,5-tetrahydro-1H-benzo[b][1,4]diazepin-3-yl}-2-methylamino-propionamide hydrochloride, (S)—N—{(S)-1-(6-bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-yl}-2-methylamino-propionamide hydrochloride, (S)—N—{(S)-1-(6-Bromo-2-methoxy-naphthalen-1-ylmethyl)-5-[4-(1-hydroxy-1-methyl-ethyl)-benzoyl]-2-oxo-2,3,4,5-tetrahydro-1H-benzo[b][1,4]diazepin-3-yl}-2-methylamino-propionamide trifluoroacetate, (S)—N—{(S)-1-(6-Bromo-2-methoxy-naphthalen-1-ylmethyl)-5-[4-(2,2-dimethyl-propionyl)-benzoyl]-2-oxo-2,3,4,5-tetrahydro-1H-benzo[b][1,4]diazepin-3-yl}-2-methylamino-propionamide hydrochloride, 3-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzamide hydrochloride, 4-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzoic acid methyl ester hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid methyl ester hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzamide hydrochloride, and 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-N-cyclohexylmethyl-benzamide hydrochloride.

A certain embodiment of the invention relates to a compound of formula I as described herein that is selected from the group consisting of (R)—N—((S)-5-(4-Acetylbenzoyl)-1-((2-methylnaphthalen-1-yl)methyl)-2-oxo-2,3,4,5-tetrahydro-1H-benzo[b][1,4]diazepin-3-yl)-2-(methylamino)propanamide hydrochloride, (R)—N—[(S)-5-(4-acetyl-benzoyl)-1-(6-bromo-2-methoxyl-naphthalen-1-ylmethyl)-2-oxo-2,3,4,5-tetrahydro-1H-benzo[b][1,4]diazepin-3-yl]-2-methylamino-propionamide hydrochloride, (S)-2-Methylamino-N—((S)-1-naphthalen-1-ylmethyl-2-oxo-5-phenylacetyl-2,3,4,5-tetrahydro-1H-benzo[b][1,4]diazepin-3-yl)-propionamide hydrochloride, (S)-2-Methylamino-N—[(S)-1-(2-methyl-naphthalen-1-ylmethyl)-2-oxo-5-(3,4,5-trimethoxy-benzoyl)-2,3,4,5-tetrahydro-1H-benzo[b][1,4]diazepin-3-yl]-propionamide hydrochloride, (S)-2-Methylamino-N—[(S)-5-(4-methyl-benzoyl)-1-(2-methyl-naphthalen-1-ylmethyl)-2-oxo-2,3,4,5-tetrahydro-1H-benzo[b][1,4]diazepin-3-yl]-propionamide hydrochloride, (S)—N—((S)-1-((5-Bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-Bromo-2-methoxynaphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-methylbenzoyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-Acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-(methylamino)propanamide hydrochloride, (S)—N—((S)-5-(4-Aminobenzoyl)-1-((2-methylnaphthalen-1-yl)methyl)-2-oxo-2,3,4,5-tetrahydro-1H-benzo[b][1,4]diazepin-3-yl)-N-methyl-2-(methylamino)propanamide hydrochloride, (S)—N—[(S)-1-(5-Bromo-2-methoxy-naphthalen-1-ylmethyl)-5-(4-fluoro-benzoyl)-2-oxo-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-5-(4-methyl-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(2-fluoro-benzoyl)-2-oxo-2,3,4,5-tetrahydro-1H-benzo[b][1,4]diazepin-3-yl]-2-methylamino-propionamide hydrochloride, (S)—N—[(S)-5-(2-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(3-Amino-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(2-naphthalen-1-ylethyl)-2-oxo-2,3,4,5-tetrahydro-1H-benzo[b][1,4]diazepin-3-yl]-2-methylamino-propionamide hydrochloride, (S)—N—[(S)-5-(4-amino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Amino-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Chloro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Cyano-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Fluoro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Methoxy-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochoride, (S)—N—[(S)-5-[2-(4-Acetyl-phenyl)-acetyl]-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Benzoyl-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—{(S)-1-(6-Bromo-2-methoxy-naphthalen-1-ylmethyl)-5-[4-(2,2-dimethyl-propionyl)-benzoyl]-2-oxo-2,3,4,5-tetrahydro-1H-benzo[b][1,4]diazepin-3-yl}-2-methylamino-propionamide hydrochloride, 4-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzoic acid methyl ester hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-carbonyl]-benzoic acid hydrochloride, and 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid methyl ester hydrochloride.

A certain embodiment of the invention relates to a compound of formula I as described herein that is selected from the group consisting of (S)-2-Methylamino-N—((S)-1-naphthalen-1-ylmethyl-2-oxo-5-phenethyl-2,3,4,5-tetrahydro-1H-benzo[b][1,4]diazepin-3-yl)-propionamide trifluoroacetate, (S)-2-Methylamino-N—[(S)-1-(2-methyl-naphthalen-1-ylmethyl)-5-(4-nitro-benzenesulfonyl)-2-oxo-2,3,4,5-tetrahydro-1H-benzo[b][1,4]diazepin-3-yl]-propionamide hydrochloride, (S)-2-Methylamino-N—[(S)-1-(2-methyl-naphthalen-1-ylmethyl)-5-methylsulfamoyl-2-oxo-2,3,4,5-tetrahydro-1H-benzo[b][1,4]diazepin-3-yl]-propionamide hydrochloride, (S)-3-((S)-2-methylamino-propionylamino)-5-(2-methyl-naphthalen-1-ylmethyl)-4-oxo-2,3,4,5-tetrahydro-benzo[b][1,4]diazepine-1-carboxylic acid methyl ester hydrochloride, (S)—N—((S)-1-((6-Bromo-2-methoxynaphthalen-1-yl)methyl)-5-(4-cyanobenzyl)-2-oxo-2,3,4,5-tetrahydro-1H-benzo[b][1,4]diazepin-3-yl)-2-(methylamino)propanamide trifluoroacetate, (S)—N—((S)-5-Benzyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—[(S)-5-(4-Acetylamino-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methoxy-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Benzenesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Dimethylsulfamoyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-methanesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-methanesulfonylmethanesulfonyl-1-(2-methyl-naphthalen-1-ylmethyl)-2-oxo-2,3,4,5-tetrahydro-1H-benzo[b][1,4]diazepin-3-yl]-2-methylamino-propionamide trifluoroacetate, Cyclic-5-[(S)-5-(2-Amino-ethyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, Cyclic-5-[(S)-5-(3-Amino-propionyl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride, Cyclic-5-[(S)-5-(3-amino-propyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, Cyclic-5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, and Cyclic-5-[(S)-5-(5-amino-pentanoyl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride.

A certain embodiment of the invention relates to a pharmaceutical composition comprising any of the compounds as described herein, or a pharmaceutically acceptable salt thereof, as an active ingredient together with a pharmaceutically acceptable carrier or excipient.

A certain embodiment of the invention relates to compounds as described herein for use as therapeutically active substance A certain embodiment of the invention relates to a use of compounds as described herein for the manufacture of a medicament for the therapeutic and/or prophylactic treatment of cancer.

A certain embodiment of the invention relates to a use of compounds as described herein for use in the therapeutic and/or prophylactic treatment of cancer.

A certain embodiment of the invention relates to a method of treating or ameliorating cancer comprising administering to a subject in need of such treatment a therapeutically effective amount of a compound as described herein.

The compounds of Formula I as well as their salts have at least one asymmetric carbon atom and therefore may be present as mixtures of different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP1 and/or cIAP2. In another aspect, the compounds of the invention bind to the BIR2 domain of XIAP, cIAP1 and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

The compounds of the present invention are thus useful in the amelioration, control or treatment of cell proliferative disorders such as, in particular, oncological disorders. These compounds and formulations containing said compounds are anticipated to be useful in the treatment or control of blood cancers, such as, for example, acute myeloid leukemia, or solid tumors, such as, for example, breast, colon, lung and prostate tumors.

A "therapeutically effective amount" or "effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

Compositions/Formulations

In an alternative embodiment, the present invention includes pharmaceutical compositions comprising at least one compound of formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The compounds of Formula I and their pharmaceutically acceptable salts and esters can be processed with pharmaceutically inert, inorganic or organic adjuvants for the production of tablets, coated tablets, dragees and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragees and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, H$_2$O, polyols, saccharose, invert sugar, glucose, etc. Suitable adjuvants for injection solutions are, for example, H$_2$O, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds in the present invention (compounds of general Formula I) can be prepared using the general reaction scheme set out in Scheme 1

Scheme 1

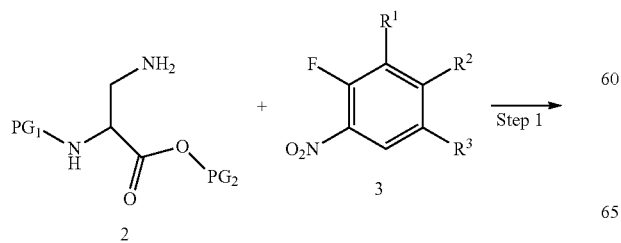

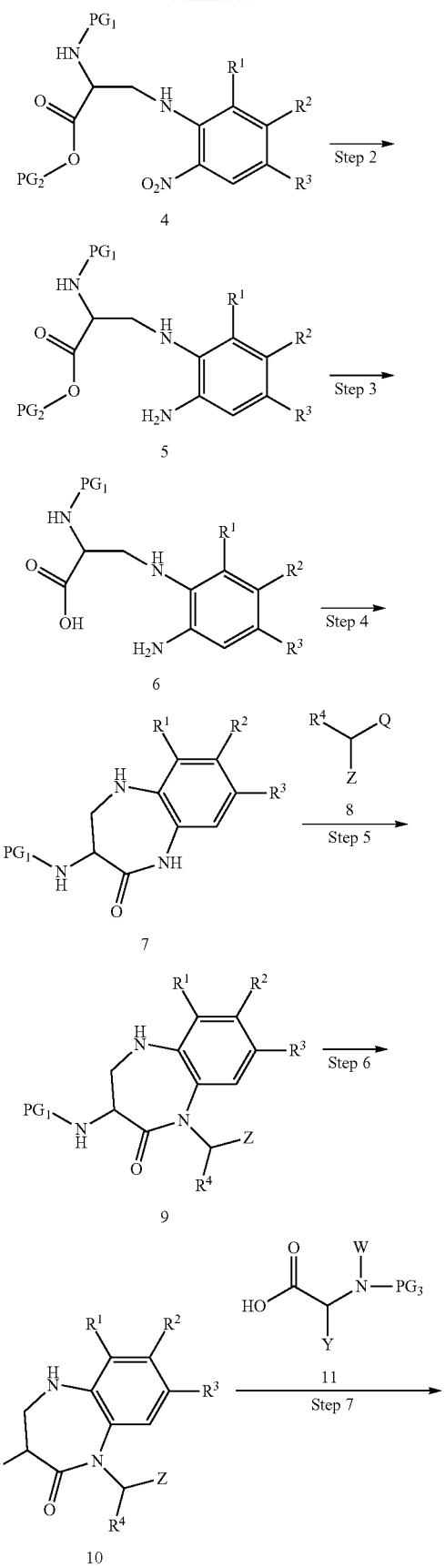

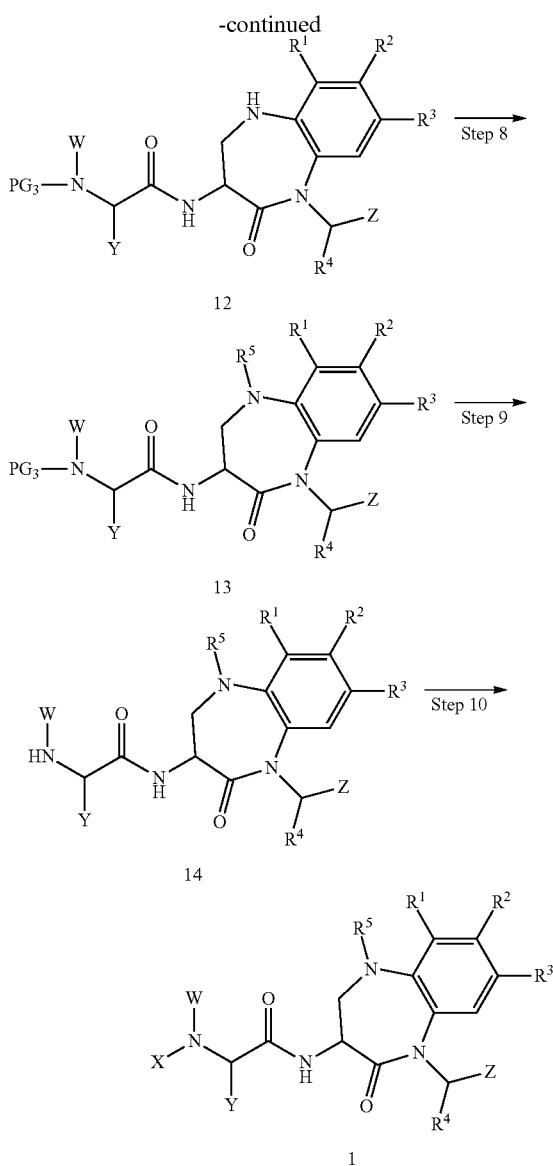

particular, carbamate-based protecting groups, e.g. tert-butyloxycarbonyl and benzyloxycarbonyl, are preferred for PG1 but other amine-protecting groups may also be effective. PG2 can be H or can be an alkyl group, e.g., methyl, ethyl, tert-butyl.

Step 2: This step involves the reduction of the nitro group in compounds of general formula 4 to provide compounds of general formula 5. Those skilled in the art will recognize there are several methods to accomplish this reduction including catalytic hydrogenation and chemical reduction. The choice of reduction method will be influenced by the substitution on the phenyl ring indicated by $R^1$, $R^2$ and $R^3$ and by the protecting groups PG1 and PG2 so that unwanted side reactions do not occur. For example, compounds of general formula 4 can be treated with an appropriate hydrogenation catalyst, e.g., 10% Pd/C in an appropriate solvent, e.g., MeOH and subjected to hydrogenation at pressures ranging from atmospheric pressure to elevated pressure, up to about 60 PSI for an amount of time sufficient to carry out this transformation. Alternatively, compounds of general formula 4 can treated with an appropriate chemical reducing agent, e.g. Zn or $SnCl_2$, in an appropriate solvent or solvent mixture, e.g., EtOAc or a mixture of EtOAc and EtOH or a mixture of EtOH and HCl, at an appropriate temperature, ranging from about 0° C. to about 80° C. for an amount of time sufficient to carry out this transformation.

Step 3: The optional carboxylic acid protecting group PG2 in compounds of general formula 5 can be removed to afford compounds of general formula 6. As mentioned above, the choice of protecting group PG2 and conditions used during step 3 for removal of PG2 is influenced by what other potentially reactive functional groups are present in compounds of general formula 5 and the requirement of avoiding undesired reactions elsewhere in the starting material or product of the reaction, i.e., compounds of general formulae 5 and 6, respectively. For example, if PG2 is an ester, e.g., methyl or ethyl, compounds of general formula 4 can be treated with a base, e.g., NaOH or LiOH, in an appropriate solvent or solvent mixture, e.g., $THF/H_2O$ or $MeOH/H_2O$ at an appropriate temperature, ranging from about 0° C. to about 80° C. for an amount of time sufficient to carry out this transformation. Those skilled in the art will recognize that there are a variety of conditions for removing protecting groups from carboxylic acids which may be identified by reference to organic chemistry text books (e.g. Protective Groups in Organic Synthesis, Theodora W. Greene et al.) or the original chemistry literature. It will be recognized that compounds of general formula 5 where PG2=H are equivalent to compounds of general formula 6.

Step 4: This step entails the conversion of compounds of general formula 6 to lactams of general formula 7. Reagents which may be employed to achieve this transformation include diimide based reagents e.g. dicyclohexylcarbodiimide, (3-dimethylamino-propyl)-ethyl-carbodiimide hydrochloride; or uronium based reagents, e.g. O-benzotriazol-1-yl-N,N,N',N'-tetramethyluronium hexaflurorophosphate or O-benzotriazol-1-yl-N,N,N',N'-bis(tetramethylene)uronium hexaflurorophosphate. Additionally, a catalyst can be optionally added to the reaction, e.g., 1-hydroxybenzotriazole or N-hydroxysuccinimide. Alternative reagents may also be effective in performing this conversion whose selection may be made by reference to the original chemistry literature or would be generally known to one knowledgeable in the art of organic synthesis.

Step 5: This step involves the reaction of compounds of general structure 7 with compounds of general structure 8 to form compounds of general structure 9, where Q is a suitable Step 1: A suitably protected 2-amino-3-aminopropionic acid of general formula 2, where PG1 is a group that renders the 2-amine N inert to reaction conditions used in the rest of the synthetic sequence and PG2 is an optional group that renders the carboxylic acid inert to reaction conditions used in the rest of the synthetic sequence, and a substituted or unsubstituted 1-fluoro-2-nitrobenzene of general formula 3 can be reacted with a base in an appropriate solvent and at an appropriate temperature for an amount of time sufficient to provide a product of general formula 4. The base can be inorganic, e.g., $NaHCO_3$, $Na_2CO_3$ or $Cs_2CO_3$, or organic, e.g., lithium bis(trimethylsilyl)amide. Solvents are chosen to be compatible with the base and other reaction conditions, such as temperature, and include, but are not limited to, e.g., THF or DMF. Temperatures suitable for this reaction can range from about 0° C. to about 150° C. Preferred choices for protecting group PG1 and PG2 may be made by reference to organic chemistry text books (e.g. Protective Groups in Organic Synthesis, Theodora W. Greene et al.), the original chemistry literature, or would be generally known to one knowledgeable in the art of organic synthesis. In leaving group, e.g., a halo, such as Br or I, or a sulfonate ester, such as methanesulfonate ester. Step 5 can be accomplished by treating compounds of general structure 7 with a base and compounds of general structure 9 in a suitable solvent for an amount of time sufficient to carry out this transformation. The base used can be inorganic, e.g., $Cs_2CO_3$ or organic, e.g., lithium bis(trimethylsilyl)amide. Solvents are chosen to be compatible with the base and other reaction conditions, such as temperature, and include, but are not limited to, e.g., THF or DMF. Temperatures suitable for this reaction can range from −78° C. to 100° C. Those skilled in the art will recognize that a catalyst can be added to the reaction mixture. Such catalysts can include, but are not limited to, e.g., NaI or tetrabutylammonium iodide.

Step 6: This step entails the removal of protecting group PG1 from compounds of general formula 9 to form amine-containing compounds of general Formula I0. As mentioned above, the choice of protecting group PG1 and conditions used during step 6 for removal of PG1 is influenced by what other potentially reactive functional groups are present in compounds of general Formula I0 and the requirement of avoiding undesired reactions elsewhere in the starting material or product of the reaction, i.e., compounds of general formulae 9 and 10, respectively. In the case where the amine-protecting group PG1 present in compounds of general formula 5 is tert-butyloxycarbonyl, the protecting group can be removed under acidic conditions such as trifluoroacetic acid in dichloromethane or hydrochloric acid in p-dioxane. Removal of the tert-butyloxycarbonyl group under acidic conditions initially liberates the corresponding salt of the compound of general Formula I0, from which the free amine of general Formula I0 can be optionally liberated after treatment with base. Alternatively, if the protecting group PG1 is benzyloxycarbonyl removal can be accomplished by catalytic hydrogenation using a suitable catalyst, e.g., 10% Pd/C and treating the mixture with a hydrogen source, e.g., $H_2$ or ammonium formate, in an appropriate solvent, e.g., EtOH. Those skilled in the art will recognize that there are a variety of conditions for removing protecting groups from nitrogen atoms which may be identified by reference to organic chemistry text books (e.g. Protective Groups in Organic Synthesis, Theodora W. Greene et al.) or the original chemistry literature.

Step 7: This step entails the coupling of a suitably protected α-amino-acid of general structure 11 to compounds of general structure 10, where PG3 is a group that renders the α-amine N inert to reaction conditions used in the rest of the synthetic sequence and W is as described above. Preferred choices for protecting group PG3 may be made by reference to organic chemistry text books (e.g. Protective Groups in Organic Synthesis, Theodora W. Greene et al.), the original chemistry literature, or would be generally known to one knowledgeable in the art of organic synthesis. In particular, carbamate-based protecting groups, e.g. tert-butyloxycarbonyl and benzyloxycarbonyl, are preferred but other amine-protecting groups may also be effective. Those skilled in the art will recognize there are several methods using known peptide coupling reaction techniques to convert compounds of general Formula I0 and compounds of general Formula I1 to compounds of general Formula I2. Typical peptide coupling reagents which may be employed include diimide based reagents e.g. dicyclohexylcarbodiimide, (3-dimethylamino-propyl)-ethyl-carbodiimide hydrochloride; or uronium based reagents, e.g. O-benzotriazol-1-yl-N,N,N',N'-tetramethyluronium hexaflurorophosphate or O-benzotriazol-1-yl-N,N,N',N'-bis(tetramethylene)uronium hexafluorophosphate. Additionally, a catalyst can be optionally added to the reaction, e.g., 1-hydroxybenzotriazole or N-hydroxysuccinimide. Alternative peptide coupling reagents may also be effective in performing this conversion. Selection of alternative peptide coupling reagents may be made by reference to the original chemistry literature or would be generally known to one knowledgeable in the art of organic synthesis.

Step 8: This step entails the optional introduction of $R^5$ onto compounds of general Formula I2 to provide compounds of general Formula I3. Conditions and reagents for this step will be influenced by other potentially reactive functional groups in compounds of general Formula I2 and the requirement of avoiding undesired reactions elsewhere in the starting material or product of the reaction, i.e., compounds of general Formulae 12 and 13, respectively. When $R^5$ is an alkyl group, compounds of general Formula I2 can be treated with an alkyl halide, e.g., iodomethane or bromopropane, in an appropriate solvent, e.g., DMF or THF and a base, e.g., $K_2CO_3$ or $Cs_2CO_3$. Temperatures suitable for this reaction can range from about 20° C. to about 120° C. Additionally, a catalyst can be added to the reaction mixture. Such catalysts can include, but are not limited to, e.g., NaI or tetrabutylammonium iodide.

Alternatively, when $R^5$ is an alkyl group, reductive amination can be used to achieve the introduction of $R^5$ onto compounds of general Formula I2. Compounds of general Formula I2 can be treated with an aldehyde, e.g., propionaldehyde or isovaleraldehyde, in an appropriate solvent, e.g., tetrahydrofuran (THF), EtOH or dichloromethane (DCM) and a reducing agent, e.g., $NaBH_4$ or $NaBH(OAc)_3$, at an appropriate temperature, ranging from about 0° C. to about 100° C., for an amount of time sufficient to carry out this transformation.

When $R^5$ is an acyl group, compounds of general Formula I2 can be treated with an acylating agent, e.g., acetyl chloride, methyl chloroformate, methyl isocyanate or glutaric anhydride, in an appropriate solvent, e.g., DCM or THF, and an optional base, e.g., triethylamine (TEA) or pyridine, at an appropriate temperature, ranging from about 0° C. to about 100° C., for an amount of time sufficient to carry out this transformation. Alternatively, compounds of general Formula I2 and a carboxylic acid, e.g., benzoic acid or malonamic acid, can be treated with a dehydrating agent, e.g., $POCl_3$ or dicyclohexylcarbodiimide, in an appropriate solvent, e.g., DCM or THF, and an optional base, e.g., (TEA) or pyridine, and an optional catalyst, e.g., 1-hydroxybenzotriazole or N-hydroxysuccinimide, at an appropriate temperature, ranging from about 0° C. to about 100° C., for an amount of time sufficient to carry out this transformation. Those skilled in the art will recognize that there are additional methods to carry out the introduction of an acyl group onto compounds of general Formula I2 which may be identified by reference to the original chemical literature.

When $R^5$ is a sulfonyl group, compounds of general Formula I2 can be treated with a sulfonating agent, e.g., methanesulfonyl chloride or methanesulfonic anhydride, in an appropriate solvent, e.g., DCM or THF, and an optional base, e.g., TEA or pyridine, at an appropriate temperature, ranging from about 0° C. to about 100° C., for an amount of time sufficient to carry out this transformation.

Step 9: This step entails the removal of protecting group PG3 from compounds of general Formula I3 to provide amine compounds of general Formula I4. The conditions and methods used for this step are analogous to those described above for Step 6.

In cases where X in general Formula I is desired to be H no further reactions are needed as compounds of general Formula I4 are equivalent to compounds of general Formula I, where X =H.

Step 10 involves the introduction of an additional substitution to the nitrogen atom bearing group W. Those skilled in the art will recognize there are several ways to accomplish this transformation. These include, but are not limited to, reductive amination or alkylation. For example, compounds of general Formula I3 can be treated with an aldehyde, e.g., acetaldehyde, benzaldehyde or 3-pyridinecarboxaldehyde and a reducing agent, e.g., $NaBH_4$ or $NaBH_3CN$ in a suitable solvent, e.g., MeOH or EtOH at an appropriate temperature, ranging from about −20° C. to about 100° C. for an amount of time sufficient to carry out this transformation. Alternatively, compounds can be treated with an alkylating agent, e.g., methyl iodide, benzyl bromide or allyl bromide, and a base, e.g., pyridine or TEA, in a suitable solvent, e.g., DCM or THF at an appropriate temperature, ranging from about −20° C. to about 100° C. for an amount of time sufficient to carry out this transformation. Those skilled in the art will recognize that a catalyst can be added to the reaction mixture. Such catalysts can include, but are not limited to, e.g., NaI or tetrabutylammonium iodide.

It will be apparent to one knowledgeable in the art of organic synthesis that when one or more of the substituents labeled W, Y or $R^1$ through $R^5$, or substituents included in their definitions, in the compounds shown in Scheme 1 are in and of themselves chemically reactive groups, or contains chemically reactive groups, then additional modification of the compounds of general Formula I through 14 which contain those reactive groups may be possible. The point in the synthetic sequence at which modification of the chemically reactive groups takes place may be chosen such that the newly elaborated group is chemically inert to the reagents to be employed during the remaining steps of the synthetic sequence and does not interfere with the remaining steps in the synthetic sequence shown in Scheme 1. Alternatively, if the newly elaborated group is not chemically inert or can interfere with the remaining steps in the synthetic sequence it may be necessary to temporarily mask the reactive functional group with an appropriate protecting group or to derivatize the functional group into a moiety which is stable to the remaining transformations in the synthetic sequence and will be present in the final product of the reaction sequence. If a protecting group is introduced which is not required in the final compound of general structure 1 then it may either be removed under the conditions remaining in the synthetic sequence shown in Scheme 1 or by introduction of an additional deprotection step into the synthetic sequence depending upon the nature of the protecting group employed.

The reaction conditions for the above reactions can vary to a certain extent. Those skilled in the art will recognize that the sequence of some reaction steps described in Scheme 1 can vary, as shown in Scheme 2, Scheme 3 and Scheme 4.

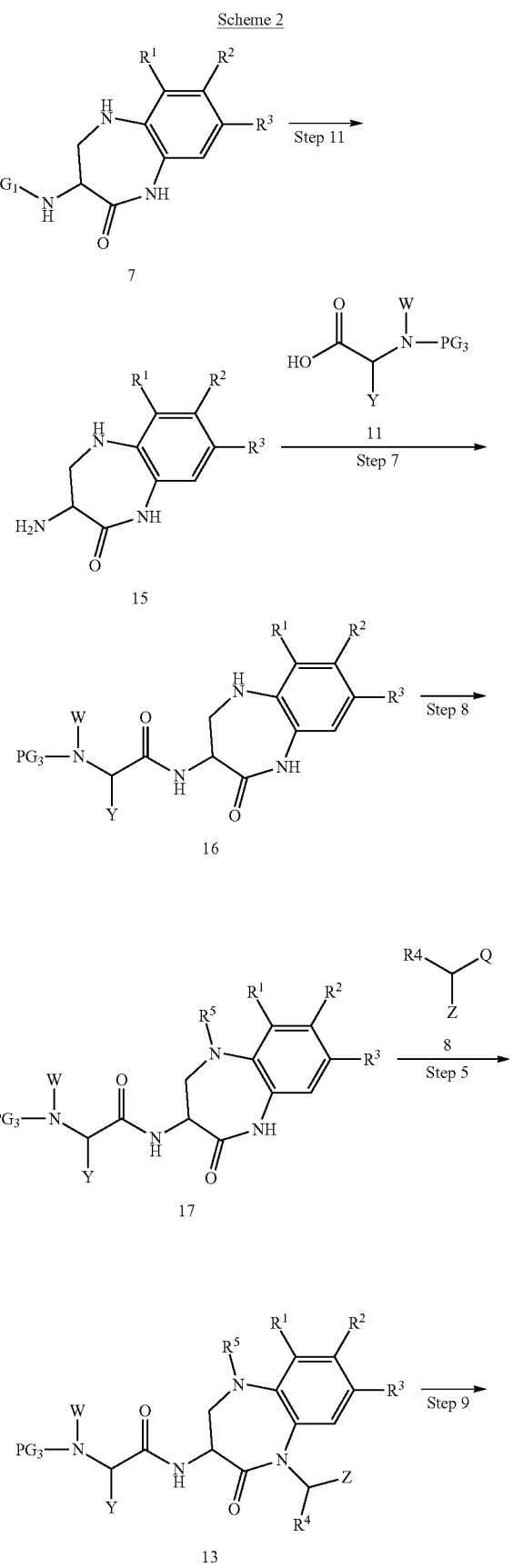

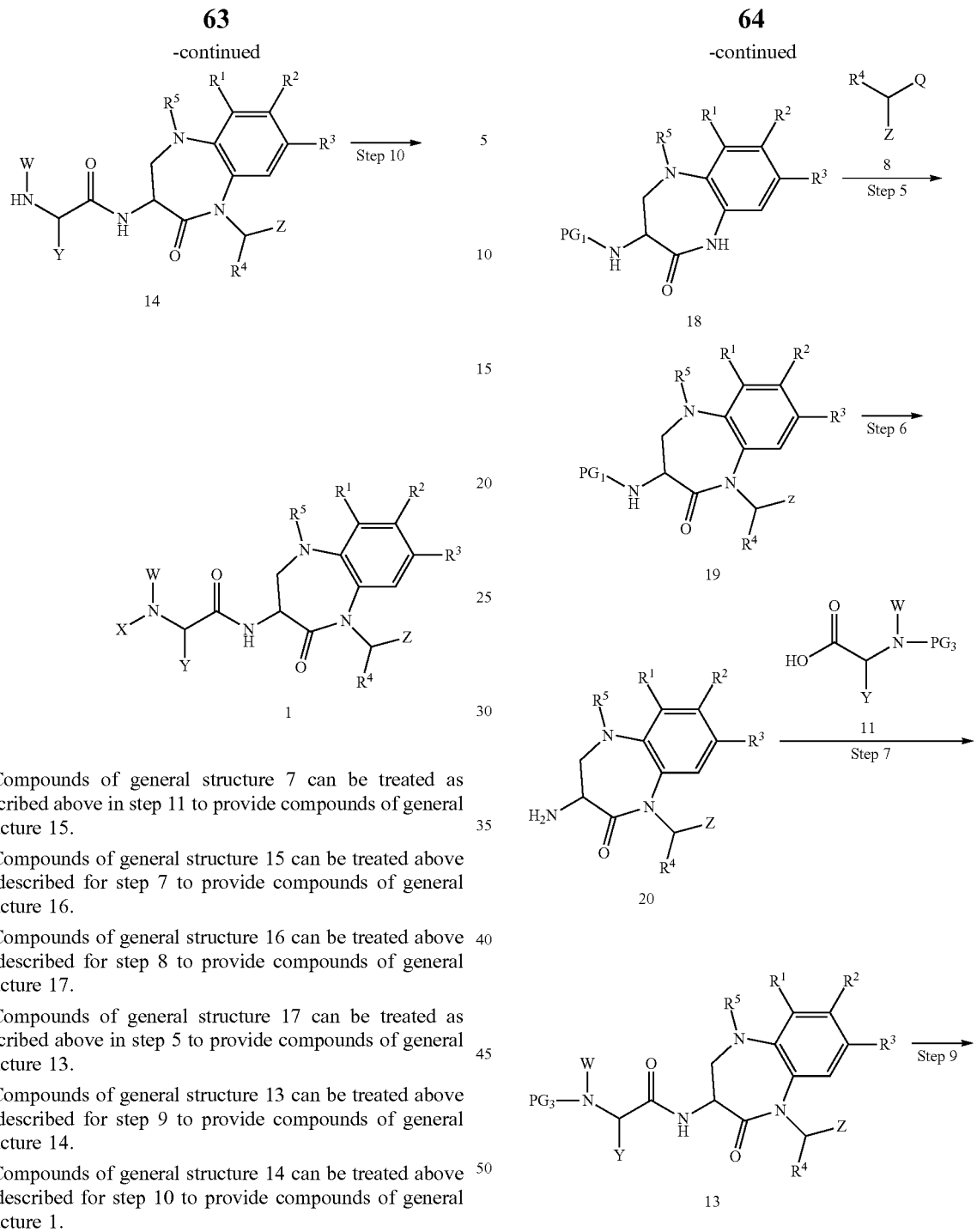

Compounds of general structure 7 can be treated as described above in step 11 to provide compounds of general structure 15.

Compounds of general structure 15 can be treated above as described for step 7 to provide compounds of general structure 16.

Compounds of general structure 16 can be treated above as described for step 8 to provide compounds of general structure 17.

Compounds of general structure 17 can be treated as described above in step 5 to provide compounds of general structure 13.

Compounds of general structure 13 can be treated above as described for step 9 to provide compounds of general structure 14.

Compounds of general structure 14 can be treated above as described for step 10 to provide compounds of general structure 1.

Scheme 3

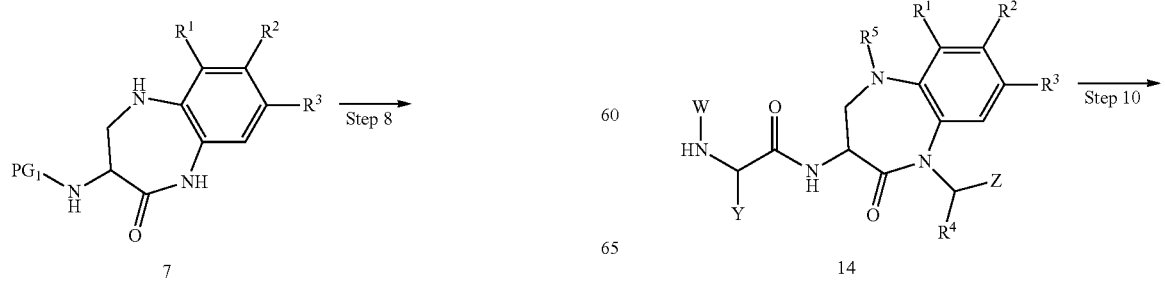

-continued

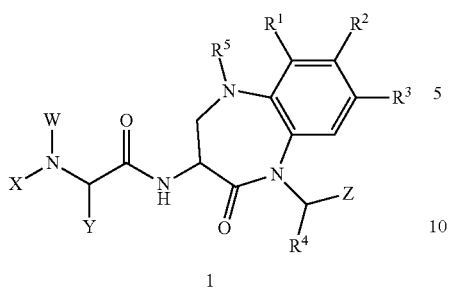

1

Compounds of general structure 7 can be treated as described above in step 8 to provide compounds of general structure 18.

Compounds of general structure 18 can be treated above as described for step 5 to provide compounds of general structure 19.

Compounds of general structure 19 can be treated above as described for step 6 to provide compounds of general structure 20.

Compounds of general structure 20 can be treated as described above in step 7 to provide compounds of general structure 13.

Compounds of general structure 13 can be treated above as described for step 9 to provide compounds of general structure 14.

Compounds of general structure 14 can be treated above as described for step 10 to provide compounds of general structure 1.

Scheme 4

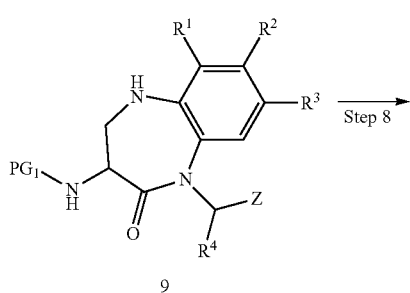

9

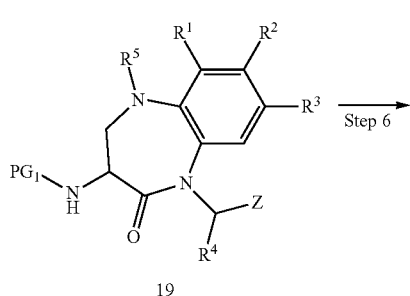

19

-continued

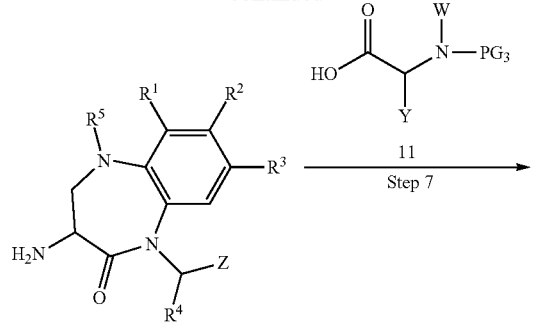

20

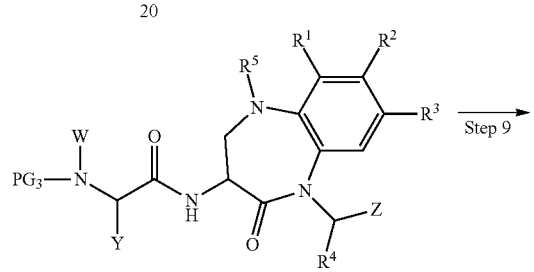

13

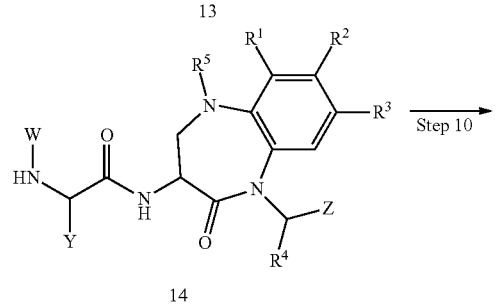

14

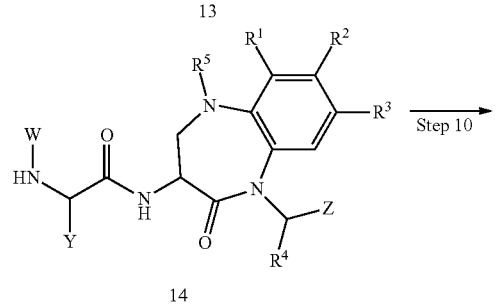

1

Compounds of general structure 9 can be treated above as described for step 8 to provide compounds of general structure 19.

Compounds of general structure 19 can be treated above as described for step 6 to provide compounds of general structure 20.

Compounds of general structure 20 can be treated as described above in step 7 to provide compounds of general structure 13.

Compounds of general structure 13 can be treated above as described for step 9 to provide compounds of general structure 14.

Compounds of general structure 14 can be treated above as described for step 10 to provide compounds of general structure 1.

Methods to perform the above described reactions and processes would be apparent to those of ordinary skill in the art based on the present disclosure, or can be deduced in analogy from the examples. Starting materials are commercially available or can be made by methods analogous to those described in the Examples below.

Crystal Forms

When the compounds of the invention are solids, it is understood by those skilled in the art that these compounds, and their salts, may exist in different crystal or polymorphic forms, all of which are intended to be within the scope of the present invention and specified formulas.

EXAMPLES

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using AutoNom 2000 Add-in v4.0 SP2 (function in ISIS Draw, Elsevier/MDL), or AutoNom 2000 TT v4.01.305 (Elsevier/MDL), or functions available in ChemDraw Pro Control 11.0.2 (CambridgeSoft Corp.), or Struct=Name feature of electronic notebooks.

Preparation of Intermediates

A. ((S)-2-Oxo-2,3,4,5-tetrahydro-1H-benzo[b][1,4]diazepin-3-yl)-carbamic acid tert-butyl ester

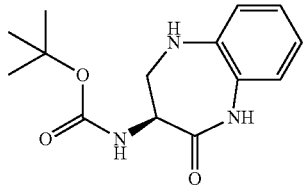 [SMILES: CC(C)(C)OC(=O)N[C@H]1CNc2ccccc2NC1=O]

Step 1: A mixture of (S)-3-amino-2-tert-butoxycarbonylamino-propionic acid (5.0 g 25 mmol, *J. Med. Chem.* 2008, 51, 4581), 2-fluoronitrobenzene (3.9 mL 37.5 mmol) and NaHCO₃ (6.3 g 75 mmol) in 50 mL of DMF was stirred at 80° C. overnight. The mixture was cooled to RT, H₂O and Et₂O were added and the aqueous layer extracted with Et₂O. The aqueous layer was adjusted to ca. pH 5 with 10% aq. NaHSO₃ solution and extracted with EtOAc, the combined organic extracts were washed with brine, dried over anhydr. Na₂SO₄, filtered and concentrated to give (S)-2-(tert-butoxycarbonylamino)-3-(2-nitro-phenylamino)-propanoic acid (7.5 g, orange solid) which was used without purification.

Step 2: A mixture of (S)-2-(tert-butoxycarbonylamino)-3-(2-nitro-phenylamino)-propanoic acid (7.5 g 23 mmol) and 0.5 g of 10% Pd/C in 100 mL of MeOH was hydrogenated under an atmosphere of H₂ at 60 psi for 4 h. The mixture was filtered through a pad of Celite, the filter cake washed with MeOH and the filtrate concentrated to give (S)-3-(2-aminophenylamino)-2-(tert-butoxycarbonylamino)-propanoic acid which was used without purification (6.3 g, black solid).

Step 3: 1-(3-Dimethylaminopropyl)-3-ethylcarbodiimide hydrochloride (EDCI, 5.3 g 27.82 mmol) was added to a solution of (S)-3-(2-aminophenylamino)-2-(tert-butoxycarbonylamino)-propanoic acid (6.3 g 21.4 mmol) in 80 mL of DMF at 0° C. The reaction was warmed and stirred at room temperature (RT) for 4 h, diluted with EtOAc and H₂O, the organic layer was washed with H₂O, dried over anhydr. Na₂SO₄, filtered and concentrated. Purification by silica gel chromatography gave the title compound (4.7 g, light yellow powder).

B. ((S)-1-Naphthalen-1-ylmethyl-2-oxo-2,3,4,5-tetrahydro-1H-benzo[b][1,4]diazepin-3-yl)-carbamic acid tert-butyl ester

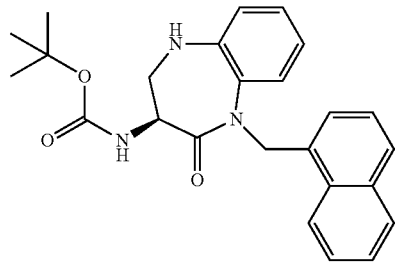 [SMILES: CC(C)(C)OC(=O)N[C@H]1CNc2ccccc2N(Cc2cccc3ccccc23)C1=O]

To a solution of (S)-2-oxo-2,3,4,5-tetrahydro-1H-benzo[b][1,4]diazepin-3-yl)-carbamic acid tert-butyl ester (0.56 g 2.0 mmol) in 8 mL of anhydr. THF at −78° C. was slowly added a solution of 1 M lithium bis(trimethylsilyl)amide (2.2 mL 2.2 mmol) in THF. The mixture was stirred at −78° C. for 30 min. and a solution of 1-bromomethyl-naphthalene (0.583 g, 2.6 mmol) in 2 mL of THF was added, the mixture stirred at −78° C. for 10 min., warmed to RT, stirred 3 h, diluted with EtOAc, washed with 10% aq. NaHSO₃, brine, dried over anhydr. Na₂SO₄, filtered and the filtrate concentrated to give a material that was purified by silica gel chromatography to give the title compound (0.65 g, white solid).

C. Methyl-[(S)-1-((S)-1-naphthalen-1-ylmethyl-2-oxo-2,3,4,5-tetrahydro-1H-benzo[b][1,4]diazepin-3-ylcarbamoyl)-ethyl]-carbamic acid tert-butyl ester

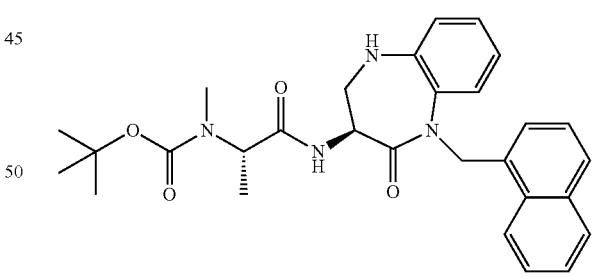

Step 1: ((S)-1-Naphthalen-1-ylmethyl-2-oxo-2,3,4,5-tetrahydro-1H-benzo[b][1,4]diazepin-3-yl)-carbamic acid tert-butyl ester (0.14 g 0.34 mmol) in 10 mL of 4 M HCl in dioxane was stirred at RT overnight. The mixture was concentrated and the residue was washed with Et₂O and dried to give of (S)-3-amino-1-naphthalen-1-ylmethyl-1,3,4,5-tetrahydro-benzo[b][1,4]diazepin-2-one hydrochloride which was used without purification (0.119 g).

Step 2: To a solution of (S)-3-amino-1-naphthalen-1-ylmethyl-1,3,4,5-tetrahydro-benzo[b][1,4]diazepin-2-one hydrochloride (0.119 g 0.34 mmol), 1-hydroxybenzotriazole hydrate (HOBT.H₂O, 0.057 g 0.374 mmol), BOC-N-Me- Ala-OH (0.068 g 0.34 mmol), DIEA (0.24 mL 1.36 mmol) in 2 mL of DMF at 0° C. was added of O-(benzotriazol-1-yl)-N,N,N',N'-bis(tetramethylene)uronium hexafluorophosphate (HBPyU, 0.159 g 0.374 mmol). The mixture was stirred at RT for 4 h, diluted with EtOAc, washed with aq. Na$_2$CO$_3$, brine, 1 M citric acid, brine, dried over anhydr. Na$_2$SO$_4$ and concentrated to give a material that was purified by silica gel chromatography to afford the title compound (0.14 g, white solid).

D. [(S)-1-(2-Methyl-naphthalen-1-ylmethyl)-2-oxo-2,3,4,5-tetrahydro-1H-benzo[b][1,4]diazepin-3-yl]-carbamic acid tert-butyl ester

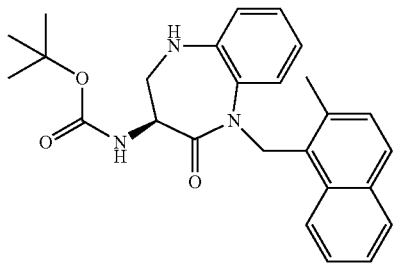 [SMILES: Cc1ccc2ccccc2c1CN1C(=O)[C@@H](NC(=O)OC(C)(C)C)CNc2ccccc21]

In a similar manner to that described for the preparation of ((S)-1-naphthalen-1-ylmethyl-2-oxo-2,3,4,5-tetrahydro-1H-benzo[b][1,4]diazepin-3-yl)-carbamic acid tert-butyl ester, except the reaction mixture was stirred at RT overnight and KI (1.8 g 10.83 mmol) was added, (S)-2-oxo-2,3,4,5-tetrahydro-1H-benzo[b][1,4]diazepin-3-yl)-carbamic acid tert-butyl ester (3.0 g 10.83 mmol) and 1-chloromethyl-2-methyl-naphthalene (5.35 g 28.2 mmol) were reacted to afford the title compound (3.2 g, light yellow solid).

E. Methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester

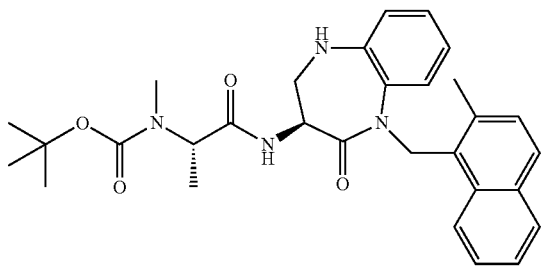 [SMILES: Cc1ccc2ccccc2c1CN1C(=O)[C@@H](NC(=O)[C@H](C)N(C)C(=O)OC(C)(C)C)CNc2ccccc21]

Step 1: In a similar manner to that described for the preparation of methyl-[(S)-1-((S)-1-naphthalen-1-ylmethyl-2-oxo-2,3,4,5-tetrahydro-1H-benzo[b][1,4]diazepin-3-yl-carbamoyl)-ethyl]-carbamic acid tert-butyl ester, Step 1, except the resulting solid obtained was lyophilized from MeCN/H$_2$O, [(S)-1-(2-methyl-naphthalen-1-ylmethyl)-2-oxo-2,3,4,5-tetrahydro-1H-benzo[b][1,4]diazepin-3-yl]-carbamic acid tert-butyl ester (1.29 g 3.0 mmol) was converted (S)-3-amino-1-(2-methyl-naphthalen-1-ylmethyl)-1,3,4,5-tetrahydro-benzo[b][1,4]diazepin-2-one hydrochloride (1.10 g) which was used without purification.

Step 2: In a similar manner to that described for the preparation of methyl-[(S)-1-((S)-1-naphthalen-1-ylmethyl-2-oxo-2,3,4,5-tetrahydro-1H-benzo[b][1,4]diazepin-3-yl-carbamoyl)-ethyl]-carbamic acid tert-butyl ester, Step 2, (S)-3-amino-1-(2-methyl-naphthalen-1-ylmethyl)-1,3,4,5-tetrahydro-benzo[b][1,4]diazepin-2-one hydrochloride (1.10 g 3 mmol) and BOC-N-Me-Ala-OH (0.64 g 3.15 mmol) were reacted to give a material that was purified by silica gel chromatography to afford the title compound (1.4 g, white solid).

F. [(S)-1-(6-Bromo-2-methoxy-naphthalen-1-ylmethyl)-2-oxo-2,3,4,5-tetrahydro-1H-benzo[b][1,4]diazepin-3-yl]-carbamic acid tert-butyl ester

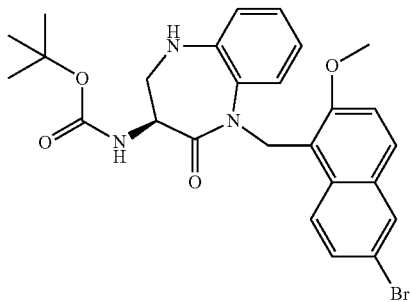 [SMILES: COc1ccc2cc(Br)ccc2c1CN1C(=O)[C@@H](NC(=O)OC(C)(C)C)CNc2ccccc21]

To a solution of methyl-[(S)-1-((S)-2-oxo-2,3,4,5-tetrahydro-1H-benzo[b][1,4]diazepin-1-ylcarbamoyl)-ethyl]-carbamic acid tert-butyl ester (1.66 g 6 mmol) in 30 mL of anhydr. THF at –78° C. was slowly added 1.0 M lithium bis(trimethylsilyl)amide solution in THF (6.6 mL 6.6 mmol), the mixture stirred at –78° C. for 30 min., NaI (1.08 g 7.2 mmol) was added and 6-bromo-1-(chloromethyl)-2-methoxynaphthalene (2.06 g 7.2 mmol) in 15 mL of THF was added and the mixture warmed to RT and stirred overnight. The mixture was cooled to 0° C., 1 M citric acid was added and the mixture extracted with EtOAc. The organic extracts were washed with 1 M citric acid, brine, aq. Na$_2$CO$_3$, dried over anhydr. Na$_2$SO$_4$, and concentrated to give a material that was purified by silica gel chromatography to afford the title compound (2.9 g, white solid).

G. {(S)-1-[(S)-1-(6-Bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester

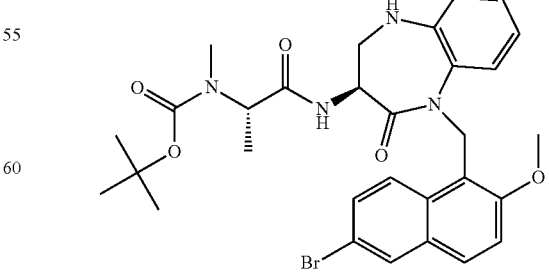

Step 1: In a similar manner to that described for the preparation of methyl-[(S)-1-((S)-1-naphthalen-1-ylmethyl- 2-oxo-2,3,4,5-tetrahydro-1H-benzo[b][1,4]diazepin-3-yl-carbamoyl)-ethyl]-carbamic acid tert-butyl ester, Step 1, [(S)-1-(2-methyl-naphthalen-1-ylmethyl)-2-oxo-2,3,4,5-tetrahydro-1H-benzo[b][1,4]diazepin-3-yl)-carbamic acid tert-butyl ester (2.84 g (5.4 mmol) was converted to (S)-3-amino-1-(6-bromo-2-methoxy-naphthalen-1-ylmethyl)-1,3,4,5-tetrahydro-benzo[b][1,4]diazepin-2-one hydrochloride (2.5 g) which was used without purification.

Step 2: To a solution of (S)-3-amino-1-(6-bromo-2-methoxy-naphthalen-1-ylmethyl)-1,3,4,5-tetrahydro-benzo[b][1,4]diazepin-2-one hydrochloride (2.5 g 5.4 mmol), HOBT.H$_2$O (0.91 g 5.94 mmol), BOC-N-Me-Ala-OH (1.21 g 5.94 mmol), DIEA (3.76 mL 21.6 mmol) in 18 mL of DMF at 0° C. was added HBPyU (2.25 g 5.94 mmol) and the mixture stirred at RT for 4 hours. The reaction was cooled to 0° C. and aq. Na$_2$CO$_3$ was added and a precipitate formed. The resulting solid was collected and washed with aq. Na$_2$CO$_3$, H$_2$O, and dried in vacuum to give the title compound (3.30 g, white solid) which was used without purification.

H. 5-{(S)-3-[(S)-2-(tert-Butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester

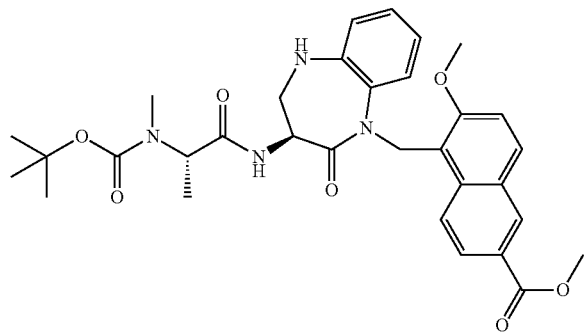 [SMILES: COC(=O)c1ccc2c(CN3C(=O)[C@@H](NC(=O)[C@H](C)N(C)C(=O)OC(C)(C)C)CNc4ccccc43)c(OC)ccc2c1]

A mixture of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.330 g 0.540 mmol), palladium(II)acetate (0.0067 g 0.0297 mmol), 4,5-bis(diphenylphosphino)-9,9-dimethylxanthene (0.0251 g 0.0433 mmol), MeOH (0.328 mL 8.11 mmol) and TEA in a 5 mL microwave tube was degassed with N$_2$, purged with CO for 30 sec. and heated to 70° C. overnight under CO. EtOAc was added and the mixture was washed with H$_2$O, brine, dried over anhydr. Na$_2$SO$_4$ and concentrated. The residue was purified by silica gel chromatography to afford the title compound (0.190 g, white solid).

I. Methyl-{(S)-1-[(S)-1-(3-methyl-butyryl)-4-oxo-2,3,4,5-tetrahydro-1H-benzo[b][1,4]diazepin-3-ylcarbamoyl]-ethyl}-carbamic acid tert-butyl ester

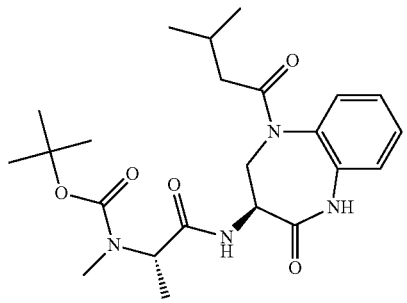 [SMILES: CC(C)CC(=O)N1C[C@H](NC(=O)[C@H](C)N(C)C(=O)OC(C)(C)C)C(=O)Nc2ccccc21]

Step 1: A solution of ((S)-2-oxo-2,3,4,5-tetrahydro-1H-benzo[b][1,4]diazepin-3-yl)-carbamic acid tert-butyl ester (1.11 g 4 mmol) in 15 mL of 4.0 M HCl in 1,4-dioxane was stirred at RT overnight, the solvent removed and the residue lyophilized from MeCN/H$_2$O to give (S)-3-amino-1,3,4,5-tetrahydro-benzo[b][1,4]diazepin-2-one hydrochloride (0.90 g) which was used without purification.

Step 2: To a solution of (S)-3-amino-1,3,4,5-tetrahydro-benzo[b][1,4]diazepin-2-one hydrochloride (0.855 g 4 mmol), HOBT.H$_2$O (0.674 g 4.4 mmol), BOC-N-Me-Ala-OH (0.894 g 4.4 mmol), and DIEA (2.79 mL 16 mmol) in 16 mL of DMF at 0° C. was added (1.67 g 4.4 mmol) of HBPyU, the mixture was stirred at RT for 1 h and diluted with H$_2$O and EtOAc. The organic layer was washed 1 M citric acid, brine, aq. Na$_2$CO$_3$, brine, dried over anhydr. Na$_2$SO$_4$, filtered and concentrated to give a material that was purified by silica gel chromatography to afford methyl-[(S)-1-((S)-2-oxo-2,3,4,5-tetrahydro-1H-benzo[b][1,4]diazepin-3-ylcarbamoyl)-ethyl]-carbamic acid tert-butyl ester (1.45 g, white solid).

Step 3: To a solution of methyl-[(S)-1-((S)-2-oxo-2,3,4,5-tetrahydro-1H-benzo[b][1,4]diazepin-3-ylcarbamoyl)-ethyl]-carbamic acid tert-butyl ester (0.145 g 0.4 mmol), pyridine (0.316 mL 1.2 mmol) in 8 mL of DCM at 0° C. was slowly added isovaleryl chloride (0.146 mL 4 mmol). After 30 min. at 0° C. the mixture was poured into 1 M citric acid and extracted with EtOAc. The organic extracts were washed with 1 M citric acid, brine, sat. Na$_2$CO$_3$, brine, dried over anhydr. Na$_2$SO$_4$, filtered and concentrated to give a material that was purified by silica gel chromatography to afford the title compound (0.150 g white, solid).

J. Methyl-[(S)-1-((S)-2-oxo-2,3,4,5-tetrahydro-1H-benzo[b][1,4]diazepin-3-ylcarbamoyl)-ethyl]-carbamic acid tert-butyl ester

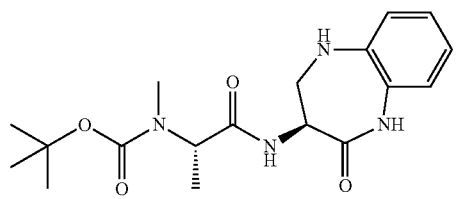 [SMILES: C[C@@H](C(=O)N[C@H]1CNc2ccccc2NC1=O)N(C)C(=O)OC(C)(C)C]

To a solution of (S)-3-amino-1,3,4,5-tetrahydro-benzo[b][1,4]diazepin-2-one hydrochloride (2.5 g (11.7 mmol), HOBT.H₂O (1.97 g (12.9 mmol), (S)-2-(tert-butoxycarbonyl-methyl-amino)-propionic acid (2.62 g 12.9 mmol) and DIEA (8.2 mL 46.8 mmol) in 45 mL of DMF at 0° C. was added HBPyU (4.88 g 12.9 mmol). The mixture was stirred at room temperature for 4 h, diluted with EtOAc, washed with aq. Na₂CO₃, brine, 1 M citric acid, brine, dried over anhydr. Na₂SO₄, filtered and concentrated to give a material that was purified by silica gel chromatography to give methyl-[(S)-1-((S)-2-oxo-2,3,4,5-tetrahydro-1H-benzo[b][1,4]diazepin-3-ylcarbamoyl)-ethyl]-carbamic acid tert-butyl ester (2.97 g, white solid).

K. (S)-Methyl-5-((3-(tert-butoxycarbonylamino)-2-oxo-2,3,4,5-tetrahydro-1H-benzo[b][1,4]diazepin-1-yl)methyl)-6-methoxy-2-naphthoate

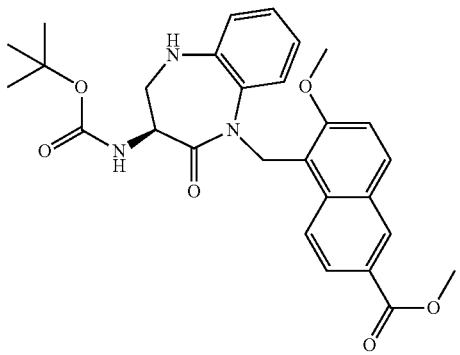 [SMILES: COC(=O)c1ccc2c(CN3C(=O)[C@@H](NC(=O)OC(C)(C)C)CNc4ccccc43)c(OC)ccc2c1]

A mixture of {(S)-1-(6-bromo-2-methoxy-naphthalen-1yl)-2-oxo-2,3,4,5-tetrahydro-1H-benzo[b][1,4]diazepin-3-ylcarbamoyl}-ethyl}-methyl-carbamic acid tert-butyl ester (1.2 g, 2.28 mmol), palladium(II)acetate (0.0205 g, 0.091 mmol), of 4,5-bis(diphenylphosphino)-9,9-dimethylxanthene (0.11 g, 0.18 mmol), MeOH (1.38 mL, 34.2 mmol) and TEA (5.8 mL) in a microwave tube was degassed with N₂, purged with CO for 30 seconds and heated at 70° C. under CO overnight. The mixture was diluted with EtOAc, washed with H₂O, brine, dried over anhydr. Na₂SO₄, filtered and concentrated to give a material that was purified by silica gel chromatography to afford the title compound (0.81 g, white solid).

L. (2-(Difluoromethoxy)naphthalen-1-yl)methyl methanesulfonate

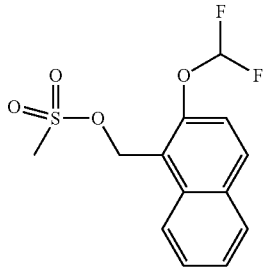 [SMILES: CS(=O)(=O)OCc1c(OC(F)F)ccc2ccccc12]

Step 1: To a suspension of 2-(difluoromethoxy)-1-naphthaldehyde (0.997 g, 4.49 mmol) in EtOH (29.9 mL) was added NaBH₄ (255 mg, 6.73 mmol). The mixture was stirred at for 3 h, diluted with H₂O and extracted with EtOAc. The combined extracts were washed with brine, dried over Na₂SO₄, filtered, and concentrated. The residue was purified by flash chromatography to provide (2-(difluoromethoxy)naphthalen-1-yl)MeOH (387 mg, 39%) as an orange solid.

Step 2: To a solution of (2-(difluoromethoxy)naphthalen-1-yl) MeOH (387 mg, 1.73 mmol) in CH₂Cl₂ (8.63 mL) was added TEA (505 µL, 3.62 mmol) and methanesulfonyl chloride (160 µL, 2.07 mmol) and the mixture stirred at for 20 h. The reaction was diluted with CH₂Cl₂, washed with H₂O and brine, dried over Na₂SO₄, filtered, and concentrated to provide (2-(difluoromethoxy)naphthalen-1-yl) methyl methanesulfonate (342 mg) as a brown oil which was used without purification.

M. (S)-tert-butyl 1-(4-nitrobenzoyl)-4-oxo-2,3,4,5-tetrahydro-1H-benzo[b][1,4]diazepin-3-ylcarbamate

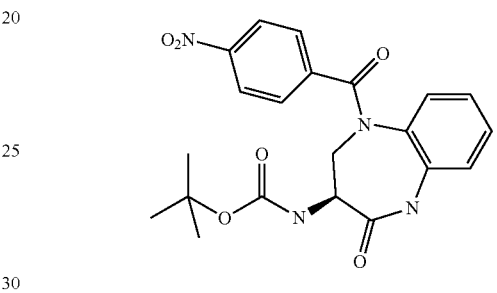

Step 1: Pyridine (12.4 mL, 153 mmol) was added to a solution of ((S)-2-oxo-2,3,4,5-tetrahydro-1H-benzo[b][1,4]diazepin-3-yl)-carbamic acid tert-butyl ester (4.24 g, 15.3 mmol) in CH₂Cl₂ (122 mL) at 0° C., and a solution of 4-nitrobenzoyl chloride (3.12 g, 16.8 mmol) in CH₂Cl₂ (30.5 mL) was added dropwise over 15 min. The mixture was stirred at 0° C. for 1 h, diluted with H₂O and extracted with CH₂Cl₂. The combined extracts were washed with 1 N aq. citric acid, H₂O, sat. aq. NaHCO₃, and brine, dried over Na₂SO₄, filtered, and concentrated. The resulting material was triturated with CH₂Cl₂ to provide (S)-tert-butyl 1-(4-nitrobenzoyl)-4-oxo-2,3,4,5-tetrahydro-1H-benzo[b][1,4]diazepin-3-ylcarbamate (5.30 g, 81%) as a white solid. LC-MS m/z 449 [M+Na]⁺.

N. tert-Butyl methyl((S)-1-((S)-1-((2-methylnaphthalen-1-yl)methyl)-5-(4-nitrobenzoyl)-2-oxo-2,3,4,5-tetrahydro-1H-benzo[b][1,4]diazepin-3-ylamino)-1-oxopropan-2-yl)carbamate

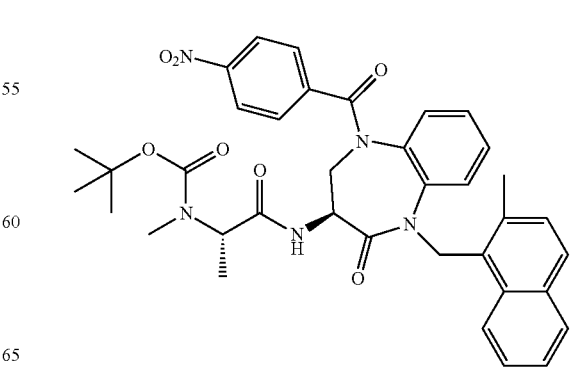

Step 1: To a solution of (S)-tert-butyl 1-(4-nitrobenzoyl)-4-oxo-2,3,4,5-tetrahydro-1H-benzo[b][1,4]diazepin-3-yl-carbamate (239 mg, 560 µmol) in DMF (2.8 mL) was added 1-(chloromethyl)-2-methylnaphthalene (118 mg, 617 µmol), Cs$_2$CO$_3$ (219 mg, 673 µmol), and NaI (101 mg, 673 µmol). The yellow suspension was stirred for 20 h. The reaction was diluted with H$_2$O and extracted with EtOAc. The combined extracts were washed with sat. aq. NaHCO$_3$, H$_2$O, and brine, dried over Na$_2$SO$_4$, filtered, and concentrated. The residue was purified by flash chromatography to provide (S)-tert-butyl 1-((2-methylnaphthalen-1-yl)methyl)-5-(4-nitrobenzoyl)-2-oxo-2,3,4,5-tetrahydro-1H-benzo[b][1,4]diazepin-3-ylcarbamate (324 mg, quant.) as a white solid. LC-MS m/z 603 [M+Na]$^+$.

Step 2: A solution of (S)-tert-butyl 1-((2-methylnaphthalen-1-yl)methyl)-5-(4-nitrobenzoyl)-2-oxo-2,3,4,5-tetrahydro-1H-benzo[b][1,4]diazepin-3-ylcarbamate (324 mg, 558 mol) in 4 M HCl in dioxane (2.79 mL) was stirred for 18 h. The reaction was concentrated and the residue was triturated with Et$_2$O to provide (S)-3-amino-1-((2-methylnaphthalen-1-yl)methyl)-5-(4-nitrobenzoyl)-4,5-dihydro-H-benzo[b][1,4]diazepin-2(3H)-one hydrochloride (235 mg, 82%) as a white solid. LC-MS m/z 481 [M+Na]$^+$.

Step 3: To a solution of (S)-3-amino-1-((2-methylnaphthalen-1-yl)methyl)-5-(4-nitrobenzoyl)-4,5-dihydro-H-benzo[b][1,4]diazepin-2(3H)-one hydrochloride (235 mg, 455 mol) in DMF (1.52 mL) was added Boc-N-methyl-L-alanine (102 mg, 500 µmol), DIEA (315 L, 1.82 mmol), and HBTU (190 mg, 500 µmol). After 1 h, the mixture was diluted with EtOAc, washed with sat. aq. NaHCO$_3$, H$_2$O, and brine, dried over Na$_2$SO$_4$, filtered, and concentrated.

The residue was purified by flash chromatography to provide the title compound (297 mg, 98%) as a white solid. LC-MS m/z 688 [M+Na]$^+$.

O. (S)-5-(4-Acetylbenzoyl)-3-amino-4,5-dihydro-1H-benzo[b][1,4]diazepin-2(3H)-one hydrochloride

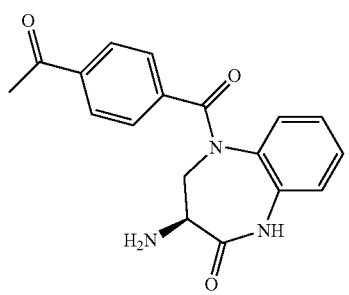 [SMILES: CC(=O)c1ccc(C(=O)N2C[C@H](N)C(=O)Nc3ccccc32)cc1]

Step 1: Phosphorus oxychloride (POCl$_3$, 1.64 mL, 18.0 mmol) was added dropwise to a solution of ((S)-2-oxo-2,3,4,5-tetrahydro-1H-benzo[b][1,4]diazepin-3-yl)-carbamic acid tert-butyl ester (2.49 g, 8.98 mmol) and 4-acetylbenzoic acid (1.62 g, 9.88 mmol) in pyridine (89.8 mL) at 0° C. After 1 h, the mixture was diluted with H$_2$O and extracted with EtOAc. The combined extracts were washed with 1 N aq. citric acid, H$_2$O, sat. aq. NaHCO$_3$, and brine, dried over Na$_2$SO$_4$, filtered, and concentrated. The residue was purified by flash chromatography to provide (S)-tert-butyl 1-(4-acetylbenzoyl)-4-oxo-2,3,4,5-tetrahydro-1H-benzo[b][1,4]diazepin-3-ylcarbamate (1.487 g, 39%) as an off-white solid. LC-MS m/z 446 [M+Na]$^+$ Step 2: A solution of (S)-tert-butyl 1-(4-acetylbenzoyl)-4-oxo-2,3,4,5-tetrahydro-1H-benzo[b][1,4]diazepin-3-yl-carbamate (1.48 g, 3.5 mmol) in 4 M HCl in dioxane (17.5 mL) was stirred for 1 h. The mixture was concentrated and the residue triturated with Et$_2$O to provide the title compound (1.17 g, 93%) as a light yellow solid. LC-MS m/z 324 (MH)$^+$ P. (S)-5-(4-Acetyl-benzoyl)-3-amino-1-(6-bromo-2-methoxy-naphthalen-1-ylmethyl)-1,3,4,5-tetrahydro-benzo[b][1,4]diazepin-2-on hydrochloride

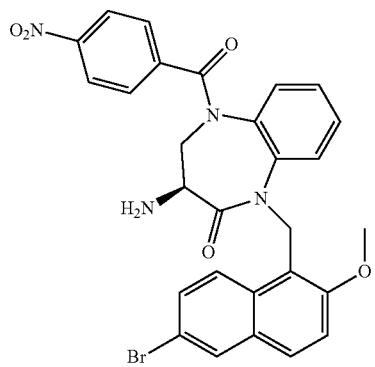 [SMILES: COc1ccc2cc(Br)ccc2c1CN1C(=O)[C@@H](N)CN(C(=O)c2ccc([N+](=O)[O-])cc2)c2ccccc21]

In a similar manner to that described for tert-butyl methyl ((S)-1-((S)-1-((2-methylnaphthalen-1-yl)methyl)-5-(4-nitrobenzoyl)-2-oxo-2,3,4,5-tetrahydro-1H-benzo[b][1,4]diazepin-3-ylamino)-1-oxopropan-2-yl)carbamate, Step 1, except 1.5 eq. of Cs$_2$CO$_3$ and NaI were used, (S)-tert-butyl 1-(4-acetylbenzoyl)-4-oxo-2,3,4,5-tetrahydro-1H-benzo[b][1,4]diazepin-3-ylcarbamate (0.26 g. 0.61 mmol) and of 6-bromo-1-(chloromethyl)-2-methoxynaphthalene (0.26 g, 0.92 mmol) were converted to [(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-yl]-carbamic acid tert-butyl ester (0.34 g, 83%) as a white solid. LC-MS m/z 672 (MH$^+$)

In a similar manner to that described for (S)-5-(4-acetyl-benzoyl)-3-amino-4,5-dihydro-1H-benzo[b][1,4]diazepin-2(3H)-one hydrochloride Step 2, of [(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-yl]-carbamic acid tert-butyl ester (0.34 g, 0.51 mmol) was converted to the title compound (0.3 g, 100%) as a white solid. LC-MS m/z 572 (MH$^+$)

Q. tert-Butyl (S)-1-((S)-1-(4-acetylbenzoyl)-4-oxo-2,3,4,5-tetrahydro-1H-benzo[b][1,4]diazepin-3-ylamino)-1-oxopropan-2-yl(methyl)carbamate

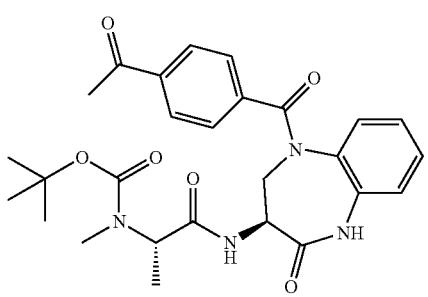 [SMILES: CC(=O)c1ccc(C(=O)N2C[C@H](NC(=O)[C@H](C)N(C)C(=O)OC(C)(C)C)C(=O)Nc3ccccc32)cc1]

Step 1: To a solution of (S)-5-(4-acetylbenzoyl)-3-amino-4,5-dihydro-H-benzo[b][1,4]diazepin-2(3H)-one hydrochloride (563 mg, 1.56 mmol) in DMF (3.91 mL) was added Boc-N-methyl-L-alanine (350 mg, 1.72 mmol), DIEA (1.08 mL, 6.26 mmol), and HBTU (653 mg, 1.72 mmol). After 30 min., the mixture was diluted with EtOAc, washed with sat. aq. NaHCO₃, H₂O, and brine, dried over Na₂SO₄, filtered, and concentrated. The residue was purified by flash chromatography to provide tert-butyl (S)-1-((S)-1-(4-acetylbenzoyl)-4-oxo-2,3,4,5-tetrahydro-1H-benzo[b][1,4]diazepin-3-ylamino)-1-oxopropan-2-yl(methyl)carbamate (748 mg, 94%) as a white solid. LC-MS m/z 531 [M+Na]⁺.

R. tert-Butyl (S)-1-((S)-1-(4-acetylbenzoyl)-4-oxo-2,3,4,5-tetrahydro-1H-benzo[b][1,4]diazepin-3-ylamino)-1-oxopropan-2-ylcarbamate

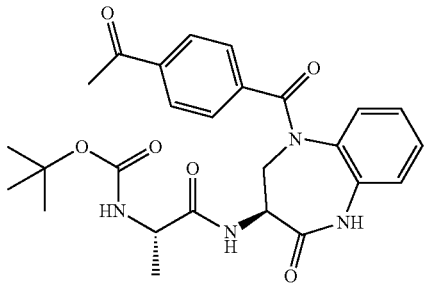 [SMILES: CC(=O)c1ccc(C(=O)N2C[C@H](NC(=O)[C@H](C)NC(=O)OC(C)(C)C)C(=O)Nc3ccccc32)cc1]

To a solution of (S)-5-(4-acetylbenzoyl)-3-amino-4,5-dihydro-H-benzo[b][1,4]diazepin-2(3H)-one hydrochloride (606 mg, 1.68 mmol) in DMF (5.61 mL) was added N-Boc-L-alanine (351 mg, 1.85 mmol), DIEA (1.17 mL, 6.74 mmol), and HBTU (703 mg, 1.85 mmol). After 30 min., the mixture was diluted with EtOAc, washed with sat. aq. NaHCO₃, H₂O, and brine, dried over Na₂SO₄, filtered, and concentrated. The residue was purified by flash chromatography to provide tert-butyl (S)-1-((S)-1-(4-acetylbenzoyl)-4-oxo-2,3,4,5-tetrahydro-1H-benzo[b][1,4]diazepin-3-ylamino)-1-oxopropan-2-ylcarbamate (792 mg, 95%) as an off-white solid. LC-MS m/z 517 [M+Na]⁺.

S. BOC-N-(methyl-d3)-Ala-OH

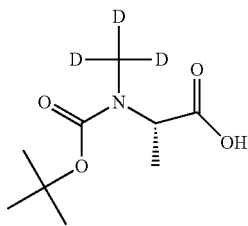 [SMILES: [2H]C([2H])([2H])N(C(=O)OC(C)(C)C)[C@@H](C)C(=O)O]

Sodium hydride (1.27 g, 31.7 mmol, Eq: 3.00) was added to a mixture of (S)-2-(tert-butoxycarbonylamino)propanoic acid (2 g, 10.6 mmol, Eq: 1.00) and iodomethane-d3 (12.3 g, 5.26 mL, 84.6 mmol, Eq: 8.00) in THF (40 mL) at 0° C. and the mixture stirred for 5 min then at RT. After 4 h the mixture was diluted with H₂O and extracted with Et₂O. The pH of the aqueous mixture was adjusted to ~2 and extracted with Et₂O and these combined extract were washed with brine, dried over Na₂SO₄ and concentrated to afford the title compound as colorless oil which solidified upon standing (2.1 g, 96% yield) and was used without purification.

T. Methyl-d3-tert-butyl (S)-1-((S)-1-(4-acetylbenzoyl)-4-oxo-2,3,4,5-tetrahydro-1H-benzo[b][1,4]diazepin-3-ylamino)-1-oxopropan-2-ylcarbamate

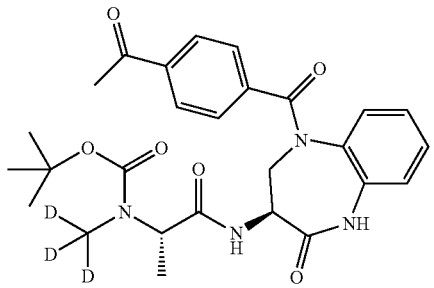 [SMILES: [2H]C([2H])([2H])N(C(=O)OC(C)(C)C)[C@@H](C)C(=O)N[C@H]1CN(C(=O)c2ccc(C(C)=O)cc2)c2ccccc2NC1=O]

To a solution of (S)-5-(4-acetylbenzoyl)-3-amino-4,5-dihydro-H-benzo[b][1,4]diazepin-2(3H)-one hydrochloride (355 mg, 987 μmol) in DMF (3.29 mL) was added BOC-N-(methyl-d3)-Ala-OH (224 mg, 1.09 mmol), DIEA (683 μL, 3.95 mmol), and HBTU (412 mg, 1.09 mmol). After 30 min., the mixture was diluted with sat. aq. NaHCO₃ and extracted with EtOAc. The combined extracts were washed with H₂O and brine, dried over Na₂SO₄, filtered, and concentrated. The residue was purified by flash chromatography to provide the title compound (381 mg, 76%) as a white solid. LC-MS m/z 534 [M+Na]⁺.

U. 6-Bromo-1-chloromethyl-2-(methoxy-d3)-naphthalene

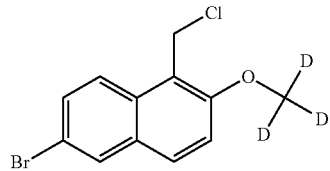 [SMILES: [2H]C([2H])([2H])Oc1ccc2cc(Br)ccc2c1CCl]

Step 1: A mixture of 6-bromo-2-naphthol (5 g, 22.4 mmol, Eq: 1.00), K₂CO₃ (4.65 g, 33.6 mmol, Eq: 1.5) and iodomethane-d3 (3.9 g, 1.67 mL, 26.9 mmol, Eq: 1.2) in DMF was stirred overnight. The mixture was diluted with H₂O resulting in a precipitate which was collected by filtration, The precipitate was dissolved in EtOAc and successively washed with 1 N NaOH and brine. The organic layer was dried over Na₂SO₄ and concentrated under to afford 6-bromo-2-(d3-methoxy)-naphthol as beige solid (5 g, 93% yield).

Step 2: Titanium tetrachloride, 1.0 M in DCM (18.3 mL, 18.3 mmol, Eq: 2.2) and dichloromethyl methyl ether (1.05 g, 817 μl, 9.16 mmol, Eq: 1.1) in DCM (70 mL) were cooled to 0° C. and 6-bromo-2-(d3-methoxy)-naphthol (2 g, 8.33 mmol, Eq: 1.00) in DCM (10 mL) was added. The mixture was warmed to RT, stirred for 2.5 h, diluted with 1 N HCl, and extracted with DCM. The combined extracts were washed with brine, dried over Na₂SO₄ and concentrated to afford 6-bromo-2-(d3-methoxy)-naphthalene-1-carbaldehyde (2.11 g, 95% yield) which was used without purification.

Step 3: Sodium borohydride (1.19 g, 31.3 mmol, Eq: 4.00) was added to a mixture of 6-bromo-2-(d3-methoxy)-naphthalene-1-carbaldehyde (2.1 g, 7.83 mmol, Eq: 1.00) in MeOH. After 10 min, the mixture was diluted with 1 N HCl and H₂O resulting in a precipitate which was collected by filtration and air-dried. This material was purified by flash chromatography (6-bromo-2-(d3-methoxy)-naphthalene-1-yl)-MeOH (1.38 g, 65%). MS m/z 253.9 (M-H₂O+H+).

Step 4: Pyridine (606 mg, 618 µl, 7.66 mmol, Eq: 1.5) and thionyl chloride (912 mg, 559 µl, 7.66 mmol, Eq: 1.5) were added to (6-bromo-2-(d3-methoxy)-naphthalene-1-yl)-MeOH (1.38 g, 5.11 mmol, Eq: 1.00) in DCM (30 mL) and the mixture was stirred overnight. The mixture was diluted with aq. NaHCO₃ and extracted with DCM. The extracts were dried over Na₂SO₄ and concentrated to afford the title compound as beige solid. (1.4 g, 95% yield).

The compounds of the invention may form a salt with an acid, for example hydrochloric acid, hydrobromicn acid or trifluoroacetic acid. In the following examples, most of the compounds are reported in the hydrochloride salt form.

Example 1

(S)-2-Methylamino-N—((S)-1-naphthalen-1-ylmethyl-2-oxo-2,3,4,5-tetrahydro-1H-benzo[b][1,4]diazepin-3-yl)-propionamide hydrochloride

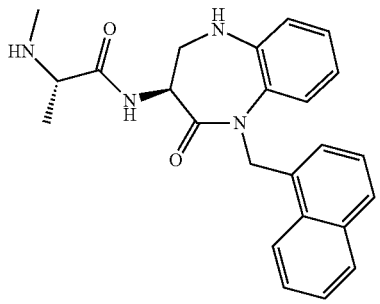 [SMILES: CN[C@@H](C)C(=O)N[C@H]1CNc2ccccc2N(Cc2cccc3ccccc23)C1=O]

A solution of methyl-[(S)-1-((S)-1-naphthalen-1-ylmethyl-2-oxo-2,3,4,5-tetrahydro-1H-benzo[b][1,4]diazepin-3-ylcarbamoyl)-ethyl]-carbamic acid tert-butyl ester (0.04 g 0.08 mmol) in 5 mL of 4.0 M HCl in 1,4-dioxane was stirred at RT overnight and concentrated to give a material that was dissolved in MeCN/H₂O and lyophilized to afford the title compound (0.033 g, white powder). MS m/z 403 (MH⁺).

Example 2

(S)—N—((S)-5-Acetyl-1-naphthalen-1-ylmethyl-2-oxo-2,3,4,5-tetrahydro-1H-benzo[b][1,4]diazepin-3-yl)-2-methylamino-propionamide hydrochloride

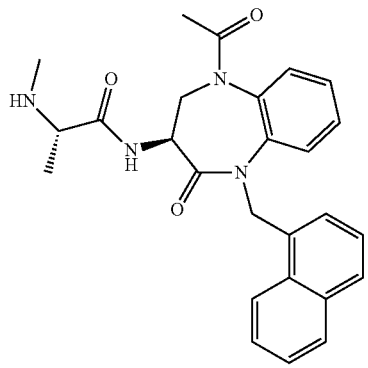 [SMILES: CN[C@@H](C)C(=O)N[C@H]1CN(C(C)=O)c2ccccc2N(Cc2cccc3ccccc23)C1=O]

Step 1: To a solution of methyl-[(S)-1-((S)-1-naphthalen-1-ylmethyl-2-oxo-2,3,4,5-tetrahydro-1H-benzo[b][1,4]diazepin-3-ylcarbamoyl)-ethyl]-carbamic acid tert-butyl ester (0.05 g 0.1 mmol) and TEA (0.028 mL 0.2 mmol) in 3 mL of dichloromethane (DCM) was slowly added acetyl chloride (0.0086 mL 0.12 mmol). The mixture was stirred at RT overnight and additional TEA (0.056 mL 0.4 mmol) and acetyl chloride (0.014 mL 0.2 mmol) were added and the mixture stirred at RT overnight. EtOAc was added and the mixture was washed with 1 M citric acid, brine, aq. Na₂CO₃, brine, dried over anhydr. Na₂SO₄, filtered and concentrated to give a material that was purified by silica gel chromatography to afford [(S)-1-((S)-5-acetyl-1-naphthalen-1-ylmethyl-2-oxo-2,3,4,5-tetrahydro-1H-benzo[b][1,4]diazepin-3-ylcarbamoyl)-ethyl]-methyl-carbamic acid tert-butyl ester (0.02 g, white solid).

Step 2: In a similar manner to that described for Example 1, [(S)-1-((S)-5-acetyl-1-naphthalen-1-ylmethyl-2-oxo-2,3,4,5-tetrahydro-1H-benzo[b][1,4]diazepin-3-ylcarbamoyl)-ethyl]-methyl-carbamic acid tert-butyl ester (0.02 g 0.037 mmol) was converted to the title compound (0.018 g, white powder). MS m/z 445 (MH⁺).

Example 3

(S)-2-Methylamino-N—[(S)-5-(3-methyl-butyryl)-1-naphthalen-1-ylmethyl-2-oxo-2,3,4,5-tetrahydro-1H-benzo[b][1,4]diazepin-3-yl]-propionamide hydrochloride

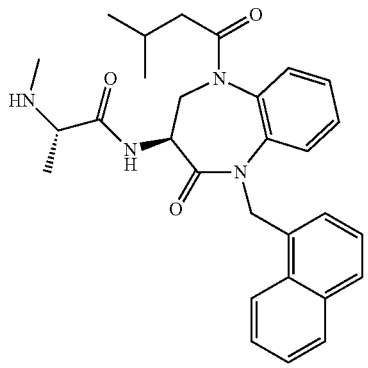 [SMILES: CN[C@@H](C)C(=O)N[C@H]1CN(C(=O)CC(C)C)c2ccccc2N(Cc2cccc3ccccc23)C1=O]

Step 1: Methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester To a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.05 g 0.1 mmol) and TEA (0.069 mL 0.5 mmol) in 3 mL of DCM, was added isovaleryl chloride (0.048 mL 0.4 mmol). After 30 min. at RT EtOAc was added the mixture was washed with 1 M citric acid, brine, aq. Na₂CO₃, brine, dried over anhydr. Na₂SO₄ and concentrated to give a material that was purified by silica gel chromatography to afford methyl-{(S)-1-[(S)-5-(3-methyl-butyryl)-1-naphthalen-1-ylmethyl-2-oxo-2,3,4,5-tetrahydro-1H-benzo[b][1,4]diazepin-3-ylcarbamoyl]-ethyl}-carbamic acid tert-butyl ester (0.048 g, white solid).

Step 2: In a similar manner to that described for Example 1, methyl-{(S)-1-[(S)-5-(3-methyl-butyryl)-1-naphthalen-1- ylmethyl-2-oxo-2,3,4,5-tetrahydro-1H-benzo[b][1,4]diazepin-3-ylcarbamoyl]-ethyl}-carbamic acid tert-butyl ester (0.048 g 0.082 mmol) was converted to the title compound (0.030 g, white powder). MS m/z 487 (MH+).

Example 4

(S)-2-Methylamino-N—((S)-1-naphthalen-1-ylmethyl-2-oxo-5-phenylacetyl-2,3,4,5-tetrahydro-1H-benzo[b][1,4]diazepin-3-yl)-propionamide hydrochloride

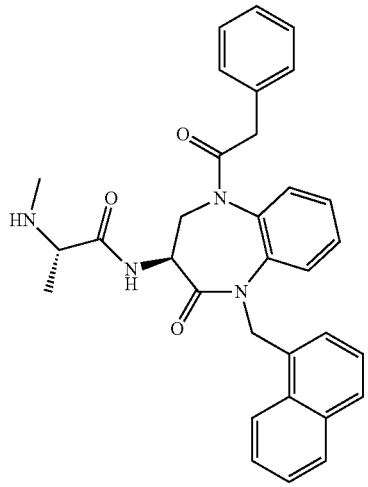 [SMILES: CN[C@@H](C)C(=O)N[C@H]1CN(C(=O)Cc2ccccc2)c2ccccc2N(Cc2cccc3ccccc23)C1=O]

Step 1: In a similar manner to that described for Example 3, Step 1, methyl-[(S)-1-((S)-1-naphthalen-1-ylmethyl-2-oxo-2,3,4,5-tetrahydro-1H-benzo[b][1,4]diazepin-3-ylcarbamoyl)-ethyl]-carbamic acid tert-butyl ester (0.050 g 0.1 mmol) and phenyl-acetyl chloride (0.040 mL 0.3 mmol) were reacted to give a material that was purified by silica gel chromatography to afford methyl-[(S)-1-((S)-1-naphthalen-1-ylmethyl-2-oxo-5-phenylacetyl-2,3,4,5-tetrahydro-1H-benzo[b][1,4]diazepin-3-ylcarbamoyl)-ethyl]-carbamic acid tert-butyl ester (0.040 g, white solid).

Step 2: In a similar manner to that described for Example 1, methyl-[(S)-1-((S)-1-naphthalen-1-ylmethyl-2-oxo-5-phenylacetyl-2,3,4,5-tetrahydro-1H-benzo[b][1,4]diazepin-3-ylcarbamoyl)-ethyl]-carbamic acid tert-butyl ester (0.040 g 0.065 mmol) was converted to the title compound (0.03 g, white solid). MS m/z 521 (MH+).

Example 5

(S)-2-Methylamino-N—((S)-5-methyl-1-naphthalen-1-ylmethyl-2-oxo-2,3,4,5-tetrahydro-1H-benzo[b][1,4]diazepin-3-yl)-propionamide hydrochloride

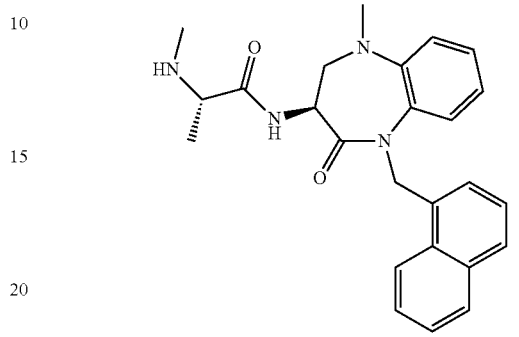

Step 1: A mixture of ((S)-1-naphthalen-1-ylmethyl-2-oxo-2,3,4,5-tetrahydro-1H-benzo[b][1,4]diazepin-3-yl)-carbamic acid tert-butyl ester (0.100 g 0.240 mmol), K$_2$CO$_3$ (0.096 g 0.72 mmol) and MeI (0.045 mL 0.72 mmol) in 1.5 mL of DMF was stirred at RT overnight. The mixture was transferred to pressure tube and K$_2$CO$_3$ (0.096 g 0.72 mmol) and MeI (0.045 mL 0.72 mmol) were added and the mixture heated at 100° C. overnight. The reaction was diluted with H$_2$O, extracted with EtOAc, the combined extracts dried over anhydr. Na$_2$SO$_4$ and concentrated to give a material that was purified by silica gel chromatography to afford ((S)-5-methyl-1-naphthalen-1-ylmethyl-2-oxo-2,3,4,5-tetrahydro-1H-benzo[b][1,4]diazepin-3-yl)-carbamic acid tert-butyl ester (0.031 g, white solid).

Step 2: In a similar manner to that described for Example 1, ((S)-5-methyl-1-naphthalen-1-ylmethyl-2-oxo-2,3,4,5-tetrahydro-1H-benzo[b][1,4]diazepin-3-yl)-carbamic acid tert-butyl ester (0.031 g 0.072 mmol) was converted to (S)-3-amino-5-methyl-1-naphthalen-1-ylmethyl-1,3,4,5-tetrahydro-benzo[b][1,4]diazepin-2-one hydrochloride (0.026 g, white powder).

Step 3: HBPyU (0.038 g 0.086 mmol) was slowly added to a solution of (S)-3-amino-5-methyl-1-naphthalen-1-ylmethyl-1,3,4,5-tetrahydro-benzo[b][1,4]diazepin-2-one hydrochloride (0.026 g 0.072 mmol), DIEA (0.040 mL 0.288 mmol), BOC-N-Me-Ala-OH (0.018 g 0.086 mmol) in 2 mL of DMF at 0° C. The mixture was stirred at 0° C. for 5 min., then RT for 2 h and H$_2$O and aq. Na$_2$CO$_3$ were added and the mixture extracted with DCM. The organic extracts were washed with brine, dried over anhydr. Na$_2$SO$_4$, filtered and concentrated to give a material that was purified by silica gel chromatography to afford methyl-[(S)-1-((S)-5-methyl-1-naphthalen-1-ylmethyl-2-oxo-2,3,4,5-tetrahydro-1H-benzo[b][1,4]diazepin-3-ylcarbamoyl)-ethyl]-carbamic acid tert-butyl ester (0.030 g, oil).

Step 4: In a similar manner to that described for Example 1, methyl-[(S)-1-((S)-5-methyl-1-naphthalen-1-ylmethyl-2-oxo-2,3,4,5-tetrahydro-1H-benzo[b][1,4]diazepin-3-ylcarbamoyl)-ethyl]-carbamic acid tert-butyl ester (0.028 g 0.054 mmol) was converted to the title compound (0.025 g, beige solid). MS m/z 417 (MH+).

Example 6

(S)-2-Methylamino-N—[(S)-5-(3-methyl-butyl)-1-naphthalen-1-ylmethyl-2-oxo-2,3,4,5-tetrahydro-1H-benzo[b][1,4]diazepin-3-yl]-propionamide hydrochloride

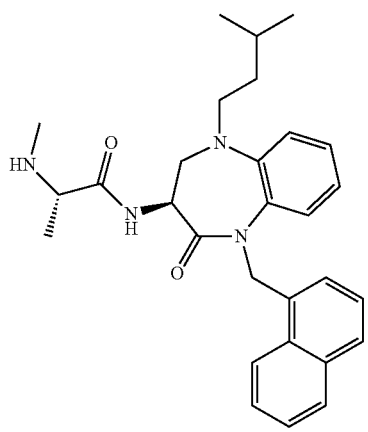 [SMILES: CN[C@@H](C)C(=O)N[C@H]1CN(CCC(C)C)c2ccccc2N(Cc2cccc3ccccc23)C1=O]

Step 1: To a solution of ((S)-1-naphthalen-1-ylmethyl-2-oxo-2,3,4,5-tetrahydro-1H-benzo[b][1,4]diazepin-3-yl)-carbamic acid tert-butyl ester (0.050 g 0.120 mmol) and isovaleraldehyde (0.026 mL 0.240 mmol) in 1.0 mL of DCM was added sodium triacetoxyborohydride (NaBH(OAc)$_3$, 0.127 mL 0.60 mmol). The mixture was stirred at RT overnight, diluted with H$_2$O, extracted with EtOAc and the extracts washed with brine, dried over anhydr. Na$_2$SO$_4$ and concentrated to give a material that was purified by silica gel chromatography to afford [(S)-5-(3-methyl-butyl)-1-naphthalen-1-ylmethyl-2-oxo-2,3,4,5-tetrahydro-1H-benzo[b][1,4]diazepin-3-yl]-carbamic acid tert-butyl ester (0.050 g).

Step 2: In a similar manner to that described for Example 1, except the lyophilization was omitted, [(S)-5-(3-methyl-butyl)-1-naphthalen-1-ylmethyl-2-oxo-2,3,4,5-tetrahydro-1H-benzo[b][1,4]diazepin-3-yl]-carbamic acid tert-butyl ester (0.050 g (0.103 mmol) was converted to (S)-3-amino-5-(3-methyl-butyl)-1-naphthalen-1-ylmethyl-1,3,4,5-tetrahydro-benzo[b][1,4]diazepin-2-one hydrochloride (0.043 g).

Step 3: In a similar manner to that described for Example 5, Step 3, (S)-3-amino-5-(3-methyl-butyl)-1-naphthalen-1-ylmethyl-1,3,4,5-tetrahydro-benzo[b][1,4]diazepin-2-one hydrochloride (0.043 g 0.103 mmol) and BOC-N-Me-Ala-OH (0.025 g 0.124 mmol) were reacted to give a material that was purified by silica gel chromatography to afford methyl-{(S)-1-[(S)-5-(3-methyl-butyl)-1-naphthalen-1-ylmethyl-2-oxo-2,3,4,5-tetrahydro-1H-benzo[b][1,4]diazepin-3-ylcarbamoyl]-ethyl}-carbamic acid tert-butyl ester (0.058 g, oil).

Step 4: In a similar manner to that described for Example 1, methyl-{(S)-1-[(S)-5-(3-methyl-butyl)-1-naphthalen-1-ylmethyl-2-oxo-2,3,4,5-tetrahydro-1H-benzo[b][1,4]diazepin-3-ylcarbamoyl]-ethyl}-carbamic acid tert-butyl ester (0.058 g 0.101 mmol) was converted to the title compound (0.060 g, beige solid). MS m/z 473 (MH$^+$).

Example 7

(S)-2-Methylamino-N—((S)-1-naphthalen-1-ylmethyl-2-oxo-5-phenethyl-2,3,4,5-tetrahydro-1H-benzo[b][1,4]diazepin-3-yl)-propionamide trifluoroacetate

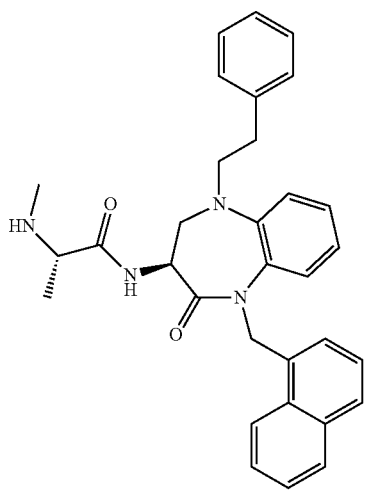 [SMILES: CN[C@@H](C)C(=O)N[C@H]1CN(CCc2ccccc2)c2ccccc2N(Cc2cccc3ccccc23)C1=O]

Step 1: In a similar manner to that described for Example 6, Step 1, except 5 eq. of NaBH(OAc)$_3$ were used, methyl-[(S)-1-((S)-1-napthalen-1-ylmethyl-2-oxo-2,3,4,5-tetrahydro-1H-benzo[b][1,4]diazepin-3-ylcarbamoyl)-ethyl]-carbamic acid tert-butyl ester (0.050 g 0.100 mmol) and phenyl acetaldehyde (0.024 mL 0.20 mmol) were reacted to give a material that was purified by silica gel chromatography to afford methyl-[(S)-1-((S)-1-naphthalen-1-ylmethyl-2-oxo-5-phenethyl-2,3,4,5-tetrahydro-1H-benzo[b][1,4]diazepin-3-ylcarbamoyl)-ethyl]-carbamic acid tert-butyl ester (0.032 g white solid).

Step 2: A solution of methyl-[(S)-1-((S)-1-naphthalen-1-ylmethyl-2-oxo-5-phenethyl-2,3,4,5-tetrahydro-1H-benzo[b][1,4]diazepin-3-ylcarbamoyl)-ethyl]-carbamic acid tert-butyl ester (0.029 g 0.048 mmol) in 2 mL of 4.0 M HCl in 1,4-dioxane was stirred at RT overnight. The mixture was concentrated and the residue was purified by reverse phase HPLC to afford the title compound (0.015 g, white solid). MS m/z 585 (MH$^+$).

Example 8

(S)-2-Methylamino-N—[(S)-5-(3-methyl-butyryl)-1-(2-methyl-naphthalen-1-ylmethyl)-2oxo-2,3,4,5-tetrahydro-1H-benzo[b][1,4]diazepin-3-yl]-propionamide hydrochloride

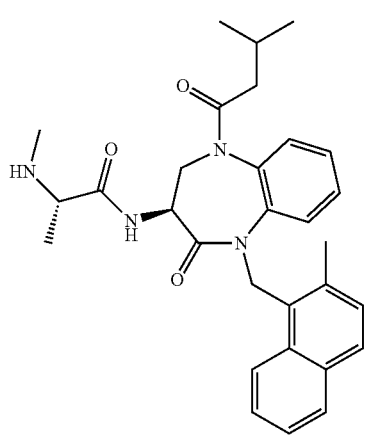 [SMILES: CN[C@@H](C)C(=O)N[C@H]1CN(C(=O)CC(C)C)c2ccccc2N(Cc2c(C)ccc3ccccc23)C1=O]

Step 1: In a similar manner to that described for Example 3, Step 1, except that after 30 min. an additional portion of isovaleryl chloride (0.012 mL 0.1 mmol) was added and the mixture stirred an additional 30 min., methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.052 g, 0.1 mmol) was converted to a material that was purified by silica gel chromatography to afford methyl-{(S)-1-[(S)-5-(3-methyl-butyl)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.048 g. white solid).

Step 2: In a similar manner to that described for Example 1, methyl-{(S)-1-[(S)-5-(3-methyl-butyl)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.045 g 0.075 mmol) was converted to the title compound (0.040 g, white solid). MS m/z 501 (MH$^+$).

Example 9

(S)-2-Methylamino-N—[(S)-1-(2-methyl-naphthalen-1-naphthalen-1 ylmethyl)-2-oxo-5-(pyridine-4-carbonyl)-2,3,4,5-tetrahydro-1H-benzo[b][1,4]diazepin-3-yl]-propionamide hydrochloride

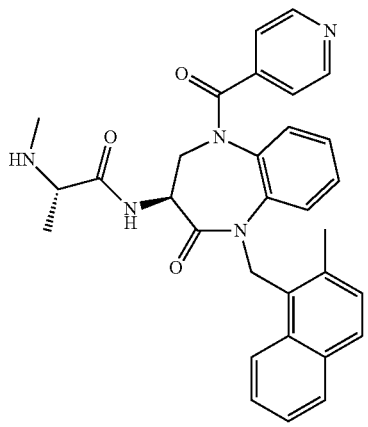 [SMILES: CN[C@@H](C)C(=O)N[C@H]1CN(C(=O)c2ccncc2)c2ccccc2N(Cc2c(C)ccc3ccccc23)C1=O]

le;3qStep 1: To a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.050 g 0.097 mmol), TEA (0.067 mL 0.48 mmol) and 2 mL of DCM was slowly added of isonicotinoyl chloride hydrochloride (0.052 mg 0.291 mmol). The reaction mixture was stirred at RT for 30 min. and diluted with EtOAc. The resulting mixture was washed with 1 M citric acid, brine, aq. Na$_2$CO$_3$, brine, dried over anhydr. Na$_2$SO$_4$, filtered and concentrated to give a material that was purified by silica gel chromatography to afford methyl-{(S)-1-[(S)-1-(2-methyl-naphthalen-1-ylmethyl)-2-oxo-5-(pyridine-4-carbonyl)-2,3,4,5-tetrahydro-1H-benzo[b][1,4]diazepin-3-ylcarbamoyl]-ethyl}-carbamic acid tert-butyl ester (0.041 g, white solid).

Step 2: In a similar manner to that described for Example 1, methyl-{(S)-1-[(S)-1-(2-methyl-naphthalen-1-ylmethyl)-2-oxo-5-(pyridine-4-carbonyl)-2,3,4,5-tetrahydro-1H-benzo[b][1,4]diazepin-3-ylcarbamoyl]-ethyl}-carbamic acid tert-butyl ester (0.038 g 0.061 mmol) was converted to the title compound (0.039 g, off-white solid). MS m/z 522 (MH$^+$).

Example 10

(S)—N—[(S)-5-[2-(2-methoxy-ethoxy)-acetyl]-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride

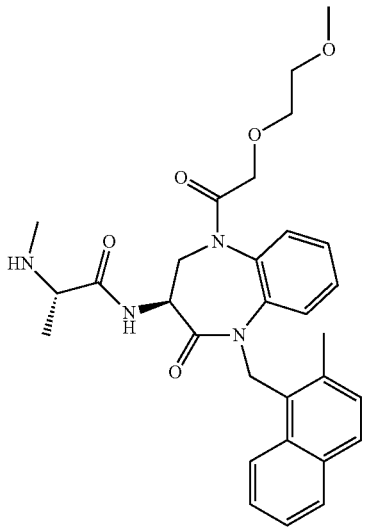 [SMILES: CN[C@@H](C)C(=O)N[C@H]1CN(C(=O)COCCOC)c2ccccc2N(Cc2c(C)ccc3ccccc23)C1=O]

In a similar manner to that described for Example 9, except the mixture was stirred overnight, methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.050 g 0.097 mmol) and (2-methoxy-ethoxy)-acetyl chloride (0.044 mg 0.30 mmol) were converted to the title compound (0.022 g, white solid). MS m/z 533 (MH$^+$).

Example 11

(S)—N—[(S)-5-(2-Carbamoyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride

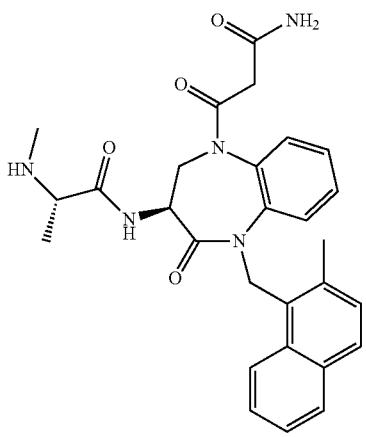 [SMILES: CN[C@@H](C)C(=O)N[C@H]1CN(C(=O)CC(N)=O)c2ccccc2N(Cc2c(C)ccc3ccccc23)C1=O]

Step 1: To a mixture of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.050 g 0.097 mmol), malonamic acid (0.012 g 0.116 mmol) and 2 mL of pyridine at 0° C. was slowly added POCl$_3$ (0.011 mL 0.116 mmol) and the mixture stirred at 0° C. for 1 h and an additional portion of malonamic acid (0.012 g 0.116 mmol) and POCl$_3$ (0.011 mL 0.116 mmol) were added. After 30 min. at 0° C. MeOH was added and the mixture concentrated to give a material that was purified by silica gel chromatography to afford {(S)-1-[(S)-5-(2-carbamoyl-acetyl)-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.0156 g, off-white solid).

Step 2: In a similar manner to that described for Example 1, {(S)-1-[(S)-5-(2-carbamoyl-acetyl)-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.015 g 0.025 mmol) was converted to the title compound (0.013 g, white solid). MS m/z 502 (MH$^+$).

Example 12

(S)-2-methylamino-N—{(S)-1(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-yl}-propionamide hydrochloride

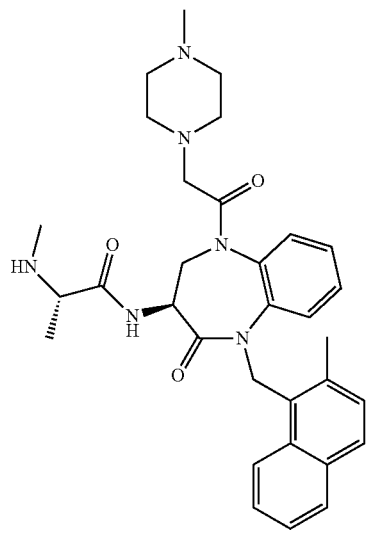 [SMILES: CN[C@@H](C)C(=O)N[C@H]1CN(C(=O)CN2CCN(C)CC2)c2ccccc2N(Cc2c(C)ccc3ccccc23)C1=O]

Step 1: To a solution of [(S)-1-(2-methyl-naphthalen-1-ylmethyl)-2-oxo-2,3,4,5-tetrahydro-1H-benzo[b][1,4]diazepin-3-yl]-carbamic acid tert-butyl ester (0.043 g 0.10 mmol) and (4-methyl-piperazin-1-yl)-acetic acid (0.0174 g 0.11 mmol) in 2 mL of pyridine at 0° C. was slowly added POCl₃ (0.012 mL 0.13 mmol). The reaction was stirred at 0° C. for 1 h and an additional portion of POCl₃ (0.0093 mL 1 mmol) was added and the mixture stirred at 0° C. for 1 h. Ice and H₂O were added, and the mixture extracted with EtOAc. The organic extracts were washed with aq. Na₂CO₃, brine, dried over anhydr. Na₂SO₄, filtered and concentrated to give a material that was purified by silica gel chromatography to afford of {(S)-1-(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-yl}-carbamic acid tert-butyl ester (0.022 g, white solid).

Step 2: In a similar manner to that described for Example 1, {(S)-1-(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-yl}-carbamic acid tert-butyl ester (0.020 g 0.035 mmol) was converted to (S)-3-amino-1-(2-methyl-naphthalen-1-ylmethyl)-5-[2-(4-methyl-piperazin-1-yl)-acetyl]-1,3,4,5-tetrahydro-benzo[b][1,4]diazepin-2-one hydrochloride (0.0165 g white solid) which was used without purification.

Step 3: In a similar manner to that described for Example 5, Step 3, except the mixture was stirred at RT 4 h, (S)-3-amino-1-(2-methyl-naphthalen-1-ylmethyl)-5-[2-(4-methyl-piperazin-1-yl)-acetyl]-1,3,4,5-tetrahydro-benzo[b][1,4]diazepin-2-one hydrochloride (0.0165 g 0.035 mmol) and BOC-N-Me-Ala-OH (0.0078 g 0.039 mmol) were reacted to give a material that was purified by silica gel chromatography to afford methyl-((S)-1-{(S)-1-(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-ylcarbamoyl}-ethyl)-carbamic acid tert-butyl ester (0.020 g, white solid).

Step 4: In a similar manner to that described for Example 1, methyl-((S)-1-{(S)-1-(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-ylcarbamoyl}-ethyl)-carbamic acid tert-butyl ester (0.020 g 0.030 mmol) was converted to the title compound (0.020 g, white solid). MS m/z 557 (MH⁺).

Example 13 a (S)—N—[(S)-5-{2-[2-(2-Methoxy-ethoxy)-ethoxy]-acetyl}-1-(2-methyl-naphthalen-1-ylmethyl)-2-oxo-2,3,4,5-tetrahydro-1H-benzo[b][1,4]diazepin-3-yl]-2-methylamino-propionamide hydrochloride

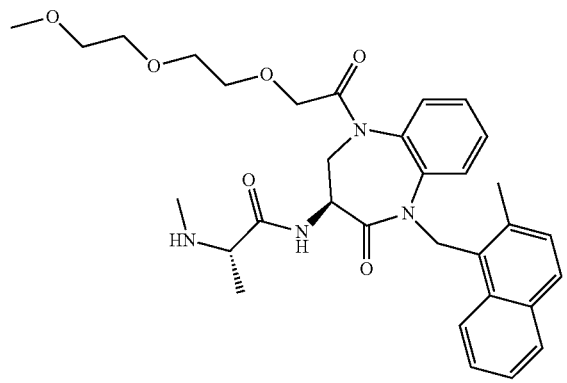 [SMILES: CN[C@@H](C)C(=O)N[C@H]1CN(C(=O)COCCOCCOC)c2ccccc2N(Cc2c(C)ccc3ccccc23)C1=O]

Step 1: To a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.052 g 0.1 mmol) and 2-[2-(2-methoxyethoxy)ethoxy]acetic acid (0.023 mL 0.15 mmol) in 2 mL of pyridine at 0° C. was slowly added POCl₃ (0.028 mL 0.30 mmol). After 1 h at 0° C., the mixture was diluted with H₂O and EtOAc. The organic layer was washed with 1 M citric acid, brine, aq. Na₂CO₃, brine, dried over anhydr. Na₂SO₄, filtered and concentrated to give a material that was purified by silica gel chromatography to afford {(S)-1-[(S)-5-{2-[2-(2-methoxy-ethoxy)-ethoxy]-acetyl}-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.040 g, white solid).

Step 2: In a similar manner to that described for Example 1, {(S)-1-[(S)-5-{2-[2-(2-methoxy-ethoxy)-ethoxy]-acetyl}-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.038 g 0.0561 mmol) was converted to the title compound (0.033 g, white solid). MS m/z 577 (MH⁺).

The compounds listed in Table 1 below were prepared in a similar manner to that described in Example 13a using the appropriate starting materials, where the conditions in step 1 can be varied so that the reaction time can range from 1 h to 24 h, the amount of acid can range from 1-6 equivalents, the temperature can range from 0° C. -RT, the amount of POCl₃ can range from 1.3-6 equivalents and the reaction time in step 2 can range from 1 h-24 h.

TABLE 1
| Example | Final Product | m/z (MH+) |
|---|---|---|
| 13 b | 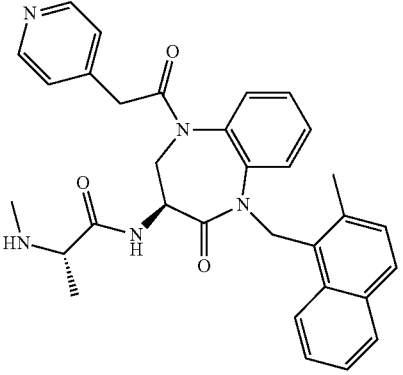 [SMILES: CN[C@@H](C)C(=O)N[C@H]1CN(C(=O)Cc2ccncc2)c2ccccc2N(Cc2c(C)ccc3ccccc23)C1=O] | 573 |
| 13 c | 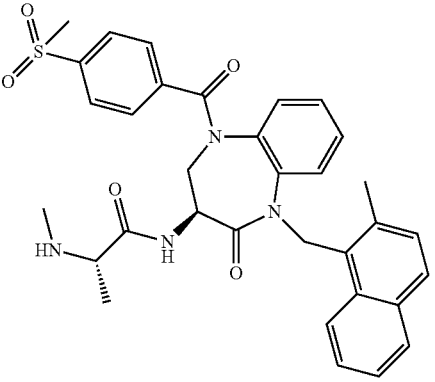 [SMILES: CN[C@@H](C)C(=O)N[C@H]1CN(C(=O)c2ccc(S(C)(=O)=O)cc2)c2ccccc2N(Cc2c(C)ccc3ccccc23)C1=O] | 599 |
| 13 d | 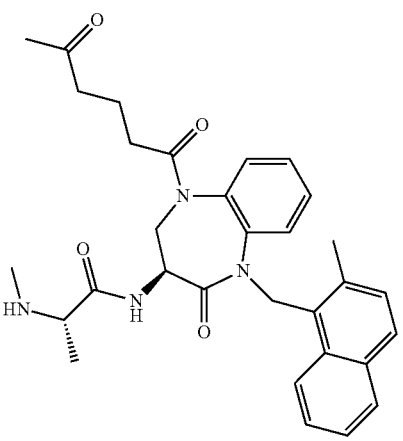 [SMILES: CN[C@@H](C)C(=O)N[C@H]1CN(C(=O)CCCC(C)=O)c2ccccc2N(Cc2c(C)ccc3ccccc23)C1=O] | 529 |

TABLE 1-continued

| Example | Final Product | m/z (MH+) |
|---|---|---|
| 13 e | | 559 |
| 13 f | | 563 |
| 13 g | | 611 |

TABLE 1-continued

| Example | Final Product | m/z (MH+) |
|---|---|---|
| 13 h | | 658 |
| 13 i | | 636 |
| 13 j | | 700 |
| 13 k | | 730 |

TABLE 1-continued

| Example | Final Product | m/z (MH+) |
|---|---|---|
| 13 l | | 658 |
| 13 m | | 661 |
| 13 n | | 627 |
| 13 o | | 672 |

TABLE 1-continued

| Example | Final Product | m/z (MH+) |
|---------|---------------|-----------|
| 13 p | | 641 |
| 13 q | | 688 |
| 13 r | | 784 |

Intermediates obtained in the course of preparing the products listed in Table 1 can be derivatized further to afford additional compounds as is exemplified infra in e.g., Example 60 et seq.

Example 14

(S)—N—[(S)-5-acetyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride

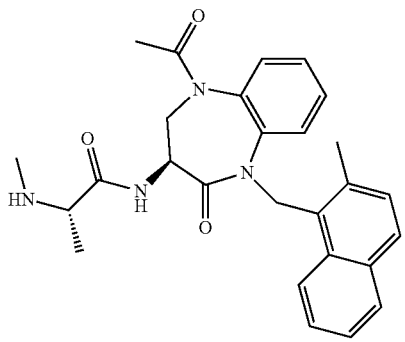 [SMILES: CN[C@@H](C)C(=O)N[C@H]1CN(C(C)=O)c2ccccc2N(Cc2c(C)ccc3ccccc23)C1=O]

Step 1: To a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.050 g 0.097 mmol), 0.078 mL (0.97 mmol) of pyridine and 2 mL of DCM was added AcCl (0.021 mL 0.291 mmol) in 0.5 mL DCM. The mixture was stirred at 0° C. for 1 h, diluted with H₂O and EtOAc and extracted with EtOAc. The combined organic extracts were washed with 1 M citric acid, brine, Na₂CO₃, brine, dried over Na₂SO₄, filtered and concentrated to give a material that was purified by silica gel chromatography to afford {(S)-1-[(S)-5-acetyl-1-(2-methyl-naphthalen-1 ylmethyl)-2-oxo-2,3,4,5-tetrahydro-1H-benzo[b][1,4]diazepin-3-ylcarbamoyl]-ethyl}-methyl-carbamic acid tert-butyl ester (0.040 g, white solid).

Step 2: In a similar manner to that described for Example 1, {(S)-1-[(S)-5-acetyl-1-(2-methyl-naphthalen-1 ylmethyl)-2-oxo-2,3,4,5-tetrahydro-1H-benzo[b][1,4]diazepin-3-ylcarbamoyl]-ethyl}-methyl-carbamic acid tert-butyl ester (0.038 g 0.068 mmol) was converted to the title compound (0.039 g, off-white solid). MS m/z 459 (MH⁺).

Example 15

5-[(S)-3-((S)-2-Methylamino-propionylamino)-5-(2-methyl-naphthalen-1-ylmethyl)-4-oxo-2,3,4,5-tetrahydro-benzo[b][1,4]diazepin-1-yl]-5-oxo-pentanoic acid hydrochloride

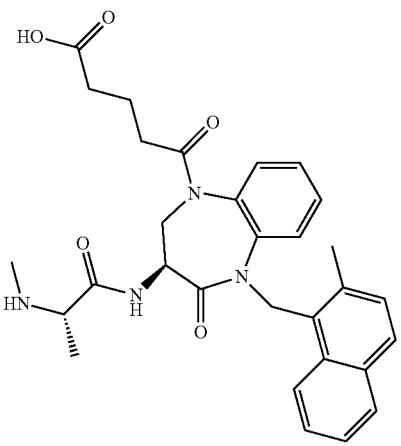 [SMILES: CN[C@@H](C)C(=O)N[C@H]1CN(C(=O)CCCC(=O)O)c2ccccc2N(Cc2c(C)ccc3ccccc23)C1=O]

Step 1: To a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.060 g 0.116 mmol) and pyridine (0.094 mL 1.16 mmol) in 2 mL of DCM at 0° C. was slowly added glutaric anhydride (0.040 g 0.348 mmol) in 0.5 mL of DCM and the mixture was heated at 50° C. overnight. The mixture was diluted with H₂O and EtOAc, extracted with EtOAc and the extracts washed with 1 M citric acid, brine, sat. Na₂CO₃, brine, dried over anhydr. Na₂SO₄, filtered and concentrated to give a material that was purified by silica gel chromatography to afford 5-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepin-1-yl]-5-oxo-pentanoic acid (0.046 g, white solid).

Step 2: In a similar manner to that described for Example 1, 5-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepin-1-yl]-5-oxo-pentanoic acid (0.043 g 0.068 mmol) was converted to the title compound (0.051 g, off-white solid). MS m/z 531 (MH⁺).

Example 16

4-[(S)-3-((S)-2-Methylamino-propionylamino)-5-(2-methyl-naphthalen-1-ylmethyl)-4-oxo-2,3,4,5-tetrahydro-benzo[b][1,4]diazepin-1-yl]-4-oxo-butyric acid hydrochloride

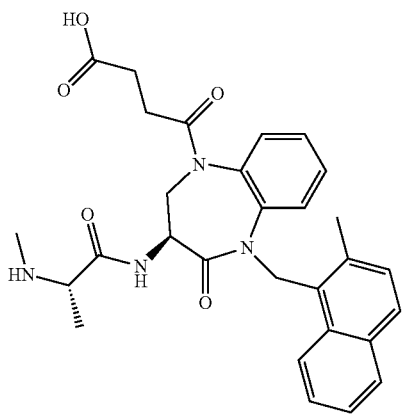 [SMILES: CN[C@@H](C)C(=O)N[C@H]1CN(C(=O)CCC(=O)O)c2ccccc2N(Cc2c(C)ccc3ccccc23)C1=O]

Step 1: To a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.060 g 0.116 mmol), mono-methyl succinate (0.046 g 0.348 mmol) and 2.4 mL of pyridine at 0° C. was slowly added POCl₃ (0.025 mL 0.267 mmol). The reaction mixture was stirred at RT for 4 h, the solvent was removed, and ice and H₂O were added. The aq. mixture was extracted with EtOAc and the extracts were washed with 1 M citric acid, brine, sat. Na₂CO₃, brine, dried over anhydr. Na₂SO₄, filtered and concentrated to give a material that was purified by silica gel chromatography to afford 4-[(S)-3-[(S)-2-(tert-butoxycarbonyl-methyl-amino)-propionylamino]-5-(2-methyl-naphthalen-ylmethyl)-4-oxo-2,3,4,5-tetrahydro-benzo[b][1,4]diazepine-1-yl]-4-oxo-butyric acid methyl ester (0.034 g, white solid).

Step 2: To a solution of 4-[(S)-3-[(S)-2-(tert-butoxycarbonyl-methyl-amino)-propionylamino]-5-(2-methyl-naphthalen-ylmethyl)-4-oxo-2,3,4,5-tetrahydro-benzo[b][1,4]diazepine-1-yl]-4-oxo-butyric acid methyl ester (0.032 g 0.051 mmol) in 1.0 mL of THF and 0.2 mL of H₂O was slowly added of 1 M LiOH (0.122 mL 0.101 mmol). The reaction mixture was stirred at RT overnight, 1 M citric acid was added and the resulting mixture was extracted with EtOAc. The combined extracts were washed with 1 M citric acid, brine, H₂O dried over anhydr. Na₂SO₄, filtered and concentrated to give 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-yl]-4-oxo-butyric acid (0.035 g, colorless oil) which was used without purification.

Step 3: In a similar manner to that described for Example 1, 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-yl]-4-oxo-butyric acid (0.035 g 0.0568 mmol) was converted to the title compound (0.031 g, white solid). MS m/z 517 (MH⁺).

Example 17

(S)-3-((S)-2-Methylamino-propionylamino)-5-(2-methyl-naphthalen-1-ylmethyl)-4-oxo-2,3,4,5-tetrahydro-benzo[b][1,4]diazepine-1-carboxylic acid methylamide hydrochloride

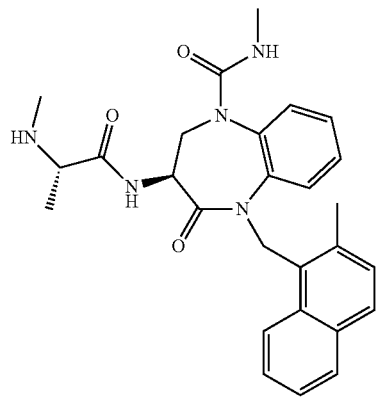 [SMILES: CNC(=O)N1C[C@H](NC(=O)[C@H](C)NC)C(=O)N(Cc2c(C)ccc3ccccc23)c2ccccc21]

Step 1: To a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.052 g 0.1 mmol) in 2 mL of DCM was added (0.009 mL 0.15 mmol) of methyl isocyanate. After 3 h, additional portions of methyl isocyanate (0.009 mL 0.15 mmol) and TEA (0.070 mL 0.50 mmol) were added and the mixture stirred at RT overnight. An additional portion of methyl isocyanate (0.018 mL 0.3 mmol) was added and the reaction was stirred at RT overnight, the solvent removed and the residue purified by silica gel chromatography to afford methyl-{(S)-1-[(S)-5-methylcarbamoyl-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.042 g, white solid).

Step 2: In a similar manner to that described for Example 1, methyl-{(S)-1-[(S)-5-methylcarbamoyl-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.040 g 0.07 mmol) was converted to the title compound (0.035 g, white solid). MS m/z 474 (MH⁺).

Example 18

(S)—N—[(S)-5-Methanesulfonylmethanesulfonyl-1-(2-methyl-naphthalen-1-ylmethyl)-2-oxo-2,3,4,5-tetrahydro-1H-benzo[b][1,4]diazepin-3-yl]-2-methylamino-propionamide trifluoroacetate

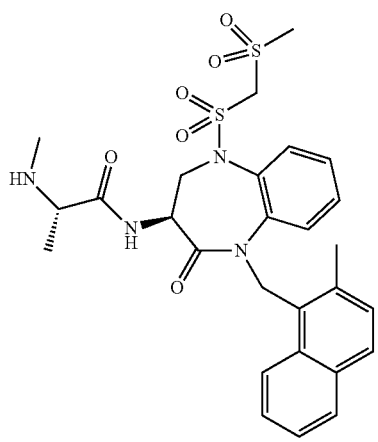 [SMILES: CN[C@@H](C)C(=O)N[C@H]1CN(S(=O)(=O)CS(C)(=O)=O)c2ccccc2N(Cc2c(C)ccc3ccccc23)C1=O]

Step 1: To a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.052 g 0.10 mmol) in 2 mL of DCM was added of methanesulfonic anhydride (0.035 g 0.20 mmol) in 0.5 mL of DCM then TEA (0.070 mL 0.5 mmol) was added dropwise. After 20 min. at RT additional portions of methanesulfonic anhydride (0.035 g 0.20 mmol) in 0.5 mL of DCM and TEA (0.07 mL 0.5 mmol) were added. After 20 min. an additional portion of methanesulfonic anhydride (0.070 g 0.4 mmol) was added. After 20 min. the mixture was diluted with EtOAc and 1 M citric acid. The organic layer was washed with 1 M citric acid, brine, aq. Na$_2$CO$_3$, brine, dried over anhydr. Na$_2$SO$_4$, filtered and concentrated to give a material that was purified by silica gel chromatography to afford {(S)-1-[(S)-5-methanesulfonylmethanesulfonyl-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.025 g, white solid).

Step 2: A solution of {(S)-1-[(S)-5-methanesulfonylmethanesulfonyl-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.045 g 0.075 mmol) in 6 mL of 4.0 M HCl in 1,4-dioxane was stirred at RT overnight. The solvent was removed and the residue was purified by reverse phase HPLC to afford the title compound (0.027 g, white solid). MS m/z 573 (MH$^+$).

Example 19

(S)—N—[(S)-5-methanesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride

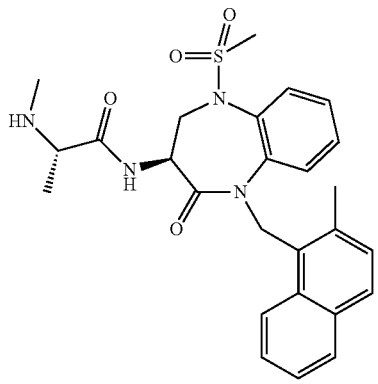 [SMILES: CN[C@@H](C)C(=O)N[C@H]1CN(S(C)(=O)=O)c2ccccc2N(Cc2c(C)ccc3ccccc23)C1=O]

Step 1: To a solution of methyl-{(S)-1-(2-methyl-naphthalen-1-ylmethyl)-2-oxo-2,3,4,5-tetrahydro-1H-benzo[b][1,4]diazepin-3-ylcarbamoyl}-ethyl}-carbamic acid tert-butyl ester (0.052 g 0.10 mmol) and pyridine (0.081 mL 1 mmol) in 2 mL of DCM was slowly added a solution of methanesulfonic anhydride (0.087 g 0.5 mmol) in 1 mL of DCM. The reaction mixture was stirred at RT for 1 h, diluted with H$_2$O and extracted with EtOAc. The extracts were washed with 1 M citric acid, brine, sat. Na$_2$CO$_3$, brine, dried over anhydr. Na$_2$SO$_4$, filtered and concentrated to give a material that was purified by silica gel chromatography to afford {(S)-1-[(S)-5-methanesulfonyl-1-(2-methyl-naphthanlen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.053 g, yellow solid).

Step 2: In a similar manner to that described for Example 1, {(S)-1-[(S)-5-methanesulfonyl-1-(2-methyl-naphthanlen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.050 g 0.084 mmol) was converted to the title compound (0.045 g, white solid). MS m/z 495 (MH$^+$).

Example 20

((S)-3-((S)-2-Methylamino-propionylamino)-5-(2-methyl-naphthalen-1-ylmethyl)-4-oxo-2,3,4,5-tetrahydro-benzo[b][1,4]diazepine-1-carboxylic acid methyl ester hydrochloride

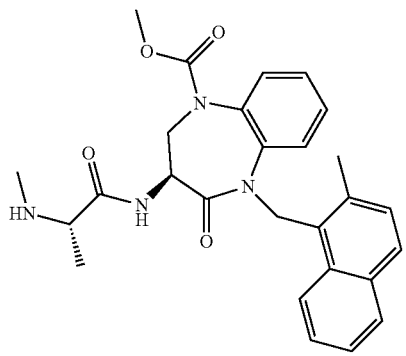 [SMILES: CN[C@@H](C)C(=O)N[C@H]1CN(C(=O)OC)c2ccccc2N(Cc2c(C)ccc3ccccc23)C1=O]

Step 1: In a similar manner to that described for Example 14, except the mixture was stirred 30 min. at 0° C., methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (0.050 g 0.097 mmol) and methyl chloroformate (0.022 mL (0.291 mmol) were converted to the title compound (0.050 g, white solid). MS m/z 475 (MH+).

Example 21

(S)—N—((S)-1-benzyl-5-(3-methylbutanoyl)-2-oxo-2,3,4,5-tetrahydro-1H-benzo[b][1,4]diazepin-3-yl)-2-(methylamino)propanamide hydrochloride

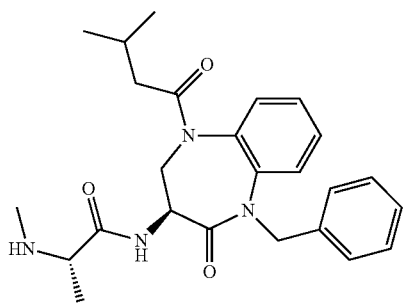 [SMILES: CN[C@@H](C)C(=O)N[C@H]1CN(C(=O)CC(C)C)c2ccccc2N(Cc2ccccc2)C1=O]

Step 1: A mixture of methyl-{(S)-1-[(S)-1-(3-methyl-butyryl)-4-oxo-2,3,4,5-tetrahydro-1H-benzo[b][1,4]diazepin-3-ylcarbamoyl]-ethyl}-carbamic acid tert-butyl ester (0.0447 g 0.1 mmol), benzyl bromide (0.0178 mL 0.150 mmol) and Cs$_2$CO$_3$ (0.0487 g 0.150 mmol) in 2 mL of DMF was heated in a microwave at 100° C. for 30 min., poured into H$_2$O and extracted with EtOAc. The organic extracts were washed with sat. Na$_2$CO$_3$, brine, dried over anhydr. Na$_2$SO$_4$, filtered and concentrated to give a material that was purified by silica gel chromatography to afford {(S)-1 [(S)-1-benzyl-5-(3-methyl-butyryl)-2-oxo-2,3,4,5-tetrahydro-1H-benzo[b][1,4]diazepin-3-ylcarbamoyl]-ethyl}-methyl-carbamic acid tert-butyl ester (0.051 g, white solid).

Step 2: In a similar manner to that described for Example 1, {(S)-1[(S)-1-benzyl-5(3-methyl-butyryl)-2-oxo-2,3,4,5-tetrahydro-1H-benzo[b][1,4]diazepin-3-ylcarbamoyl]-ethyl}-methyl-carbamic acid tert-butyl ester (0.050 g 0.093 mmol) was converted to the title compound (0.043 g, white solid). MS m/z 437 (MH+).

Example 22

(S)—N—[(S)-1-(2-Methoxy-benzyl)-5-(3-methyl-butyryl)-2-oxo-2,3,4,5-tetrahydro-1H-benzo[b][1,4]diazepin-3-yl]-2-methylamino-propionamide hydrochloride

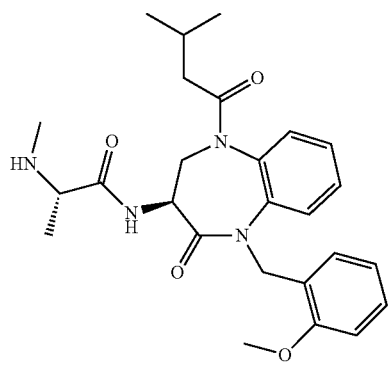 [SMILES: CN[C@@H](C)C(=O)N[C@H]1CN(C(=O)CC(C)C)c2ccccc2N(Cc2ccccc2OC)C1=O]

Step 1: A mixture of methyl-{(S)-1-[(S)-1-(3-methyl-butyryl)-4-oxo-2,3,4,5-tetrahydro-1H-benzo[b][1,4]diazepin-3-ylcarbamoyl]-ethyl}-carbamic acid tert-butyl ester (0.0447 g 0.1 mmol), 2-methoxybenzyl chloride (0.0235 g 0.150 mmol), Cs$_2$CO$_3$ (0.0489 g (0.150 mmol) and NaI (0.0225 g 0.150 mmol) in 2 mL of DMF was heated in microwave at 100° C. for 50 min., poured into H$_2$O and extracted with EtOAc. The organic extracts were washed with sat. Na$_2$CO$_3$, brine, dried over anhydr. Na$_2$SO$_4$, filtered and concentrated to give a material that was purified by silica gel chromatography to afford {(S)-1-[(S)-1-(2-methoxy-benzyl)-5-(3-methyl-butyryl)-2-oxo-2,3,4,5-tetrahydro-1H-benzo[b][1,4]diazepin-3-ylcarbamoyl]-ethyl}-methyl-carbamic acid tert-butyl ester (0.031 g, white solid).

Step 2: In a similar manner to that described for Example 1, {(S)-1[(S)-1-(2-methoxy-benzyl)-5-(3-methyl-butyryl)-2-oxo-2,3,4,5-tetrahydro-1H-benzo[b][1,4]diazepin-3-ylcarbamoyl]-ethyl}-methyl-carbamic acid tert-butyl ester (0.025 g 0.0441 mmol) was converted to the title compound (0.022 g, white solid). MS m/z 430 (MH+).

Example 23

(S)-2-Methylamino-N—[(S)-5-(3-methyl-butyryl)-2-oxo-1-phenethyl-2,3,4,5-tetrahydro-1H-benzo[b][1,4]diazepin-3-yl]-propionamide hydrochloride

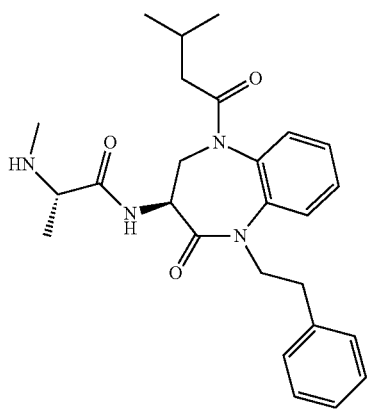 [SMILES: CN[C@@H](C)C(=O)N[C@H]1CN(C(=O)CC(C)C)c2ccccc2N(CCc2ccccc2)C1=O]

In a similar manner to that described for Example 22, except in Step 1 NaI was omitted and the reaction was heated for 30 min., methyl-{(S)-1-[(S)-1-(3-methyl-butyryl)-4-oxo-2,3,4,5-tetrahydro-1H-benzo[b][1,4]diazepin-3-ylcarbamoyl]-ethyl}-carbamic acid tert-butyl ester (0.050 g 0.112 mmol), and (2-bromoethyl)benzene (0.023 mL 0.168 mmol) were converted to the title compound (0.041 g, light yellow solid). MS m/z 451 (MH$^+$).

Example 24

(S)—N—[(S)-1-(2-Methoxy-naphthalen-1-ylmethyl)-5-(3-methyl-butyryl)-2-oxo-2,3,4,5-tetrahydro-1H-benzo[b][1,4]diazepin-3-yl]-2-methylamino-propionamide hydrochloride

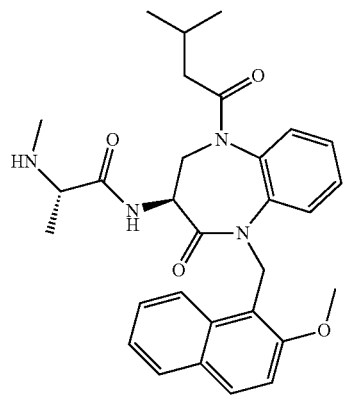 [SMILES: CN[C@@H](C)C(=O)N[C@H]1CN(C(=O)CC(C)C)c2ccccc2N(Cc2c(OC)ccc3ccccc23)C1=O]

In a similar manner to that described for Example 22, except in Step 1 NaI was omitted and the reaction was heated for 30 min., methyl-{(S)-1-[(S)-1-(3-methyl-butyryl)-4-oxo-2,3,4,5-tetrahydro-1H-benzo[b][1,4]diazepin-3-ylcarbamoyl]-ethyl}-carbamic acid tert-butyl ester (0.050 g 0.112 mmol) and 1-(bromomethyl)-2-methoxynaphthalene (0.0844 g (0.336 mmol) were converted to the title compound (0.050 g, off-white solid). MS m/z 517 (MH$^+$).

Example 25

(S)-2-Methylamino-N—[(S)-5-(3-methyl-butyryl)-1-(1-naphthalen-1-yl-ethyl)-2-oxo-2,3,4,5-tetrahydro-1H-benzo[b][1,4]diazepin-3-yl]-propionamide hydrochloride, mixture of diastereomers

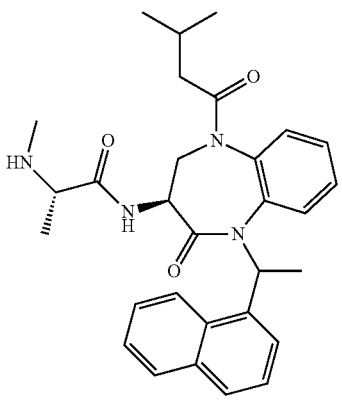 [SMILES: CN[C@@H](C)C(=O)N[C@H]1CN(C(=O)CC(C)C)c2ccccc2N(C(C)c2cccc3ccccc23)C1=O]

In a similar manner to that described for Example 22, except in Step 1 NaI was omitted and the reaction was heated for 1 h and in Step 2 the reaction was stirred for 3 h, methyl-{(S)-1-[(S)-1-(3-methyl-butyryl)-4-oxo-2,3,4,5-tetrahydro-1H-benzo[b][1,4]diazepin-3-ylcarbamoyl]-ethyl}-carbamic acid tert-butyl ester (0.050 g (0.112 mmol) an 1-(1-bromoethyl)naphthalene (0.079 g (0.336 mmol) were converted to the title compound (0.019 g, white solid). MS m/z 403 (MH$^+$).

Example 26

(S)—N—[(S)-1-(6-Bromo-2-methoxy-naphthalen-1-ylmethyl)-5-(3-methyl-butyryl)-2-oxo-2,3,4,5-tetrahydro-1H-benzo[b][1,4]diazepin-3-yl]-2-methylamino-propionamide hydrochloride

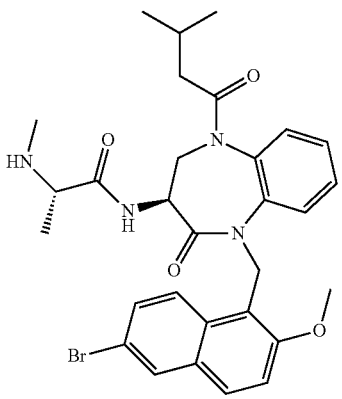 [SMILES: CN[C@@H](C)C(=O)N[C@H]1CN(C(=O)CC(C)C)c2ccccc2N(Cc2c(OC)ccc3cc(Br)ccc23)C1=O]

In a similar manner to that described for Example 22, except in Step 1 the reaction was heated for 30 min., methyl-{(S)-1-[(S)-1-(3-methyl-butyryl)-4-oxo-2,3,4,5-tetrahydro-1H-benzo[b][1,4]diazepin-3-ylcarbamoyl]-ethyl}-carbamic acid tert-butyl ester (0.050 g 0.112 mmol) and 6-bromo-1-(chloromethyl)-2-methoxynaphthalene (0.048 g 0.168 mmol) were converted to the title compound (0.060 g, off-white solid). MS m/z 596 (MH+).

Example 27

(S)—N—((S)-1-((6-bromo-2-methoxynaphthalen-1-yl)methyl)-2-oxo-5-(5-oxohexanoyl)-2,3,4,5-tetrahydro-1H-benzo[b][1,4]diazepin-3-yl)-2-(methylamino)propanamide hydrochloride

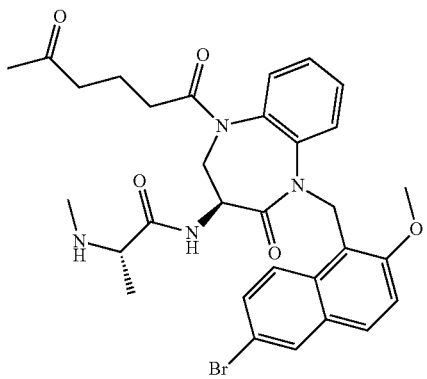 [SMILES: CN[C@@H](C)C(=O)N[C@H]1CN(C(=O)CCCC(C)=O)c2ccccc2N(Cc2c(OC)ccc3cc(Br)ccc23)C1=O]

Step 1: To a solution of methyl-[(S)-1-((S)-2-oxo-2,3,4,5-tetrahydro-1H-benzo[b][1,4]diazepin-3-ylcarbamoyl)-ethyl]-carbamic acid tert-butyl ester (0.500 g 1.38 mmol) and 4-acetylbutyric acid (0.494 mL 4.14 mmol) in 20 mL of pyridine at 0° C. was slowly added POCl₃ (0.167 mL 1.79 mmol). The mixture was stirred at RT overnight, the solvent removed and ice and H₂O was added. The resulting mixture was extracted with EtOAc, the organic extracts were washed with 1 M citric acid, brine, sat. Na₂CO₃, brine, dried over anhydr. Na₂SO₄, filtered and concentrated to give a material that was purified by silica gel chromatography to afford methyl-{(S)-1-[(S)-4-oxo-1-(5-oxo-hexanoyl)-2,3,4,5-tetrahydro-1H-benzo[b][1,4]diazepin-3-ylcarbamoyl]-ethyl}-carbamic acid tert-butyl ester (0.348 g, white solid).

Step 2: A mixture of methyl-{(S)-1-[(S)-4-oxo-1-(5-oxohexanoyl)-2,3,4,5-tetrahydro-1H-benzo[b][1,4]diazepin-3-ylcarbamoyl]-ethyl}-carbamic acid tert-butyl ester (0.0949 g 0.2 mmol), 6-bromo-1-(chloromethyl)-2-methoxynaphthalene (0.0857 g, 0.300 mmol), Cs₂CO₃ (0.0977 g 0.300 mmol) and NaI (0.045 g 0.300 mmol) in 2 mL of DMF was stirred at RT overnight. The mixture was poured into H₂O and extracted with EtOAc, the extracts washed with sat. Na₂CO₃, brine, dried over anhydr. Na₂SO₄, filtered and concentrated to give a material that was purified by silica gel chromatography to afford {(S)-1-[(S)-1-(6-bromo-2-methoxy-naphthalen-1-ylmethyl)-2-oxo-5-(5-oxohexanoyl)-2,3,4,5-tetrahydro-1H-benzo[b][1,4]diazepin-3-ylcarbamoyl]-ethyl}-methyl-carbamic acid tert-butyl ester (0.130 g, white solid).

Step 3: In a similar manner to that described for Example 1, {(S)-1-[(S)-1-(6-bromo-2-methoxy-naphthalen-1-ylmethyl)-2-oxo-5-(5-oxo-hexanoyl)-2,3,4,5-tetrahydro-1H-benzo[b][1,4]diazepin-3-ylcarbamoyl]-ethyl}-methyl-carbamic acid tert-butyl ester (0.030 g 0.0415 mmol) was converted to the title compound (0.028 g, white solid). MS m/z 624 (MH+).

Example 28

4-[(S)-5-(6-Bromo-2-methoxy-naphthalen-1-ylmethyl)-3-((S)-2-methylamino-propionylamino)-4-oxo-2,3,4,5-tetrahydro-benzo[b][1,4]diazepine-1-carbonyl]-benzoic acid methyl ester hydrochloride

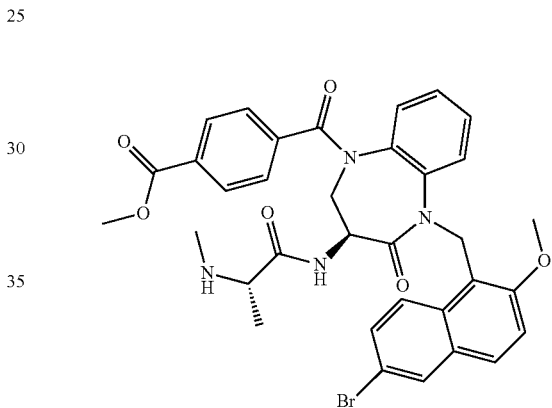

Step 1: To a solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.200 g 0.327 mmol) and mono-methyl terephthalate (0.0884 g 0.491 mmol) in 10 mL of pyridine at 0° C. was slowly added POCl₃ (0.064 mL 0.687 mmol). After 4 h at 0° C., 1 M citric acid was slowly added and the mixture extracted with EtOAc, the extracts washed with 1 M citric acid, brine, sat. Na₂CO₃, brine, dried over anhydr. Na₂SO₄, filtered and concentrated to give a material that was purified by silica gel chromatography to afford 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepin-1-carbonyl}-benzoic acid methyl ester (0.135 g, white solid).

Step 2: In a similar manner to that described for Example 1, 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepin-1-carbonyl}-benzoic acid methyl ester (0.011 g 0.0142 mmol) was converted to the title compound (0.012 g, white solid). MS m/z 674 (MH+).

Example 29

4-[(S)-5-(6-Bromo-2-methoxy-naphthalen-1-ylmethyl)-3-((S)-2-methylamino-propionylamino)-4-oxo-2,3,4,5-tetrahydro-benzo[b][1,4]diazepine-1-carbonyl]-benzoic acid hydrochloride

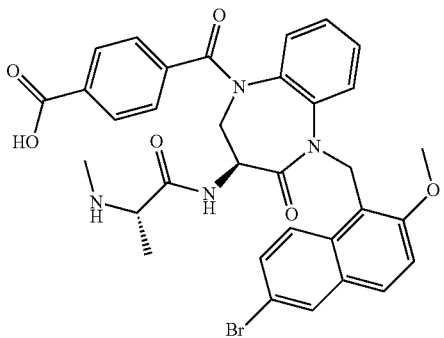 [SMILES: CN[C@@H](C)C(=O)N[C@H]1CN(C(=O)c2ccc(C(=O)O)cc2)c2ccccc2N(Cc2c(OC)ccc3cc(Br)ccc23)C1=O]

Step 1: To a solution of 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepin-1-carbonyl}-benzoic acid methyl ester (0.120 g 0.155 mmol) in 6 mL of THF and 0.6 mL of H₂O was added 1 M LiOH (0.371 mL 0.310 mmol). The mixture was stirred at RT overnight and 1 M citric acid was added, the mixture extracted with EtOAc, the extracts washed with 1 M citric acid, brine, dried over anhydr. Na₂SO₄, filtered and concentrated to give 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepin-1-carbonyl}-benzoic acid (0.120 g, white solid) which was used without purification.

Step 2: In a similar manner to that described for Example 1, 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepin-1-carbonyl}-benzoic acid (0.030 g 0.0388 mmol) was converted to the title compound (0.030 g, white solid). MS m/z 660 (MH⁺).

Example 30

4-[(S)-5-(6-Bromo-2-methoxy-naphthalen-1-ylmethyl)-3-((S)-2-methylamino-propionylamino)-4-oxo-2,3,4,5-tetrahydro-benzo[b][1,4]diazepine-1-carbonyl]-benzamide hydrochloride

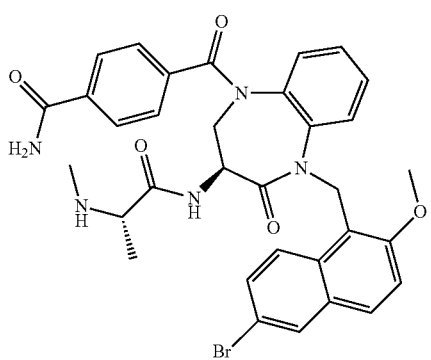 [SMILES: CN[C@@H](C)C(=O)N[C@H]1CN(C(=O)c2ccc(C(N)=O)cc2)c2ccccc2N(Cc2c(OC)ccc3cc(Br)ccc23)C1=O]

Step 1: To a mixture of 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepin-1-carbonyl}-benzoic acid (0.045 g 0.0592 mmol), NH₄Cl (0.00634 g 0.118 mmol) and DIEA (0.0414 mL 0.237 mmol) in 2 mL DMF was slowly added HBPyU (0.0281 g 0.0652 mmol). After 1 h, H₂O was added to the mixture at 0° C., and the resulting mixture extracted with DCM. The extracts were washed with sat. Na₂CO₃, brine, dried over anhydr. Na₂SO₄, filtered and concentrated to give a material that was purified by silica gel chromatography to afford {(S)-1-[(S)-1-(6-bromo-2-methoxy-naphthalen-1-ylmethyl)-5-(4-carbamoyl-benzoyl)-2-oxo-2,3,4,5-tetrahydro-1H-benzo[b][1,4]diazepin-3-ylcarbamoyl]-ethyl}-methyl-carbamic acid tert-butyl ester (0.032 g, white solid).

Step 2: In a similar manner to that described for Example 1 except the mixture was stirred for 4 h, {(S)-1-[(S)-1-(6-bromo-2-methoxy-naphthalen-1-ylmethyl)-5-(4-carbamoyl-benzoyl)-2-oxo-2,3,4,5-tetrahydro-1H-benzo[b][1,4]diazepin-3-ylcarbamoyl]-ethyl}-methyl-carbamic acid tert-butyl ester (0.030 g 0.0395 mmol) was converted to the title compound (0.031 g, off-white solid). MS m/z 659 (MH⁺).

Example 31

4-[(S)-5-(6-Bromo-2-methoxy-naphthalen-1-ylmethyl)-3-((S)-2-methylamino-propionylamino)-4-oxo-2,3,4,5-tetrahydro-benzo[b][1,4]diazepine-1-carbonyl]-N-cyclohexylmethyl-benzamide hydrochloride

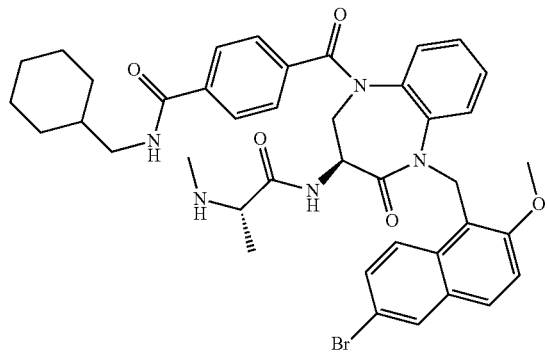 [SMILES: CN[C@@H](C)C(=O)N[C@H]1CN(C(=O)c2ccc(C(=O)NCC3CCCCC3)cc2)c2ccccc2N(Cc2c(OC)ccc3cc(Br)ccc23)C1=O]

Step 1: To a solution of 4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepin-1-carbonyl}-benzoic acid (0.045 g 0.0592 mmol), cyclohexanemethylamine (0.0154 mL 0.118 mmol) and DIEA (0.0414 mL 0.237 mmol) in 2 mL of DMF at 0° C. was added HBPyU (0.017 g 0.0592 mmol). After 1 h at RT, the mixture was cooled to 0° C. and H₂O was added to the mixture which was then extracted with DCM. The extracts were washed with aq. Na₂CO₃, brine, dried over anhydr. Na₂SO₄, filtered and concentrated to give a material that was purified by silica gel chromatography to afford ((S)-1-{(S)-1-(6-bromo-2-methoxy-naphthalen-1-ylmethyl)-5-[4-(cyclohexylmethyl-carbamoyl)-benzoyl]-2-oxo-2,3,4,5-tetrahydro-1H-benzo[b][1,4]diazepin-3-ylcarbamoyl]-ethyl}-methyl-carbamic acid tert-butyl ester (0.048 g, colorless oil).

Step 2: In a similar manner to that described for Example 1, except the mixture was stirred for 3 h, ((S)-1-{(S)-1-(6-bromo-2-methoxy-naphthalen-1-ylmethyl)-5-[4-(cyclohexylmethyl-carbamoyl)-benzoy]-2-oxo-2,3,4,5-tetrahydro-1H-benzo[b][1,4]diazepin-3-ylcarbamoyl]-ethyl}-methyl-carbamic acid tert-butyl ester (0.048 g 0.0562 mmol) was converted to the title compound (0.044 g, white solid). MS m/z 755 (MH$^+$).

Example 32

(S)—N—{(S)-1-(6-Bromo-2-methoxy-naphthalen-1-ylmethyl)-2-oxo-5-[4-(2,2,2-trifluoro-1-hydroxy-ethyl)-benzoyl]-2,3,4,5-tetrahydro-1H-benzo[b][1,4]diazepin-3-yl}-2-methylamino-propionamide hydrochloride, mixture of diastereomers

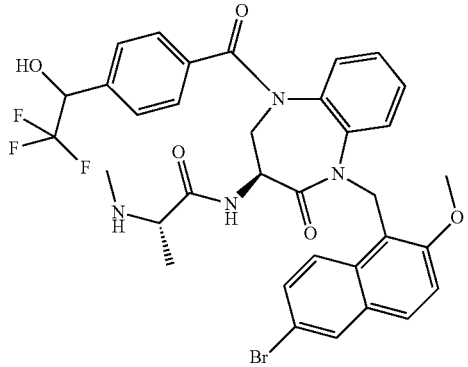 [SMILES: CN[C@@H](C)C(=O)N[C@H]1CN(C(=O)c2ccc(C(O)C(F)(F)F)cc2)c2ccccc2N(Cc2c(OC)ccc3cc(Br)ccc23)C1=O]

Step 1: To a solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.080 g 0.131 mmol) and 4-(trifluoroacetyl)benzoic acid (0.043 g 0.196 mmol) in 3 mL of pyridine at 0° C. was slowly added of POCl$_3$ (0.0244 mL 0.262 mmol) and the mixture was stirred at RT overnight. Ice and H$_2$O were added and the resulting mixture extracted with EtOAc. The extracts were washed with 1 M citric acid, brine, sat. Na$_2$CO$_3$, brine, dried over anhydr. Na$_2$SO$_4$, filtered and concentrated to give a material that was purified by silica gel chromatography to afford ((S)-1-{(S)-1-(6-bromo-2-methoxy-naphthalen-1-ylmethyl)-2-oxo-5-[4-(2,2,2-trifluoro-acetyl)-benzoyl]-2,3,4,5-tetrahydro-1H-benzo[b][1,4]diazepin-3-ylcarbamoyl}-ethyl)-methyl-carbamic acid tert-butyl ester (0.052 g, white solid).

Step 2: To a solution of ((S)-1-{(S)-1-(6-bromo-2-methoxy-naphthalen-1-ylmethyl)-2-oxo-5-[4-(2,2,2-trifluoro-acetyl)-benzoyl]-2,3,4,5-tetrahydro-1H-benzo[b][1,4]diazepin-3-ylcarbamoyl}-ethyl)-methyl-carbamic acid tert-butyl ester (0.050 g 0.0616 mmol) in 2 mL of THF was added NaBH$_4$ (0.005 g 0.123 mmol). The reaction mixture was stirred at RT for 72 h then H$_2$O was added and the mixture extracted with DCM. The organic extracts were washed with H$_2$O, brine, dried over anhydr. Na$_2$SO$_4$, filtered and concentrated to give ((S)-1-{(S)-1-(6-bromo-2-methoxy-naphthalen-1-ylmethyl)-2-oxo-5-[4-(2,2,2-trifluoro-1-hydroxy-ethyl)-benzoyl]-2,3,4,5-tetrahydro-1H-benzo[b][1,4]diazepin-3-ylcarbamoyl}-ethyl)-methyl-carbamic acid tert-butyl ester (0.041 g, white solid) which was used without purification.

Step 3: In a similar manner to that described for Example 1, ((S)-1-{(S)-1-(6-bromo-2-methoxy-naphthalen-1-ylmethyl)-2-oxo-5-[4-(2,2,2-trifluoro-1-hydroxy-ethyl)-benzoyl]-2,3,4,5-tetrahydro-1H-benzo[b][1,4]diazepin-3-ylcarbamoyl}-ethyl)-methyl-carbamic acid tert-butyl ester (0.039 g 0.0479 mmol) was converted to the title compound (0.041 g, white solid). MS m/z 714 (MH$^+$).

Example 33

(S)—N—{(S)-1-(6-Bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-yl}-2-methylamino-propionamide hydrochloride

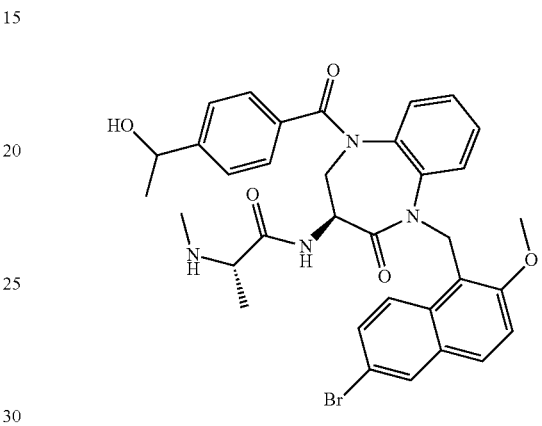

Step 1: To a solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.150 g 0.245 mmol) and 4-acetylbenzoic acid (0.0604 g 0.368 mmol) in 6 mL of pyridine at 0° C. was slowly added POCl$_3$ (0.0686 mL 0.736 mmol) and the mixture stirred at RT overnight. Ice and H$_2$O was slowly added and the mixture extracted with EtOAc. The extracts were washed with 1 M citric acid, brine, sat. Na$_2$CO$_3$, brine, dried over anhydr. Na$_2$SO$_4$, filtered and concentrated to give a material that was purified by silica gel chromatography {(S)-1-[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.109 g, white solid).

Step 2: To a solution of {(S)-1-[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.050 g 0.066 mmol) in 1 mL of THF was added NaBH$_4$ (0.005 g (0.132 mmol) and the mixture stirred at RT overnight. H$_2$O was added and the mixture extracted with DCM. The extracts were washed with brine, sat. Na$_2$CO$_3$, dried over anhydr. Na$_2$SO$_4$, filtered and concentrated to give ((S)-1-{(S)-1-(6-bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-ylcarbamoyl]-ethyl}-methyl-carbamic acid tert-butyl ester (0.046 g, white solid) which was used without purification.

Step 3: In a similar manner to that described for Example 1 except the mixture was stirred 4 h, ((S)-1-{(S)-1-(6-bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-ylcarbamoyl]-ethyl}-methyl-carbamic acid tert-butyl ester (0.044 g 0.0579 mmol) was converted to the title compound as a mixture of diastereomers (0.046 g, white solid). MS m/z 660 (MH$^+$).

Example 34

(S)—N—[(S)-5-(Adamantane-1-carbonyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride

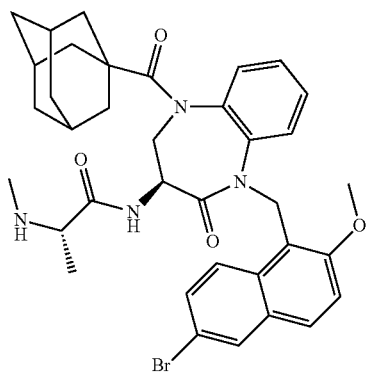 [SMILES: CN[C@@H](C)C(=O)N[C@H]1CN(C(=O)C23CC4CC(CC(C4)C2)C3)c2ccccc2N(Cc2c(OC)ccc3cc(Br)ccc23)C1=O]

Step 1: To a mixture of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.050 g 0.0818 mmol) and pyridine (0.132 mL 1.64 mmol) in 4 mL of DCM was added dropwise 1-adamantanecarbonyl chloride (0.0975 g 0.491 mmol). The reaction mixture was stirred at RT for 24 h, diluted with 50 mL of 1 M citric acid and extracted with EtOAc. The combined extracts were washed with 1 M citric acid, brine, sat. Na$_2$CO$_3$, brine, dried over anhydr. Na$_2$SO$_4$, filtered and concentrated to give a material that was purified by silica gel chromatography to afford {(S)-1-[(S)-5-(adamantan-1-carbonyl)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.025 g, light yellow solid).

Step 2: In a similar manner to that described for Example 1 except the mixture was stirred for 5 h, {(S)-1-[(S)-5-(adamantan-1-carbonyl)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.025 g 0.0323 mmol) was converted to the title compound (0.020 g, light yellow solid). MS m/z 674 (MH$^+$).

Example 35

(S)—N—((S)-5-(4-aminobenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide dihydrochloride

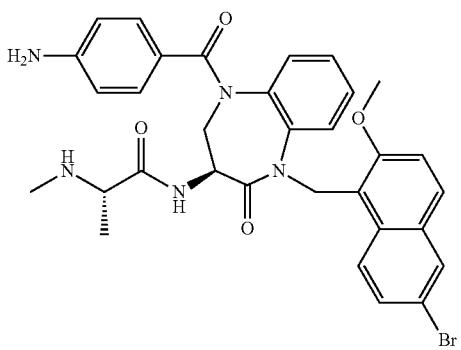 [SMILES: CN[C@@H](C)C(=O)N[C@H]1CN(C(=O)c2ccc(N)cc2)c2ccccc2N(Cc2c(OC)ccc3cc(Br)ccc23)C1=O]

Step 1: To a solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.050 g 0.0818 mmol), 4-(tert-butoxycarbonylamino)benzoic acid (0.029 g 0.123 mmol) in 1 mL of pyridine at 0° C. was slowly added POCl$_3$ (0.023 mL 0.245 mmol). The mixture was stirred at 0° C. for 1 h, diluted with 1 M citric acid and extracted with EtOAc. The extracts were washed with 1 M citric acid, brine, sat. Na$_2$CO$_3$, brine, dried over anhydr. Na$_2$SO$_4$, filtered and concentrated to give a material that was purified by silica gel chromatography to afford (4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepine-1-carbonyl}-phenyl)-carbamic acid tert-butyl ester (0.068 g, white solid).

Step 2: In a similar manner to that described for Example 1, (4-{(S)-5-(6-bromo-2-methoxy-naphthalen-1-ylmethyl)-3-[(S)-2-(tert-butoxycarbonyl-methyl-amino)-propionylamino]-4-oxo-2,3,4,5-tetrahydro-benzo[b][1,4]diazepine-1-carbonyl}-phenyl)-carbamic acid tert-butyl ester (0.012 g 0.014 mmol) was converted to the title compound (0.010 g, white solid). MS m/z 631 (MH$^+$).

Example 36

(S)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)azetidine-2-carboxamide hydrochloride

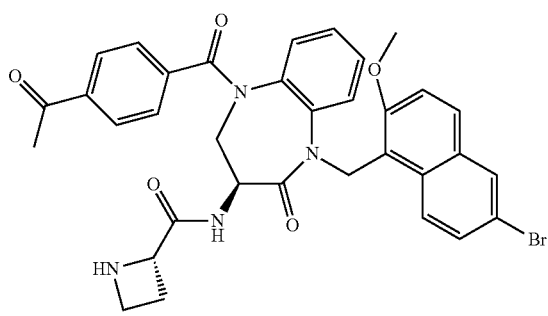 [SMILES: COc1ccc2cc(Br)ccc2c1CN1C(=O)[C@@H](NC(=O)[C@@H]2CCN2)CN(C(=O)c2ccc(C(C)=O)cc2)c2ccccc21]

Step 1: To a solution of (S)-5-(4-acetyl-benzoyl)-3-amino-1-(6-bromo-2-methoxy-naphthalen-1-ylmethyl)-1,3,4,5-tetrahydro-benzo[b][1,4]diazepin-2-one hydrochloride (0.040 g 0.0657 mmol), (S)-azetidine-1,2-dicarboxylic acid-1-tert-butyl ester (0.0145 g (0.0723 mmol), DIEA (0.046 mL (0.263 mmol), and HOBT.H₂O (0.011 g 0.072 mmol) in 25 mL of DMF at 0° C. was slowly added HBPyU (0.031 g 0.0723 mmol), the reaction warmed to RT and stirred overnight. The mixture was cooled to 0° C., 1 M citric acid was slowly added and the mixture was extracted with EtOAc. The extracts were washed with 1 M citric acid, brine, sat. Na₂CO₃, brine, dried over anhydr. Na₂SO₄, filtered and concentrated to give a material that was purified by silica gel chromatography to afford (S)-2-[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-ylcarbamoyl]-azetindine-1-carboxylic acid tert-butyl ester (0.043 g, white solid).

Step 2: In a similar manner to that described for Example 1, (S)-2-[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-ylcarbamoyl]-azetindine-1-carboxylic acid tert-butyl ester (0.043 g 0.057 mmol) was converted to the title compound (0.040 g, white powder). MS m/z 656 (MH⁺).

Example 37

(R)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride

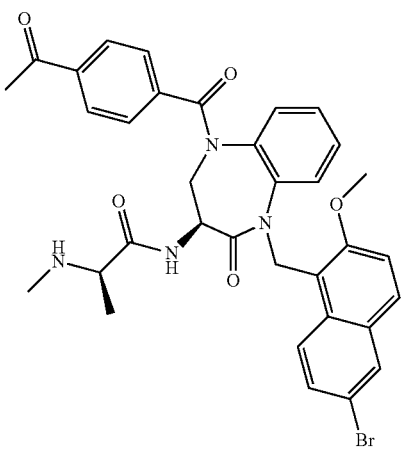 [SMILES: CN[C@H](C)C(=O)N[C@H]1CN(C(=O)c2ccc(C(C)=O)cc2)c2ccccc2N(Cc2c(OC)ccc3cc(Br)ccc23)C1=O]

In a similar manner to that described for Example 36 except in Step 2 the reaction was stirred for 5 h, (S)-5-(4-acetyl-benzoyl)-3-amino-1-(6-bromo-2-methoxy-naphthalen-1-ylmethyl)-1,3,4,5-tetrahydro-benzo[b][1,4]diazepin-2-one hydrochloride (0.040 g 0.0657 mmol) and (R)-2-(tert-butoxycarbonyl-methyl-amino)-propionic acid (0.0147 g 0.0723 mmol) were converted to the title compound (0.036 g, white powder). MS m/z 658 (MH⁺).

Example 38

(S)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(dimethylamino)propanamide

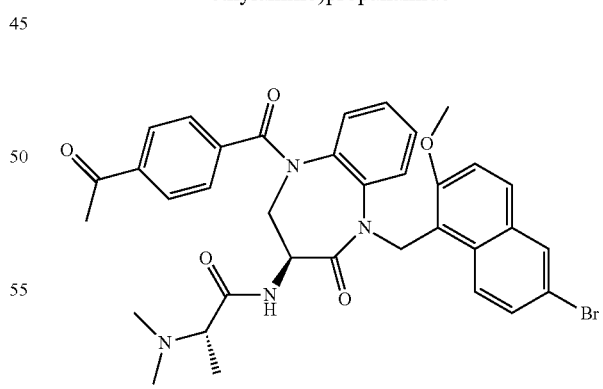

In a similar manner to that described for Example 36, Step 1, except the reaction was diluted with H₂O after stirring overnight, (S)-5-(4-acetyl-benzoyl)-3-amino-1-(6-bromo-2-methoxy-naphthalen-1-ylmethyl)-1,3,4,5-tetrahydro-benzo[b][1,4]diazepin-2-one hydrochloride (0.040 g 0.0657 mmol) and (S)-2-(dimethylamino)propanoic acid hydrochloride (0.012 g 0.079 mmol) were reacted to give a material that was purified by silica gel chromatography to afford the title compound (0.033 g, white solid). MS m/z 672 (MH+).

Example 39

(S)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)-2-aminopropanamide hydrochloride

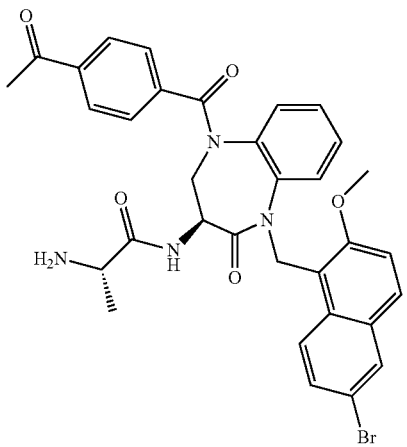 [SMILES: COc1ccc2cc(Br)ccc2c1CN1C(=O)[C@@H](NC(=O)[C@H](C)N)CN(C(=O)c2ccc(C(C)=O)cc2)c2ccccc21]

In a similar manner to that described for Example 36 except in Step 2 the reaction was stirred for 5 h, (S)-5-(4-acetyl-benzoyl)-3-amino-1-(6-bromo-2-methoxy-naphthalen-1-ylmethyl)-1,3,4,5-tetrahydro-benzo[b][1,4]diazepin-2-one hydrochloride (0.040 g 0.0657 mmol) and (S)-2-tert-butoxycarbonylamino-propionic acid (0.0137 g 0.0723 mmol) was converted to the title compound (0.033 g, white powder). MS m/z 644 (MH+).

Example 40

(S)—N—((S)-5-(4-acetylbenzoyl)-1-(2-(naphthalen-1-yl)ethyl)-2-oxo-2,3,4,5-tetrahydro-1H-benzo[b][1,4]diazepin-3-yl)-2-(methylamino)propanamide

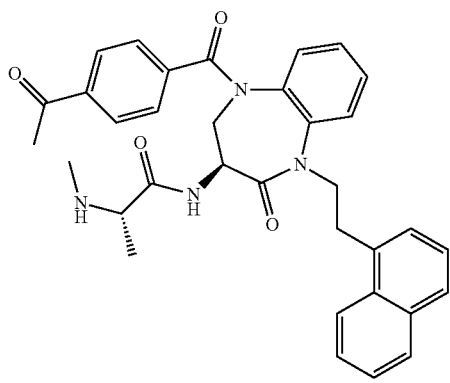 [SMILES: CN[C@@H](C)C(=O)N[C@H]1CN(C(=O)c2ccc(C(C)=O)cc2)c2ccccc2N(CCc2cccc3ccccc23)C1=O]

Step 1: A mixture of ((S)-1-{(S)-1-[4-(1-hydroxy-ethyl)-benzoyl]-4-oxo-2,3,4,5-tetrahydro-1H-benzo[b][1,4]diazepin-3-ylcarbamoyl}-ethyl)-methyl-carbamic acid tert-butyl ester (0.038 g 0.0747 mmol), 1-(2-bromoethyl)naphthalene (0.016 mL 0.112 mmol), NaI (0.0168 g 0.112 mmol), Cs₂CO₃ (0.0365 g 0.112 mmol) and 1 mL of DMF was stirred at RT overnight, diluted with H₂O and extracted with EtOAc. The extracts were washed with sat. Na₂CO₃, brine, dried over anhydr. Na₂SO₄ and concentrated to give a material that was purified by silica gel chromatography to afford {(S)-1-[(S)-5-(4-acetyl-benzoyl)-1-(2-naphthalen-1-yl-ethyl)-2-oxo-2,3,4,5-tetrahydro-1H-benzo[b][1,4]diazepin-3-ylcarbamoyl]-ethyl I-methyl-carbamic acid tert-butyl ester (0.026 g, white solid).

Step 2: In a similar manner to that described for Example 1 except the mixture was stirred for 5 h and the residue was washed with Et₂O before lyophilization, {(S)-1-[(S)-5-(4-Acetyl-benzoyl)-1-(2-naphthalen-1-yl-ethyl)-2-oxo-2,3,4,5-tetrahydro-1H-benzo[b][1,4]diazepin-3-ylcarbamoyl]-ethyl}-methyl-carbamic acid tert-butyl ester (0.026 g 0.0392 mmol) was converted to the title compound (0.025 g, white solid). MS m/z 563 (MH+).

Example 41

(S)—N—[(S)-5-(4-Amino-benzoyl)-1-(2-methoxy-naphthalen-1-ylmethyl)-2-oxo-2,3,4,5-tetrahydro-1H-benzo[b][1,4]diazepin-3-yl]-2-methylaminopropionamide hydrochloride

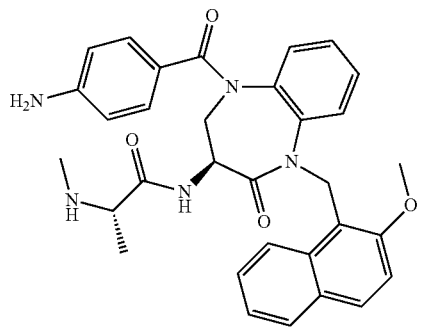 [SMILES: CN[C@@H](C)C(=O)N[C@H]1CN(C(=O)c2ccc(N)cc2)c2ccccc2N(Cc2c(OC)ccc3ccccc23)C1=O]

Step 1: In a similar manner to that described for Example 13 Step 1 except 2 eq. of POCl₃ were used, the mixture was stirred at RT overnight and ice and H₂O were added to quench the reaction, {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.100 g 0.164 mmol) and 4-nitrobenzoic acid (0.041 g 0.245 mmol) were reacted to give a material that was purified by silica gel chromatography to give {(S)-1-[(S)-1-(2-methoxy-naphthalen-1-ylmethyl)-5-(4-nitro-benzoyl)-2-oxo-2,3,4,5-tetrahydro-1H-benzo[b][1,4]diazepin-3-ylcarbamoyl]-ethyl}-methyl-carbamic acid tert-butyl ester (0.075 g, white solid).

Step 2: A mixture of {(S)-1-[(S)-1-(2-methoxy-naphthalen-1-ylmethyl)-5-(4-nitro-benzoyl)-2-oxo-2,3,4,5-tetrahydro-1H-benzo[b][1,4]diazepin-3-ylcarbamoyl]-ethyl}-methyl-carbamic acid tert-butyl ester (0.073 g 0.096 mmol) and 10% Pd/C (0.014 g) in 4 mL of MeOH was hydrogenated at 50 psi for 2 h. The mixture was filtered through Celite, the filter cake washed with MeOH and the filtrate concentrated to give {(S)-1-[(S)-5-(4-amino-benzoyl)-1-(2-methoxy-naphthalen-1-ylmethyl)-2-oxo-2,3,4,5-tetrahydro-1H-benzo[b][1,4]diazepin-3-ylcarbamoyl]-ethyl}-methylcarbamic acid tert-butyl ester (0.065 g, light brown solid) which was used without purification.

Step 3: In a similar manner to that described for Example 1, {(S)-1-[(S)-5-(4-amino-benzoyl)-1-(2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.023 g 0.0353 mmol) was converted to the title compound (0.026 g, yellow solid). MS m/z 552 (MH+).

Alternate Synthesis

Step 1: To a solution of (S)-tert-butyl 1-(4-nitrobenzoyl)-4-oxo-2,3,4,5-tetrahydro-1H-benzo[b][1,4]diazepin-3-yl-carbamate (3.289 g, 7.71 mmol) in DMF (38.6 mL) was added 1-(chloromethyl)-2-methoxynaphthalene (1.75 g, 8.48 mmol), Cs$_2$CO$_3$ (3.02 g, 9.26 mmol), and NaI (1.39 g, 9.26 mmol). After 6 h additional 1-(chloromethyl)-2-methoxynaphthalene (400 mg, 1.94 mmol) and Cs$_2$CO$_3$ (750 mg, 2.30 mmol) were added and the mixture stirred for an additional 16 h. The mixture was diluted with H$_2$O and extracted with EtOAc. The combined extracts were washed with sat. aq. NaHCO$_3$, H$_2$O, and brine, dried over Na$_2$SO$_4$, filtered, and concentrated. The residue was purified by flash chromatography to provide (S)-tert-butyl 1-((2-methoxynaphthalen-1-yl)methyl)-5-(4-nitrobenzoyl)-2-oxo-2,3,4,5-tetrahydro-1H-benzo[b][1,4]diazepin-3-ylcarbamate (4.663 g, 100%) as a light yellow solid. LC-MS m/z 619 [M+Na]+.

Step 2: A solution of (S)-tert-butyl 1-((2-methoxynaphthalen-1-yl)methyl)-5-(4-nitrobenzoyl)-2-oxo-2,3,4,5-tetrahydro-1H-benzo[b][1,4]diazepin-3-ylcarbamate (4.656 g, 7.8 mmol) in 4 M HCl in dioxane (39.0 mL) was stirred for 16 h. The reaction was concentrated and the residue was triturated with Et$_2$O to provide (S)-3-amino-1-((2-methoxynaphthalen-1-yl)methyl)-5-(4-nitrobenzoyl)-4,5-dihydro-H-benzo[b][1,4]diazepin-2(3H)-one hydrochloride (4.005 g, 96%) as a light yellow solid. LC-MS m/z 497 (MH+).

Step 3: To solution of (S)-3-amino-1-((2-methoxynaphthalen-1-yl)methyl)-5-(4-nitrobenzoyl)-4,5-dihydro-H-benzo[b][1,4]diazepin-2(3H)-one hydrochloride (3.900 g, 7.32 mmol) in DMF (24.4 mL) at 0° C. was added Boc-N-methyl-L-alanine (1.64 g, 8.05 mmol), DIEA (5.06 mL, 29.3 mmol), and HBTU (3.05 g, 8.05 mmol) and the mixture warmed to RT. After 30 min. the mixture was added dropwise to a stirred 0° C. solution of sat. aq. NaHCO$_3$ and H$_2$O 1:1 resulting in a precipitate. The precipitate was collected by filtration, washed with H$_2$O and dissolved in EtOAc. This solution was washed with H$_2$O, brine, dried over Na$_2$SO$_4$, filtered, and concentrated. The residue was purified by flash chromatography to provide tert-butyl (S)-1-((S)-1-((2-methoxynaphthalen-1-yl)methyl)-5-(4-nitrobenzoyl)-2-oxo-2,3,4,5-tetrahydro-1H-benzo[b][1,4]diazepin-3-ylamino)-1-oxopropan-2-yl(methyl)carbamate (4.399 g, 88%) as a light yellow solid. LC-MS m/z 704 [M+Na]+.

Step 4: To a suspension of tert-butyl (S)-1-((S)-1-((2-methoxynaphthalen-1-yl)methyl)-5-(4-nitrobenzoyl)-2-oxo-2,3,4,5-tetrahydro-1H-benzo[b][1,4]diazepin-3-ylamino)-1-oxopropan-2-yl(methyl)carbamate (2.756 g, 4.04 mmol) in EtOH (40.4 mL) was added tin(II) chloride dihydrate (4.56 g, 20.2 mmol) and the mixture heated to 30° C. After 4 h the mixture concentrated and the residue was dissolved in CH$_2$Cl$_2$. This solution was washed with 1:1 H$_2$O/sat. aq. NaHCO$_3$ and the aqueous layer was extracted with CH$_2$Cl$_2$. The combined extracts were washed with H$_2$O, brine, dried over Na$_2$SO$_4$, filtered, and concentrated. The residue was purified by flash chromatography to provide tert-butyl (S)-1-((S)-5-(4-aminobenzoyl)-1-((2-methoxynaphthalen-1-yl)methyl)-2-oxo-2,3,4,5-tetrahydro-1H-benzo[b][1,4]diazepin-3-ylamino)-1-oxopropan-2-yl(methyl)carbamate (2.30 g, 87%) as a white solid. LC-MS m/z 674 [M+Na]+.

Step 5: To a solution of tert-butyl (S)-1-((S)-5-(4-aminobenzoyl)-1-((2-methoxynaphthalen-1-yl)methyl)-2-oxo-2,3,4,5-tetrahydro-1H-benzo[b][1,4]diazepin-3-ylamino)-1-oxopropan-2-yl(methyl)carbamate (2.81 g, 4.31 mmol) in MeOH (4.31 mL) was added 4 M HCl in dioxane (38.8 mL). After 1 h the mixture was concentrated and the residue was triturated with Et$_2$O. The residue was taken up in 10% MeCN—H$_2$O and lyophilized to provide (S)—N—((S)-5-(4-aminobenzoyl)-1-((2-methoxynaphthalen-1-yl)methyl)-2-oxo-2,3,4,5-tetrahydro-H-benzo[b][1,4]diazepin-3-yl)-2-(methylamino)propanamide hydrochloride (2.365 g, 93%) as a white solid. LC-MS m/z 552 (MH+).

Example 42

(S)—N—[(S)-5-(4-Acetylamino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride

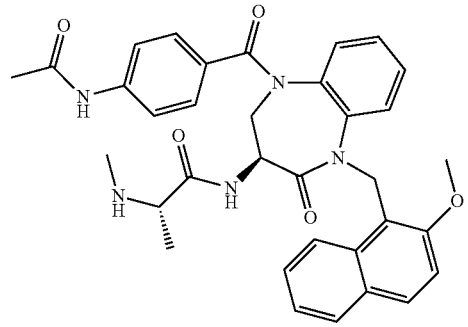 [SMILES: CN[C@@H](C)C(=O)N[C@H]1CN(C(=O)c2ccc(NC(C)=O)cc2)c2ccccc2N(Cc2c(OC)ccc3ccccc23)C1=O]

Step 1: To a mixture of {(S)-1-[(S)-5-(4-amino-benzoyl)-1-(2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.050 g 0.0767 mmol) and pyridine (0.0186 mL 0.230 mmol) in 2 mL of DCM was added acetic anhydride (0.0217 g 0.230 mmol). The mixture was stirred at RT 72 h, sat. Na$_2$CO$_3$ was added and the mixture extracted with DCM. The organic extracts were washed with sat. Na$_2$CO$_3$, brine, dried over anhydr. Na$_2$SO$_4$, filtered and concentrated to give a material that was purified by silica gel chromatography to afford {(S)-1-[(S)-5-(4-acetylamino-benzoyl)-1-(2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.037 g, white solid).

Step 2: In a similar manner to that described for Example 1 except the mixture was stirred for 4 h, {(S)-1-[(S)-5-(4-acetylamino-benzoyl)-1-(2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.035 g 0.0504 mmol) was converted to the title compound (0.036 g, white solid). MS m/z 594 (MH+).

Example 43

5-[(S)-5-(4-Acetyl-benzoyl)-3-((S)-2-methylamino-propionylamino)-2-oxo-2,3,4,5-tetrahydro-benzo[b][1,4]diazepin-1-ylmethyl]-6-methoxy-naphthalen-2-carboxylic acid methyl ester hydrochloride

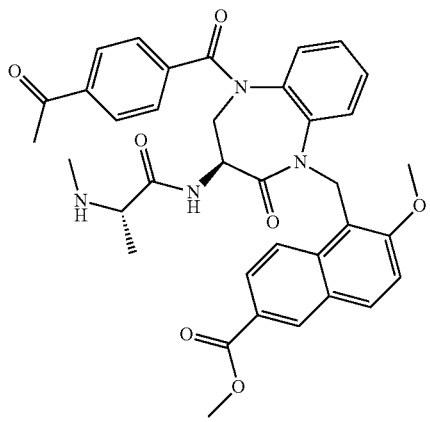 [SMILES: CN[C@@H](C)C(=O)N[C@H]1CN(C(=O)c2ccc(C(C)=O)cc2)c2ccccc2N(Cc2c(OC)ccc3cc(C(=O)OC)ccc23)C1=O]

Step 1: A mixture of {(S)-1-[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (0.200 g 0.264 mmol), palladium acetate (0.00024 g 0.0106 mmol), bis(diphenylphosphino)-9,9-dimethylxanthene (0.0122 g 0.021 mmol) and 4 mL of TEA were combined, the vessel was evacuated, purged with $N_2$ and MeOH (0.107 mL 0.00264 mmol) was added to the mixture. The vessel was purged with CO gas for 30 seconds and heated to 70° C. for 15 h. EtOAc was added and the mixture washed with $H_2O$ and brine. The organic layer was dried over anhydr. $Na_2SO_4$, filtered and concentrated. The residue was purified by silica gel chromatography, to give 5-{(S)-5-(4-acetyl-benzoy)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalen-2-carboxylic acid methyl ester (0.070 g).

Step 2: In a similar manner to that described for Example 1, 5-{(S)-5-(4-acetyl-benzoy)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalen-2-carboxylic acid methyl ester (0.015 g 0.0204 mmol) was converted to the title compound (0.013 g, white solid). MS m/z 637 (MH$^+$).

Example 44

5-[[(3S)-1-(4-acetylbenzoyl)-3-[[(2S)-2-(methylamino)propanoyl]amino]-4-oxo-2,3-dihydro-1,5-benzodiazepin-5-yl]methyl]-6-methoxy-naphthalene-2-carboxylic acid; hydrochloride

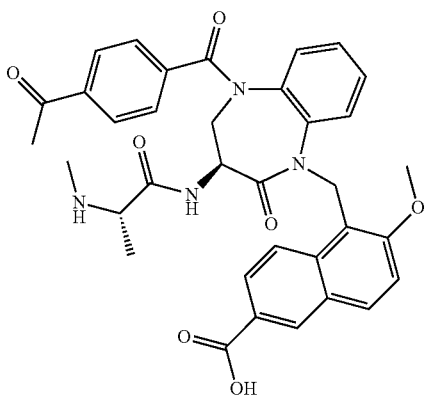 [SMILES: CN[C@@H](C)C(=O)N[C@H]1CN(C(=O)c2ccc(C(C)=O)cc2)c2ccccc2N(Cc2c(OC)ccc3cc(C(=O)O)ccc23)C1=O]

Step 1: To a solution of 5-{(S)-5-(4-acetyl-benzoy)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalen-2-carboxylic acid methyl ester (0.050 g 0.0679 mmol) in 2 mL of THF and 0.3 mL of $H_2O$ was added 1 M LiOH (0.272 mL 0.271 mmol). After 3 h, 1 M citric acid was added, the mixture extracted with EtOAc and the extracts washed with 1 M citric acid, brine, dried over $Na_2SO_4$, filtered and concentrated to afford 5-{(S)-5-(4-acetyl-benzoy)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalen-2-carboxylic acid (0.040 g, white solid) which was used without purification.

Step 2: In a similar manner to that described for Example 1, 5-{(S)-5-(4-acetyl-benzoy)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalen-2-carboxylic acid (0.025 g 0.0346 mmol) was converted to the title compound (0.022 g, white solid). MS m/z 623 (MH$^+$).

Example 45

5-(((S)-5-(4-acetylbenzoyl)-3-((S)-2-(methylamino)propanamido)-2-oxo-2,3,4,5-tetrahydro-1H-benzo[b][1,4]diazepin-1-yl)methyl)-N-hydroxy-6-methoxy-2-naphthamide 2,2,2-trifluoroacetate

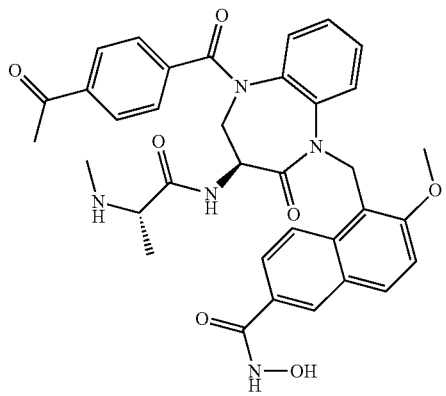 [SMILES: CN[C@@H](C)C(=O)N[C@H]1CN(C(=O)c2ccc(C(C)=O)cc2)c2ccccc2N(Cc2c(OC)ccc3cc(C(=O)NO)ccc23)C1=O]

Step 1: In a similar manner to that described for Example { }Step 1 except 2 eq. each of HOBT.H₂O and HBPyU were used, 5-{(S)-5-(4-acetyl-benzoy)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalen-2-carboxylic acid (0.038 g 0.0526 mmol) and O-(tetrahydro-2H-pyran-2-yl)hydroxylamine (0.00739 g 0.0631 mmol) were reacted to give a material that was purified by silica gel chromatography to afford ((S)-1-{(S)-5-(4-acetyl-benzoy)-1-[2-methoxy-6-(tetrahydro-pyran-2-yloxycarbamoyl)-naphthalen-1-ylmethyl]-2-oxo-2,3,4,5-tetrahydro-1H-benzo[b][1,4]diazepin-3-ylcarbamoyl}-ethyl)-methyl-carbamic acid tert-butyl ester (0.041 g, white solid).

Step 2: In a similar manner to that described for Example 1, ((S)-1-{(S)-5-(4-acetyl-benzoy)-1-[2-methoxy-6-(tetrahydro-pyran-2-yloxycarbamoyl}-naphthalen-1-ylmethyl]-2-oxo-2,3,4,5-tetrahydro-1H-benzo[b][1,4]diazepin-3-ylcarbamoyl-ethyl)-methyl-carbamic acid tert-butyl ester (0.035 g 0.0426 mmol) was treated to give a material that was purified by HPLC to afford the title compound (0.012, yellow solid). MS m/z 638 (MH⁺).

Example 46

6-Methoxy-5-[(S)-3 ((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid methyl ester hydrochloride

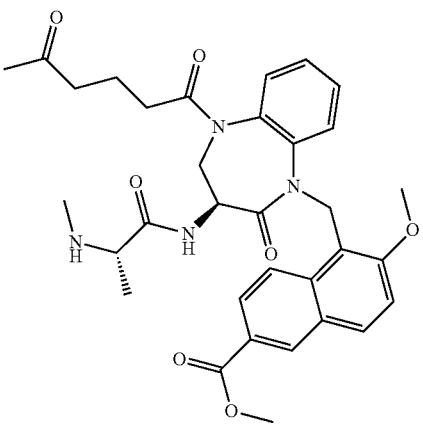 [SMILES: CN[C@@H](C)C(=O)N[C@H]1CN(C(=O)CCCC(C)=O)c2ccccc2N(Cc2c(OC)ccc3cc(C(=O)OC)ccc23)C1=O]

Step 1: In a similar manner to that described for 5-{(S)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester except 0.04 eq. Pd(OAc)₂ and 10 eq. MeOH were used, {(S)-1-[(S)-1-(6-bromo-2-methoxy-naphthalen-1-ylmethyl)-2-oxo-5-(5-oxo-hexanoyl)-2,3,4,5-tetrahydro-1H-benzo[b][1,4]diazepin-3-ylcarbamoyl]-ethyl}-methyl-carbamic acid tert-butyl ester (0.0724 0.1 mmol) was reacted to give a material that was purified by silica gel chromatography to afford 5-[(S)-3-[(S)-2-(tert-butoxycarbonyl-methyl-amino)-propionylamino]-2-oxo-5-(5-oxo-hexanoyl)-2,3,4,5-tetrahydro-1H-benzo[b][1,4]diazepin-1-ylmethyl]-6-methoxy-naphthalene-2-carboxylic acid methyl ester (0.035 g, white solid).

Step 2: In a similar manner to that described for Example 1, 5-[(S)-3-[(S)-2-(tert-butoxycarbonyl-methyl-amino)-propionylamino]-2-oxo-5-(5-oxo-hexanoyl)-2,3,4,5-tetrahydro-1H-benzo[b][1,4]diazepin-1-ylmethyl]-6-methoxy-naphthalene-2-carboxylic acid methyl ester (0.010 g 0.0142 mmol) was converted to the title compound (0.007 g, white solid). MS m/z 603 (MH⁺).

Example 47

6-Methoxy-5-[(S)-3 ((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid hydrochloride

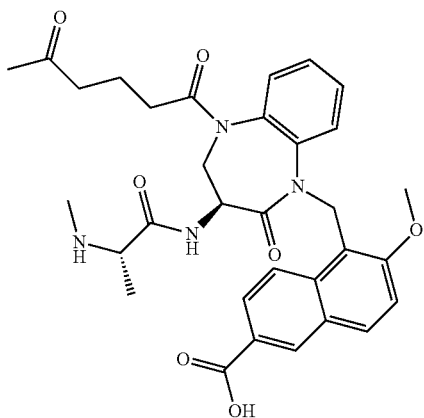 [SMILES: CN[C@@H](C)C(=O)N[C@H]1CN(C(=O)CCCC(C)=O)c2ccccc2N(Cc2c(OC)ccc3cc(C(=O)O)ccc23)C1=O]

Step 1: To a solution of 0.025 g (0.0356 mmole) 5-[(S)-3-[(S)-2-(tert-butoxycarbonyl-methyl-amino)-propionylamino]-2-oxo-5-(5-oxo-hexanoyl)-2,3,4,5-tetrahydro-1H-benzo[b][1,4]diazepin-1-ylmethyl]-6-methoxy-naphthalene-2-carboxylic acid methyl ester in 1.0 mL of THF and 0.2 mL of water was added 0.143 mL (0.142 mmol) of 1 M LiOH. After 3 h 1M citric acid was added and the mixture extracted with EtOAc. The extracts were washed with 1M citric acid, brine, anhydr. $Na_2SO_4$, filtered and concentrated. The residue was purified by silica gel chromatography to afford 5-[(S)-3-[(S)-2-(tert-butoxycarbonyl-methyl-amino)-propionylamino]-2-oxo-5-(5-oxo-hexanoyl)-2,3,4,5-tetrahydro-1H-benzo[b][1,4]diazepin-1-ylmethyl]-6-methoxy-naphthalene-2-carboxylic acid (0.025 g white solid).

Step 2: In a similar manner to that described for Example 1, 5-[(S)-3-[(S)-2-(tert-butoxycarbonyl-methyl-amino)-propionylamino]-2-oxo-5-(5-oxo-hexanoyl)-2,3,4,5-tetrahydro-1H-benzo[b][1,4]diazepin-1-ylmethyl]-6-methoxy-naphthalene-2-carboxylic acid (0.025 g 0.0363 mmol) was converted to the title compound (0.023 g, white solid). MS m/z 589 ($MH^+$).

Example 48

5-[(S)-5-[4-(9H-Fluoren-9-ylmethoxycarbonylamino)-butyryl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride

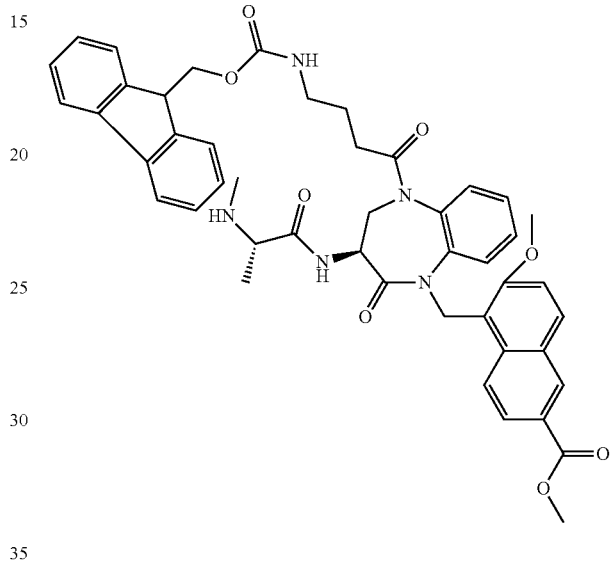

Step 1: A solution of 5-{(S)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxyl-naphthalene-2-carboxylic acid methyl ester (0.150 g, 0.254 mmol), of 4-(9H-fluoren-9-ylmethoxycarbonylamino)-butyric acid (0.124 g 0.381 mmol) in 4.5 mL of pyridine was stirred at 0° C. for 10 min., $POCl_3$ (0.0473 mL 0.508 mmol) was added and the mixture stirred at RT overnight. The solvent was removed; ice and $H_2O$ was added, the mixture extracted with EtOAc, the extracts were washed with citric acid, brine, dried over anhydr. $Na_2SO_4$, filtered and concentrated to give a material that was purified by silica gel chromatography to afford 5-{(S)-3-[(S)-2-(tert-butoxycarbonyl-methyl-amino)-propionylamino]-5-[4-(9H-fluoren-9-ylmethoxycarbonylamino)-butyryl]-2-oxo-2,3,4,5-tetrahydro-benzo[b][1,4]diazepin-1-ylmethyl}-6-methoxyl-naphthalene-2-carboxylic acid methyl ester (0.138 g white solid).

Step 2: In a similar manner to that described for Example 1 except the material was not lyophilized, 5-{(S)-3-[(S)-2-(tert-butoxycarbonyl-methyl-amino)-propionylamino]-5-[4-(9H-fluoren-9-ylmethoxycarbonylamino)-butyryl]-2-oxo-2,3,4,5-tetrahydro-benzo[b][1,4]diazepin-1-ylmethyl}-6-methoxyl-naphthalene-2-carboxylic acid methyl ester (15 mg 0.017 mmol) was converted to the title compound (14 mg, white solid). MS m/z 798 ($MH^+$).

Example 49

5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride

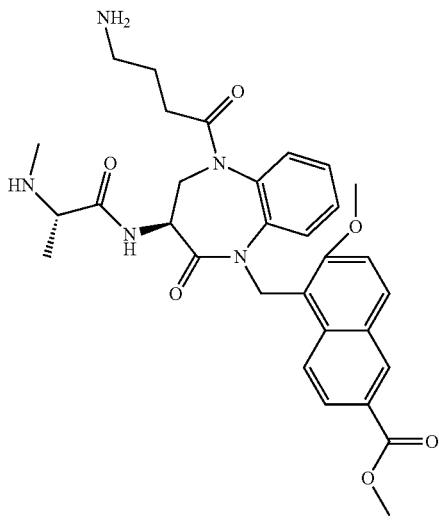 [SMILES: CN[C@@H](C)C(=O)N[C@H]1CN(C(=O)CCCN)c2ccccc2N(Cc2c(OC)ccc3cc(C(=O)OC)ccc23)C1=O]

Step 1: A solution of 5-{(S)-3-[(S)-2-(tert-butoxycarbonyl-methyl-amino)-propionylamino]-5-[4-(9H-fluoren-9-yl-methoxycarbonylamino)-butyryl]-2-oxo-2,3,4,5-tetrahydro-benzo[b][1,4]diazepin-1-ylmethyl}-6-methoxyl-naphthalene-2-carboxylic acid methyl ester (0.130 g 0.145 mmol) in 4.0 mL of piperidine/DCM 1:1 was stirred at RT for 3 h, diluted with DCM washed with sat. Na$_2$CO$_3$, dried over anhydr. Na$_2$SO$_4$, filtered and concentrated to give a material that was purified by silica gel chromatography to afford 5-{(S)-5-(4-amino-butyryl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (0.074 g white solid).

Step 2: In a similar manner to that described for Example 1 except the material was not lyophilized, 5-{(S)-5-(4-amino-butyryl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (15 mg 0.022 mmol) was converted to the title compound (14 mg, white solid). MS m/z 576 (MH$^+$).

Example 50

5-(((S)-5-(4-aminobutanoyl)-3-((S)-2-(methylamino) propanamido)-2-oxo-2,3,4,5-tetrahydro-1H-benzo[b][1,4]diazepin-1-yl)methyl)-6-methoxy-2-naphthoic acid hydrochloride

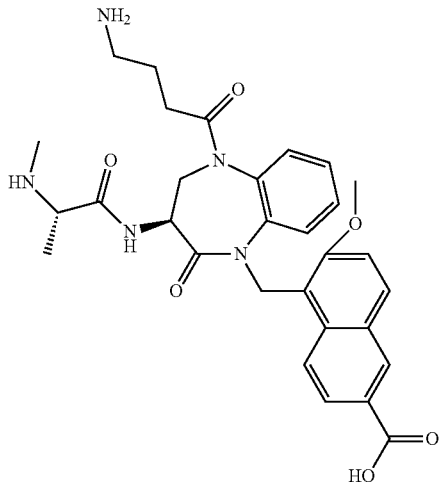 [SMILES: CN[C@@H](C)C(=O)N[C@H]1CN(C(=O)CCCN)c2ccccc2N(Cc2c(OC)ccc3cc(C(=O)O)ccc23)C1=O]

Step 1: To a solution of 5-{(S)-5-(4-amino-butyryl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (0.070 g 0.104 mmol) in 1.0 mL of MeOH was added 1 M LiOH (0.415 mL 0.414 mmol). The reaction mixture was stirred at RT for 15 h, adjusted to pH ca. 7.0 with 1 N HCl and lyophilized to give 5-{(S)-5-(4-amino-butyryl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid (0.081 g) which was used without purification (white solid).

Step 2; In a similar manner to that described for Example 1 except the material was not lyophilized, 5-{(S)-5-(4-amino-butyryl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid (15 mg 0.023 mmol) was converted to the title compound (9 mg, white solid). MS m/z 562 (MH$^+$).

Example 51

Cyclic-5-[(S)-5-(4-Amino-butyryl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride

Example 52

5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride

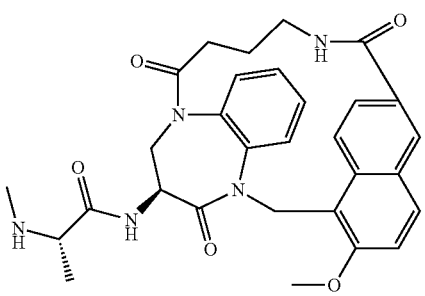 [SMILES: CN[C@@H](C)C(=O)N[C@H]1CN2C(=O)CCCNC(=O)c3ccc4c(c(OC)ccc4c3)CN(C1=O)c1ccccc12]

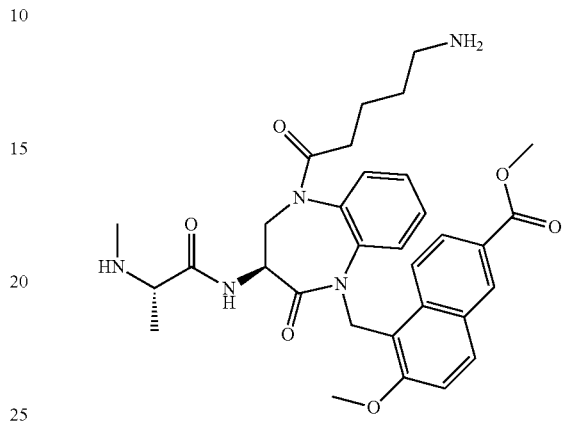

Step 1: To a solution of 5-{(S)-5-(4-amino-butyryl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid (0.0662 g 0.100 mmol) in 15 mL of DMF was added DIEA (0.0524 mL 0.300 mmol) and pentafluorophenyl diphenylphosphinate (0.0576 g 0.150 mmol). The mixture was stirred at RT overnight, diluted with $H_2O$ and EtOAc, the organic layer washed with 1 M citric acid, brine, sat. $Na_2CO_3$, brine, dried over anhydr. $Na_2SO_4$, filtered and concentrated to give a material that was purified by silica gel chromatography to afford cyclic-5-{(S)-5-(4-amino-butyryl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic amide (0.030 g, white solid).

Step 2: In a similar manner to that described for Example 1 except the reaction was stirred for 5 h, cyclic-5-{(S)-5-(4-amino-butyryl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic amide (0.030 g (0.0466 mmol) was converted to cyclic-5-[(S)-5-(4-amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride (0.026 g, white powder).

Step 3: Cyclic-5-[(S)-5-(4-amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride (0.025 g) was purified by supercritical fluid chromatography (SFC) to give cyclic-5-[(S)-5-(4-amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide (0.019 g, white solid). MS m/z 544 ($MH^+$).

Step 1: A solution of 5-{(S)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxyl-naphthalene-2-carboxylic acid methyl ester (0.300 g 0.508 mmol), 4-(9H-fluoren-9-ylmethoxycarbonylamino)-butyric acid (0.259 g 0.762 mmol) in 9.01 mL of pyridine was cooled to 0° C. and $POCl_3$ (0.142 mL 1.52 mmol) was added. After 1 h the solvent was removed; ice and $H_2O$ was added and the mixture extracted with EtOAc, the extracts washed with citric acid, brine, dried over anhydr. $Na_2SO_4$, filtered and concentrated to give a material that was purified by silica gel chromatography to afford 5-{(S)-3-[(S)-2-(tert-butoxycarbonyl-methyl-amino)-propionylamino]-5-[5-(9H-fluoren-9-ylmethoxycarbonylamino)-pentanoyl]-2-oxo-2,3,4,5-tetrahydro-benzo[b][1,4]diazepin-1-ylmethyl}-6-methoxyl-naphthalene-2-carboxylic acid methyl ester (0.308 g white solid).

Step 2: In a similar manner to that described for Example 49, Step 1, except the reaction was stirred 1 h, 5-{(S)-3-[(S)-2-(tert-butoxycarbonyl-methyl-amino)-propionylamino]-5-[5-(9H-fluoren-9-ylmethoxycarbonylamino)-pentanoyl]-2-oxo-2,3,4,5-tetrahydro-benzo[b][1,4]diazepin-1-ylmethyl}-6-methoxyl-naphthalene-2-carboxylic acid methyl ester (0.288 g 0.316 mmol) was converted to a material that was purified by silica gel chromatography to afford 5-{(S)-5-(5-amino-pentanoyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (0.218 g).

Step 3: In a similar manner to that described for Example 1 except the reaction was stirred for 4 h, 5-{(S)-5-(5-amino-pentanoyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (0.015 g 0.0217 mmol) was converted to the title compound (0.0126 g, light brown solid). MS m/z 590 ($MH^+$).

Example 53

5-(((S)-5-(5-aminopentanoyl)-3-((S)-2-(methyl-amino)propanamido)-2-oxo-2,3,4,5-tetrahydro-1H-benzo[b][1,4]diazepin-1-yl)methyl)-6-methoxy-2-naphthoic acid hydrochloride

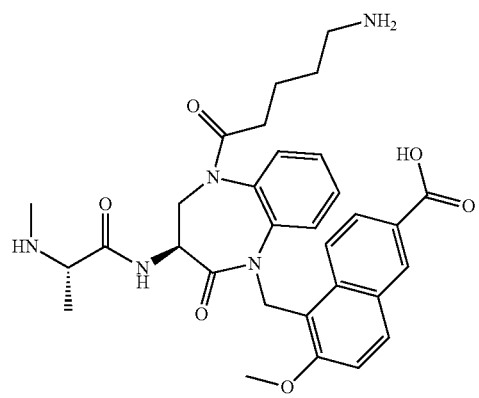 [SMILES: CN[C@@H](C)C(=O)N[C@H]1CN(C(=O)CCCCN)c2ccccc2N(Cc2c(OC)ccc3cc(C(=O)O)ccc23)C1=O]

Step 1: To a solution of 5-{(S)-5-(5-amino-pentanoyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (0.203 g 0.222 mmol) in 1.6 mL of MeOH and 0.40 mL of H$_2$O was added 1 M LiOH (0.889 mL 0.889 mmol). The mixture was stirred at RT for 15 h and the solvent was removed. The residue was dissolved in H$_2$O with small amount of MeCN and filtered. The filtrate was purified by reverse phase chromatography to afford 5-{(S)-5-(5-amino-pentanoyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid (0.121 g, white solid).

Step 2: In a similar manner to that described for Example 1 except the reaction was stirred for 4 h, 5-{(S)-5-(5-amino-pentanoyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid (0.015 g 0.0222 mmol) was converted to the title compound (0.0146 g, light brown solid). MS m/z 576 (MH$^+$).

Example 54

Cyclic-5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride

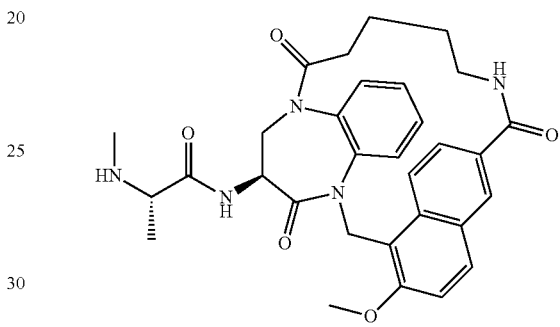

Step 1: In a similar manner to that described for Example 50 Step 1 except the reaction was stirred 2 h, 5-{(S)-5-(5-amino-pentanoyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid (0.116 g, 0.171 mmol) was converted to a material that was purified by silica gel chromatography to afford cyclic-5-{(S)-5-(5-amino-pentanoyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic amide (0.0498 g white solid).

Step 2: In a similar manner to that described for Example 1, cyclic-5-{(S)-5-(5-amino-pentanoyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic amide 0.0498 g (0.0757 mmol) was converted to the title compound (0.0415 g, off-white powder). MS m/z 558 (MH$^+$).

137

Example 55

5-[(S)-5-[4-(9H-Fluoren-9-ylmethoxycarbonylamino)-benzoyl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride

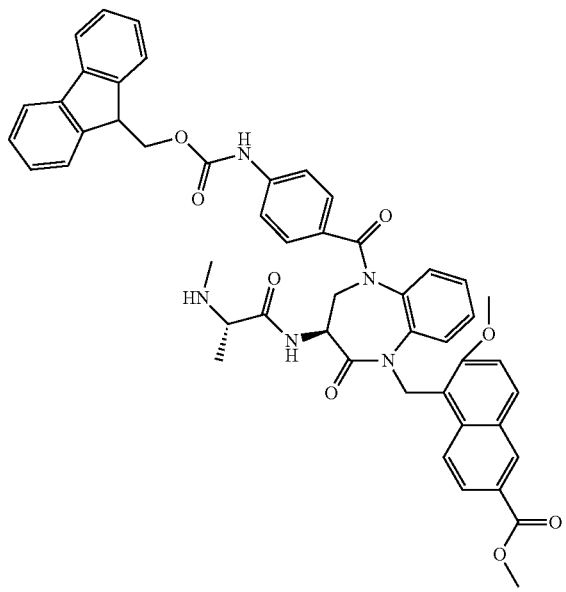 [SMILES: CN[C@@H](C)C(=O)N[C@H]1CN(C(=O)c2ccc(NC(=O)OCC3c4ccccc4-c4ccccc43)cc2)c2ccccc2N(Cc2c(OC)ccc3cc(C(=O)OC)ccc23)C1=O]

Step 1: In a similar manner to that described for Example 14, Step 1, except pyridine was omitted and the reaction was stirred for 2 h, 5-{(S)-3-[(S)-2-(tert-butoxycarbonyl-methyl-amino)-propionylamino]-2-oxo-2,3,4,5-tetrahydro-benzo[b][1,4]diazepin-1-yl}-6-methoxyl-naphthalene-2-carboxylic acid methyl ester (0.100 g 0.17 mmol) and (9H-fluoren-9-yl)methyl 4-(chlorocarbonyl)phenylcarbamate (0.19 mL 0.5 mmol) were reacted to give a material that was purified by silica gel chromatography to afford 5-{(S)-3-[(S)-2-(tert-butoxycarbonyl-methyl-amino)-propionylamino]-5-[4-(9H-fluoren-9-ylmethoxycarbonylamino)-benzoyl]-2-oxo-2,3,4,5-tetrahydro-benzo[b][1,4]diazepin-1-ylmethyl}-6-methoxy-naphthalene-2-carboxylic acid methyl ester (0.098 g, white solid).

Step 2: In a similar manner to that described for Example 1, 5-{(S)-3-[(S)-2-(tert-butoxycarbonyl-methyl-amino)-propionylamino]-5-[4-(9H-fluoren-9-ylmethoxycarbonylamino)-benzoyl]-2-oxo-2,3,4,5-tetrahydro-benzo[b][1,4]diazepin-1-ylmethyl}-6-methoxy-naphthalene-2-carboxylic acid (0.015 g, 0.016 mmol) was converted to the title compound (0.015 g, white solid). MS m/z 832 (MH+).

138

Example 56

5-[(S)-5-(4-Amino-benzoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride

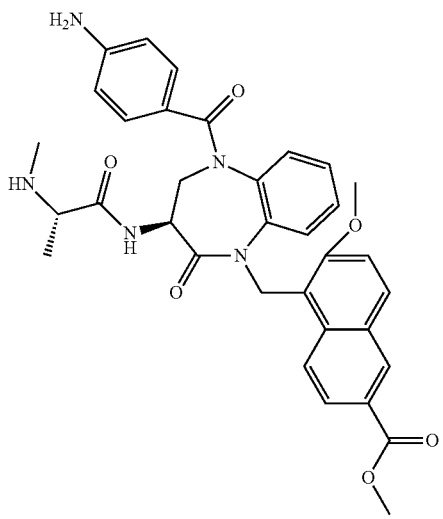 [SMILES: CN[C@@H](C)C(=O)N[C@H]1CN(C(=O)c2ccc(N)cc2)c2ccccc2N(Cc2c(OC)ccc3cc(C(=O)OC)ccc23)C1=O]

In a similar manner to that described for Example 49, 5-{(S)-3-[(S)-2-(tert-butoxycarbonyl-methyl-amino)-propionylamino]-5-[4-(9H-fluoren-9-ylmethoxycarbonylamino)-benzoyl]-2-oxo-2,3,4,5-tetrahydro-benzo[1,4]diazepin-1-ylmethyl}-6-methoxy-naphthalene-2-carboxylic acid methyl ester (0.025 g, 0.027 mmol) was converted to the title compound (0.013 g, white solid). MS m/z 610 (MH+).

Example 57

5-(((S)-5-(4-aminobenzoyl)-3-((S)-2-(methylamino)propanamido)-2-oxo-2,3,4,5-tetrahydro-1H-benzo[b][1,4]diazepin-1-yl)methyl)-6-methoxy-2-naphthoic acid hydrochloride

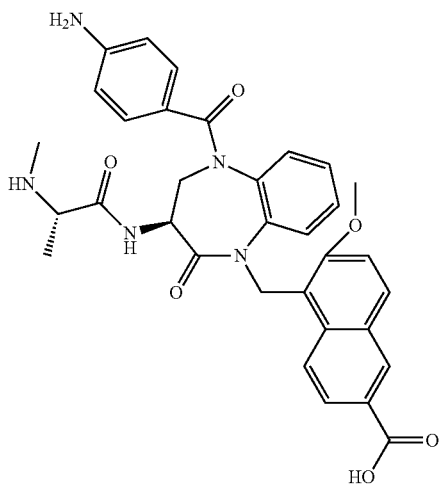 [SMILES: CN[C@@H](C)C(=O)N[C@H]1CN(C(=O)c2ccc(N)cc2)c2ccccc2N(Cc2c(OC)ccc3cc(C(=O)O)ccc23)C1=O]

In a similar manner to that described for Example 50, 5-{(S)-5-(4-amino-benzoyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (0.005 g, 0.007 mmol) was converted to the title compound (0.004 g, white solid). MS m/z 596 (MH+).

Example 58

Cyclic-5-[(S)-5-(3-amino-propyl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride

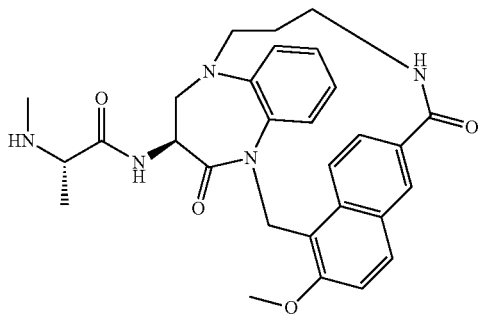 [SMILES: CN[C@@H](C)C(=O)N[C@H]1CN2CCCNC(=O)c3ccc4c(c(OC)ccc4c3)CN(C1=O)c1ccccc12]

Step 1: To a solution of (S)-methyl-5-((3-(tert-butoxycarbonylamino)-2-oxo-2,3,4,5-tetrahydro-1H-benzo[b][1,4]diazepin-1-yl)methyl)-6-methoxy-2-naphthoate (0.50 g 1.0 mmol) and benzyl 3-oxopropylcarbamate (0.41 g 2.0 mmol) in 1.24 mL of DCM was added NaBH(OAc)₃ (1.05 g 5.0 mmol) and the mixture stirred at RT overnight. The mixture was diluted with EtOAc, washed with H₂O, brine, dried over anhydr. Na₂SO₄, filtered and concentrated to give a material that was purified by silica gel chromatography to afford 5-[(S)-5-(3-benzyloxycarbonylamino-propyl)-3-tert-butoxycarbonylamino-2-oxo-2,3,4,5-tetrahydro-benzo[b][1,4]diazepin-1-ylmethyl]-6-methoxy-naphthalene-2-carboxylic acid methyl ester (0.17 g, white solid).

Step 2: A mixture of 5-[(S)-5-(3-benzyloxycarbonylamino-propyl)-3-tert-butoxycarbonylamino-2-oxo-2,3,4,5-tetrahydro-benzo[b][1,4]diazepin-1-ylmethyl]-6-methoxy-naphthalene-2-carboxylic acid methyl ester (0.162 g 0.232 mmol) and 10% Pd/C (0.025 g) in 1 mL of MeOH was hydrogenated at 40 psi for 2 h. The mixture was filtered through Celite, the filter cake washed with MeOH and the filtrate concentrated to give 5-[(S)-5-(3-amino-propyl)-3-tert-butoxycarbonylamino-2-oxo-2,3,4,5-tetrahydro-benzo[b][1,4]diazepin-1-ylmethyl]-6-methoxy-naphthalene-2-carboxylic acid methyl ester (0.130 g off-white solid) which was used without purification.

Step 3: To a solution of 5-[(S)-5-(3-amino-propyl)-3-tert-butoxycarbonylamino-2-oxo-2,3,4,5-tetrahydro-benzo[b][1,4]diazepin-1-ylmethyl]-6-methoxy-naphthalene-2-carboxylic acid methyl ester (0.130 g 0.230 mmol) in 2.08 mL of MeOH was added 1 M LiOH (0.921 m (0.921 mmol). After 3 h, the solvent was removed, the residue was dissolved in H₂O and lyophilized to give a material that was purified by reverse phase HPLC to give 5-[(S)-5-(3-amino-propyl)-3-tert-butoxycarbonylamino-2-oxo-2,3,4,5-tetrahydro-benzo[b][1,4]diazepin-1-ylmethyl]-6-methoxy-naphthalene-2-carboxylic acid trifluoroacetate (0.080 g, white powder).

Step 4: To a solution of 5-[(S)-5-(3-amino-propyl)-3-tert-butoxycarbonylamino-2-oxo-2,3,4,5-tetrahydro-benzo[b][1,4]diazepin-1-ylmethyl]-6-methoxy-naphthalene-2-carboxylic acid trifluoroacetate (0.080 g 0.124 mmol) in 18.6 mL of DMF was added DIEA (0.0649 mL 0.372 mmol) and pentafluorophenyl diphenylphosphinate (0.0714 g 0.186 mmol). After 3 h at RT the mixture was diluted with H₂O and EtOAc, the organic layer was washed with 1 M citric acid, brine, sat. Na₂CO₃ and brine, dried over Na₂SO₄, filtered and concentrated to give a material that was purified by silica gel chromatography to afford cyclic-5-[(S)-5-(3-amino-propyl)-3-tert-butoxycarbonylamino-2-oxo-2,3,4,5-tetrahydro-benzo[b][1,4]diazepin-1-ylmethyl]-6-methoxy-naphthalene-2-carboxylic amide (0.063, white solid).

Step 5: In a similar manner to that described for Example 1 except the reaction was stirred for 1.5 h, cyclic-5-[(S)-5-(3-amino-propyl)-3-tert-butoxycarbonylamino-2-oxo-2,3,4,5-tetrahydro-benzo[b][1,4]diazepin-1-ylmethyl]-6-methoxy-naphthalene-2-carboxylic amide (0.063 g 0.119 mmol) was converted to cyclic-5-[(S)-3-amino-5-(3-amino-propyl)-2-oxo-2,3,4,5-tetrahydro-benzo[b][1,4]diazepin-1-ylmethyl]-6-methoxy-naphthalene-2-carboxylic amide hydrochloride (0.044 g, white powder).

Step 6: In a similar manner to that described for methyl-[(S)-1-((S)-1-naphthalen-1-ylmethyl-2-oxo-2,3,4,5-tetrahydro-1H-benzo[b][1,4]diazepin-3-ylcarbamoyl)-ethyl]-carbamic acid tert-butyl ester except the mixture was stirred at RT 4 h, cyclic-5-[(S)-3-amino-5-(3-amino-propyl)-2-oxo-2,3,4,5-tetrahydro-benzo[b][1,4]diazepin-1-ylmethyl]-6-methoxy-naphthalene-2-carboxylic amide hydrochloride (0.044 g 0.1 mmol) and BOC-N-Me-Ala-OH (0.023 g 0.11 mmol) were reacted to give a material that was purified by silica gel chromatography to afford cyclic-5-{(S)-5-(3-amino-propyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic amide (0.039 g white solid).

Step 7: In a similar manner to that described for Example 1 except the reaction was stirred for 4 h, cyclic-5-{(S)-5-(3-amino-propyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic amide (0.039 g 0.063 mmol) was converted to the title compound (0.028 g, off-white powder). MS m/z 516 (MH+).

Example 59

Cyclic-5-[(S)-5-(2-Amino-ethyl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride

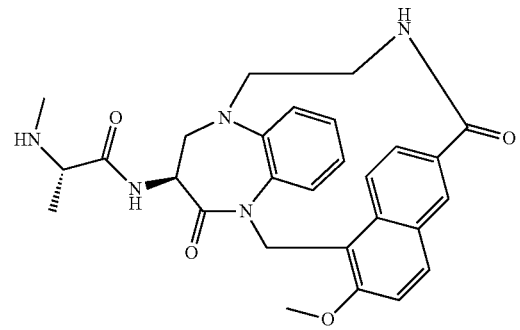 [SMILES: CN[C@@H](C)C(=O)N[C@H]1CN2CCNC(=O)c3ccc4c(c(OC)ccc4c3)CN(C1=O)c1ccccc12]

In a similar manner to that described for Example 58, except benzyl 3-oxoethylcarbamate was used instead of benzyl 3-oxopropylcarbamate, (S)-methyl-5-((3-(tert-butoxycarbonylamino)-2-oxo-2,3,4,5-tetrahydro-1H-benzo[b][1,4]diazepin-1-yl)methyl)-6-methoxy-2-naphthoate was converted to the title compound. m/z 502 (MH$^+$).

Example 60

6-((S)-3-((S)-2-(methylamino)propanamido)-5-((2-methylnaphthalen-1-yl)methyl)-4-oxo-2,3,4,5-tetrahydro-1H-benzo[b][1,4]diazepin-1-yl)-6-oxo-hexanoic acid hydrochloride

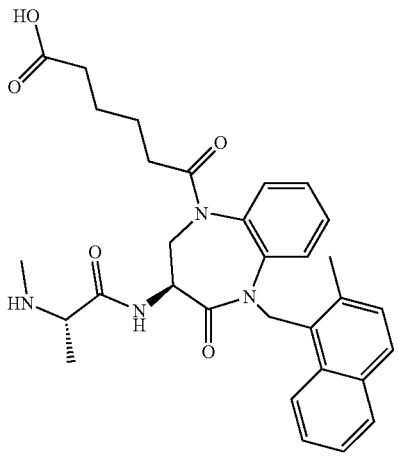 [SMILES: CN[C@@H](C)C(=O)N[C@H]1CN(C(=O)CCCCC(=O)O)c2ccccc2N(Cc2c(C)ccc3ccccc23)C1=O]

Step 1: To a solution of 6-[(S)-3-[(S)-2-(tert-butoxycarbonyl-methyl-amino)-propionylamino]-5-(2-methyl-naphthalen-ylmethyl)-4-oxo-2,3,4,5-tetrahydro-benzo[b][1,4]diazepin-1-yl]-6-oxo-hexanoic acid methyl ester (0.035 g 0.053 mmol) in 1.0 mL of THF and 0.2 mL of H$_2$O was added of 1 M LiOH (0.106 mL 0.106 mmol) and the mixture stirred at RT for 3 h. 1 M citric acid was added, the mixture extracted with EtOAc. The extracts were washed with 1 M citric acid, brine, dried over anhydr. Na$_2$SO$_4$, filtered and concentrated to give a material that was purified by silica gel chromatography to afford 6-[(S)-3-[(S)-2-(tert-butoxycarbonyl-methyl-amino)-propionylamino]-5-(2-methyl-naphthalen-1 ylmethyl)-4-oxo-2,3,4,5-tetrahydro-benzo[b][1,4]diazepin-1-yl]-6-oxo-hexanoic acid (0.030 g, white solid).

In a similar manner to that described for Example 1, 6-[(S)-3-[(S)-2-(tert-butoxycarbonyl-methyl-amino)-propionylamino]-5-(2-methyl-naphthalen-1 ylmethyl)-4-oxo-2,3,4,5-tetrahydro-benzo[b][1,4]diazepin-1-yl]-6-oxo-hexanoic acid (0.030 g (0.047 mmol) was converted to the title compound (0.027 g, white solid). MS m/z 545 (MH$^+$).

Example 61

5-[(S)-5-(3-Amino-propionyl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic acid methyl ester hydrochloride

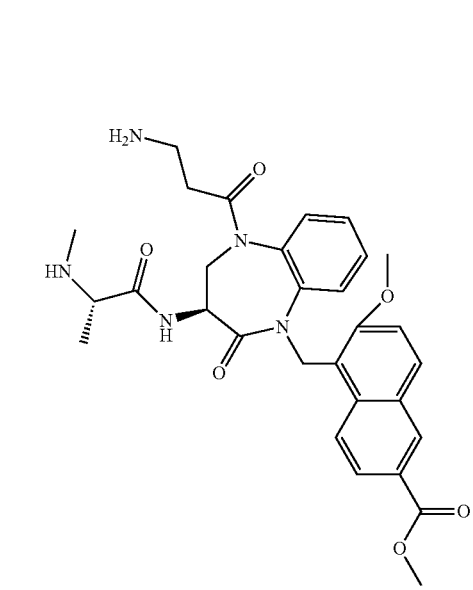 [SMILES: CN[C@@H](C)C(=O)N[C@H]1CN(C(=O)CCN)c2ccccc2N(Cc2c(OC)ccc3cc(C(=O)OC)ccc23)C1=O]

Step 1: A solution of 5-{(S)-3-[(S)-2-(tert-butoxycarbonyl-methyl-amino)-propionylamino]-5-[3-(9H-fluoren-9-yl-methoxycarbonylamino)-propionyl]-2-oxo-2,3,4,5-tetrahydro-benzo[b][1,4]diazepin-1-ylmethyl}-6-methoxyl-naphthalene-2-carboxylic acid methyl ester (0.297 g 0.336 mmol) in 9.28 mL of piperidine/DCM 1:1 was stirred at RT for 2 h, the mixture was diluted with DCM, extracted with aq. Na$_2$CO$_3$, dried over anhydr. Na$_2$SO$_4$, filtered and concentrated to give a material that was purified by silica gel chromatography to afford 5-{(S)-5-(3-amino-propionyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (0.214 g, light yellow powder).

Step 2: In a similar manner to that described for Example 1, 5-{(S)-5-(3-amino-propionyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (15 mg 0.023 mmol was converted to the title compound (14 mg, white solid). MS m/z 562 (MH$^+$).

Example 62

5-(((S)-5-(3-aminopropanoyl)-3-((S)-2-(methyl-amino)propanamido)-2-oxo-2,3,4,5-tetrahydro-1H-benzo[b][1,4]diazepin-1-yl)methyl)-6-methoxy-2-naphthoic acid hydrochloride

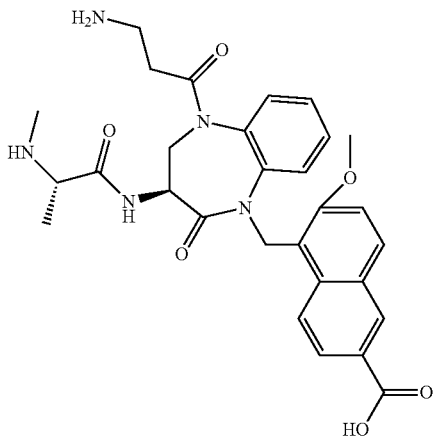 [SMILES: CN[C@@H](C)C(=O)N[C@H]1CN(C(=O)CCN)c2ccccc2N(Cc2c(OC)ccc3cc(C(=O)O)ccc23)C1=O]

Step 1: To a solution of 5-{(S)-5-(3-amino-propionyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid methyl ester (0.184 g 0.278 mmol) in 2.0 mL of MeOH and 0.5 mL H$_2$O was added of 1 M LiOH (0.834 mL 0.834 mmol) and the mixture stirred at RT for 72 h. The mixture was concentrated and adjusted to ca. pH 7.0 with 1 N HCl and lyophilized to give to give a material that was purified by HPLC to afford 5-{(S)-5-(3-amino-propionyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid (0.090 g, white solid).

Step 2: In a similar manner to that described for Example 1 except the material was not lyophilized, 5-{(S)-5-(3-amino-propionyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid (22 mg 0.040 mmol) was converted to the title compound (24 mg, white solid). MS m/z 585 (MH$^+$).

Example 63

Cyclic-5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride

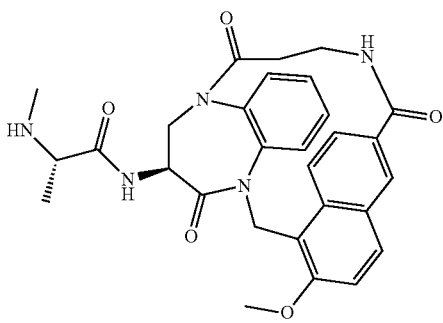 [SMILES: CN[C@@H](C)C(=O)N[C@H]1CN2C(=O)CCNC(=O)c3ccc4c(c(OC)ccc4c3)CN(C1=O)c1ccccc12]

In a similar manner to that described for Example 51 except in Step 2 the mixture was stirred for 4 h, 5-{(S)-5-(3-amino-propionyl)-3-[(S)-2-(tert-butoxycarbonyl-methyl-amino)-propionylamino]-2-oxo-2,3,4,5-tetrahydro-benzo[b][1,4]diazepin-1-ylmethyl}-6-methoxy-naphthalene-2-carboxylic acid (0.090 g 0.139 mmol) was converted to the title compound (0.0506 g, light brown solid). MS m/z 530 (MH$^+$).

Example 64

(S)—N—((S)-5-(4-acetylbenzoyl)-1-((2-methyl-naphthalen-1-yl)methyl)-2-oxo-2,3,4,5-tetrahydro-1H-benzo[b][1,4]diazepin-3-yl)-2-aminopropanamide hydrochloride

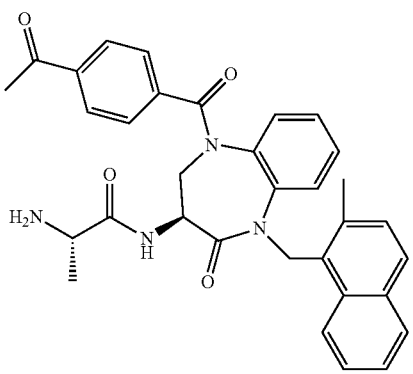 [SMILES: CC(=O)c1ccc(C(=O)N2C[C@H](NC(=O)[C@H](C)N)C(=O)N(Cc3c(C)ccc4ccccc34)c3ccccc32)cc1]

Step 1: To a 0° C. solution of ((S)-2-oxo-2,3,4,5-tetrahydro-1H-benzo[b][1,4]diazepin-3-yl)-carbamic acid tert-butyl ester (3.63 g, 13.1 mmol) and 4-acetylbenzoic acid (2.36 g, 14.4 mmol) in pyridine (131 mL) was added POCl₃ (2.4 mL, 26 mmol). After 1 h at 0° C., the mixture was diluted H₂O and extracted with EtOAc. The combined extracts were washed with 1 N aq. citric acid, H₂O, sat. aq. NaHCO₃, and brine, dried over Na₂SO₄, filtered, and concentrated. The residue was purified by flash chromatography. This resulting material was repurified by flash chromatography to provide (S)-tert-butyl 1-(4-acetylbenzoyl)-4-oxo-2,3,4,5-tetrahydro-1H-benzo[b][1,4]diazepin-3-ylcarbamate (4.18 g, 75%) as an off-white solid. LC-MS m/z 446 [M+Na]⁺.

Step 2: To a solution of (S)-tert-butyl 1-(4-acetylbenzoyl)-4-oxo-2,3,4,5-tetrahydro-1H-benzo[b][1,4]diazepin-3-yl-carbamate (4.18 g, 9.87 mmol) in DMF (49.4 mL) was added 1-(chloromethyl)-2-methylnaphthalene (2.82 g, 14.8 mmol), Cs₂CO₃ (4.82 g, 14.8 mmol), and NaI (2.22 g, 14.8 mmol). After 2.5 h the mixture was diluted with H₂O and extracted with EtOAc. The combined extracts were washed with sat. aq. NaHCO₃, H₂O, and brine, dried over Na₂SO₄, filtered, and concentrated. The residue was purified by flash chromatography to provide (S)-tert-butyl 5-(4-acetylbenzoyl)-1-((2-methylnaphthalen-1-yl)methyl)-2-oxo-2,3,4,5-tetrahydro-1H-benzo[b][1,4]diazepin-3-ylcarbamate (5.02 g, 88%) as a white foam. LC-MS m/z 600 [M+Na]⁺.

Step 3: A solution of (S)-tert-butyl 5-(4-acetylbenzoyl)-1-((2-methylnaphthalen-1-yl)methyl)-2-oxo-2,3,4,5-tetrahydro-1H-benzo[b][1,4]diazepin-3-ylcarbamate (5.02 g, 8.69 mmol) in 4 M HCl in dioxane (43.5 mL) was stirred for 16 h, the mixture concentrated and the residue triturated with Et₂O to provide (S)-5-(4-acetylbenzoyl)-3-amino-1-((2-methylnaphthalen-1-yl)methyl)-4,5-dihydro-H-benzo[b][1,4]diazepin-2(3H)-one hydrochloride (4.24 g, 95%) as a white solid. LC-MS m/z 468 (MH)⁺.

Step 4: To a suspension of (S)-5-(4-acetylbenzoyl)-3-amino-1-((2-methylnaphthalen-1-yl)methyl)-4,5-dihydro-H-benzo[b][1,4]diazepin-2(3H)-one hydrochloride (100 mg, 0.195 mmol) in DMF (648 μl) was added N-Boc-L-alanine (40.5 mg, 0.214 mmol), DIEA (135 μl, 0.778 mmol), and HBTU (81.2 mg, 0.214 mmol). After 2 h, the mixture was diluted with EtOAc, washed with sat. aq. NaHCO₃, H₂O, and brine, dried over Na₂SO₄, filtered, and concentrated. The residue was purified by flash chromatography to provide tert-butyl (S)-1-((S)-5-(4-acetylbenzoyl)-1-((2-methylnaphthalen-1-yl)methyl)-2-oxo-2,3,4,5-tetrahydro-1H-benzo[b][1,4]diazepin-3-ylamino)-1-oxopropan-2-ylcarbamate (106 mg, 84%) as a white solid. LC-MS m/z 671 [M+Na]⁺.

Step 5: A solution of tert-butyl (S)-1-((S)-5-(4-acetylbenzoyl)-1-((2-methylnaphthalen-1-yl)methyl)-2-oxo-2,3,4,5-tetrahydro-1H-benzo[b][1,4]diazepin-3-ylamino)-1-oxopropan-2-ylcarbamate (103.8 mg, 0.1600 mmol) in 4 M HCl in dioxane (800 μL) was stirred for 1 h. The reaction was concentrated and the residue was triturated with Et₂O. The residue was taken up in MeCN—H₂O and lyophilized to provide the title compound (76.5 mg, 82%) as a white solid. LC-MS m/z 549 (MH)⁺.

Example 65

(S)-2-amino-N—((S)-5-(4-aminobenzoyl)-1-((2-methoxynaphthalen-1-yl)methyl)-2-oxo-2,3,4,5-tetrahydro-1H-benzo[b][1,4]diazepin-3-yl)propanamide

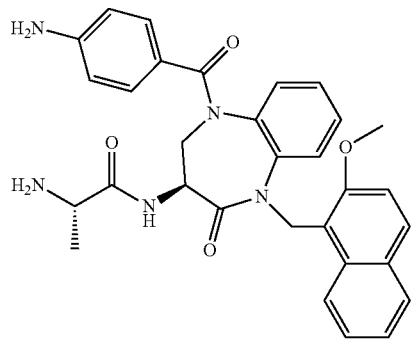 [SMILES: COc1ccc2ccccc2c1CN1C(=O)[C@@H](NC(=O)[C@H](C)N)CN(C(=O)c2ccc(N)cc2)c2ccccc21]

Step 1: In a similar manner to that described for Example 64 Step 2 except 1.2 eq. of Cs₂CO₃ and NaI were used and the mixture was stirred 16 h, (S)-tert-butyl 1-(4-nitrobenzoyl)-4-oxo-2,3,4,5-tetrahydro-1H-benzo[b][1,4]diazepin-3-ylcarbamate (3.68 g, 8.64 mmol) and 6-bromo-1-(chloromethyl)-2-methoxynaphthalene (2.71 g, 9.5 mmol) were converted to (S)-tert-butyl 1-((6-bromo-2-methoxynaphthalen-1-yl)methyl)-5-(4-nitrobenzoyl)-2-oxo-2,3,4,5-tetrahydro-1H-benzo[b][1,4]diazepin-3-ylcarbamate (5.05 g, 87%) as a yellow foam. LC-MS m/z 697/699 [M+Na]⁺.

Step 2: A solution of (S)-tert-butyl 1-((6-bromo-2-methoxynaphthalen-1-yl)methyl)-5-(4-nitrobenzoyl)-2-oxo-2,3,4,5-tetrahydro-1H-benzo[b][1,4]diazepin-3-ylcarbamate (5.05 g, 7.48 mmol) in 4 M HCl in dioxane (37.4 mL) was stirred for 16 h. The mixture was concentrated and the residue was triturated with Et₂O to provide (S)-3-amino-1-((6-bromo-2-methoxynaphthalen-1-yl)methyl)-5-(4-nitrobenzoyl)-4,5-dihydro-H-benzo[b][1,4]diazepin-2(3H)-one hydrochloride (4.57 g, quant.) as a light yellow solid. LC-MS m/z 575/577 (MH)⁺.

Step 3: In a similar manner to that described for Example 64, Step 4, except the mixture was stirred 30 min., (S)-3-amino-1-((6-bromo-2-methoxynaphthalen-1-yl)methyl)-5-(4-nitrobenzoyl)-4,5-dihydro-H-benzo[b][1,4]diazepin-2(3H)-one hydrochloride (186 mg, 304 mol) in DMF (1.01 mL) and (S)-2-(tert-butoxycarbonylamino)propanoic acid (63.3 mg, 334 mol), DIEA (210 μL, 1.22 mmol) were converted to tert-butyl (S)-1-((S)-1-((6-bromo-2-methoxynaphthalen-1-yl)methyl)-5-(4-nitrobenzoyl)-2-oxo-2,3,4,5-tetrahydro-1H-benzo[b][1,4]diazepin-3-ylamino)-1-oxopropan-2-ylcarbamate (186 mg, 82%) as a white solid. LC-MS m/z 768/770 [M+Na]⁺.

Step 4: A mixture of tert-butyl (S)-1-((S)-1-((6-bromo-2-methoxynaphthalen-1-yl)methyl)-5-(4-nitrobenzoyl)-2-oxo-2,3,4,5-tetrahydro-1H-benzo[b][1,4]diazepin-3-ylamino)-1-oxopropan-2-ylcarbamate (186 mg, 249 μmol) in MeOH, EtOAc, and DMF (2 mL) was sparged with Ar for 30 min, then 10% Pd/C (26.5 mg, 24.9 μmol) was added. The mixture was shaken under H₂ at 40 psi for 3 h. The mixture was filtered through Celite, the filter cake washed with MeOH and the filtrate concentrated. The residue was purified by flash chromatography. The resulting material was purified by preparative HPLC to provide, after extraction from sat. aq. NaHCO₃ using CH₂Cl₂, tert-butyl (S)-1-((S)-5-(4-aminobenzoyl)-1-((2-methoxynaphthalen-1-yl)methyl)-2-oxo-2,3,4,5-tetrahydro-1H-benzo[b][1,4]diazepin-3-ylamino)-1-oxopropan-2-ylcarbamate (71.3 mg, 45%) as a white solid. LC-MS m/z 660 [M+Na]⁺.

Step 5: A solution of tert-butyl (S)-1-((S)-5-(4-aminobenzoyl)-1-((2-methoxynaphthalen-1-yl)methyl)-2-oxo-2,3,4,5-tetrahydro-1H-benzo[b][1,4]diazepin-3-ylamino)-1-oxopropan-2-ylcarbamate (71.3 mg, 112 μmol) in 4 M HCl in dioxane (1.12 mL) was stirred for 4 h. The reaction was concentrated and the residue was taken up in MeCN—H₂O and lyophilized to provide the title compound (63.7 mg, 99%) as a white solid. LC-MS m/z 538 (MH)⁺.

Example 66

(2S)-2-(methylamino)-N-[(3S)-5-[(2-methyl-1-naphthyl)methyl]-1-(4-nitrobenzoyl)-4-oxo-2,3-dihydro-1,5-benzodiazepin-3-yl]propanamide hydrochloride

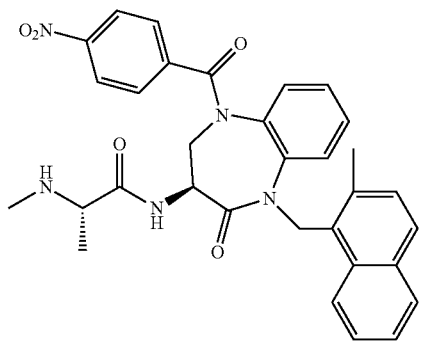

A solution of tert-butyl methyl((S)-1-((S)-1-((2-methylnaphthalen-1-yl)methyl)-5-(4-nitrobenzoyl)-2-oxo-2,3,4,5-tetrahydro-1H-benzo[b][1,4]diazepin-3-ylamino)-1-oxopropan-2-yl)carbamate (106.8 mg, 160 μmol) in 4 M HCl in dioxane (1.6 mL) was stirred at RT for 2 h, the mixture concentrated and the residue taken up in H₂O-MeCN and lyophilized to provide (S)-2-(methylamino)-N—((S)-1-((2-methylnaphthalen-1-yl)methyl)-5-(4-nitrobenzoyl)-2-oxo-2,3,4,5-tetrahydro-1H-benzo[b][1,4]diazepin-3-yl)propanamide hydrochloride (92.7 mg, 96%) as a white solid. LC-MS m/z 566 (MH)⁺.

Example 67

(S)—N—((S)-5-(4-aminobenzoyl)-1-((2-methylnaphthalen-1-yl)methyl)-2-oxo-2,3,4,5-tetrahydro-1H-benzo[b][1,4]diazepin-3-yl)-2-(methylamino)propanamide hydrochloride

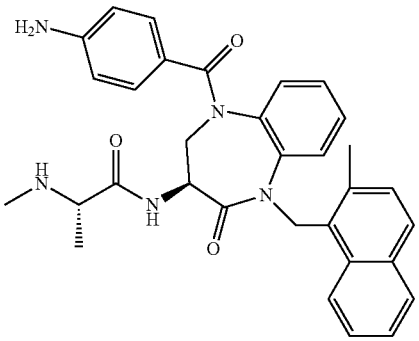 [SMILES: CN[C@@H](C)C(=O)N[C@H]1CN(C(=O)c2ccc([N+](=O)[O-])cc2)c2ccccc2N(Cc2c(C)ccc3ccccc23)C1=O]

Step 1: To a solution of tert-butyl methyl((S)-1-((S)-1-((2-methylnaphthalen-1-yl)methyl)-5-(4-nitrobenzoyl)-2-oxo-2,3,4,5-tetrahydro-1H-benzo[b][1,4]diazepin-3-ylamino)-1-oxopropan-2-yl)carbamate (190 mg, 285 μmol) in EtOH (2.85 mL) was added tin(II) chloride dihydrate (322 mg, 1.43 mmol) and the mixture heated to 30° C. After 4 h, the mixture was diluted with 1:1 sat. aq. NaHCO₃—H₂O, and extracted with CH₂Cl₂. The combined extracts were washed with H₂O and brine, dried over Na₂SO₄, filtered, and concentrated. The residue was purified by flash chromatography to provide tert-butyl (S)-1-((S)-5-(4-aminobenzoyl)-1-((2-methylnaphthalen-1-yl)methyl)-2-oxo-2,3,4,5-tetrahydro-1H-benzo[b][1,4]diazepin-3-ylamino)-1-oxopropan-2-yl(methyl)carbamate (171 mg, 94%) as a white solid. LC-MS m/z 658 [M+Na]⁺.

Step 2: A solution of tert-butyl (S)-1-((S)-5-(4-aminobenzoyl)-1-((2-methylnaphthalen-1-yl)methyl)-2-oxo-2,3,4,5-tetrahydro-1H-benzo[b][1,4]diazepin-3-ylamino)-1-oxopropan-2-yl(methyl)carbamate (169 mg, 266 μmol) in 4 M HCl in dioxane (2.39 mL) and MeOH (266 μL) was stirred for 2 h, concentrated and the residue was taken up in H₂O-MeCN and lyophilized to provide the title compound (141 mg, 93%) as a white solid. LC-MS m/z 536 (MH)⁺

Example 68

(R)—N—((S)-5-(4-acetylbenzoyl)-1-((2-methyl-naphthalen-1-yl)methyl)-2-oxo-2,3,4,5-tetrahydro-1H-benzo[b][1,4]diazepin-3-yl)-2-(methylamino)propanamide hydrochloride

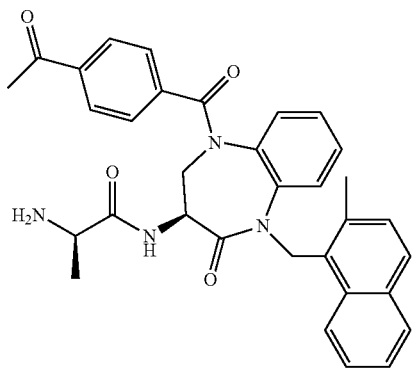 [SMILES: CC(=O)c1ccc(C(=O)N2C[C@H](NC(=O)[C@@H](C)N)C(=O)N(Cc3c(C)ccc4ccccc34)c3ccccc32)cc1]

Step 1: In a similar manner to that described for Example 64 Step 4, (S)-5-(4-acetylbenzoyl)-3-amino-1-((2-methylnaphthalen-1-yl)methyl)-4,5-dihydro-1H-benzo[b][1,4]diazepin-2(3H)-one hydrochloride (57.0 mg, 111 μmol) in DMF (370 μL) and Boc-N-methyl-D-alanine (24.8 mg, 122 μmol were converted to tert-butyl (R)-1-((S)-5-(4-acetylbenzoyl)-1-((2-methylnaphthalen-1-yl)methyl)-2-oxo-2,3,4,5-tetrahydro-1H-benzo[b][1,4]diazepin-3-ylamino)-1-oxopropan-2-yl(methyl)carbamate (55.8 mg, 76%) as a white solid. LC-MS m/z 685 [M+Na]+.

Step 2: A solution of tert-butyl (R)-1-((S)-5-(4-acetylbenzoyl)-1-((2-methylnaphthalen-1-yl)methyl)-2-oxo-2,3,4,5-tetrahydro-1H-benzo[b][1,4]diazepin-3-ylamino)-1-oxopropan-2-yl(methyl)carbamate (54.3 mg, 81.9 μmol) in 4 M HCl in dioxane (410 μL) was stirred for 30 min. concentrated, taken up in H$_2$O and lyophilized to provide the title compound (44.0 mg, 90%) as a white solid. LC-MS m/z 563 (MH)+.

Example 69 a (S)—N—((S)-5-(4-Acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-(methylamino)propanamide hydrochloride

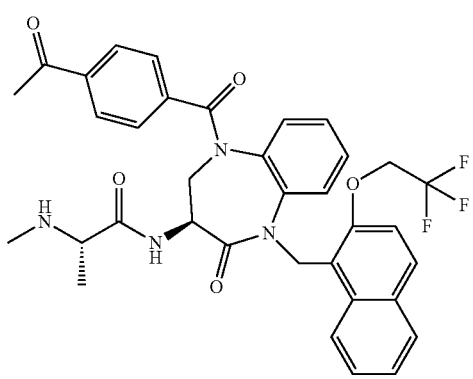 [SMILES: CN[C@@H](C)C(=O)N[C@H]1CN(C(=O)c2ccc(C(C)=O)cc2)c2ccccc2N(Cc2c(OCC(F)(F)F)ccc3ccccc23)C1=O]

Step 1: In a similar manner to that described for Example 64, Step 2, except 1.2 eq. of Cs$_2$CO$_3$ and NaI were used, tert-butyl (S)-1-((S)-1-(4-acetylbenzoyl)-4-oxo-2,3,4,5-tetrahydro-1H-benzo[b][1,4]diazepin-3-ylamino)-1-oxopropan-2-yl(methyl)carbamate (75.2 mg, 148 μmol) and 1-(chloromethyl)-2-(2,2,2-trifluoroethoxy)naphthalene (44.7 mg, 163 μmol) were converted to tert-butyl (S)-1-((S)-5-(4-acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-ylamino)-1-oxopropan-2-yl(methyl)carbamate (82.4 mg, 75%) as a white solid. LC-MS m/z 769 [M+Na]+.

Step 2: A solution of tert-butyl (S)-1-((S)-5-(4-acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-ylamino)-1-oxopropan-2-yl(methyl)carbamate (80.4 mg, 108 μmol) in 4 M HCl in dioxane (538 μL) was stirred at rt for 1 h. The mixture was concentrated and the residue was triturated with Et$_2$O, the solid taken up in H$_2$O and lyophilized to provide the title compound (64.9 mg, 88%) as a white solid. LC-MS m/z 647 (MH)+.

The compounds in Table 2 below were prepared in a similar manner to that described in Example 69 (a) using the appropriate alkyl chloride, bromide, or mesylate as the alkylating reagent. The conditions in Step 1 were varied so that the amount of alkylating reagent ranged from 1.1-1.2 equivalents, the amount of Cs$_2$CO$_3$ ranged from 1.2-1.3 equivalents, and the amount of NaI ranged from 1.2-1.3 equivalents except in Example 69b where no NaI was used. The total reaction time for Step 1 ranged from 3-20 h. The product from Example 69c contained an impurity that was carried into the next step. For Example 69b, the conditions of Step 2 the 4 M HCl in dioxane was replaced by a 4:1 mixture of 2 M HCl in Et$_2$O and CH$_2$Cl$_2$ to which MeOH was added after 2 h. Example 69c was purified by preparative HPLC and the product was extracted from sat. aq. NaHCO$_3$ using CH$_2$Cl$_2$. The resulting material was dissolved in MeOH, treated with 2 M HCl in Et$_2$O and concentrated to obtain the HCl salt. For Examples 69d-g, the 4 M HCl in dioxane was replaced by a 4:1 mixture of 2 M HCl in Et$_2$O and MeOH and reaction time ranged from 1.5-3 h.

TABLE 2

| Example | Final Product | LC-MS m/z (MH)+ |
| --- | --- | --- |
| 69b | | 615 |

TABLE 2-continued

| Example | Final Product | LC-MS m/z (MH)+ |
|---|---|---|
| 69c | 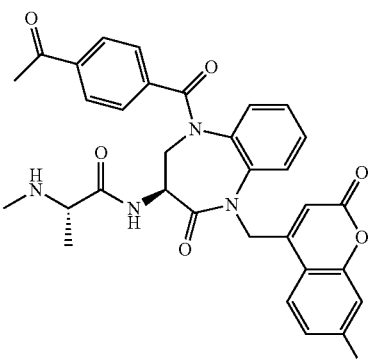 | 597 |
| 69d | 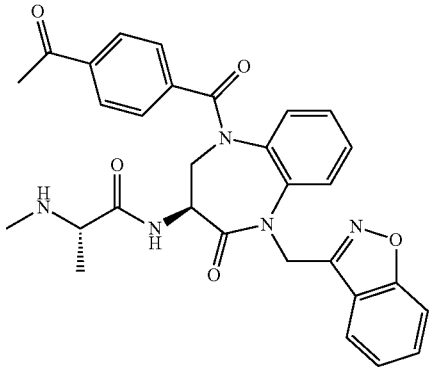 [SMILES: CN[C@@H](C)C(=O)N[C@H]1CN(C(=O)c2ccc(C(C)=O)cc2)c2ccccc2N(Cc2noc3ccccc23)C1=O] | 540 |
| 69e | 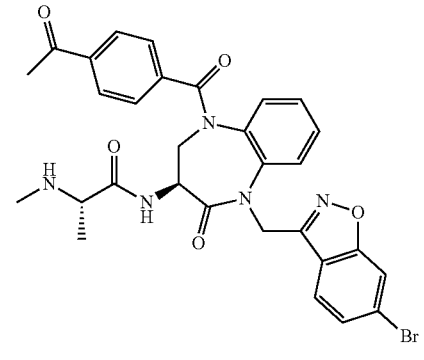 [SMILES: CN[C@@H](C)C(=O)N[C@H]1CN(C(=O)c2ccc(C(C)=O)cc2)c2ccccc2N(Cc2noc3cc(Br)ccc23)C1=O] | 618/620 |
| 69f | 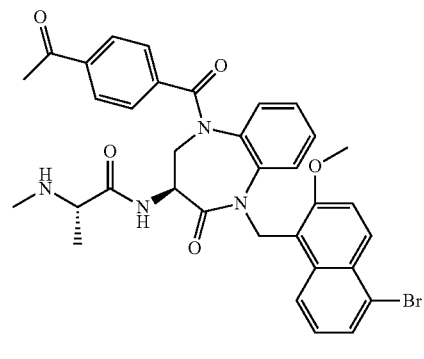 [SMILES: CN[C@@H](C)C(=O)N[C@H]1CN(C(=O)c2ccc(C(C)=O)cc2)c2ccccc2N(Cc2c(OC)ccc3c(Br)cccc23)C1=O] | 657/659 |

TABLE 2-continued

| Example | Final Product | LC-MS m/z (MH)+ |
|---|---|---|
| 69g | 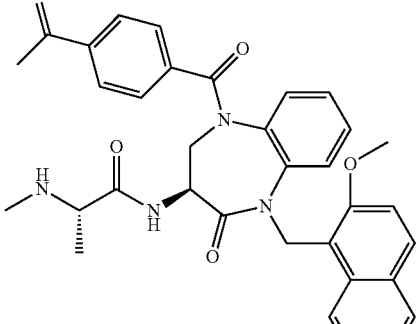 | 579 |

The compounds in Table 3 below were prepared in a similar manner to that described in Example 69a starting from tert-butyl (S)-1-((S)-1-(4-acetylbenzoyl)-4-oxo-2,3,4,5-tetrahydro-1H-benzo[b][1,4]diazepin-3-ylamino)-1-oxo-propan-2-ylcarbamate and using the appropriate alkyl chloride, bromide, or mesylate as the alkylating reagent in Step 1. For Example 69i NaI was omitted in Step 1. The reaction time for Step 1 ranged from 4-20 h. For Example 69i, the 4 M HCl in dioxane was replaced by a 4:1 mixture of 2 M HCl in Et$_2$O and CH$_2$Cl$_2$ to which MeOH was added after 3 h. For Example 69k, the 4 M HCl in dioxane was replaced by a 4:1 mixture of 2 M HCl in Et$_2$O and MeOH. The reaction time for Step 2 ranged from 1-4.5 h.

TABLE 3

| Example | Final Product | LC-MS m/z (MH)+ |
|---|---|---|
| 69h | 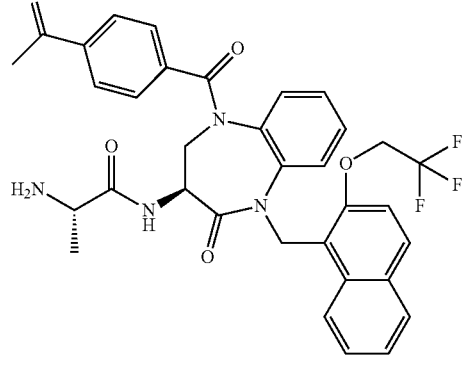 | 633 |

TABLE 3-continued

| Example | Final Product | LC-MS m/z (MH)+ |
|---|---|---|
| 69i | [structure] | 601 |
| 69j | [structure] | 583 |
| 69k | [structure] | 526 |

The compounds in Table 4 below were prepared in a similar manner to that described in Example 69a, starting from methyl-d3-tert-butyl (S)-1-((S)-1-(4-acetylbenzoyl)-4-oxo-2,3,4,5-tetrahydro-1H-benzo[b][1,4]diazepin-3-ylamino)-1-oxopropan-2-ylcarbamate using the appropriate alkyl chloride or mesylate as the alkylating reagent. The conditions in Step 1 were varied so that 1.2 equivalents of alkylating reagent, 1.3 equivalents of Cs$_2$CO$_3$, and 1.3 equivalents of NaI were used except in Example 69n where NaI was omitted. The total reaction time for Step 1 was 16 h. The conditions of Step 2 were varied so that the 4 M HCl in dioxane was replaced by an equivalent volume of a 4:1 mixture of 2 M HCl in Et$_2$O and MeOH. The total reaction time for Step 2 ranged from 1.5-2 h.

TABLE 4

| Example | Final Product | LC-MS m/z (MH)+ |
|---|---|---|
| 69l | [structure] | 660/662 |

| Example | Final Product | LC-MS m/z (MH)+ |
|---|---|---|
| 69m | | 660/662 |
| 69n | | 618 |

Example 70

4-(((S)-5-(4-Acetylbenzoyl)-3-((S)-2-(methylamino) propanamido)-2-oxo-2,3,4,5-tetrahydro-1H-benzo[b] [1,4]diazepin-1-yl)methyl)-3-(2,2,2-trifluoroethoxy) quinoline 1-oxide hydrochloride

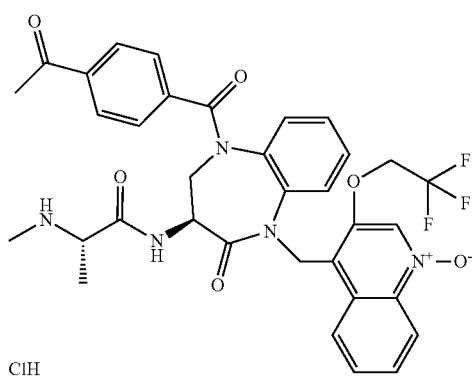 [SMILES: CN[C@@H](C)C(=O)N[C@H]1CN(C(=O)c2ccc(C(C)=O)cc2)c2ccccc2N(Cc2c(OCC(F)(F)F)c[n+]([O-])c3ccccc23)C1=O ; Cl]

Step 1: To a suspension of 3-hydroxyquinoline-4-carboxylic acid (4.977 g, 26.3 mmol) in CH₂Cl₂ (263 mL) was added MeOH (53.4 mL, 1.32 µmol), 1-(3-dimethylaminopropyl)-3-ethylcarbodiimide hydrochloride (EDCI, 5.55 g, 28.9 mmol), and 4-dimethylamino-pyridine (321 mg, 2.63 mmol). After 40 h, the mixture was concentrated and the residue was taken up in EtOAc and washed with H₂O. The aqueous layer was extracted with EtOAc. The combined extracts were washed with brine, dried over Na₂SO₄, filtered, and concentrated. The residue was purified by flash chromatography to provide methyl 3-hydroxyquinoline-4-carboxylate (2.56 g, 48% yield) as an off-white solid. LC-MS m/z 204 (MH)+.

Step 2: To a solution of methyl 3-hydroxyquinoline-4-carboxylate (2.56 g, 12.6 mmol) in DMF (126 mL) was added 2,2,2-trifluoroethyl 4-methylbenzenesulfonate (4.8 g, 18.9 mmol) and K₂CO₃ (4.35 g, 31.5 mmol) and the mixture heated to 80° C. After 16 h, the mixture was cooled, diluted with a mixture of H₂O and brine, and extracted with EtOAc. The combined organic extracts were washed with brine, dried over Na₂SO₄, filtered, and concentrated. The residue was purified by flash chromatography to provide methyl 3-(2,2,2-trifluoroethoxy)quinoline-4-carboxylate (0.505 g, 14%) as a light yellow solid. LC-MS m/z 286 (MH)+.

Step 3: To a solution of methyl 3-(2,2,2-trifluoroethoxy) quinoline-4-carboxylate (244 mg, 855 µmol) in THF (6.42 mL) and EtOH (2.14 mL) was added lithium borohydride (93.2 mg, 4.28 mmol). After 22 h, the mixture was diluted with H₂O and extracted with EtOAc. The combined extracts were washed with 1 M HCl and brine, dried over Na₂SO₄, filtered, and concentrated. The residue was purified by flash chromatography to provide (3-(2,2,2-trifluoroethoxy)quinolin-4-yl)MeOH (43.5 mg, 20%) as a white solid. The combined aqueous layers from the above procedure were made basic with 1 M NaOH and extracted with EtOAc. The combined extracts were washed with brine, dried over Na₂SO₄, filtered, and concentrated to give a residue that was triturated with CH₂Cl₂ to provide additional (3-(2,2,2-trifluoroethoxy)quinolin-4-yl)MeOH (56.9 mg, 26%) as a white solid. LC-MS m/z 258 (MH)+. Step 4: To a suspension of (3-(2,2,2-trifluoroethoxy)quinolin-4-yl)MeOH (98.8 mg, 384 mol) in CH$_2$Cl$_2$ (3.84 mL) was added TEA (107 L, 768 μmol) and methanesulfonyl chloride (35.7 L, 461 μmol). After 45 min., the mixture was diluted with CH$_2$Cl$_2$, washed with H$_2$O and brine, dried over Na$_2$SO$_4$, filtered, and concentrated. The material obtained was added to a solution of tert-butyl (S)-1-((S)-1-(4-acetylbenzoyl)-4-oxo-2,3,4,5-tetrahydro-1H-benzo[b][1,4]diazepin-3-ylamino)-1-oxopropan-2-yl(methyl)carbamate (120 mg, 236 μmol) in DMF (590 μL) and Cs$_2$CO$_3$ (99.9 mg, 307 μmol) was added. After 3 h, the mixture was diluted with EtOAc and washed with H$_2$O and brine, dried over Na$_2$SO$_4$, filtered, and concentrated. The residue was purified by flash chromatography to provide tert-butyl (S)-1-((S)-5-(4-acetylbenzoyl)-2-oxo-1-((3-(2,2,2-trifluoroethoxy)quinolin-4-yl)methyl)-2,3,4,5-tetrahydro-1H-benzo[b][1,4]diazepin-3-ylamino)-1-oxopropan-2-yl(methyl)carbamate (153 mg, 87%) as a white solid. LC-MS m/z 770 [M+Na]$^+$.

Step 5: To a solution of tert-butyl (S)-1-((S)-5-(4-acetylbenzoyl)-2-oxo-1-((3-(2,2,2-trifluoroethoxy)quinolin-4-yl)methyl)-2,3,4,5-tetrahydro-1H-benzo[b][1,4]diazepin-3-ylamino)-1-oxopropan-2-yl(methyl)carbamate (51.6 mg, 69.0 μmol) in CH$_2$Cl$_2$ (690 μL) was added 3-chloroperoxybenzoic acid (32.5 mg, 145 μmol). After 3 h, the mixture was diluted with CH$_2$Cl$_2$, washed with 1 M NaOH and brine, dried over Na$_2$SO$_4$, filtered, and concentrated to provide 4-(((S)-5-(4-acetylbenzoyl)-3-((S)-2-(tert-butoxycarbonyl(methyl)amino)propanamido)-2-oxo-2,3,4,5-tetrahydro-1H-benzo[b][1,4]diazepin-1-yl)methyl)-3-(2,2,2-trifluoroethoxy)quinoline 1-oxide (48.3 mg, 92%) as a light yellow solid. LC-MS m/z 764 (MH)$^+$.

Step 6: A solution of 4-(((S)-5-(4-acetylbenzoyl)-3-((S)-2-(tert-butoxycarbonyl(methyl)amino)propanamido)-2-oxo-2,3,4,5-tetrahydro-1H-benzo[b][1,4]diazepin-1-yl)methyl)-3-(2,2,2-trifluoroethoxy)quinoline 1-oxide (23.4 mg, 30.6 μmol) in 4 M HCl in dioxane (306 μL) was stirred for 40 min. and the mixture was concentrated. The residue was diluted with Et$_2$O, the mixture concentrated and the residue taken up in H$_2$O and lyophilized to provide the title compound (18.5 mg, 86%) as a white solid. LC-MS m/z 664 (MH)$^+$.

Example 71

(S)—N—((S)-5-(4-Aminobenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride

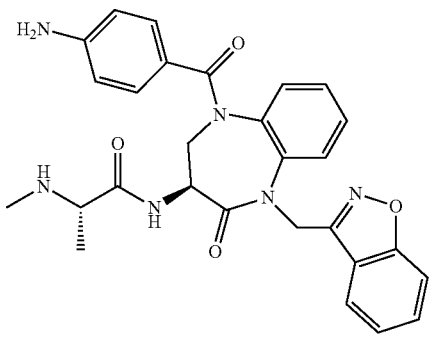 [SMILES: CN[C@@H](C)C(=O)N[C@H]1CN(C(=O)c2ccc(N)cc2)c2ccccc2N(Cc2noc3ccccc23)C1=O]

Step 1: To a −78° C. solution of ((S)-2-oxo-2,3,4,5-tetrahydro-1H-benzo[b][1,4]diazepin-3-yl)-carbamic acid tert-butyl ester (807 mg, 2.91 mmol) in THF (19.4 mL) was added lithium bis(trimethylsilyl)amide (3.2 mL, 1.0 M solution in THF, 3.2 mmol), dropwise. The mixture was stirred at −78° C. for 15 min, then a mixture of NaI (523 mg, 3.49 mmol) and 3-(bromomethyl)benzo[d]isoxazole (740 mg, 3.49 mmol) in THF (9.7 mL) was added dropwise over 10 min. The mixture was stirred at −78° C. for 50 min., warmed to RT and stirred for 4.5 h. The mixture was diluted with 1 N citric acid and extracted with EtOAc. The combined extracts were washed with sat. aq. NaHCO$_3$, brine, dried over Na$_2$SO$_4$, filtered, and concentrated. The residue was purified by flash chromatography. The resulting material was repurified by flash chromatography to provide a ~4:1 mixture of (S)-tert-butyl 1-(benzo[d]isoxazol-3-ylmethyl)-2-oxo-2,3,4,5-tetrahydro-1H-benzo[b][1,4]diazepin-3-ylcarbamate and (S)-tert-butyl 1-(benzo[d]isoxazol-3-ylmethyl)-4-oxo-2,3,4,5-tetrahydro-1H-benzo[b][1,4]diazepin-3-ylcarbamate (742 mg, 63%) as a yellow foam. LC-MS m/z 431 [M+Na]$^+$.

Step 2: A solution of a ~4:1 mixture of (S)-tert-butyl 1-(benzo[d]isoxazol-3-ylmethyl)-2-oxo-2,3,4,5-tetrahydro-1H-benzo[b][1,4]diazepin-3-ylcarbamate and (S)-tert-butyl 1-(benzo[d]isoxazol-3-ylmethyl)-4-oxo-2,3,4,5-tetrahydro-1H-benzo[b][1,4]diazepin-3-ylcarbamate (740.1 mg, 1.81 mmol) in 4 M HCl in dioxane (9.06 mL) was stirred for 30 min. The mixture was concentrated and the residue was triturated with Et$_2$O to provide a light brown solid. This material was taken up in DMF (6.04 mL) and DIEA (1.25 mL, 7.25 mmol), Boc-N-methyl-L-alanine (405 mg, 1.99 mmol) and HBTU (756 mg, 1.99 mmol) were added. After 1 h, the mixture was diluted with sat. aq. Na$_2$CO$_3$ and extracted with EtOAc. The combined extracts were washed with H$_2$O, brine, dried over Na$_2$SO$_4$, filtered and concentrated. The residue was purified by flash chromatography to provide a ~4:1 mixture of tert-butyl (S)-1-((S)-1-(benzo[d]isoxazol-3-ylmethyl)-2-oxo-2,3,4,5-tetrahydro-1H-benzo[b][1,4]diazepin-3-ylamino)-1-oxopropan-2-yl(methyl)carbamate and tert-butyl (S)-1-((S)-1-(benzo[d]isoxazol-3-ylmethyl)-4-oxo-2,3,4,5-tetrahydro-1H-benzo[b][1,4]diazepin-3-ylamino)-1-oxopropan-2-yl(methyl)carbamate (569 mg, 64%) as an off-white solid. LC-MS m/z 516 [M+Na]$^+$.

Step 3: To a 0° C. solution of a ~4:1 mixture of tert-butyl (S)-1-((S)-1-(benzo[d]isoxazol-3-ylmethyl)-2-oxo-2,3,4,5-tetrahydro-1H-benzo[b][1,4]diazepin-3-ylamino)-1-oxopropan-2-yl(methyl)carbamate and tert-butyl (S)-1-((S)-1-(benzo[d]isoxazol-3-ylmethyl)-4-oxo-2,3,4,5-tetrahydro-1H-benzo[b][1,4]diazepin-3-ylamino)-1-oxopropan-2-yl(methyl)carbamate (70.6 mg, 143 μmol) in CH$_2$Cl$_2$ (1.43 mL) was added pyridine (116 μL, 1.43 mmol), followed by 4-nitrobenzoyl chloride (29.2 mg, 157 μmol). After 1 h at 0° C., the mixture was diluted with H$_2$O and extracted with CH$_2$Cl$_2$. The combined extracts were washed with 1 N aq. citric acid, sat. aq. NaHCO$_3$, and brine, dried over Na$_2$SO$_4$, filtered, and concentrated. The residue was purified by flash chromatography to afford the title compound (66.1 mg, 72%) as a white solid. LC-MS m/z 665 [M+Na]$^+$.

Step 4: In a similar manner to that described for Example 67, Step 1, tert-butyl (S)-1-((S)-1-(benzo[d]isoxazol-3-ylmethyl)-5-(4-nitrobenzoyl)-2-oxo-2,3,4,5-tetrahydro-1H-benzo[b][1,4]diazepin-3-ylamino)-1-oxopropan-2-yl(methyl)carbamate (64.5 mg, 100 μmol) was converted to tert-butyl (S)-1-((S)-5-(4-aminobenzoyl)-1-(benzo[d]isoxazol-3-ylmethyl)-2-oxo-2,3,4,5-tetrahydro-1H-benzo[b][1,4]diazepin-3-ylamino)-1-oxopropan-2-yl(methyl)carbamate (50.6 mg, 82%) as a white solid. LC-MS m/z 635 [M+Na]$^+$.

Step 5: To a solution of tert-butyl (S)-1-((S)-5-(4-aminobenzoyl)-1-(benzo[d]isoxazol-3-ylmethyl)-2-oxo-2,3,4,5-tetrahydro-1H-benzo[b][1,4]diazepin-3-ylamino)-1-oxopropan-2-yl(methyl)carbamate (49.2 mg, 80.3 μmol) in MeOH (161 μL) was added 2 M HCl in Et$_2$O (642 μL). After 3 h, the mixture was concentrated and the residue was triturated with Et$_2$O, the material taken up in H$_2$O and lyophilized to afford the title compound (37.2 mg, 84%) as a white solid. LC-MS m/z 513 (MH)$^+$.

Example 72

Methyl 4-((S)-5-(benzo[d]isoxazol-3-ylmethyl)-3-((S)-2-(methylamino)propanamido)-4-oxo-2,3,4,5-tetrahydro-1H-benzo[b][1,4]diazepine-1-carbonyl)benzoate hydrochloride

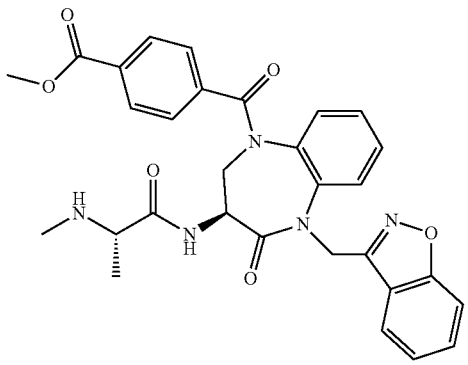 [SMILES: CN[C@@H](C)C(=O)N[C@H]1CN(C(=O)c2ccc(C(=O)OC)cc2)c2ccccc2N(Cc2noc3ccccc23)C1=O]

Step 1: To a 0° C. solution of ~4:1 mixture of tert-butyl (S)-1-((S)-1-(benzo[d]isoxazol-3-ylmethyl)-2-oxo-2,3,4,5-tetrahydro-1H-benzo[b][1,4]diazepin-3-ylamino)-1-oxopropan-2-yl(methyl)carbamate and tert-butyl (S)-1-((S)-1-(benzo[d]isoxazol-3-ylmethyl)-4-oxo-2,3,4,5-tetrahydro-1H-benzo[b][1,4]diazepin-3-ylamino)-1-oxopropan-2-yl(methyl)carbamate (209.4 mg, 424 μmol) in CH$_2$Cl$_2$ (4.24 mL) was added pyridine (343 L, 4.24 mmol), followed by methyl 4-(chlorocarbonyl)benzoate (92.7 mg, 467 μmol). After 1 h at 0° C. the mixture was diluted with H$_2$O and extracted with CH$_2$Cl$_2$. The combined extracts were washed with 1 N aq. citric acid, sat. aq. NaHCO$_3$, and brine, dried over Na$_2$SO$_4$, filtered, and concentrated. The residue was purified by flash chromatography. The resulting material was repurified by flash chromatography to provide methyl 4-((S)-5-(benzo[d]isoxazol-3-ylmethyl)-3-((S)-2-(tert-butoxycarbonyl(methyl)amino) propanamido)-4-oxo-2,3,4,5-tetrahydro-1H-benzo[b][1,4]diazepine-1-carbonyl)benzoate (194 mg, 70%) as a white solid. LC-MS m/z 678 [M+Na]$^+$.

Step 2: In a similar manner to that described for Example 71, Step 5, methyl 4-((S)-5-(benzo[d]isoxazol-3-ylmethyl)-3-((S)-2-(tert-butoxycarbonyl(methyl)amino) propanamido)-4-oxo-2,3,4,5-tetrahyd-1H-benzo[b][1,4]diazepine-1-carbonyl)benzoate (44.7 mg, 68.2 μmol) was converted to methyl 4-((S)-5-(benzo[d]isoxazol-3-ylmethyl)-3-((S)-2-(methylamino)propanamido)-4-oxo-2,3,4,5-tetrahydro-1H-benzo[b][1,4]diazepine-1-carbonyl)benzoate hydrochloride (28.7 mg, 71%) as a white solid. LC-MS m/z 556 (MH)$^+$.

Example 73

(S)—N—((S)-1-((5-Bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride

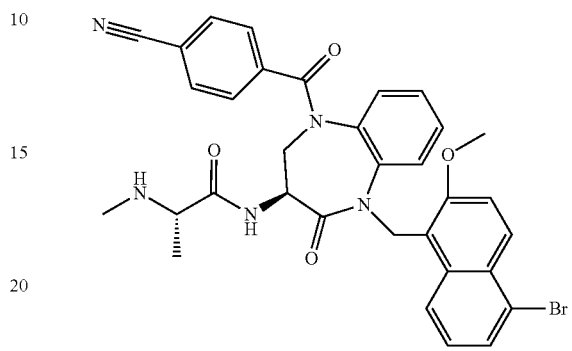

Step 1: To a 0° C. solution of ((S)-2-oxo-2,3,4,5-tetrahydro-1H-benzo[b][1,4]diazepin-3-yl)-carbamic acid tert-butyl ester (400 mg, 1.44 mmol) in pyridine (14.4 mL) was added 4-cyanobenzoic acid (233 mg, 1.59 mmol), and POCl$_3$ (264 μL, 2.88 mmol). After 1 h at 0° C. the mixture was diluted with H$_2$O and extracted with EtOAc. The combined extracts were washed with 1 N aq. citric acid, H$_2$O, sat. aq. NaHCO$_3$, and brine, dried over Na$_2$SO$_4$, filtered, and concentrated. The residue was purified by flash chromatography to provide (S)-tert-butyl 1-(4-cyanobenzoyl)-4-oxo-2,3,4,5-tetrahydro-1H-benzo[b][1,4]diazepin-3-ylcarbamate (337 mg, 58%) as an off-white solid. LC-MS m/z 429 [M+Na]$^+$.

Step 2: In a similar manner to that described for Example 71, Step 2, (S)-tert-butyl 1-(4-cyanobenzoyl)-4-oxo-2,3,4,5-tetrahydro-1H-benzo[b][1,4]diazepin-3-yl-carbamate (453 mg, 1.11 mmol) and Boc-N-methyl-L-alanine (249 mg, 1.23 mmol) were converted to tert-butyl (S)-1-((S)-1-(4-cyanobenzoyl)-4-oxo-2,3,4,5-tetrahydro-1H-benzo[b][1,4]diazepin-3-ylamino)-1-oxopropan-2-yl(methyl)carbamate (431 mg, 79%) as a white solid. LC-MS m/z 514 [M+Na]$^+$.

Step 3: In a similar manner to that described for Example 64, Step 2, except 1.3 eq. of Cs$_2$CO$_3$ and NaI were used and the mixture was stirred for 16 h, tert-butyl (S)-1-((S)-1-(4-cyanobenzoyl)-4-oxo-2,3,4,5-tetrahydro-1H-benzo[b][1,4]diazepin-3-ylamino)-1-oxopropan-2-yl(methyl)carbamate (144 mg, 293 μmol) and 5-bromo-1-(chloromethyl)-2-methoxynaphthalene (100 mg, 352 μmol) were converted to tert-butyl (S)-1-((S)-1-((5-bromo-2-methoxynaphthalen-1-yl)methyl)-5-(4-cyanobenzoyl)-2-oxo-2,3,4,5-tetrahydro-1H-benzo[b][1,4]diazepin-3-ylamino)-1-oxopropan-2-yl(methyl)carbamate (155 mg, 71%) as a white solid. LC-MS m/z 762/764 [M+Na]$^+$.

Step 4: In a similar manner to that described for Example 71, Step 5, except the mixture was stirred for 2 h and the trituration with Et$_2$O was omitted, tert-butyl (S)-1-((S)-1-((5-bromo-2-methoxynaphthalen-1-yl)methyl)-5-(4-cyanobenzoyl)-2-oxo-2,3,4,5-tetrahydro-1H-benzo[b][1,4]diazepin-3-ylamino)-1-oxopropan-2-yl(methyl)carbamate (155 mg, 209 μmol) was converted to the title compound (125.7 mg, 89% yield) as a white solid. LC-MS m/z 640/642 (MH)$^+$.

161

Example 74

(S)—N—((S)-5-(4-Cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide

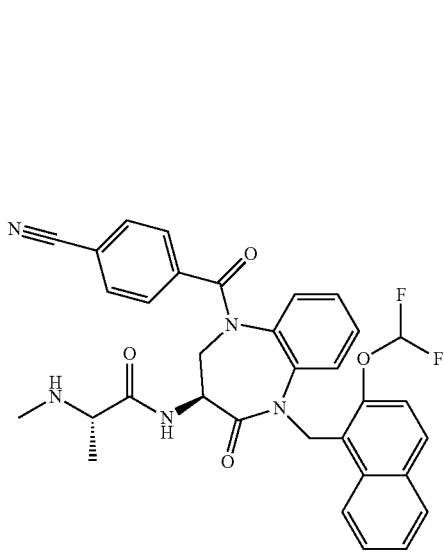 [SMILES: CN[C@@H](C)C(=O)N[C@H]1CN(C(=O)c2ccc(C#N)cc2)c2ccccc2N(Cc2c(OC(F)F)ccc3ccccc23)C1=O]

Step 1: In a similar manner to that described for Example 64, Step 2, except 1.3 eq. of Cs₂CO₃ were used and NaI was omitted and the mixture was stirred 16 h, tert-butyl (S)-1-((S)-1-(4-cyanobenzoyl)-4-oxo-2,3,4,5-tetrahydro-1H-benzo[b][1,4]diazepin-3-ylamino)-1-oxopropan-2-yl(methyl)carbamate (144 mg, 293 µmol) and (2-(difluoromethoxy)naphthalen-1-yl)methyl methanesulfonate (106 mg, 352 µmol) were converted to tert-butyl (S)-1-((S)-5-(4-cyanobenzoyl)-1-((2-(difluoromethoxy)naphthalen-1-yl)methyl)-2-oxo-2,3,4,5-tetrahydro-1H-benzo[b][1,4]diazepin-3-ylamino)-1-oxopropan-2-yl(methyl)carbamate (162 mg, 79%) as a white solid. LC-MS m/z 720 [M+Na]⁺.

Step 2: To a solution of tert-butyl (S)-1-((S)-5-(4-cyanobenzoyl)-1-((2-(difluoromethoxy)naphthalen-1-yl)methyl)-2-oxo-2,3,4,5-tetrahydro-1H-benzo[b][1,4]diazepin-3-ylamino)-1-oxopropan-2-yl(methyl)carbamate (162 mg, 232 µmol) in MeOH (232 µL) was added 2 M HCl in Et₂O (929 µL). The reaction was stirred at RT for 2 h. The reaction was concentrated and purified by reverse phase HPLC to provide, after extraction from sat. aq. NaHCO₃ using CH₂Cl₂, the title compound (65.7 mg, 47%) as a white solid. LC-MS m/z 598 (MH)⁺.

162

Example 75 a (S)—N—((S)-1-((6-Bromo-2-methoxynaphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride

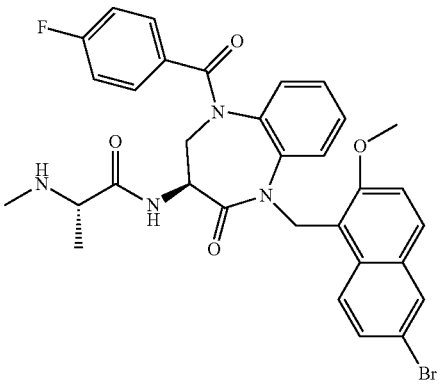 [SMILES: CN[C@@H](C)C(=O)N[C@H]1CN(C(=O)c2ccc(F)cc2)c2ccccc2N(Cc2c(OC)ccc3cc(Br)ccc23)C1=O]

Step 1: To a 0° C. solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methylcarbamic acid tert-butyl ester (149 mg, 244 µmol) in CH₂Cl₂ (2.44 mL) was added pyridine (59.6 µL, 731 mol) and 4-fluorobenzoyl chloride (32.1 µL, 268 µmol). The reaction was stirred at 0° C. for 30 min., warmed to RT and stirred for 1.5 h. Additional 4-fluorobenzoyl chloride (15.6 µL, 134 mol) was added and the mixture was stirred for an additional 22 h. The mixture was diluted with CH₂Cl₂, washed with 1 N citric acid, sat. aq. NaHCO₃, brine, dried over Na₂SO₄, filtered, and concentrated. The residue was purified by flash chromatography to provide tert-butyl (S)-1-((S)-1-((6-bromo-2-methoxynaphthalen-1-yl)methyl)-5-(4-fluorobenzoyl)-2-oxo-2,3,4,5-tetrahydro-H-benzo[b][1,4]diazepin-3-ylamino)-1-oxopropan-2-yl(methyl)carbamate (170 mg, 95%) as a white solid. LC-MS m/z 755/757 [M+Na]⁺.

Step 2: In a similar manner to that described for Example 71, Step 5, except the trituration with Et₂O was omitted and the residue was taken up in MeCN—H₂O and lyophilized, tert-butyl (S)-1-((S)-1-((6-bromo-2-methoxynaphthalen-1-yl)methyl)-5-(4-fluorobenzoyl)-2-oxo-2,3,4,5-tetrahydro-1H-benzo[b][1,4]diazepin-3-ylamino)-1-oxopropan-2-yl(methyl)carbamate (170 mg, 232 µmol) was converted to the title compound (132.7 mg, 86%) as an off-white solid. LC-MS m/z 633/635 (MH)⁺.

The compounds in Table 5 below were prepared in a similar manner to that described in Example 75a, using the appropriate acid chloride. The conditions in Step 1 were varied so that the total amount of acid chloride ranged from 1.1-1.7 equivalents and the total reaction time ranged from 1.5-20 h. The total reaction time for Step 2 ranged from 2-4 h.

TABLE 5

| Example | Final Product | LC-MS m/z (MH)+ |
|---|---|---|
| 75b | | 629/631 |
| 75c | | 606/608 |
| 75d | | 623/625 |

Example 76 a (S)—N—((S)-1-((6-Bromo-2-methoxynaphthalen-1-yl)methyl)-2-oxo-5-(2-(pyridin-3-yl)acetyl)-2,3,4,5-tetrahydro-1H-benzo[b][1,4]diazepin-3-yl)-2-(methylamino)propanamide hydrochloride

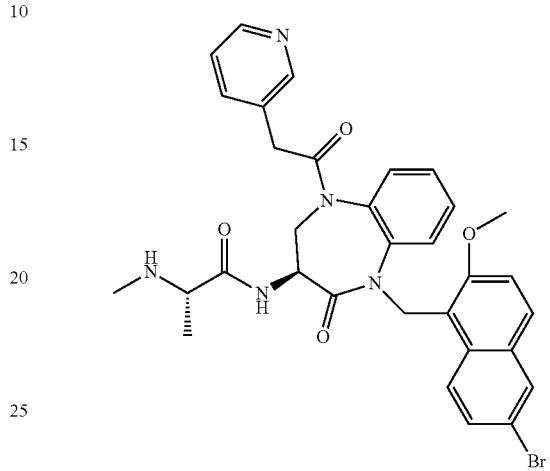

Step 1: To a 0° C. solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (125 mg, 204 μmol) in pyridine (2.04 mL) was added 2-(pyridin-3-yl)acetic acid (30.8 mg, 225 μmol) and POCl₃ (37.4 L, 409 μmol). The mixture was stirred at 0° C. for 1 h, diluted with EtOAc, washed with 1 N aq. citric acid, H₂O, sat. aq. NaHCO₃, and brine, dried over Na₂SO₄, filtered, and concentrated. The residue was purified by flash chromatography to provide tert-butyl (S)-1-((S)-1-((6-bromo-2-methoxynaphthalen-1-yl)methyl)-2-oxo-5-(2-(pyridin-3-yl)acetyl)-2,3,4,5-tetrahydro-1H-benzo[b][1,4]diazepin-3-ylamino)-1-oxopropan-2-yl(methyl)carbamate (149 mg, quant.) as a white solid. LC-MS m/z 730/732 (MH)+.

Step 2: In a similar manner to that described for Example 71, Step 5, except the trituration with Et₂O was omitted and the residue was taken up in MeCN—H₂O and lyophilized, tert-butyl (S)-1-((S)-1-((6-bromo-2-methoxynaphthalen-1-yl)methyl)-2-oxo-5-(2-(pyridin-3-yl)acetyl)-2,3,4,5-tetrahydro-1H-benzo[b][1,4]diazepin-3-ylamino)-1-oxopropan-2-yl(methyl)carbamate (149 mg, 204 μmol) was converted to the title compound (116.4 mg, 86%) as a white solid. LC-MS m/z 630/632 (MH)+

The compounds in Table 6 below were prepared in a similar manner to that described in Example 76a, using the appropriate carboxylic acid. The conditions in Step 1 were varied so that the total reaction time ranged from 1 h-3 days. Examples 76c-76c were purified by preparative HPLC. The conditions of Step 2 in Examples 76d and 76e were varied so that the 4 M HCl in dioxane was replaced by an equivalent volume of a 4:1 mixture of CH₂Cl₂ and TFA. The total reaction time for Step 2 ranged from 1-4 h.

TABLE 6

| Example | Final Product | LC-MS m/z (MH)+ |
|---|---|---|
| 76b | | 631/633 |
| 76c | | 617/619 |
| 76d | | 672/674 |

TABLE 6-continued

| Example | Final Product | LC-MS m/z (MH)+ |
|---|---|---|
| 76e | | 619/621 |

Example 77

(S)—N—((S)-5-Benzyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate Step 1: To a solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methylcarbamic acid tert-butyl ester (60 mg, 98.1 μmol) in DMF (245 μL) was added benzyl bromide (14.0 μL, 118 μmol), Cs₂CO₃ (44.8 mg, 137 μmol), and NaI (20.6 mg, 137 μmol). After 16 h, the mixture was diluted with a mixture of H₂O, MeOH, and DMSO and purified by reverse phase HPLC to provide tert-butyl (S)-1-((S)-5-benzyl-1-((6-bromo-2-methoxynaphthalen-1-yl)methyl)-2-oxo-2,3,4,5-tetrahydro-1H-benzo[b][1,4]diazepin-3-ylamino)-1-oxopropan-2-yl(methyl)carbamate (18 mg, 26%) as a white foam. LC-MS m/z 723/725 [M+Na]+.

Step 2: To a solution of tert-butyl (S)-1-((S)-5-benzyl-1-((6-bromo-2-methoxynaphthalen-1-yl)methyl)-2-oxo-2,3,4,5-tetrahydro-1H-benzo[b][1,4]diazepin-3-ylamino)-1-oxopropan-2-yl(methyl)carbamate (18 mg, 25.7 μmol) in CH₂Cl₂ (103 μL) was added TFA (25.7 μL). After 2 h, the mixture was concentrated and the residue was taken up in MeCN—H₂O and lyophilized to provide the title compound (16.3 mg, 89%) as an off-white solid. LC-MS m/z 601/603 (MH)⁺.

Example 78

(S)—N—((S)-1-((6-Bromo-2-methoxynaphthalen-1-yl)methyl)-5-(4-cyanobenzyl)-2-oxo-2,3,4,5-tetrahydro-1H-benzo[b][1,4]diazepin-3-yl)-2-(methylamino)propanamide trifluoroacetate

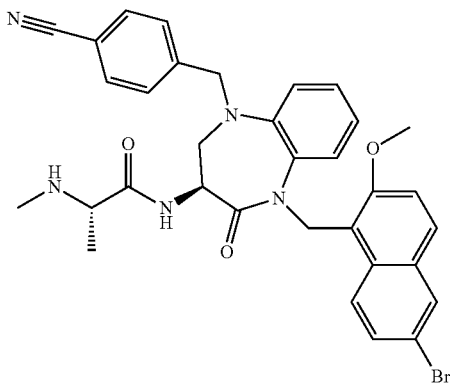 [SMILES: CN[C@@H](C)C(=O)N[C@H]1CN(Cc2ccc(C#N)cc2)c2ccccc2N(Cc2c(OC)ccc3cc(Br)ccc23)C1=O]

Step 1: To a solution of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methylcarbamic acid tert-butyl ester (105 mg, 172 µmol) in DMF (429 µL) was added 4-(bromomethyl)benzonitrile (47.1 mg, 240 µmol), Cs₂CO₃ (83.9 mg, 258 µmol), and NaI (38.6 mg, 258 µmol). After 20 h, the mixture was diluted with EtOAc, washed with H₂O, brine, dried over Na₂SO₄, filtered, and concentrated. The residue was purified by flash chromatography to afford a material was repurified by flash chromatography. The resulting material was purified by reverse phase HPLC to provide tert-butyl (S)-1-((S)-1-((6-bromo-2-methoxynaphthalen-1-yl)methyl)-5-(4-cyanobenzyl)-2-oxo-2,3,4,5-tetrahydro-1H-benzo[b][1,4]diazepin-3-ylamino)-1-oxopropan-2-yl(methyl)carbamate (33.8 mg, 27%) as a white foam. LC-MS m/z 748/750 [M+Na]⁺.

Step 2: In a similar manner to that described for Example 77, Step 2, except the mixture was stirred 1 h, tert-butyl (S)-1-((S)-1-((6-bromo-2-methoxynaphthalen-1-yl)methyl)-5-(4-cyanobenzyl)-2-oxo-2,3,4,5-tetrahydro-1H-benzo[b][1,4]diazepin-3-ylamino)-1-oxopropan-2-yl(methyl)carbamate (33 mg, 45.4 µmol) was converted to the title compound (27.7 mg, 82%) as an off-white solid. LC-MS m/z 626/628 (MH)⁺.

Example 79

(S)—N—((S)-5-(4-Acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)butanamide hydrochloride

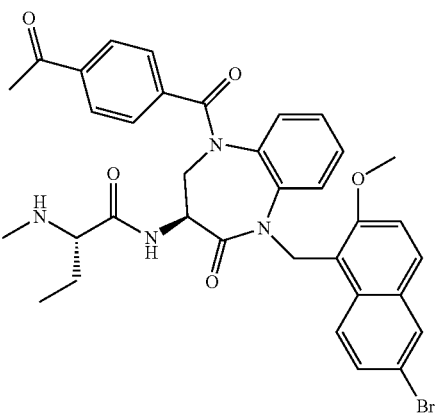 [SMILES: CC[C@H](NC)C(=O)N[C@H]1CN(C(=O)c2ccc(C(C)=O)cc2)c2ccccc2N(Cc2c(OC)ccc3cc(Br)ccc23)C1=O]

Step 1: To a 0° C. solution of [(S)-1-(6-bromo-2-methoxy-naphthalen-1-ylmethyl)-2-oxo-2,3,4,5-tetrahydro-1H-benzo[b][1,4]diazepin-3-yl]-carbamic acid tert-butyl ester (631 mg, 1.2 mmol) in pyridine (12.0 mL) was added 4-acetylbenzoic acid (216 mg, 1.32 mmol) followed by POCl₃ (219 µl, 2.4 mmol), dropwise. After 1 h at 0° C. the mixture was diluted with EtOAc, washed with 1 N aq. citric acid, H₂O, sat. aq. NaHCO₃, and brine, dried over Na₂SO₄, filtered, and concentrated. The residue was purified by flash chromatography to provide (S)-tert-butyl 5-(4-acetylbenzoyl)-1-((6-bromo-2-methoxynaphthalen-1-yl)methyl)-2-oxo-2,3,4,5-tetrahydro-1H-benzo[b][1,4]diazepin-3-ylcarbamate (513 mg, 64%) as a white solid. LC-MS m/z 694/696 [M+Na]⁺.

Step 2: A solution of (S)-tert-butyl 5-(4-acetylbenzoyl)-1-((6-bromo-2-methoxynaphthalen-1-yl)methyl)-2-oxo-2,3,4,5-tetrahydro-1H-benzo[b][1,4]diazepin-3-ylcarbamate (513 mg, 763 µmol) in 4 M HCl in dioxane (3.81 mL) was stirred for 2 h. The mixture was added to Et₂O resulting in a precipitate. The precipitate was collected by filtration and washed with Et₂O to provide (S)-5-(4-acetylbenzoyl)-3-amino-1-((6-bromo-2-methoxynaphthalen-1-yl)methyl)-4,5-dihydro-1H-benzo[b][1,4]diazepin-2(3H)-one hydrochloride (456 mg, 98%) as a white solid. LC-MS m/z 572/574 (MH)⁺.

Step 3: In a similar manner to that described for Example 64, Step 4, (S)-5-(4-acetylbenzoyl)-3-amino-1-((6-bromo-2-methoxynaphthalen-1-yl)methyl)-4,5-dihydro-1H-benzo[b][1,4]diazepin-2(3H)-one hydrochloride (64 mg, 105 µmol) and (S)-2-(tert-butoxycarbonyl(methyl)amino)butanoic acid (25.1 mg, 116 µmol) were converted to tert-butyl (S)-1-((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-ylamino)-1-oxobutan-2-yl(methyl)carbamate (87.5 mg, 100%) as a white foam. LC-MS m/z 793/795 [M+Na]⁺.

Step 4: To a solution of tert-butyl (S)-1-((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-ylamino)-1-oxobutan-2-yl(methyl)carbamate (87 mg, 113 µmol) in MeOH (113 µL) was added 2 M HCl in dioxane (451 µL). After 2 h, the mixture was concentrated, the residue was taken up in MeCN—H₂O and lyophilized to provide the title compound (69.2 mg, 87%) as a white solid. LC-MS m/z 671/673 (MH)⁺.

Example 80

(S)—N—((S)-5-(4-Acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(ethylamino)propanamide hydrochloride

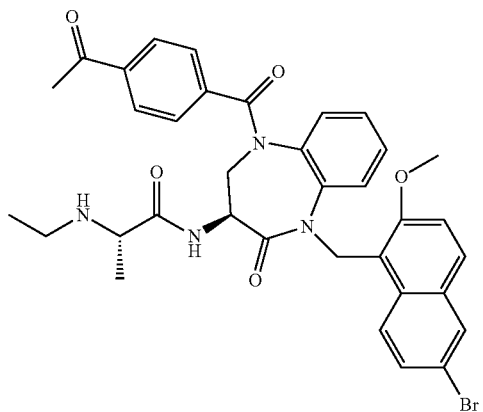 [SMILES: CCN[C@@H](C)C(=O)N[C@H]1CN(C(=O)c2ccc(C(C)=O)cc2)c2ccccc2N(Cc2c(OC)ccc3cc(Br)ccc23)C1=O]

Step 1: In a similar manner to that described for Example 64, Step 4, except the mixture was stirred 30 min., (S)-5-(4-acetylbenzoyl)-3-amino-1-((6-bromo-2-methoxynaphthalen-1-yl)methyl)-4,5-dihydro-H-benzo[b][1,4]diazepin-2(3H)-one hydrochloride (64 mg, 105 µmol) and (S)-2-(tert-butoxycarbonyl(ethyl)amino) propanoic acid (25.1 mg, 116 µmol) were converted to tert-butyl (S)-1-((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-ylamino)-1-oxopropan-2-yl(ethyl)carbamate (79.5 mg, 98%) as a white foam. LC-MS m/z 793/795 [M+Na]⁺.

Step 2: 2 M HCl in dioxane (409 µL) was added to a mixture of tert-butyl (S)-1-((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-ylamino)-1-oxopropan-2-yl(ethyl)carbamate (79 mg, 102 µmol) in MeOH (102 µL). After 2 h the mixture was concentrated the residue was taken up in MeCN—H₂O and lyophilized to afford title compound (58.7 mg, 81%) as a white solid. LC-MS m/z 671/673 (MH)⁺.

Example 81

(S)—N—((S)-1-((5-Bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride

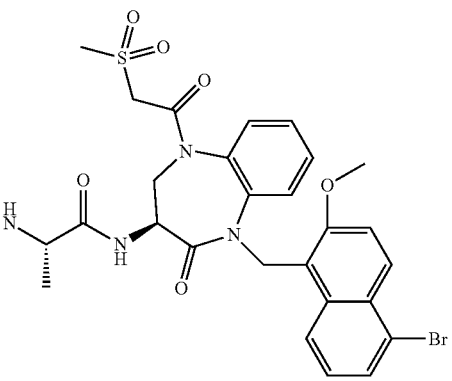

Step 1: To a 0° C. solution of ((S)-2-oxo-2,3,4,5-tetrahydro-1H-benzo[b][1,4]diazepin-3-yl)-carbamic acid tert-butyl ester (530 mg, 1.91 mmol) in pyridine (19.1 mL) was added methanesulfonylacetic acid (290 mg, 2.1 mmol), followed by POCl₃ (350 µL, 3.82 mmol). After 1.5 h at 0° C. the mixture was diluted with H₂O and extracted with EtOAc. The combined extracts were washed with 1 N aq. citric acid, H₂O, sat. aq. NaHCO₃, and brine, dried over Na₂SO₄, filtered, and concentrated. The residue was purified by flash chromatography to provide (S)-tert-butyl 1-(2-(methylsulfonyl)acetyl)-4-oxo-2,3,4,5-tetrahydro-1H-benzo[b][1,4]diazepin-3-ylcarbamate (755 mg, 99%) as a white solid. LC-MS m/z 420 [M+Na]⁺.

Step 2: A solution of (S)-tert-butyl 1-(2-(methylsulfonyl)acetyl)-4-oxo-2,3,4,5-tetrahydro-1H-benzo[b][1,4]diazepin-3-ylcarbamate (509 mg, 1.28 mmol) in 4 M HCl in dioxane (5.12 mL) was stirred at rt for 3 h, during which time solids precipitated. The reaction was diluted with Et₂O and the solids were collected by filtration and washed with Et₂O to provide (S)-3-amino-5-(2-(methylsulfonyl)acetyl)-4,5-dihydro-1H-benzo[b][1,4]diazepin-2(3H)-one hydrochloride (370 mg, 87%) as a white solid.

Step 3: In a similar manner to that described for Example 64, Step 4, except the mixture was stirred 30 min. at 0° C., (S)-3-amino-5-(2-(methylsulfonyl)acetyl)-4,5-dihydro-H-benzo[b][1,4]diazepin-2(3H)-one hydrochloride (368 mg, 1.1 mmol) and (S)-2-(tert-butoxycarbonyl(methyl)amino) propanoic acid (246 mg, 1.21 mmol were converted to tert-butyl methyl((S)-1-((S)-1-(2-(methylsulfonyl)acetyl)-4-oxo-2,3,4,5-tetrahydro-1H-benzo[b][1,4]diazepin-3-ylamino)-1-oxopropan-2-yl)carbamate (416 mg, 78%) as a white solid. LC-MS m/z 505 [M+Na]⁺.

Step 4: In a similar manner to that described for Example 64, Step 2, except 1.3 eq. of Cs₂CO₃ and NaI were used and the mixture was stirred 20 h, tert-butyl methyl((S)-1-((S)-1-(2-(methylsulfonyl)acetyl)-4-oxo-2,3,4,5-tetrahydro-1H-benzo[b][1,4]diazepin-3-ylamino)-1-oxopropan-2-yl)carbamate (60 mg, 124 µmol) and 5-bromo-1-(chloromethyl)-2-methoxynaphthalene were converted to tert-butyl (S)-1-((S)-1-((5-bromo-2-methoxynaphthalen-1-yl)methyl)-5-(2-(methylsulfonyl)acetyl)-2-oxo-2,3,4,5-tetrahydro-1H-benzo

[b][1,4]diazepin-3-ylamino)-1-oxopropan-2-yl(methyl) carbamate (61.3 mg, 67%) as a white solid. LC-MS m/z 753/755 [M+Na]+.

Step 5: In a similar manner to that described for Example 71, Step 5, except the trituration with Et2O was omitted and the residue was taken up in MeCN—H2O and lyophilized, tert-butyl (S)-1-((S)-1-((5-bromo-2-methoxynaphthalen-1-yl)methyl)-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (60 mg, 82.0 µmol) was converted to the title compound (49.3 mg, 90%) as a white solid. LC-MS m/z 631/633 (MH)+.

Example 82

(S)—N—((S)-1-((2-Methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride

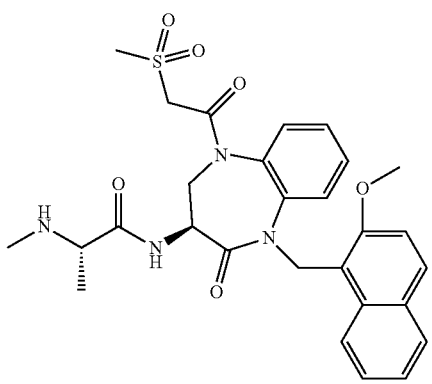 [SMILES: CN[C@@H](C)C(=O)N[C@H]1CN(C(=O)CS(C)(=O)=O)c2ccccc2N(Cc2c(OC)ccc3ccccc23)C1=O]

Step 1: In a similar manner to that described for Example 64, Step 2, except 1.3 eq. of Cs2CO3 and NaI were used and the mixture was stirred 20 h, tert-butyl methyl((S)-1-((S)-1-(2-(methylsulfonyl)acetyl)-4-oxo-2,3,4,5-tetrahydro-1H-benzo[b][1,4]diazepin-3-ylamino)-1-oxopropan-2-yl)carbamate (60 mg, 124 µmol) and 1-(chloromethyl)-2-methoxynaphthalene (30.8 mg, 149 µmol) were converted to tert-butyl (S)-1-((S)-1-((2-methoxynaphthalen-1-yl)methyl)-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (53.8 mg, 66%) as a white solid. LC-MS m/z 675 [M+Na]+.

Step 2: In a similar manner to that described for Example 71, Step 5, except the trituration with Et2O was omitted and the residue was taken up in MeCN—H2O and lyophilized, tert-butyl (S)-1-((S)-1-((2-methoxynaphthalen-1-yl)methyl)-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (52 mg, 79.7 µmol) was converted to the title compound (45.0 mg, 96%) as a white solid. LC-MS m/z 553 (MH)+.

Example 83

(S)—N—((S)-1-((2-(Difluoromethoxy)naphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride

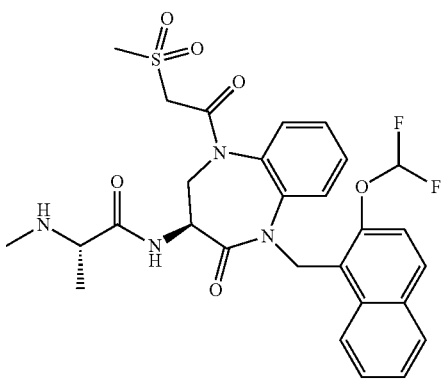 [SMILES: CN[C@@H](C)C(=O)N[C@H]1CN(C(=O)CS(C)(=O)=O)c2ccccc2N(Cc2c(OC(F)F)ccc3ccccc23)C1=O]

Step 1: To a solution of tert-butyl methyl((S)-1-((S)-1-(2-(methylsulfonyl)acetyl)-4-oxo-2,3,4,5-tetrahydro-1H-benzo[b][1,4]diazepin-3-ylamino)-1-oxopropan-2-yl)carbamate (60 mg, 124 µmol) in DMF (311 µL) was added (2-(difluoromethoxy) naphthalen-1-yl)methyl methanesulfonate (45.1 mg, 149 µmol) and Cs2CO3 (52.7 mg, 162 µmol). After 2 h the mixture was diluted with EtOAc, washed with H2O and brine, dried over Na2SO4, filtered, and concentrated. The residue was purified by flash chromatography to provide tert-butyl (S)-1-((S)-1-((2-(difluoromethoxy) naphthalen-1-yl)methyl)-5-(2-(methylsulfonyl) acetyl)-2-oxo-2,3,4,5-tetrahydro-1H-benzo[b][1,4]diazepin-3-ylamino)-1-oxopropan-2-yl(methyl)carbamate (52 mg, 61%) as a white solid. LC-MS m/z 711 [M+Na]+.

Step 2: In a similar manner to that described for Example 71, Step 5, except the trituration with Et2O was omitted and the residue was taken up in MeCN—H2O and lyophilized, tert-butyl (S)-1-((S)-1-((2-(difluoromethoxy)naphthalen-1-yl)methyl)-5-(2-(methylsulfonyl)acetyl)-2-oxo-2,3,4,5-tetrahydro-1H-benzo[b][1,4]diazepin-3-ylamino)-1-oxopropan-2-yl(methyl)carbamate (52 mg, 75.5 µmol) was converted to the title compound (41.8 mg, 89%) as a white solid. LC-MS m/z 589 (MH)+.

Example 84

(2S)—N-[(3S)-5-[[6-bromo-2-(trideuteriomethoxy)-1-naphthyl]methyl]-1-(4-cyanobenzoyl)-4-oxo-2,3-dihydro-1,5-benzodiazepin-3-yl]-2-(methylamino)propanamide hydrochloride

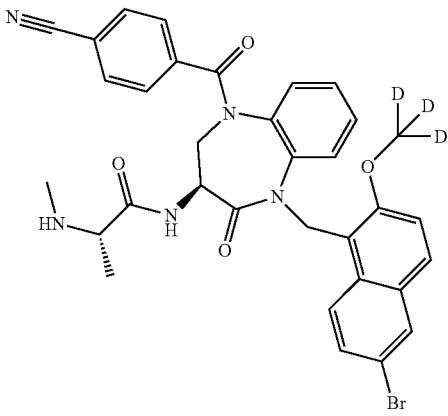 [SMILES: [2H]C([2H])([2H])Oc1ccc2cc(Br)ccc2c1CN1C(=O)[C@@H](NC(=O)[C@H](C)NC)CN(C(=O)c2ccc(C#N)cc2)c2ccccc21]

Step 1: To a −78° C. solution of ((S)-2-oxo-2,3,4,5-tetrahydro-1H-benzo[b][1,4]diazepin-3-yl)-carbamic acid tert-butyl ester (290 mg, 1.05 mmol) in THF (10 mL) was added a 1.0 M solution of lithium bis(trimethylsilyl)amide in THF (1.15 mL, 1.15 mmol). The mixture was stirred at −78° C. for 20 min. and a mixture of NaI (188 mg, 1.25 mmol) and 6-bromo-1-chloromethyl-2-(methoxy-d3)-naphthalene (332 mg, 1.15 mmol) in THF (5 mL) was added. After 50 min. at −78° C. the mixture was warmed to RT and stirred for 16 h. The mixture was diluted with 1 N citric acid and extracted with EtOAc. The combined extracts were washed with a sat. aq. NaHCO₃ solution and brine, the extracts dried over Na₂SO₄, filtered and concentrated. The residue was purified by flash chromatography to afford [(S)-1-(6-bromo-2-(d3-methoxy)-naphthalen-1-ylmethyl)-2-oxo-2,3,4,5-tetrahydro-1H-benzo[b][1,4]diazepin-3-yl]-carbamic acid tert-butyl ester (306 mg, 55%) as a white foam. LCMS m/z 529 (MH)⁺.

Step 2: A solution of [(S)-1-(6-bromo-2-(d3-methoxy)-naphthalen-1-ylmethyl)-2-oxo-2,3,4,5-tetrahydro-1H-benzo[b][1,4]diazepin-3-yl]-carbamic acid tert-butyl ester (304 mg, 574 mol) in 4 M HCl in dioxane (3 mL) was stirred for 30 min. and concentrated to afford (S)-3-amino-1-(6-bromo-2-(d3-methoxy)-naphthalen-1-ylmethyl)-1,3,4,5-tetrahydro-benzo[b][1,4]diazepin-2-one hydrochloride as a light yellow solid (267 mg) which was used without purification.

Step 3: In a similar manner to that described for Example 64, Step 4, except the mixture was stirred 20 h, (S)-3-amino-1-(6-bromo-2-(d3-methoxy)-naphthalen-1-ylmethyl)-1,3,4,5-tetrahydro-benzo[b][1,4]diazepin-2-one hydrochloride (267 mg, 573 μmol) and Boc-N-methyl-L-alanine (128 mg, 631 μmol), DIEA (397 μl, 2.29 mmol) were converted to {(S)-1-[(S)-1-(6-bromo-2-(d3-methoxy)-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (248 mg, 70%) as a light yellow oil. LCMS m/z 614 (MH)⁺.

Step 4: To solution of {(S)-1-[(S)-1-(6-bromo-2-(d3-methoxy)-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (120 mg, 195 μmol) and 4-cyanobenzoic acid (29 mg, 195 μmol) in pyridine (2 mL) at 0° C. was added POCl₃ (36 μl, 391 μmol). After 1 h the mixture was diluted with H₂O and extracted with EtOAc. The extracts were washed with 1 N citric acid, H₂O, sat. aq. NaHCO₃, and brine, dried over Na₂SO₄, filtered, and the filtrate concentrated. The residue was purified by flash chromatography to afford {(S)-1-[(S)-1-(6-bromo-2-(d3-methoxy)-naphthalen-1-ylmethyl)-5-(4-cyano-benzoyl)-2-oxo-2,3,4,5-tetrahydro-1H-benzo[b][1,4]diazepin-3-ylcarbamoyl]-ethyl}-methyl-carbamic acid tert-butyl ester (63 mg, 43%) as a light yellow gum. LCMS m/z 765 (M+Na)⁺.

Step 5: A solution of {(S)-1-[(S)-1-(6-bromo-2-(d3-methoxy)-naphthalen-1-ylmethyl)-5-(4-cyano-benzoyl)-2-oxo-2,3,4,5-tetrahydro-1H-benzo[b][1,4]diazepin-3-ylcarbamoyl]-ethyl}-methyl-carbamic acid tert-butyl ester (63 mg, 84.7 μmol) in MeOH (500 al) was treated with 2 M HCl in Et₂O (1.33 mL) and stirred for 4 h, concentrated, diluted with MeCN and concentrated. The residue was dissolved in H₂O and lyophilized to afford the title compound (54 mg, 94%) as a light yellow lyophilized powder. LCMS m/z 643 (MH)⁺.

Example 85

(2S)—N-[(3S)-5-[[6-bromo-2-(trideuteriomethoxy)-1-naphthyl]methyl]-4-oxo-1-[2-(3-pyridyl)acetyl]-2,3-dihydro-1,5-benzodiazepin-3-yl]-2-(methylamino)propanamide hydrochloride

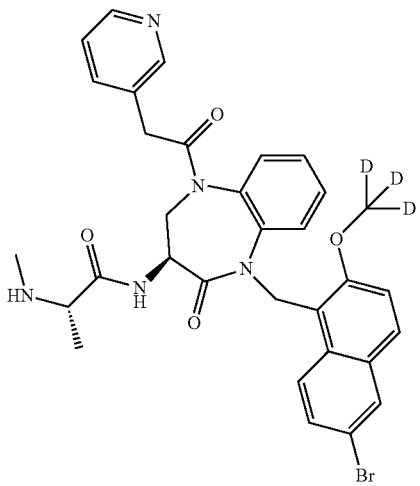 [SMILES: [2H]C([2H])([2H])Oc1ccc2cc(Br)ccc2c1CN1C(=O)[C@@H](NC(=O)[C@H](C)NC)CN(C(=O)Cc2cccnc2)c2ccccc21]

Step 1: In a similar manner to that described for Example 84, Step 4, {(S)-1-[(S)-1-(6-bromo-2-(d3-methoxy)-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester, 120 mg, 195 mol) and 2-(pyridine-3-yl)acetic acid (27 mg, 195 μmol) were converted to {(S)-1-[(S)-1-(6-bromo-2-(d3-methoxy)-naphthalen-1-ylmethyl)-2-oxo-5-(2-pyridin-3-yl-acetyl)-2,3,4,5-tetrahydro-1H-benzo[b][1,4]diazepin-3-ylcarbamoyl]-ethyl}-methyl-carbamic acid tert-butyl ester (84 mg, 59%) as a colorless gum. LCMS m/z 755 (M+Na)⁺.

Step 2: In a similar manner to that described for Example 84, Step 5, {(S)-1-[(S)-1-(6-bromo-2-(d3-methoxy)-naphthalen-1-ylmethyl)-2-oxo-5-(2-pyridin-3-yl-acetyl)-2,3,4,5-tetrahydro-1H-benzo[b][1,4]diazepin-3-ylcarbamoyl]-ethyl}-methyl-carbamic acid tert-butyl ester (84 mg, 114

μmol) was converted to the title compound (68 mg, 89%) as a white powder. LCMS m/z 633 (MH)+.

Example 86

(S)—N—((S)-1-((6-bromo-2-methoxynaphthalen-1-yl)methyl)-2-oxo-5-(2-(tetrahydro-2H-pyran-4-yl)acetyl)-2,3,4,5-tetrahydro-1H-benzo[b][1,4]diazepin-3-yl)-2-(methylamino)propanamide hydrochloride

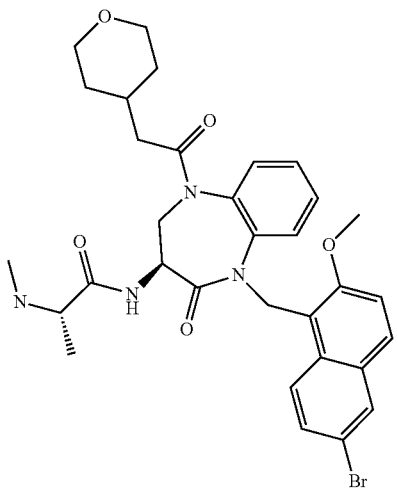 [SMILES: CN[C@@H](C)C(=O)N[C@H]1CN(C(=O)CC2CCOCC2)c2ccccc2N(Cc2c(OC)ccc3cc(Br)ccc23)C1=O]

Step 1: In a similar manner to that described for Example 84, Step 4, ((S)-2-oxo-2,3,4,5-tetrahydro-1H-benzo[b][1,4]diazepin-3-yl)-carbamic acid tert-butyl ester (325 mg, 1.17 mmol) and 2-(tetrahydro-2H-pyran-4-yl)acetic acid (169 mg, 1.17 mmol) were converted to [(S)-4-oxo-1-(2-tetrahydro-pyran-4-yl-acetyl)-2,3,4,5-tetrahydro-1H-benzo[b][1,4]diazepin-3-yl]-carbamic acid tert-butyl ester (265 mg, 56%) as a light brown foam. LCMS m/z 426 (M+Na)+.

Step 2: In a similar manner to that described for Example 84, Step 2, except the mixture was stirred 1 h, [(S)-4-oxo-1-(2-tetrahydro-pyran-4-yl-acetyl)-2,3,4,5-tetrahydro-1H-benzo[b][1,4]diazepin-3-yl]-carbamic acid tert-butyl ester (265 mg, 657 μmol) was converted to (S)-3-amino-5-(2-tetrahydro-pyran-4-yl-acetyl)-1,3,4,5-tetrahydro-benzo[b][1,4]diazepin-2-one hydrochloride (223 mg) as a light yellow solid which was used without purification.

Step 3: In a similar manner to that described for Example 64, Step 4, except 1.2 eq. of HBTU was used and the mixture was stirred 1 h, (S)-3-amino-5-(2-tetrahydro-pyran-4-yl-acetyl)-1,3,4,5-tetrahydro-benzo[b][1,4]diazepin-2-one hydrochloride (223 mg, 656 μmol, Eq) and Boc-N-methyl-L-alanine (133 mg, 656 μmol) were converted to methyl-{(S)-1-[(S)-4-oxo-1-(2-tetrahydro-pyran-4-yl-acetyl)-2,3,4,5-tetrahydro-1H-benzo[b][1,4]diazepin-3-ylcarbamoyl]-ethyl}-carbamic acid tert-butyl ester (313 mg, 98%). LCMS m/z 511 (M+Na)+.

Step 4: In a similar manner to that described for Example 64, Step 2, except 1.3 eq. of Cs2CO3 and NaI were used and the mixture was stirred 16 h, methyl-{(S)-1-[(S)-4-oxo-1-(2-tetrahydro-pyran-4-yl-acetyl)-2,3,4,5-tetrahydro-1H-benzo[b][1,4]diazepin-3-ylcarbamoyl]-ethyl}-carbamic acid tert-butyl ester (150 mg, 307 μmol) and 6-bromo-1-(chloromethyl)-2-methoxynaphthalene (105 mg, 368 μmol) were converted to {(S)-1-[(S)-1-(6-bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-ylcarbamoyl]-ethyl}-methyl-carbamic acid tert-butyl ester (115 mg, 51%) as an off-white foam. LCMS m/z 759 (M+Na)+.

Step 5: In a similar manner to that described for Example 84, Step 5, {(S)-1-[(S)-1-(6-bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-ylcarbamoyl]-ethyl}-methyl-carbamic acid tert-butyl ester (110 mg, 149 μmol) was converted to the title compound (88 mg, 88%) as a light yellow powder. LCMS m/z 637 (MH)+.

Example 87

(S)—N—((S)-1-((5-bromo-2-methoxynaphthalen-1-yl)methyl)-2-oxo-5-(2-(tetrahydro-2H-pyran-4-yl)acetyl)-2,3,4,5-tetrahydro-1H-benzo[b][1,4]diazepin-3-yl)-2-(methylamino)propanamide hydrochloride

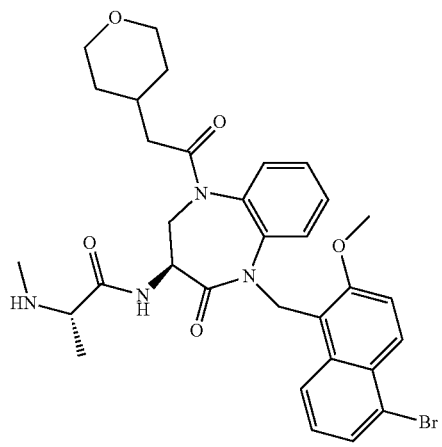 [SMILES: CN[C@@H](C)C(=O)N[C@H]1CN(C(=O)CC2CCOCC2)c2ccccc2N(Cc2c(OC)ccc3c(Br)cccc23)C1=O]

Step 1: In a similar manner to that described for Example 64, Step 2, except 1.3 eq. of Cs2CO3 and NaI were used and the mixture was stirred 16 h, methyl-{(S)-1-[(S)-4-oxo-1-(2-tetrahydro-pyran-4-yl-acetyl)-2,3,4,5-tetrahydro-1H-benzo[b][1,4]diazepin-3-ylcarbamoyl]-ethyl}-carbamic acid tert-butyl ester (150 mg, 307 μmol) and 5-bromo-1-(chloromethyl)-2-methoxynaphthalene (105 mg, 368 μmol) were converted to {(S)-1-[(S)-1-(5-bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-ylcarbamoyl]-ethyl}-methyl-carbamic acid tert-butyl ester (138 mg, 61%) as an off-white foam. LCMS m/z 759 (M+Na)+.

Step 2: In a similar manner to that described for Example 84, Step 5, {(S)-1-[(S)-1-(5-bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-ylcarbamoyl]-ethyl}-methyl-carbamic acid tert-butyl ester (133 mg, 180 μmol) was converted to the title compound (111 mg, 91%) as a white powder. LCMS m/z 637 (MH)+.

Example 88

(S)—N—((S)-1-((5-bromo-2-methoxynaphthalen-1-yl)methyl)-2-oxo-5-(2-(pyridin-3-yl)acetyl)-2,3,4,5-tetrahydro-1H-benzo[b][1,4]diazepin-3-yl)-2-(methylamino)propanamide hydrochloride

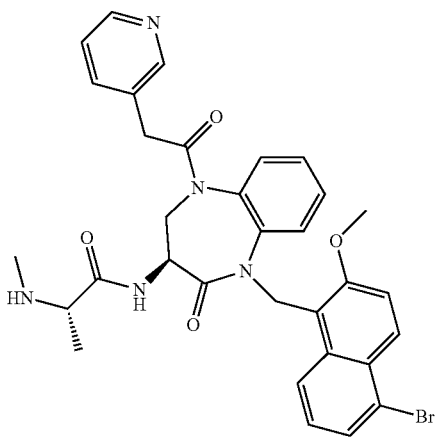 [SMILES: CN[C@@H](C)C(=O)N[C@H]1CN(C(=O)Cc2cccnc2)c2ccccc2N(Cc2c(OC)ccc3c(Br)cccc23)C1=O]

Step 1: In a similar manner to that described for Example 84, Step 4, ((S)-2-oxo-2,3,4,5-tetrahydro-1H-benzo[b][1,4]diazepin-3-yl)-carbamic acid tert-butyl ester (325 mg, 1.17 mmol) and 2-(pyridin-3-yl)acetic acid (161 mg, 1.17 mmol) were converted to [(S)-4-oxo-1-(2-pyridin-3-yl-acetyl)-2,3,4,5-tetrahydro-1H-benzo[b][1,4]diazepin-3-yl]-carbamic acid tert-butyl ester (423 mg, 91%) as an off-white foam. LCMS m/z 397 (MH)$^+$.

Step 2: A mixture of [(S)-4-oxo-1-(2-pyridin-3-yl-acetyl)-2,3,4,5-tetrahydro-1H-benzo[b][1,4]diazepin-3-yl]-carbamic acid tert-butyl ester (223 mg, 563 μmol) in 4 M HCl in dioxane (2.0 mL) and MeOH (0.5 mL) was stirred for 30 min. The mixture was concentrated, diluted with MeCN and concentrated to afford (S)-3-amino-5-(2-pyridin-3-yl-acetyl)-1,3,4,5-tetrahydro-benzo[b][1,4]diazepin-2-one hydrochloride (187 mg) as a light yellow solid which was used without purification.

Step 3: In a similar manner to that described for Example 64, Step 4, except 5 eq. of DIEA were used and the mixture was stirred 1 h, (S)-3-amino-5-(2-pyridin-3-yl-acetyl)-1,3,4,5-tetrahydro-benzo[b][1,4]diazepin-2-one hydrochloride (187 mg, 562 μmol) and Boc-N-methyl-L-alanine (114 mg, 562 μmol) were converted to methyl-{(S)-1-[(S)-4-oxo-1-(2-pyridin-3-yl-acetyl)-2,3,4,5-tetrahydro-1H-benzo[b][1,4]diazepin-3-ylcarbamoyl]-ethyl}-carbamic acid tert-butyl ester (260 mg, 96%) as a light yellow viscous oil. LCMS m/z 482 (MH)$^+$.

Step 4: In a similar manner to that described for Example 64, Step 2, except 1.3 eq. of Cs$_2$CO$_3$ and NaI were used and the mixture was stirred 16 h, methyl-{(S)-1-[(S)-4-oxo-1-(2-pyridin-3-yl-acetyl)-2,3,4,5-tetrahydro-1H-benzo[b][1,4]diazepin-3-ylcarbamoyl]-ethyl}-carbamic acid tert-butyl ester (124 mg, 258 μmol) and 5-bromo-1-(chloromethyl)-2-methoxynaphthalene were converted to {(S)-1-[(S)-1-(5-bromo-2-methoxy-naphthalen-1-ylmethyl)-2-oxo-5-(2-pyridin-3-yl-acetyl)-2,3,4,5-tetrahydro-1H-benzo[b][1,4]diazepin-3-ylcarbamoyl]-ethyl}-methyl-carbamic acid tert-butyl ester (24 mg, 13%) as a light yellow foam. LCMS m/z 752 (Na+H)$^+$.

Step 5: In a similar manner to that described for Example 86 Step 5, {(S)-1-[(S)-1-(5-bromo-2-methoxy-naphthalen-1-ylmethyl)-2-oxo-5-(2-pyridin-3-yl-acetyl)-2,3,4,5-tetrahydro-1H-benzo[b][1,4]diazepin-3-ylcarbamoyl]-ethyl}-methyl-carbamic acid tert-butyl ester (24 mg, 33 μmol) was converted to the title compound. LCMS m/z 630 (MH)$^+$.

Example 89 a (S)—N—[(S)-1-(6-Bromo-2-methoxy-naphthalen-1-ylmethyl)-2-oxo-5-(pyridine-2-carbonyl)-2,3,4,5-tetrahydro-1H-benzo[b][1,4]diazepin-3-yl]-2-methylamino-propionamide hydrochloride

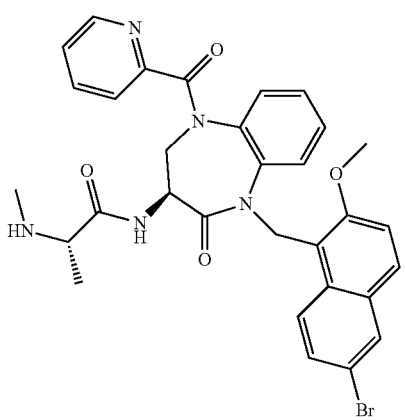 [SMILES: CN[C@@H](C)C(=O)N[C@H]1CN(C(=O)c2ccccn2)c2ccccc2N(Cc2c(OC)ccc3cc(Br)ccc23)C1=O]

Step 1: In a similar manner to that described for Example 84, Step 4, {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (60 mg, 98 μmol) and picolinic acid (12 mg, 98 μmol were converted to {(S)-1-[(S)-1-(6-bromo-2-methoxy-naphthalen-1-ylmethyl)-2-oxo-5-(pyridine-2-carbonyl)-2,3,4,5-tetrahydro-1H-benzo[b][1,4]diazepin-3-ylcarbamoyl]-ethyl}-methyl-carbamic acid tert-butyl ester (56 mg, 80%) as a colorless oil. LCMS m/z 716 (MH)$^+$.

Step 2: A solution of {(S)-1-[(S)-1-(6-bromo-2-methoxy-naphthalen-1-ylmethyl)-2-oxo-5-(pyridine-2-carbonyl)-2,3,4,5-tetrahydro-1H-benzo[b][1,4]diazepin-3-ylcarbamoyl]-ethyl}-methyl-carbamic acid tert-butyl ester (53 mg, 74 μmol) in MeOH (500 μl) was treated with 2 M HCl in Et$_2$O (1.5 mL). After 3.5 h the mixture was concentrated, the residue diluted with MeCN and concentrated. The residue was dissolve in H$_2$O and lyophilized to afford the title compound (39 mg, 81%) as a yellow powder. LCMS m/z 616 (MH)$^+$.

The compounds listed in Table 7 below were prepared in a similar manner to that described in Example 89a, where the conditions in step 1 are used substituting the appropriate acid as indicated in Table 6, supra. Step 2 can be varied such that the amount of MeOH can range from 150-500 μl and the amount of 2 M HCl in Et$_2$O can range from 400 μl-1.5 mL.

TABLE 7

| Example | Acid | Final Product | LCMS m/z (MH)+ |
|---|---|---|---|
| 89b | (pyridine-3-carboxylic acid) | (product structure) | 616 |
| 89c | (2-pyridylacetic acid) | (product structure) | 630 |
| 89d | (2-chloro-5-pyridylacetic acid) | (product structure) | 664 |

TABLE 7-continued

| Example | Acid | Final Product | LCMS m/z (MH)+ |
|---------|------|---------------|----------------|
| 89e | | | 619 |

Example 90 a (S)—N—[(S)-1-(6-Bromo-2-methoxy-naphthalen-1-ylmethyl)-5-(2-fluoro-benzoyl)-2-oxo-2,3,4,5-tetrahydro-1H-benzo[b][1,4]diazepin-3-yl]-2-methyl-amino-propionamide hydrochloride

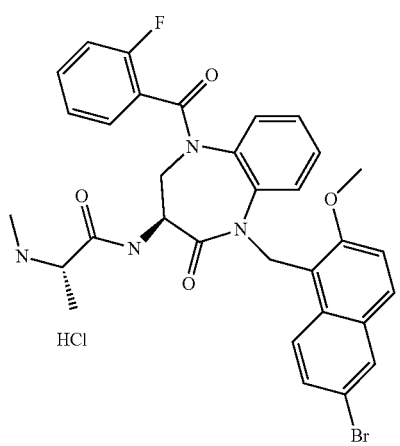 [SMILES: CN[C@@H](C)C(=O)N[C@H]1CN(C(=O)c2ccccc2F)c2ccccc2N(Cc2c(OC)ccc3cc(Br)ccc23)C1=O ; Cl]

Step 1: In a similar manner to that described for Example 84, Step 4, except the mixture was stirred at 0° C. for 2 h, {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (60 mg, 98 μmol) and 2-fluorobenzoic acid (14 mg, 98 μmol) were converted to {(S)-1-[(S)-1-(6-bromo-2-methoxy-naphthalen-1-ylmethyl)-5-(2-fluoro-benzoyl)-2-oxo-2,3,4,5-tetrahydro-1H-benzo[b][1,4]diazepin-3-ylcarbamoyl]-ethyl}-methyl-carbamic acid tert-butyl ester (29 mg, 40%) as a light yellow oil. LCMS m/z 755 (M+Na)+.

Step 2: In a similar manner to that described for Example 84, Step 5, {(S)-1-[(S)-1-(6-bromo-2-methoxy-naphthalen-1-ylmethyl)-5-(2-fluoro-benzoyl)-2-oxo-2,3,4,5-tetrahydro-1H-benzo[b][1,4]diazepin-3-ylcarbamoyl]-ethyl}-methyl-carbamic acid tert-butyl ester (29 mg, 39 μmol) was converted to the title compound (27 mg) as an off-white powder. LCMS m/z 633 (MH)+.

The compounds listed in Table 8 below were prepared in a similar manner to that described in Example 90a, where the conditions in step 1 are used substituting the appropriate acid as indicated in Table 8 and purification is carried out using the Analogix Intelliflash 280 system with the appropriate conditions. Step 2 can be varied such that the amount of MeOH can range from 200-500 al and the amount of 2 M hydrochloric acid in Et₂O can range from 500 al to 1.5 mL.

TABLE 8

| Example | Acid | Final Product | LCMS m/z (MH)+ |
|---|---|---|---|
| 90b | 3-fluorobenzoic acid | | 633 |
| 90c | 3-cyanobenzoic acid | | 640 |
| 90d | 4-(methylsulfonyl)benzoic acid | | 693 |

TABLE 8-continued
| Example | Acid | Final Product | LCMS m/z (MH)+ |
|---|---|---|---|
| 90e | 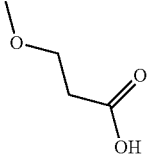 | 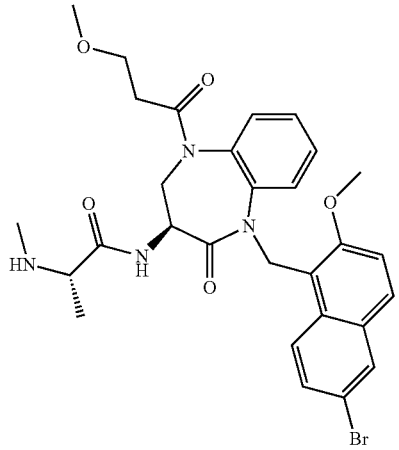 [SMILES: CN[C@@H](C)C(=O)N[C@H]1CN(C(=O)CCOC)c2ccccc2N(Cc2c(OC)ccc3cc(Br)ccc23)C1=O] | 597 |
| 90f | 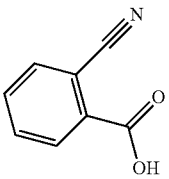 [SMILES: N#Cc1ccccc1C(=O)O] | 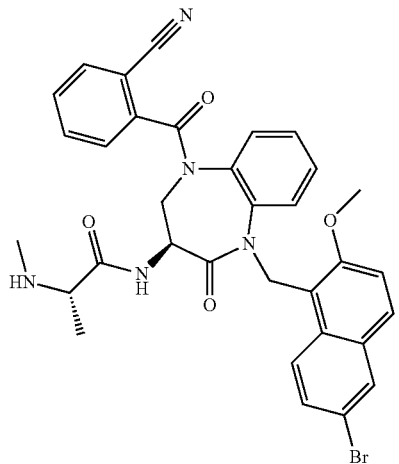 [SMILES: CN[C@@H](C)C(=O)N[C@H]1CN(C(=O)c2ccccc2C#N)c2ccccc2N(Cc2c(OC)ccc3cc(Br)ccc23)C1=O] | 640 |

Example 91 a (S)—N—[(S)-5-Benzoyl-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride

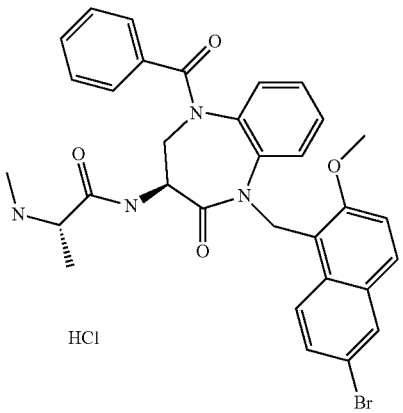 [SMILES: CN[C@@H](C)C(=O)N[C@H]1CN(C(=O)c2ccccc2)c2ccccc2N(Cc2c(OC)ccc3cc(Br)ccc23)C1=O ; Cl]

Step 1: Benzoyl chloride (13 μL, 108 μmol) was added to a mixture of {(S)-1-[(S)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (60 mg, 98 μmol) and pyridine (24 μL, 294 μmol) in DCM (1 mL) at 0° C. After 30 min, the mixture was warmed to RT and stirred for 1.5 h, diluted with DCM, washed with 1 N citric acid, sat. aq. NaHCO$_3$, and brine, dried over Na$_2$SO$_4$, filtered, and the filtrate concentrated. The residue was purified by flash chromatography to afford {(S)-1-[(S)-5-benzoyl-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (45 mg, 64%) as a white foam. LCMS m/z 737 (M+Na)$^+$.

Step 2: In a similar manner to that described for Example 84, Step 5, {(S)-1-[(S)-5-benzoyl-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (43 mg, 60 μmol) was converted to the title compound (38 mg, 97%) as an off-white lyophilized powder. LCMS m/z 615 (MH)$^+$.

The compounds listed in Table 9 below were prepared in a similar manner to that described in Example 91a, where the conditions in step 1 are used substituting the appropriate acid chloride (1.0-1.1 equiv) as indicated in Table 9. Step 2 can be varied such that the amount of MeOH can range from 500-700 μl and the amount of 2 M HCl in Et$_2$O can range from 1.2 mL to 1.8 mL.

TABLE 9

| Example | Acid Chloride | Final Product | LCMS m/z (MH)$^+$ |
|---|---|---|---|
| 91b | (acetyl chloride structure) | (final product structure) | 553 |
| 91c | (5-methylfuran-2-carbonyl chloride structure) | (final product structure) | 619 |

| Example | Acid Chloride | Final Product | LCMS m/z (MH)+ |
|---|---|---|---|
| 91d | | | 683 |

Example 92

(S)—N—[(S)-1-(5-Bromo-2-methoxy-naphthalen-1-ylmethyl)-5-(4-fluoro-benzoyl)-2-oxo-2,3,4,5-tetrahydro-1H-benzo[b][1,4]diazepin-3-yl]-2-methylamino-propionamide hydrochloride

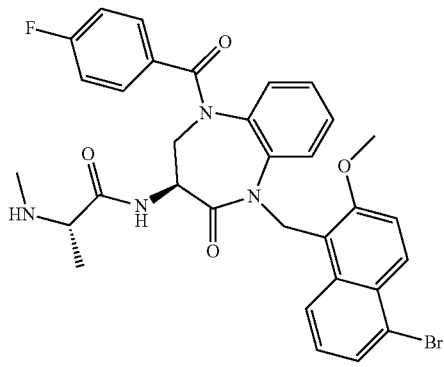 [SMILES: CN[C@@H](C)C(=O)N[C@H]1CN(C(=O)c2ccc(F)cc2)c2ccccc2N(Cc2c(OC)ccc3c(Br)cccc23)C1=O]

Step 1: A solution of 4-fluorobenzoyl chloride (99 μl, 829 μmol) in DCM (1 mL) was added to a mixture of ((S)-2-oxo-2,3,4,5-tetrahydro-1H-benzo[b][1,4]diazepin-3-yl)-carbamic acid tert-butyl ester (200 mg, 721 μmol) in DCM (5 mL) and pyridine (588 μl, 7.21 mmol) at 0° C. After 1 h the mixture was diluted with H₂O and extracted with EtOAc. The combined extracts were washed with 1 N citric acid, H₂O, sat. aq. NaHCO₃ and brine, dried over Na₂SO₄, filtered, and the filtrate concentrated. The reaction was repeated using the same amounts of reagents and the material from both reactions was combined. The resulting material was washed with DCM resulting in a solid that was filtered and collected to afford [(S)-1-(4-fluoro-benzoyl)-4-oxo-2,3,4,5-tetrahydro-1H-benzo[b][1,4]diazepin-3-yl]-carbamic acid tert-butyl ester (371 mg, 64%) as a white solid. LCMS m/z 422 (M+Na)+.

Step 2: A mixture of [(S)-1-(4-fluoro-benzoyl)-4-oxo-2,3,4,5-tetrahydro-1H-benzo[b][1,4]diazepin-3-yl]-carbamic acid tert-butyl ester (371 mg, 929 μmol) in 4 M HCl in dioxane (3.5 mL) was stirred for 60 min., concentrated, diluted with MeCN and concentrated to afford (S)-3-amino-5-(4-fluoro-benzoyl)-1,3,4,5-tetrahydro-benzo[b][1,4]diazepin-2-one hydrochloride (312 mg) which was used without purification.

Step 3: In a similar manner to that described for Example 64, Step 4, (S)-3-amino-5-(4-fluoro-benzoyl)-1,3,4,5-tetrahydro-benzo[b][1,4]diazepin-2-one hydrochloride (312 mg, 929 μmol) and Boc-N-methyl-L-alanine (189 mg, 929 μmol) were converted to {(S)-1-[(S)-1-(4-fluoro-benzoyl)-4-oxo-2,3,4,5-tetrahydro-1H-benzo[b][1,4]diazepin-3-ylcarbamoyl]-ethyl}-methyl-carbamic acid tert-butyl ester (499 mg, 100%) as a light brown foam.

Step 4: In a similar manner to that described for Example 64, Step 2, except 1.3 eq. of Cs₂CO₃ and NaI were used and the mixture was stirred 16 h, {(S)-1-[(S)-1-(4-fluoro-benzoyl)-4-oxo-2,3,4,5-tetrahydro-1H-benzo[b][1,4]diazepin-3-ylcarbamoyl]-ethyl}-methyl-carbamic acid tert-butyl ester (150 mg, 310 μmol) and 5-bromo-1-(chloromethyl)-2-methoxynaphthalene (106 mg, 372 μmol) were converted to {(S)-1-[(S)-1-(5-bromo-2-methoxy-naphthalen-1-ylmethyl)-5-(4-fluoro-benzoyl)-2-oxo-2,3,4,5-tetrahydro-1H-benzo[b][1,4]diazepin-3-ylcarbamoyl]-ethyl}-methyl-carbamic acid tert-butyl ester (131 mg, 58%) as a light yellow foam. LCMS m/z 755 (M+Na)+

Step 5: A solution of {(S)-1-[(S)-1-(5-bromo-2-methoxy-naphthalen-1-ylmethyl)-5-(4-fluoro-benzoyl)-2-oxo-2,3,4,5-tetrahydro-1H-benzo[b][1,4]diazepin-3-ylcarbamoyl]-ethyl}-methyl-carbamic acid tert-butyl ester (128 mg, 174 μmol) in MeOH (1.5 mL) was treated with a with 2 M HCl in Et₂O (4 mL). After 3.5 h, the mixture was concentrated, the residue diluted with MeCN and concentrated. The residue was dissolved in H₂O and lyophilized to afford the title compound (105 mg, 90%) as a powder. LCMS m/z 633 (MH)+.

Example 93

(S)—N—[(S)-1-(5-Bromo-2-methoxy-naphthalen-1-ylmethyl)-5-(4-methyl-benzoyl)-2-oxo-2,3,4,5-tetrahydro-1H-benzo[b][1,4]diazepin-3-yl]-2-methylamino-propionamide hydrochloride

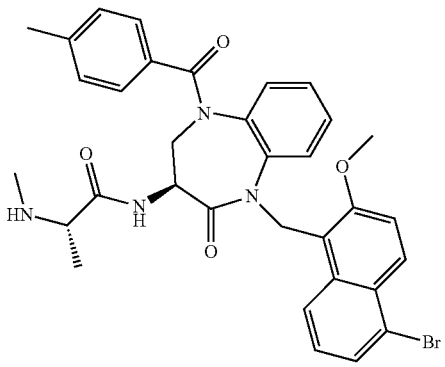 [SMILES: CN[C@@H](C)C(=O)N[C@H]1CN(C(=O)c2ccc(C)cc2)c2ccccc2N(Cc2c(OC)ccc3c(Br)cccc23)C1=O]

Step 1: A solution of 4-methylbenzoyl chloride (110 µl, 829 µmol) in DCM (1 mL) was added to a mixture of ((S)-2-oxo-2,3,4,5-tetrahydro-1H-benzo[b][1,4]diazepin-3-yl)-carbamic acid tert-butyl ester (200 mg, 721 µmol) and pyridine (588 µl, 7.21 mmol) in DCM (5 mL) at 0° C. After 1 h, the mixture was diluted with H$_2$O and extracted with EtOAc. The combined extracts were washed with 1 N citric acid, H$_2$O, sat. aq. NaHCO$_3$, and brine, dried over Na$_2$SO$_4$, filtered, and the filtrate concentrated. The resulting material was washed with DCM which afforded a solid that was collected by filtration to afford [(S)-1-(4-methyl-benzoyl)-4-oxo-2,3,4,5-tetrahydro-1H-benzo[b][1,4]diazepin-3-yl]-carbamic acid tert-butyl ester (180 mg, 63%) as a white solid. LCMS m/z 418 (M+23)$^+$.

Step 2: In a similar manner to that described for Example 92, Step 2, [(S)-1-(4-methyl-benzoyl)-4-oxo-2,3,4,5-tetrahydro-1H-benzo[b][1,4]diazepin-3-yl]-carbamic acid tert-butyl ester (180 mg, 455 µmol) was converted to (S)-3-amino-5-(4-methyl-benzoyl)-1,3,4,5-tetrahydro-benzo[b][1,4]diazepin-2-one hydrochloride (151 mg) which was used without purification.

Step 3: In a similar manner to that described for Example 64, Step 4, except the mixture was stirred for 3 h, (S)-3-amino-5-(4-methyl-benzoyl)-1,3,4,5-tetrahydro-benzo[b][1,4]diazepin-2-one hydrochloride (151 mg, 455 µmol) and Boc-N-methyl-L-alanine (93 mg, 455 µmol) were converted to methyl-{(S)-1-[(S)-1-(4-methyl-benzoyl)-4-oxo-2,3,4,5-tetrahydro-1H-benzo[b][1,4]diazepin-3-ylcarbamoyl]-ethyl}-carbamic acid tert-butyl ester (210 mg, 96%) as colorless gum. LCMS m/z 381 (MH)$^+$.

Step 4: In a similar manner to that described for Example 64, Step 2, except 1.3 eq. of Cs$_2$CO$_3$ and NaI were used and the mixture was stirred 16 h, methyl-{(S)-1-[(S)-1-(4-methyl-benzoyl)-4-oxo-2,3,4,5-tetrahydro-1H-benzo[b][1,4]diazepin-3-ylcarbamoyl]-ethyl}-carbamic acid tert-butyl ester (125 mg, 260 µmol) and 5-bromo-1-(chloromethyl)-2-methoxynaphthalene (2.89 mg, 312 µmol) were converted to {(S)-1-[(S)-1-(5-bromo-2-methoxy-naphthalen-1-ylmethyl)-5-(4-methyl-benzoyl)-2-oxo-2,3,4,5-tetrahydro-1H-benzo[b][1,4]diazepin-3-ylcarbamoyl]-ethyl}-methyl-carbamic acid tert-butyl ester (136 mg, 72%) as a light yellow foam. LCMS m/z 751 (M+Na)$^+$.

Step 5: In a similar manner to that described for Example 92, Step 5, {(S)-1-[(S)-1-(5-bromo-2-methoxy-naphthalen-1-ylmethyl)-5-(4-methyl-benzoyl)-2-oxo-2,3,4,5-tetrahydro-1H-benzo[b][1,4]diazepin-3-ylcarbamoyl]-ethyl}-methyl-carbamic acid tert-butyl ester (133 mg, 182 mol) was converted to the title compound (113 mg, 93%) as an off white lyophilized powder. LCMS m/z 629 (MH)$^+$.

Example 94

(S)—N—{(S)-1-(5-Bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-yl}-2-methylamino-propionamide, mixture of diastereomers

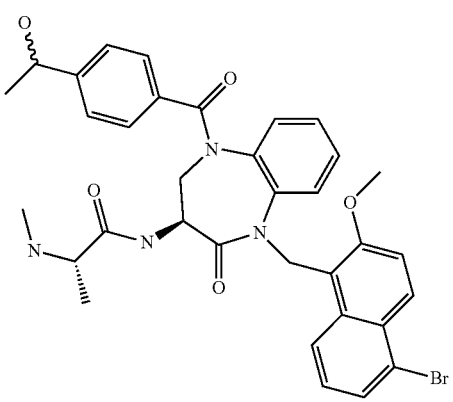 [SMILES: CN[C@@H](C)C(=O)N[C@H]1CN(C(=O)c2ccc(C(C)O)cc2)c2ccccc2N(Cc2c(OC)ccc3c(Br)cccc23)C1=O]

Step 1: A solution of {(S)-1-[(S)-5-(4-acetyl-benzoyl)-1-(5-bromo-2-methoxy-naphthalen-1-ylmethyl)-2-oxo-2,3,4,5-tetrahydro-1H-benzo[b][1,4]diazepin-3-ylcarbamoyl-ethyl}-methyl-carbamic acid tert-butyl ester (250 mg, 330 µmol) in THF (7 mL) was treated with NaBH$_4$ (25.0 mg, 660 µmol). After 16 h, the mixture was diluted with H$_2$O and extracted with DCM. The combined extracts were washed with brine and dried over MgSO$_4$, filtered and the filtrate concentrated. The residue was purified by flash chromatography to afford ((S)-1-{(S)-1-(5-bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-ylcarbamoyl}-ethyl)-methyl-carbamic acid tert-butyl ester (180 mg, 72%) as a light yellow foam. LCMS m/z 781 (M+Na)$^+$.

Step 2: A solution of ((S)-1-{(S)-1-(5-bromo-2-methoxy-naphthalen-1-ylmethyl)-5-[4-(1-hydroxy-ethyl)-benzoyl]-2-oxo-2,3,4,5-tetrahydro-1H-benzo[b][1,4]diazepin-3-ylcarbamoyl}-ethyl)-methyl-carbamic acid tert-butyl ester (180 mg, 237 µmol) in MeOH (1.5 mL) at room temperature was treated with 2 M HCl in Et$_2$O (3.75 mL). After 4 h the mixture was concentrated, the residue dissolved in EtOAc and the organic solution was washed with sat. aq. NaHCO$_3$ solution. The aqueous washes were extracted with EtOAc and the combined extracts dried over MgSO$_4$, filtered and the filtrate concentrated. The resulting material was purified by SFC to afford the title compound (91 mg, 58%) as a light yellow foam. LCMS m/z 659 (MH)$^+$.

Example 95

(S)—N—{(S)-1-(6-Bromo-2-methoxy-naphthalen-1-ylmethyl)-5-[4-(1-hydroxy-1-methyl-ethyl)-benzoyl]-2-oxo-2,3,4,5-tetrahydro-1H-benzo[b][1,4]diazepin-3-yl}-2-methylamino-propionamide trifluoroacetate

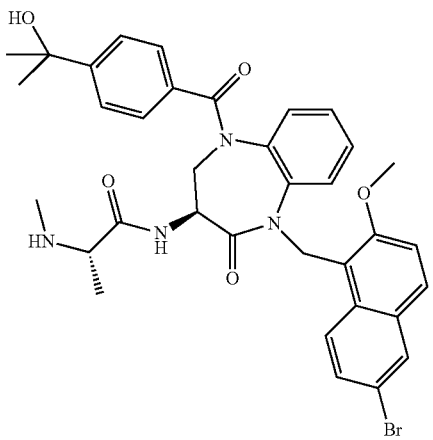 [SMILES: CN[C@@H](C)C(=O)N[C@H]1CN(C(=O)c2ccc(C(C)(C)O)cc2)c2ccccc2N(Cc2c(OC)ccc3cc(Br)ccc23)C1=O]

Step 1: A solution of {(S)-1-[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (145 mg, 191 µmol) in THF (3 mL) cooled to −78° C. and 3 M methyl magnesium bromide in Et$_2$O (159 µl, 478 µmol) was added. The mixture was stirred at −78° C. for 1 h, warmed to 0° C., stirred for 3 h and additional portion of 3 M solution of methyl magnesium bromide (159 µl, 478 µmol) was added. After 1.5 h the mixture was diluted with H$_2$O and a sat. NH$_4$Cl, extracted with EtOAc, dried over MgSO$_4$ and concentrated. The residue was purified by flash chromatography to afford ((S)-1-{(S)-1-(6-bromo-2-methoxy-naphthalen-1-ylmethyl)-5-[4-(1-hydroxy-1-methyl-ethyl)-benzoyl]-2-oxo-2,3,4,5-tetrahydro-1H-benzo[b][1,4]diazepin-3-ylcarbamoyl}-ethyl)-methyl-carbamic acid tert-butyl ester (63 mg, 43%) as a white foam. LCMS m/z 795 (M+Na)$^+$.

Step 2: A solution of ((S)-1-{(S)-1-(6-bromo-2-methoxy-naphthalen-1-ylmethyl)-5-[4-(1-hydroxy-1-methyl-ethyl)-benzoyl]-2-oxo-2,3,4,5-tetrahydro-1H-benzo[b][1,4]diazepin-3-ylcarbamoyl}-ethyl)-methyl-carbamic acid tert-butyl ester (60 mg, 78 µmol) in MeOH (0.7 mL) was treated with 2 M HCl in Et$_2$O (1.7 mL). After 3.5 h the mixture was concentrated, the residue diluted with MeCN and concentrated. The resulting material was purified by reverse phase HPLC and lyophilized to afford the title compound (19 mg, 31%) as a white powder. LCMS m/z 673 (MH)$^+$.

Example 96 a

4-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzoic acid methyl ester hydrochloride

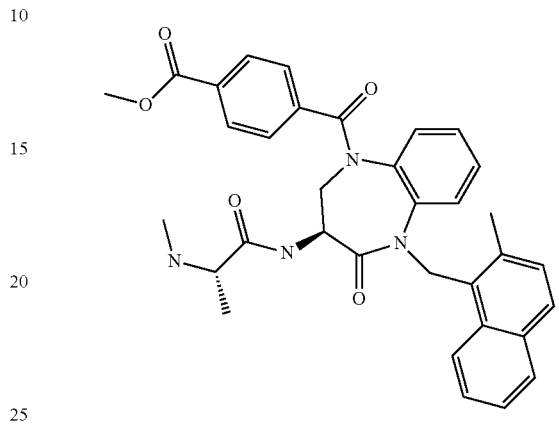

Step 1: To a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (100 mg, 0.19 mmol) in pyridine (8 mL) at 0° C. was added terephthalic acid monomethyl ester (70 mg, 0.39 mmol) and POCl$_3$ (0.037 mL, 0.41 mmol) and the mixture warmed to RT. After 4 h the mixture was concentrated, the residue diluted with ice and H$_2$O and extracted with EtOAc. The extracts were washed with sat. aq. NaHCO$_3$ solution, brine and dried over Na$_2$SO$_4$ and concentrated. The residue was purified by flash chromatography to afford 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-carbonyl]-benzoic acid methyl ester (84 mg, 64%) as an off white solid. LCMS m/z 679 (MH)$^+$.

Step 2: To a solution of 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-carbonyl]-benzoic acid methyl ester (100 mg, 0.15 mmol) in dioxane (3 mL) at 0° C. was added a 2 M HCl in dioxane (6 mL). After 4 h the mixture was concentrated and the residue triturated with Et$_2$O to afford the title compound (42 mg, 46%). LCMS m/z 579 (MH)$^+$.

The compounds listed in Table 10 below were prepared in a similar manner to that described in Example 96a, where the appropriate substituted acid as indicated in Table 10 was used and can range from 1.5-3.9 equiv, the amount of pyridine can vary from 4-8 mL, the amount of POCl$_3$ can vary from 2.1-4.1 equivalents and the reaction time can range from 2-4 h. In Step 2, the amount of dioxane used can range from 1-4 mL, the amount of 2 M HCl in dioxane solution used can range from 2-7 mL, and the products can be optionally purified by reverse phase HPLC using 0.1% aqueous NH$_4$OAc/MeCN affording the free base of the product.

TABLE 10

| Example | Acid Used in Step 1 | Final Product | LCMS m/z (MH)+ |
|---|---|---|---|
| 96b | [structure: 1H-tetrazol-5-yl acetic acid] | [structure: final product · HCl] | 527 |
| 96c | [structure: tetrahydropyran-4-yl acetic acid] | [structure: final product · HCl] | 543 |
| 96d | [structure: 4-cyanobenzoic acid] | [structure: final product] | 546 |

TABLE 10-continued

| Example | Acid Used in Step 1 | Final Product | LCMS m/z (MH)+ |
|---|---|---|---|
| 96e | | | 541 •HCl |
| 96f | | | 555 |
| 96g | | | 563 |

TABLE 10-continued

| Example | Acid Used in Step 1 | Final Product | LCMS m/z (MH)+ |
|---|---|---|---|
| 96h | | | 536 |
| 96i | | | 539 |
| 96j | | | 536 |
| 96k | | •HCl | 535 |

TABLE 10-continued

| Example | Acid Used in Step 1 | Final Product | LCMS m/z (MH)+ |
|---------|---------------------|---------------|----------------|
| 961 | 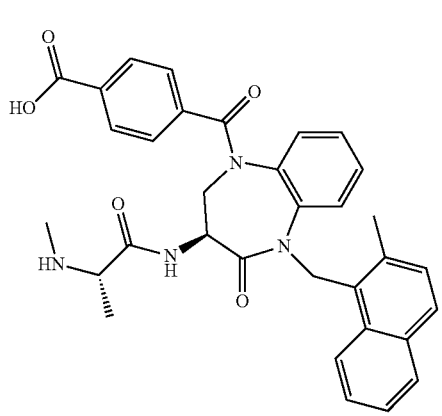 [SMILES: CN[C@@H](C)C(=O)N[C@H]1CN(C(=O)c2ccc(C(=O)O)cc2)c2ccccc2N(Cc2c(C)ccc3ccccc23)C1=O] (partial) | | 551 |

Example 97

4-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzoic acid hydrochloride

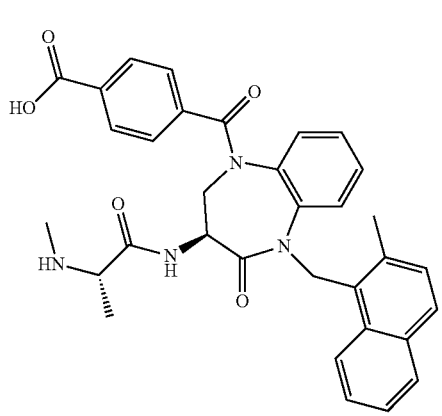 [SMILES: CN[C@@H](C)C(=O)N[C@H]1CN(C(=O)c2ccc(C(=O)O)cc2)c2ccccc2N(Cc2c(C)ccc3ccccc23)C1=O]

Step 1: LiOH (19 mg, 0.44 mmol) was added to a solution of 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-carbonyl]-benzoic acid methyl ester (150 mg, 0.22 mmol) in THF (4 mL) and H$_2$O (0.4 mL). After 16 h the mixture was evaporated and the residue treated with 1 N citric acid and extracted with EtOAc. The extracts were concentrate and purified by flash chromatography to afford 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-carbonyl]-benzoic acid (60 mg, 41%). LCMS m/z 665 (MH)+.

Step 2: In a similar manner to that described for Example 96, Step 2, 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-carbonyl]-benzoic acid (100 mg, 0.15 mmol) was converted to the title compound (47 mg, 52%). LCMS m/z 565 (MH)+.

Example 98 a (S)—N—[(S)-5-(4-Acetylamino-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride

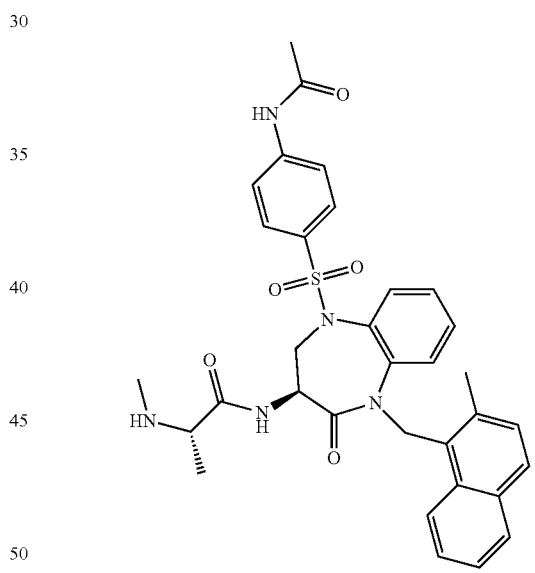

Step 1: 4-Acetylamino-benzenesulfonyl chloride (170 mg, 0.73 mmol) was added to a mixture of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (150 mg, 0.29 mmol), pyridine (0.073 mL, 0.87 mmol) and a catalytic amount of 4-dimethylaminopyridine in dichloroethane. After 16 h the mixture was diluted with H$_2$O and extracted with EtOAc. The extracts were washed with sat. Na$_2$CO$_3$, brine, dried over Na$_2$SO$_4$, filtered, and concentrated. The residue was purified by flash chromatography to afford {(S)-1-[(S)-5-(4-acetylamino-benzenesulfonyl)-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (55 mg, 31%). LCMS m/z 714 (MH)+.

Step 2: In a similar manner to that described for Example 96, Step 2, {(S)-1-[(S)-5-(4-acetylamino-benzenesulfonyl)-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (50 mg, 0.07 mmol) was converted to the title compound (41 mg, 90%). LCMS m/z 614 (MH)+.

The compounds listed in Table 11 below were prepared in a similar manner to that described in Example 98a using the appropriate sulfonyl chloride as indicated. In Step 2, the amount of dioxane used can range from 1-2 mL, the amount of 2 M HCl in dioxane used can range from 2-4 mL.

TABLE 11

| Example | Sulfonyl Chloride | Final Product | LCMS m/z (MH)+ |
|---|---|---|---|
| 98b | (structure) | (structure) | 510 |
| 98c | (structure) | (structure) | 599 |
| 98d | (structure) | (structure) | 602 |

TABLE 11-continued

| Example | Sulfonyl Chloride | Final Product | LCMS m/z (MH)+ |
|---|---|---|---|
| 98e | | | 557 |
| 98f | | | 587 |

Intermediates obtained in the course of preparing the products listed in Table 1 can be derivatized further to afford additional compounds, as exemplified below.

Example 99

3-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzamide hydrochloride

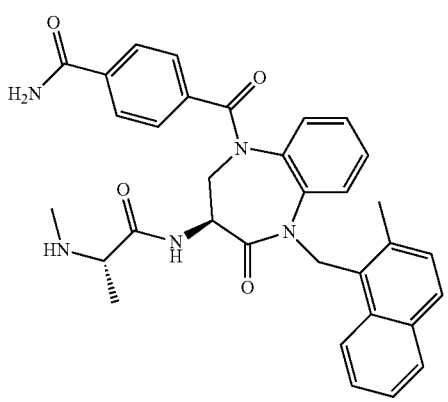 [SMILES: CN[C@@H](C)C(=O)N[C@H]1CN(C(=O)c2ccc(C(N)=O)cc2)c2ccccc2N(Cc2c(C)ccc3ccccc23)C1=O]

Step 1: To a solution of 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-carbonyl]-benzoic acid (140 mg, 0.21 mmol) in DMF (5 mL) was added NH$_4$Cl (23 mg, 0.42 mmol), DIEA (0.145 mL, 0.84 mmol), HBPYU (100 mg, 0.23 mmol). After 4 h the mixture was diluted with H$_2$O and extracted with EtOAc. The extracts were concentrated and the residue purified by flash chromatography to afford {(S)-1-[(S)-5-(3-carbamoyl-benzoyl)-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (70 mg, 59%). LCMS m/z 664 (MH)+.

Step 2: In a similar manner to that described for Example 96, Step 2, {(S)-1-[(S)-5-(3-carbamoyl-benzoyl)-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (70 mg, 0.11 mmol) was converted to the title compound (53 mg, 84%). LCMS m/z 564 (MH)+.

Example 100

(S)—N—[(S)-5-Dimethylsulfamoyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride

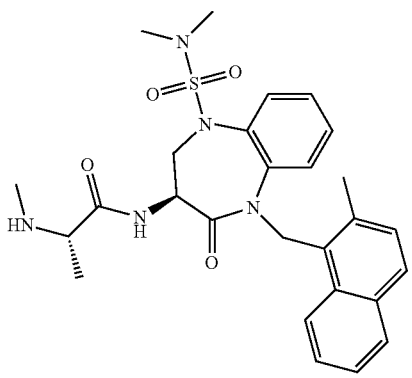 [SMILES: CN[C@@H](C)C(=O)N[C@H]1CN(S(=O)(=O)N(C)C)c2ccccc2N(Cc2c(C)ccc3ccccc23)C1=O]

Step 1: To a stirred solution of methyl-{(S)-1-[(S)-1-(2-methyl-naphthalen-1-ylmethyl)-5-methylsulfamoyl-2-oxo-2,3,4,5-tetrahydro-1H-benzo[b][1,4]diazepin-3-ylcarbamoyl]-ethyl}-carbamic acid tert-butyl ester (60 mg, 0.1 mmol) in DMF (3 mL) was added Cs$_2$CO$_3$ (64 mg, 0.2 mmol) and the mixture cooled to 0° C. MeI (31 mg, 0.22 mmol) was added and the mixture warmed to RT. After 16 h the mixture was diluted with H$_2$O and extracted with EtOAc. The combined extracts were washed with brine, dried over Na$_2$SO$_4$ and concentrated. The residue was purified by flash chromatography to afford {(S)-1-[(S)-5-dimethylsulfamoyl-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (40 mg, 65%) as an off white solid. LCMS m/z 624 (MH)$^+$.

Step 2: In a similar manner to that described for Example 96, Step 2, {(S)-1-[(S)-5-dimethylsulfamoyl-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (40 mg, 0.06 mmol) was converted to the title compound (32 mg, 89%). LCMS m/z 524 (MH)$^+$.

Example 101

(S)—N—[(S)-5-(2-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide

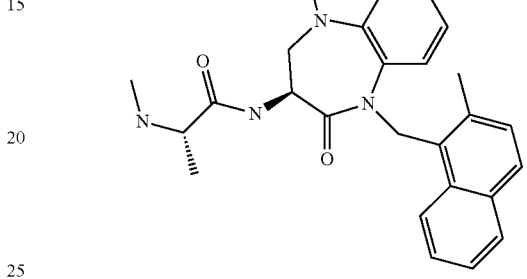

Step 1: In a similar manner to that described for Example 84, Step 4, methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (300 mg, 0.58 mmol) in pyridine (10 mL) and 2-bromobenzoic acid (175 mg, 0.87 mmol) was converted to {(S)-1-[(S)-5-(2-bromo-benzoyl)-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (240 mg, 59%) as an off white solid: LCMS m/z 700 (MH)$^+$.

Step 2: A solution of {(S)-1-[(S)-5-(2-bromo-benzoyl)-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (300 mg, 0.43 mmol) in dry toluene (15 mL) was degassed with N$_2$ for 20 min. and tributyl(1-ethoxyvinyl)tin (202 mg, 0.558 mmol) and Pd(PPh$_3$)$_4$ (99 mg, 0.086 mmol) were added. The mixture was degassed with N$_2$ for 20 min and heated to 80° C. After 4 h the mixture was filtered through Celite, the filter cake washed with toluene and the filtrate concentrated. The residue was purified by preparative HPLC to afford {(S)-1-[(S)-5-[2-(1-ethoxy-vinyl)-benzoyl]-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (100 mg, 34%). LCMS m/z 691 (MH)$^+$.

Step 3: In a similar manner to that described for Example 96, Step 2, {(S)-1-[(S)-5-[2-(1-ethoxy-vinyl)-benzoyl]-1-(2-methyl-naphthalen-1-ylmethyl)-2-oxo-2,3,4,5-tetrahydro-1H-benzo[b][1,4]diazepin-3-ylcarbamoyl]-ethyl}-methyl-carbamic acid tert-butyl ester (100 mg, 0.14 mmol) was converted to the title compound (80 mg, 92%). LCMS m/z 563 (MH)$^+$

Example 102

(S)—N—[(S)-5-(4-Hydroxymethyl-benzoyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride

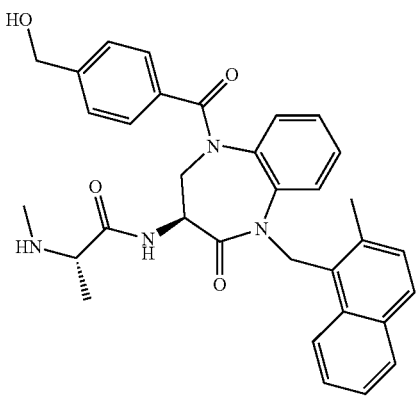 [SMILES: CN[C@@H](C)C(=O)N[C@H]1CN(C(=O)c2ccc(CO)cc2)c2ccccc2N(Cc2c(C)ccc3ccccc23)C1=O]

Step 1: Thionyl chloride (0.056 mL, 0.77 mmol) was added dropwise to a solution of 4-[(acetyloxyl)methyl]benzoic acid (50 mg, 0.258 mmol) in DCM (5 mL) at 0° C. and the mixture warmed to RT. After 2 h the mixture was concentrated, the residue diluted with toluene and concentrated. The residue was dissolved in DCM (2.5 mL) cooled to 0° C. and DIEA (0.13 mL, 0.77 mmol) was added followed by a solution of methyl-{(S)-1-[(S)-1-(2-methyl-naphthalen-1-ylmethyl)-2-oxo-2,3,4,5-tetrahydro-1H-benzo[b][1,4]diazepin-3-ylcarbamoyl]-ethyl}-carbamic acid tert-butyl ester (93 mg, 0.18 mmol) in DCM (2 mL) and the mixture warmed to RT. After 16 h the mixture was diluted with DCM, washed with H₂O, brine, dried over Na₂SO₄ and concentrated. The residue was purified by flash chromatography to afford acetic acid 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-carbonyl]-benzyl ester (44 mg, 36%). LCMS m/z 693 (MH)⁺.

Step 2: To a solution of acetic acid 4-[(S)-3-[(S)-2-(tert-butoxycarbonyl-methyl-amino)-propionylamino]-5-(2-methyl-naphthalen-1-ylmethyl)-4-oxo-2,3,4,5-tetrahydro-benzo[b][1,4]diazepine-1-carbonyl]-benzyl ester (404 mg, 0.064 mmol) in MeOH (3 mL) was added K₂CO₃ (18 mg, 0.127 mmol). After 1 h the mixture was concentrated and the residue dissolved in DCM. This solution was washed with H₂O, brine, dried over Na₂SO₄ and concentrated to afford {(S)-1-[(S)-5-(4-hydroxymethyl-benzoyl)-1-(2-methyl-naphthalen-1-ylmethyl)-2-oxo-2,3,4,5tetrahydro-1H-benzo[b][1,4]diazepin-3-ylcarbamoyl]-ethyl}-methyl-carbamic acid tert-butyl ester (37 mg, 90%) which was used without purification. LCMS m/z 651 (MH)⁺.

Step 3: To a stirred solution of {(S)-1-[(S)-5-(4-hydroxymethyl-benzoyl)-1-(2-methyl-naphthalen-1-ylmethyl)-2-oxo-2,3,4,5tetrahydro-1H-benzo[b][1,4]diazepin-3-ylcarbamoyl]-ethyl}-methyl-carbamic acid tert-butyl ester (37 mg, 0.057 mmol) in dioxane (2 mL) at 0° C. was added 2 N HCl in dioxane (4 mL) and the mixture warmed to RT. After 4 h the mixture was concentrated and the residue triturated with Et₂O to afford (S)—N—[(S)-5-(4-hydroxymethyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride (26 mg, 72%). LCMS m/z 551 (MH)⁺.

Examples 103-192 can be synthesized with analogous methods as described herein for previous examples.

TABLE 12

| Example | Name | Structure |
|---|---|---|
| 103 | (2S)-N-((3S)-1-((6-bromo-2-methoxynaphthalen-1-yl)methyl)-5-(4-(1-hydroxyethyl)benzoyl)-2-oxo-2,3,4,5-tetrahydro-1H-benzo[b][1,4]diazepin-3-yl)-2-(methylamino)propanamide | Chiral |

TABLE 12-continued

| Example | Name | Structure | |
|---|---|---|---|
| 104 | (2S)-N-((3S)-1-((6-bromo-2-methoxynaphthalen-1-yl)methyl)-5-(4-(1-hydroxyethyl)benzoyl)-2-oxo-2,3,4,5-tetrahydro-1H-benzo[b][1,4]diazepin-3-yl)-2-(methylamino)propanamide | 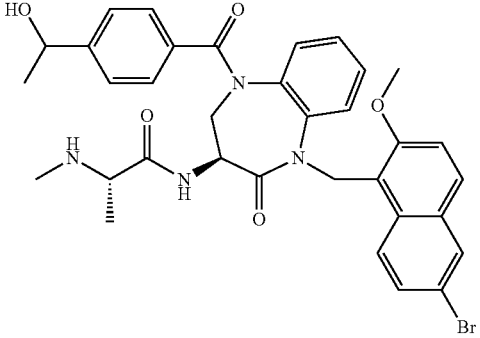 | Chiral |
| 105 | (2S)-N-[(3S)-1-(4-acetylbenzoyl)-5-[2-(naphthalen-1-ylamino)-2-oxoethyl]-4-oxo-2,3-dihydro-1,5-benzodiazepin-3-yl]-2-(methylamino)propanamide;2,2,2-trifluoroacetic acid | 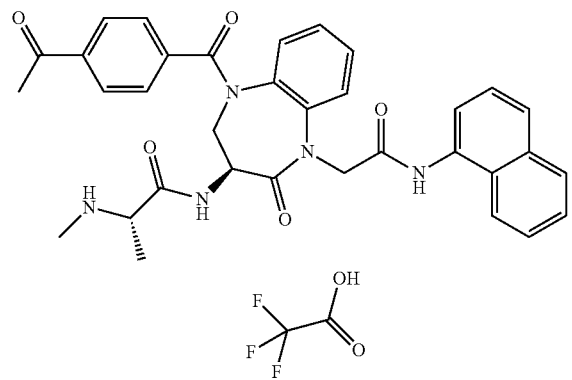 | Chiral |
| 106 | (2S)-N-[(3S)-1-(4-acetylbenzoyl)-4-oxo-5-[2-oxo-2-(1,3-thiazol-2-ylamino)ethyl]-2,3-dihydro-1,5-benzodiazepin-3-yl]-2-(methylamino)propanamide;2,2,2-trifluoroacetic acid | 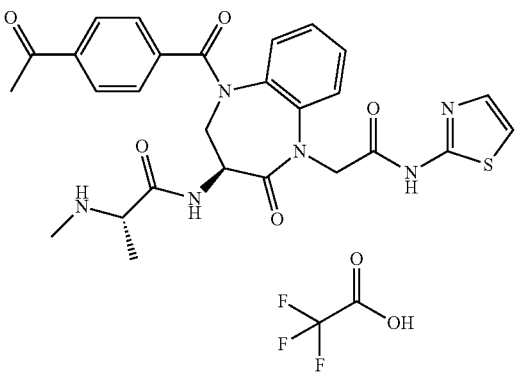 [SMILES: CN[C@@H](C)C(=O)N[C@H]1CN(C(=O)c2ccc(C(C)=O)cc2)c2ccccc2N(CC(=O)Nc2nccs2)C1=O ; O=C(O)C(F)(F)F] | |

TABLE 12-continued

| Example | Name | Structure |
|---|---|---|
| 107 | (S)-N-((S)-1-((6-bromo-2-methoxynaphthalen-1-yl)methyl)-5-(4-nitrobenzoyl)-2-oxo-2,3,4,5-tetrahydro-1H-benzo[b][1,4]diazepin-3-yl)-N-methyl-2-(methylamino)propanamide hydrochloride | 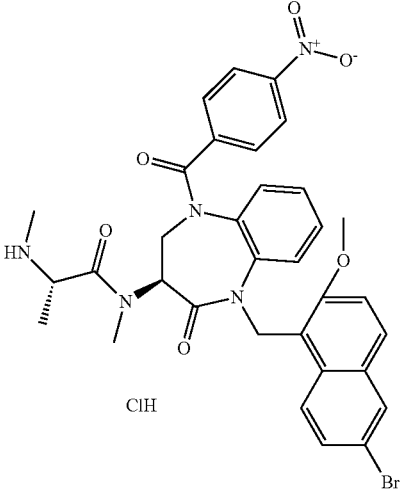 |
| 108 | Cyclic-5-[(S)-5-(3-Amino-acetyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride | 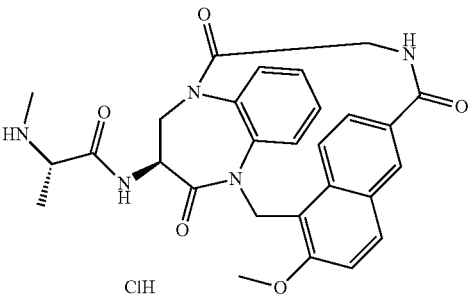 |
| 109 | (2S)-N-[(3S)-1-(4-acetylbenzoyl)-5-[2-(1,3-benzothiazol-2-ylamino)-2-oxoethyl]-4-oxo-2,3-dihydro-1,5-benzodiazepin-3-yl]-2-(methylamino)propanamide;2,2,2-trifluoroacetic acid | 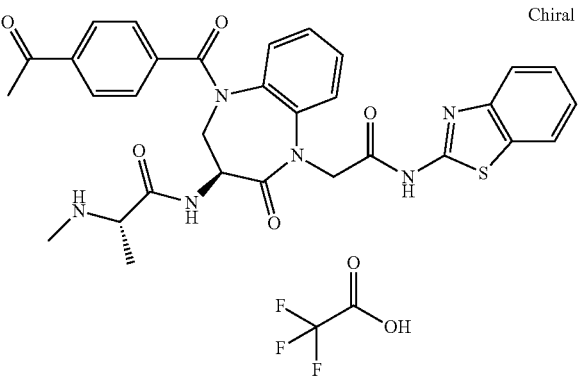 [SMILES: CN[C@@H](C)C(=O)N[C@H]1CN(C(=O)c2ccc(C(C)=O)cc2)c2ccccc2N(CC(=O)Nc2nc3ccccc3s2)C1=O ; O=C(O)C(F)(F)F] |
| 110 | (2S)-N-[5-(1-adamantylmethyl)-1-[(2-methoxynaphthalen-1-yl)methyl]-2,4-dioxo-1,5-benzodiazepin-3-yl]-2-(methylamino)propanamide | 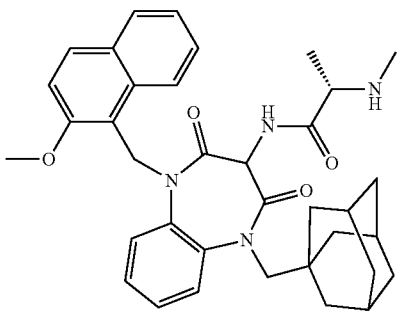 |

TABLE 12-continued

| Example | Name | Structure |
|---|---|---|
| 111 | (2S)-N-[5-(1-adamantylmethyl)-1-[(2-methoxynaphthalen-1-yl)methyl]-2,4-dioxo-1,5-benzodiazepin-3-yl]-2-aminopropanamide | 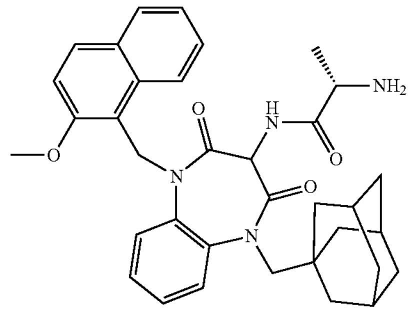 [SMILES: COc1ccc2ccccc2c1CN1C(=O)C(NC(=O)[C@H](C)N)C(=O)N(CC23CC4CC(CC(C4)C2)C3)c2ccccc21] |
| 112 | Cyclic-5-[(S)-5-(3-Amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride | Chiral |
| 113 | (2S)-N-[5-(1-adamantylmethyl)-1-[(2-methoxynaphthalen-1-yl)methyl]-2,4-dioxo-1,5-benzodiazepin-3-yl]-2-(methylamino)butanamide | 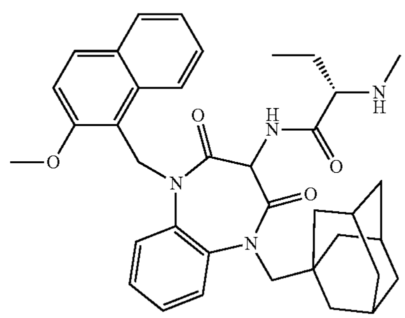 |
| 114 | (2S)-N-(1-methyl-5-((2-methylnaphthalen-1-yl)methyl)-2,4-dioxo-2,3,4,5-tetrahydro-1H-benzo[b][1,4]diazepin-3-yl)-2-(methylamino)butanamide | 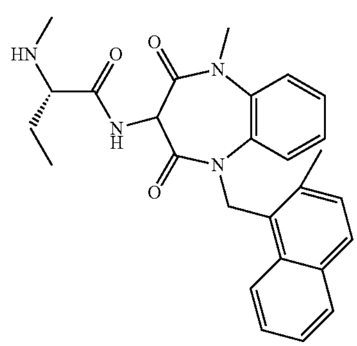 [SMILES: CC[C@H](NC)C(=O)NC1C(=O)N(C)c2ccccc2N(Cc2c(C)ccc3ccccc23)C1=O] |

TABLE 12-continued

| Example | Name | Structure |
|---|---|---|
| 115 | (2S)-2-(methylamino)-N-(1-((2-methylnaphthalen-1-yl)methyl)-2,4-dioxo-5-phenyl-2,3,4,5-tetrahydro-1H-benzo[b][1,4]diazepin-3-yl)butanamide | 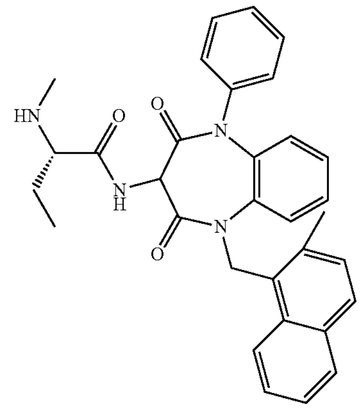 [SMILES: CC[C@H](NC)C(=O)NC1C(=O)N(Cc2c(C)ccc3ccccc23)c2ccccc2N(c2ccccc2)C1=O] |
| 116 | (2S)-2-(methylamino)-N-(1-((2-methylnaphthalen-1-yl)methyl)-2,4-dioxo-5-phenyl-2,3,4,5-tetrahydro-1H-benzo[b][1,4]diazepin-3-yl)propanamide | 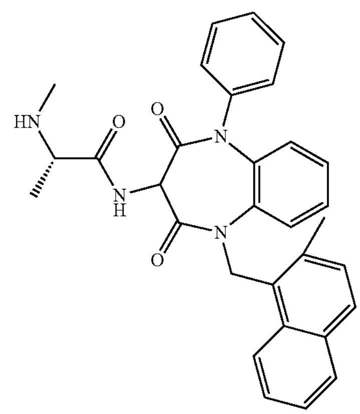 [SMILES: CN[C@@H](C)C(=O)NC1C(=O)N(Cc2c(C)ccc3ccccc23)c2ccccc2N(c2ccccc2)C1=O] |
| 117 | (2S)-N-[(3S)-1-(4-aminophenyl)sulfonyl-5-[(2-methylnaphthalen-1-yl)methyl]-4-oxo-2,3-dihydro-1,5-benzodiazepin-3-yl]-2-(methylamino)propanamide;hydrochloride | Chiral |

| Example | Name | Structure |
|---|---|---|
| 118 | (2S)-N-[(3S)-1-[3-(1-hydroxyethyl)benzoyl]-5-[(2-methylnaphthalen-1-yl)methyl]-4-oxo-2,3-dihydro-1,5-benzodiazepin-3-yl]-2-(methylamino)propanamide;hydrochloride | Chiral |
| 119 | (2S)-N-[(3S)-1-[3-(1-hydroxyethyl)benzoyl]-5-[(2-methylnaphthalen-1-yl)methyl]-4-oxo-2,3-dihydro-1,5-benzodiazepin-3-yl]-2-(methylamino)propanamide;hydrochloride | Chiral |
| 120 | (S)-N-((S)-5-(4-acetylbenzoyl)-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide 2,2,2-trifluoroacetate | Chiral |

TABLE 12-continued

| Example | Name | Structure |
|---------|------|-----------|
| 121 | (S)-N-((S)-5-(4-aminobenzoyl)-7-chloro-1-((2-methylnaphthalen-1-yl)methyl)-2-oxo-2,3,4,5-tetrahydro-1H-benzo[b][1,4]diazepin-3-yl)-2-(methylamino)propanamide hydrochloride | Chiral |
| 122 | (S)-N-((S)-5-(4-aminobenzoyl)-7-chloro-1-((2-methoxynaphthalen-1-yl)methyl)-2-oxo-2,3,4,5-tetrahydro-1H-benzo[b][1,4]diazepin-3-yl)-2-(methylamino)propanamide hydrochloride | Chiral |
| 123 | (S)-N-((S)-5-(4-aminobenzoyl)-1-((5-bromo-2-methoxynaphthalen-1-yl)methyl)-7-chloro-2-oxo-2,3,4,5-tetrahydro-1H-benzo[b][1,4]diazepin-3-yl)-2-(methylamino)propanamide hydrochloride | Chiral |

TABLE 12-continued
| Example | Name | Structure |
|---------|------|-----------|
| 124 | (S)-N-((S)-5-(4-aminobenzoyl)-1-((6-bromo-2-methoxynaphthalen-1-yl)methyl)-7-chloro-2-oxo-2,3,4,5-tetrahydro-1H-benzo[b][1,4]diazepin-3-yl)-2-(methylamino)propanamide hydrochloride | 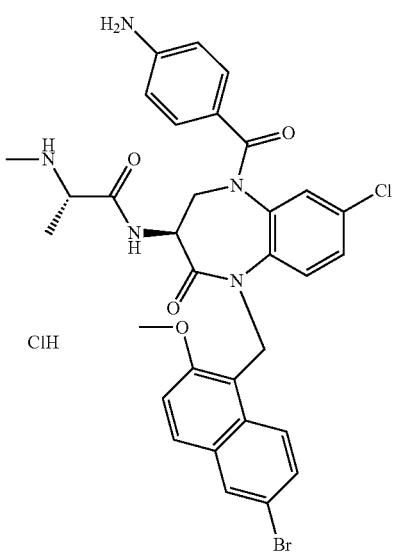 |
| 125 | (S)-N-((S)-5-(4-acetylbenzoyl)-1-((5-bromo-2-methoxynaphthalen-1-yl)methyl)-7-chloro-2-oxo-2,3,4,5-tetrahydro-1H-benzo[b][1,4]diazepin-3-yl)-2-(methylamino)propanamide hydrochloride | 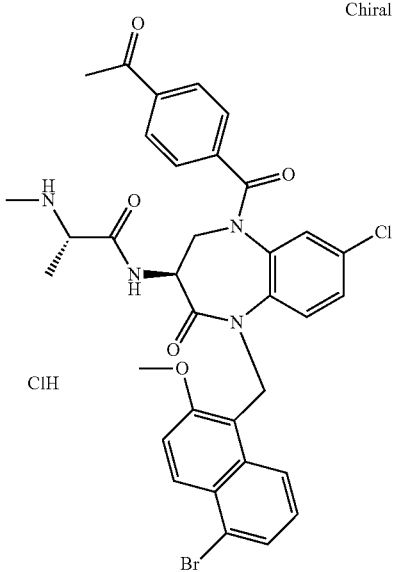 [SMILES: CN[C@@H](C)C(=O)N[C@H]1CN(C(=O)c2ccc(C(C)=O)cc2)c2cc(Cl)ccc2N(Cc2c(OC)ccc3c(Br)cccc23)C1=O ; Cl] |

TABLE 12-continued

| Example | Name | Structure |
|---|---|---|
| 126 | (S)-N-((S)-1-((5-bromo-2-methoxynaphthalen-1-yl)methyl)-7-chloro-5-(4-fluorobenzoyl)-2-oxo-2,3,4,5-tetrahydro-1H-benzo[b][1,4]diazepin-3-yl)-2-(methylamino)propanamide hydrochloride | 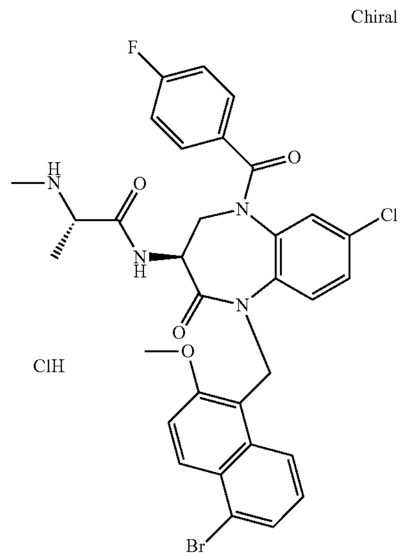 [SMILES: CN[C@@H](C)C(=O)N[C@H]1CN(C(=O)c2ccc(F)cc2)c2cc(Cl)ccc2N(Cc2c(OC)ccc3c(Br)cccc23)C1=O ; Cl] |
| 127 | (S)-N-((S)-1-((5-bromo-2-methoxynaphthalen-1-yl)methyl)-7-chloro-5-(4-cyanobenzoyl)-2-oxo-2,3,4,5-tetrahydro-1H-benzo[b][1,4]diazepin-3-yl)-2-(methylamino)propanamide hydrochloride | 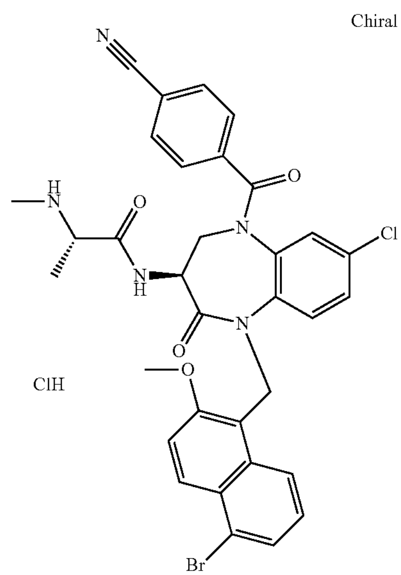 [SMILES: CN[C@@H](C)C(=O)N[C@H]1CN(C(=O)c2ccc(C#N)cc2)c2cc(Cl)ccc2N(Cc2c(OC)ccc3c(Br)cccc23)C1=O ; Cl] |
| 128 | (2S)-N-(1-((6-bromo-2-methoxynaphthalen-1-yl)methyl)-2,4-dioxo-5-phenyl-2,3,4,5-tetrahydro-1H-benzo[b][1,4]diazepin-3-yl)-2-(methylamino)propanamide | 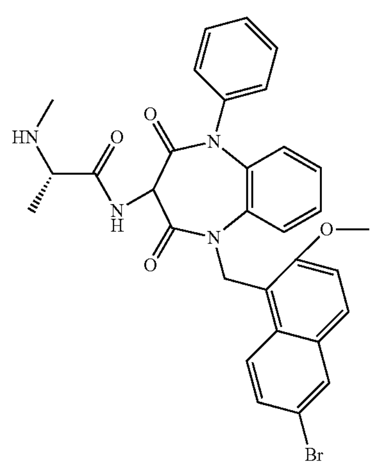 [SMILES: CN[C@@H](C)C(=O)NC1C(=O)N(Cc2c(OC)ccc3cc(Br)ccc23)c2ccccc2N(c2ccccc2)C1=O] |

TABLE 12-continued

| Example | Name | Structure |
|---|---|---|
| 129 | (2S)-N-(1-((5-bromo-2-methoxynaphthalen-1-yl)methyl)-2,4-dioxo-5-phenyl-2,3,4,5-tetrahydro-1H-benzo[b][1,4]diazepin-3-yl)-2-(methylamino)propanamide | 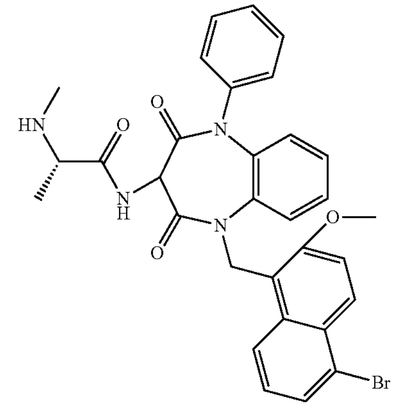 [SMILES: CN[C@@H](C)C(=O)NC1C(=O)N(Cc2c(OC)ccc3c(Br)cccc23)c2ccccc2N(c2ccccc2)C1=O] |
| 130 | (S)-N-((S)-1-((6-bromo-2-methoxynaphthalen-1-yl)methyl)-7-chloro-5-(4-fluorobenzoyl)-2-oxo-2,3,4,5-tetrahydro-1H-benzo[b][1,4]diazepin-3-yl)-2-(methylamino)propanamide hydrochloride | Chiral |
| 131 | (S)-N-((S)-1-((6-bromo-2-methoxynaphthalen-1-yl)methyl)-7-chloro-5-(4-cyanobenzoyl)-2-oxo-2,3 tetrahydro-1H-benzo[b][1,4]diazepin-yl)-2-(methylamino)propanamide hydrochloride | Chiral |

TABLE 12-continued

| Example | Name | Structure |
|---|---|---|
| 132 | (2S)-N-(1-((6-bromo-2-methoxynaphthalen-1-yl)methyl)-2,4-dioxo-5-phenyl-2,3,4,5-tetrahydro-1H-benzo[b][1,4]diazepin-3-yl)-2-(ethylamino)butanamide | 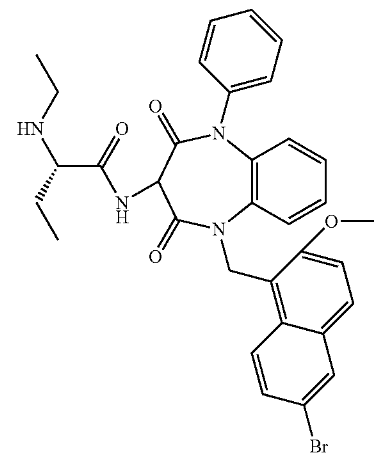 [SMILES: CCN[C@@H](CC)C(=O)NC1C(=O)N(Cc2c(OC)ccc3cc(Br)ccc23)c2ccccc2N(c2ccccc2)C1=O] |
| 133 | (2S)-2-amino-N-(1-((6-bromo-2-methoxynaphthalen-1-yl)methyl)-2,4-dioxo-5-phenyl-2,3,4,5-tetrahydro-1H-benzo[b][1,4]diazepin-3-yl)butanamide | 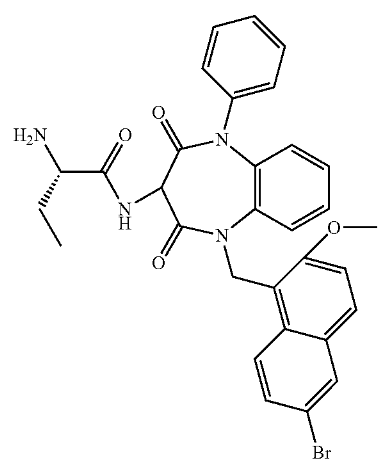 [SMILES: CC[C@H](N)C(=O)NC1C(=O)N(Cc2c(OC)ccc3cc(Br)ccc23)c2ccccc2N(c2ccccc2)C1=O] |
| 134 | (2S)-N-(1-((5-bromo-2-methoxynaphthalen-1-yl)methyl)-2,4-dioxo-5-phenyl-2,3,4,5-tetrahydro-1H-benzo[b][1,4]diazepin-3-yl)-2-(ethylamino)butanamide | | ns

TABLE 12-continued

| Example | Name | Structure |
|---------|------|-----------|
| 135 | (S)-N-((S)-1-((6-bromo-2-(2,2,2-trifluoroethoxy)naphthalen-1-yl)methyl)-7-chloro-5-(4-cyanobenzoyl)-2-oxo-2,3,4,5-tetrahydro-1H-benzo[b][1,4]diazepin-3-yl)-2-(methylamino)propanamide hydrochloride | Chiral |
| 136 | (S)-N-((S)-1-((6-bromo-2-(2,2,2-trifluoroethoxy)naphthalen-1-yl)methyl)-7-chloro-5-(4-fluorobenzoyl)-2-oxo-2,3,4,5-tetrahydro-1H-benzo[b][1,4]diazepin-3-yl)-2-(methylamino)propanamide hydrochloride | Chiral |
| 137 | (2S)-2-amino-N-(1-((5-bromo-2-methoxynaphthalen-1-yl)methyl)-2,4-dioxo-5-phenyl-2,3,4,5-tetrahydro-1H-benzo[b][1,4]diazepin-3-yl)butanamide | 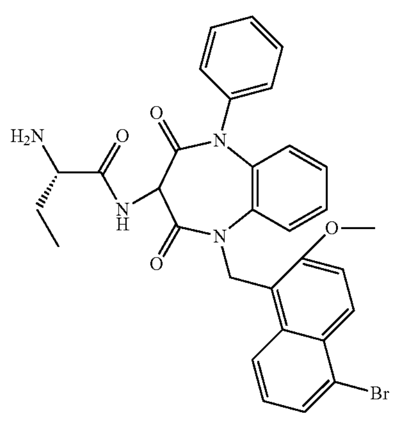 [SMILES: CC[C@H](N)C(=O)NC1C(=O)N(Cc2c(OC)ccc3c(Br)cccc23)c2ccccc2N(c2ccccc2)C1=O] |

TABLE 12-continued

| Example | Name | Structure |
|---|---|---|
| 138 | (2S)-N-(1-((5-bromo-2-methoxynaphthalen-1-yl)methyl)-2,4-dioxo-5-phenyl-2,3,4,5-tetrahydro-1H-benzo[b][1,4]diazepin-3-yl)-2-(2-hydroxyethylamino)butanamide | 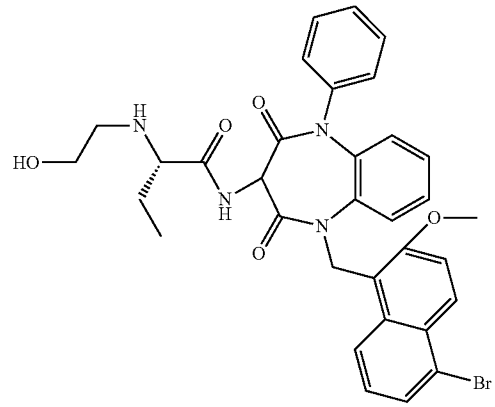 [SMILES: CC[C@H](NCCO)C(=O)NC1C(=O)N(Cc2c(OC)ccc3c(Br)cccc23)c2ccccc2N(c2ccccc2)C1=O] |
| 139 | (S)-N-((S)-7-chloro-5-(4-cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride | Chiral |
| 140 | (S)-N-((S)-7-chloro-1-((2-(difluoromethoxy)naphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride | Chiral |

TABLE 12-continued

| Example | Name | Structure |
|---|---|---|
| 141 | (2S)-N-[(3S)-1-(1H-indazole-5-carbonyl)-5-[(2-methylnaphthalen-1-yl)methyl]-4-oxo-2,3-dihydro-1,5-benzodiazepin-3-yl]-2-(methylamino)propanamide | 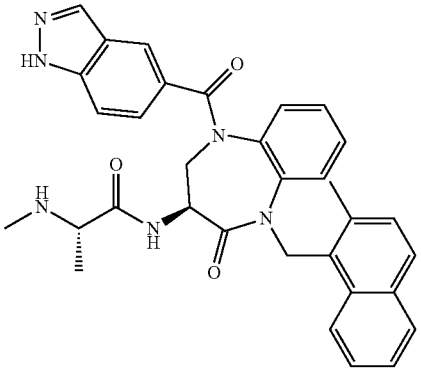 Chiral |
| 142 | (S)-N-((S)-7-cyano-5-(4-cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride | 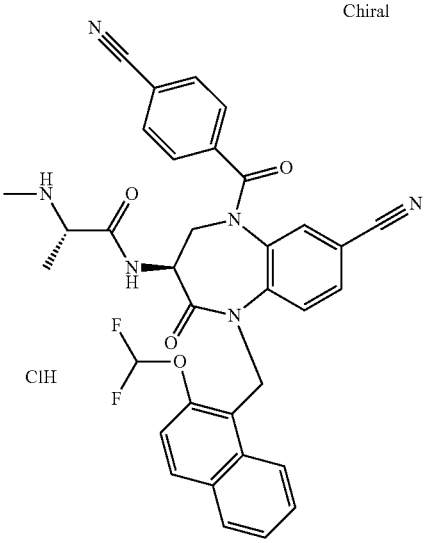 [SMILES: CN[C@@H](C)C(=O)N[C@H]1CN(C(=O)c2ccc(C#N)cc2)c2cc(C#N)ccc2N(Cc2c(OC(F)F)ccc3ccccc23)C1=O ; Cl] Chiral |
| 143 | (S)-N-((S)-1-((5-bromo-2-methoxynaphthalen-1-yl)methyl)-7-cyano-5-(4-cyanobenzoyl)-2-oxo-2,3,4,5-tetrahydro-1H-benzo[b][1,4]diazepin-3-yl)-2-(methylamino)propanamide hydrochloride | 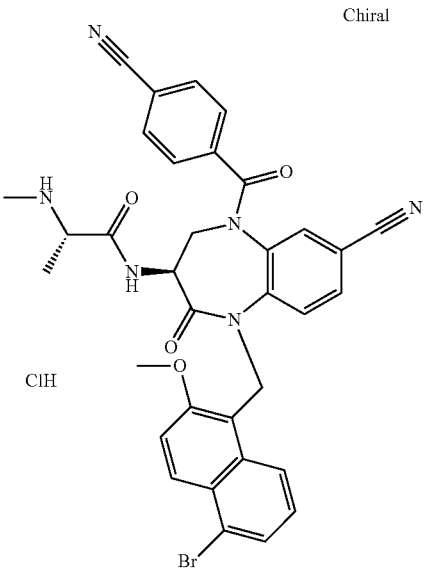 [SMILES: CN[C@@H](C)C(=O)N[C@H]1CN(C(=O)c2ccc(C#N)cc2)c2cc(C#N)ccc2N(Cc2c(OC)ccc3c(Br)cccc23)C1=O ; Cl] Chiral |

TABLE 12-continued

| Example | Name | Structure |
|---|---|---|
| 144 | (S)-N-((S)-1-((6-bromo-2-methoxynaphthalen-1-yl)methyl)-7-cyano-5-(4-cyanobenzoyl)-2-oxo-2,3,4,5-tetrahydro-1H-benzo[b][1,4]diazepin-3-yl)-2-(methylamino)propanamide hydrochloride | 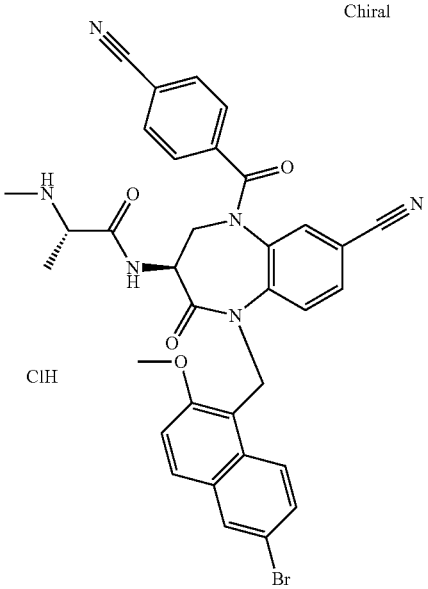 [SMILES: CN[C@@H](C)C(=O)N[C@H]1CN(C(=O)c2ccc(C#N)cc2)c2cc(C#N)ccc2N(Cc2c(OC)ccc3cc(Br)ccc23)C1=O ; Cl] |
| 145 | (2S)-N-[(3S)-1-(1H-indole-5-carbonyl)-5-[(2-methylnaphthalen-1-yl)methyl]-4-oxo-2,3-dihydro-1,5-benzodiazepin-3-yl]-2-(methylamino)propanamide | 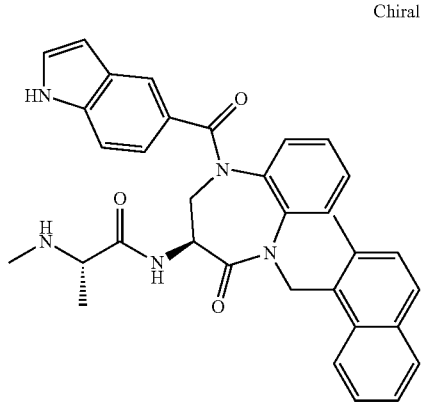 [SMILES: CN[C@@H](C)C(=O)N[C@H]1CN(C(=O)c2ccc3[nH]ccc3c2)c2ccccc2N(Cc2c(C)ccc3ccccc23)C1=O] |
| 146 | (2S)-N-[(3S)-1-(1H-indole-4-carbonyl)-5-[(2-methylnaphthalen-1-yl)methyl]-4-oxo-2,3-dihydro-1,5-benzodiazepin-3-yl]-2-(methylamino)propanamide | 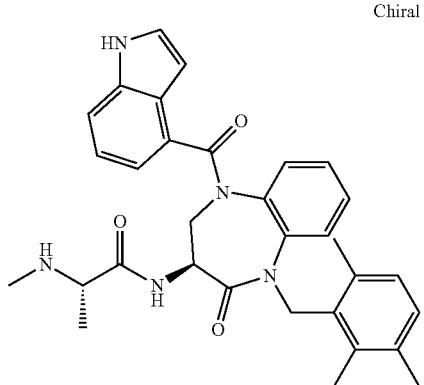 |

TABLE 12-continued

| Example | Name | Structure |
|---------|------|-----------|
| 147 | (2S)-N-[(3S)-1-(1H-indazole-4-carbonyl)-5-[(2-methylnaphthalen-1-yl)methyl]-4-oxo-2,3-dihydro-1,5-benzodiazepin-3-yl]-2-(methylamino)propanamide | Chiral 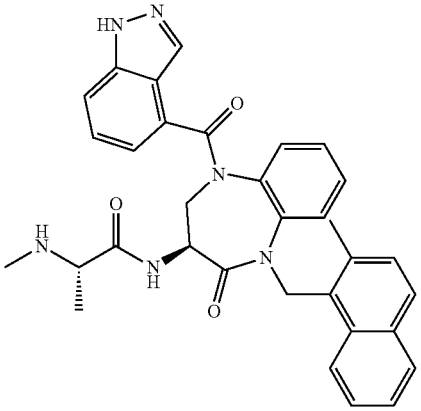 |
| 148 | (2S)-N-[(3S)-1-[2-[(1S)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide;(2S)-N-[(3S)-1-[2-[(1R)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide | Chiral 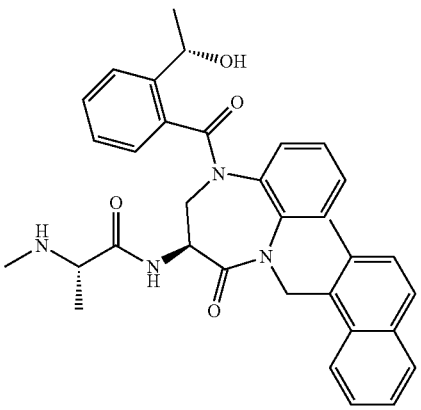 [SMILES: CN[C@@H](C)C(=O)N[C@H]1CN(C(=O)c2ccccc2[C@@H](C)O)c2ccccc2N(Cc2c(C)ccc3ccccc23)C1=O] 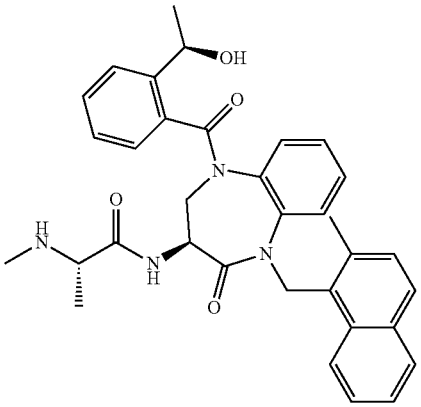 [SMILES: CN[C@@H](C)C(=O)N[C@H]1CN(C(=O)c2ccccc2[C@@H](C)O)c2ccccc2N(Cc2c(C)ccc3ccccc23)C1=O] |

TABLE 12-continued

| Example | Name | Structure |
|---|---|---|
| 149 | (S)-N-((S)-1-((6-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)propanamide | 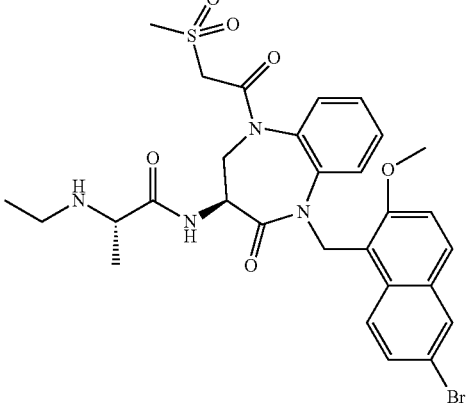 Chiral |
| 150 | (S)-N-((S)-1-((5-bromo-2-methoxynaphthalen-1-yl)methyl)-7-cyano-5-(4-fluorobenzoyl)-2-oxo-2,3,4,5-tetrahydro-1H-benzo[b][1,4]diazepin-3-yl)-2-(methylamino)propanamide hydrochloride | 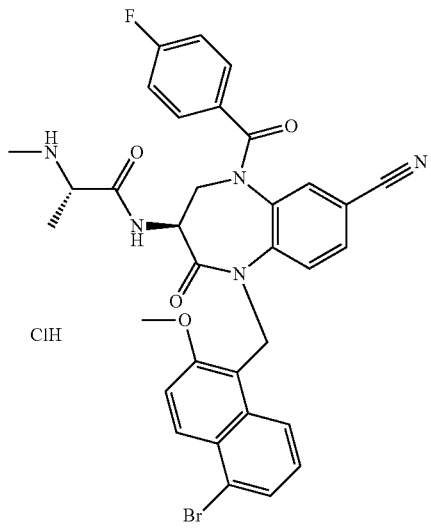 Chiral |
| 151 | (S)-N-((S)-7-cyano-1-((2-(difluoromethoxy)naphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride | 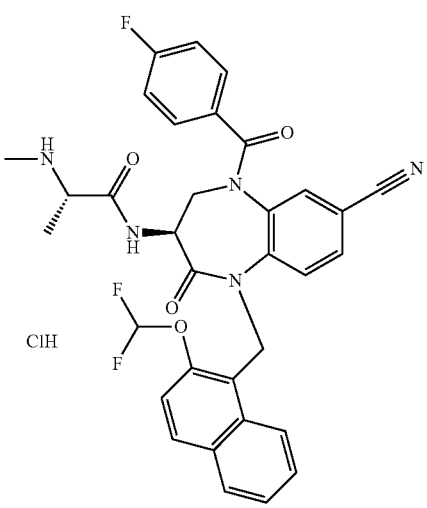 Chiral |

TABLE 12-continued

| Example | Name | Structure |
|---|---|---|
| 152 | (2S)-N-[(3S)-1-(1H-indole-6-carbonyl)-5-[(2-methylnaphthalen-1-yl)methyl]-4-oxo-2,3-dihydro-1,5-benzodiazepin-3-yl]-2-(methylamino)propanamide | Chiral |
| 153 | (2S)-N-[(3S)-1-[2-[(1S)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide;(2S)-N-[(3S)-1-[2-[(1R)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide | Chiral |

TABLE 12-continued

| Example | Name | Structure |
|---|---|---|
| 154 | (S)-N-((S)-1-((6-bromo-2-methoxynaphthalen-1-yl)methyl)-7-cyano-5-(4-fluorobenzoyl)-2-oxo-2,3,4,5-tetrahydro-1H-benzo[b][1,4]diazepin-3-yl)-2-(methylamino)propanamide hydrochloride | Chiral 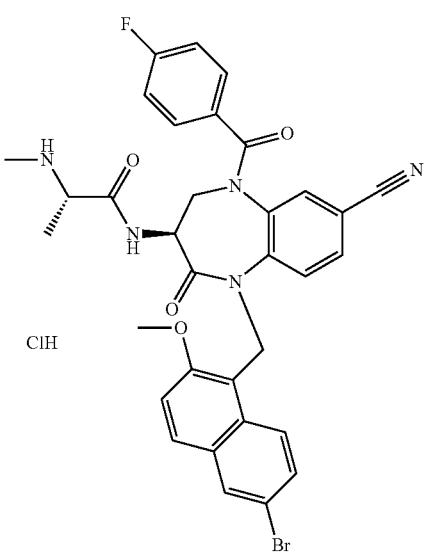 |
| 155 | (S)-N-((S)-1-((5-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride | 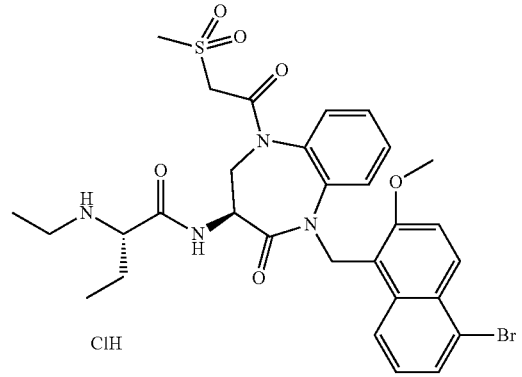 [SMILES: CCN[C@@H](CC)C(=O)N[C@H]1CN(C(=O)CS(C)(=O)=O)c2ccccc2N(Cc2c(OC)ccc3c(Br)cccc23)C1=O ; Cl] |
| 156 | (S)-N-((S)-1-((5-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)propanamide hydrochloride | 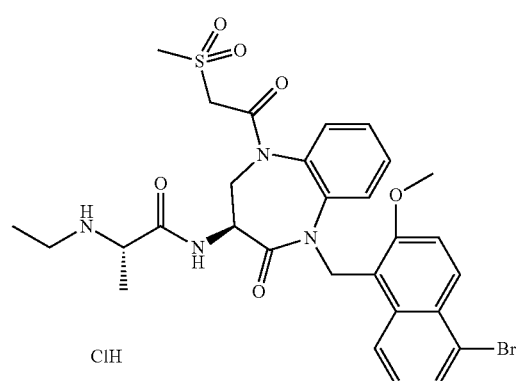 |

| Example | Name | Structure |
|---|---|---|
| 157 | (S)-N-((S)-1-((6-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride | 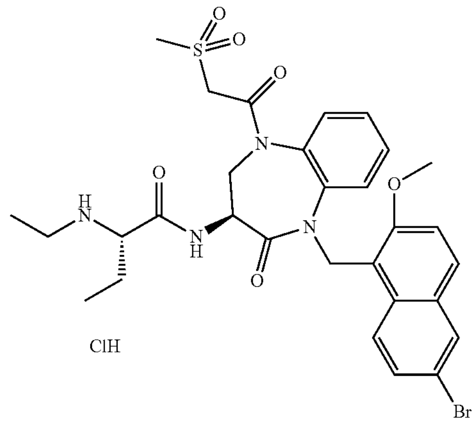 [SMILES: CCN[C@@H](CC)C(=O)N[C@H]1CN(C(=O)CS(C)(=O)=O)c2ccccc2N(Cc2c(OC)ccc3cc(Br)ccc23)C1=O ; Cl] |
| 158 | (2S)-N-[(3S)-1-(1H-indazole-6-carbonyl)-5-[(2-methylnaphthalen-1-yl)methyl]-4-oxo-2,3-dihydro-1,5-benzodiazepin-3-yl]-2-(methylamino)propanamide | Chiral |
| 159 | (S)-N-((S)-1-((1-(2-cyanophenyl)-1H-indazol-3-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride | 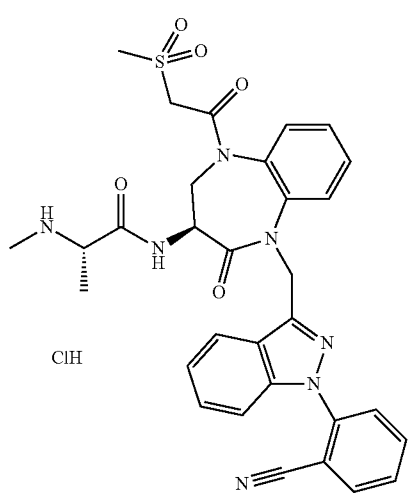 [SMILES: CN[C@@H](C)C(=O)N[C@H]1CN(C(=O)CS(C)(=O)=O)c2ccccc2N(Cc2nn(-c3ccccc3C#N)c3ccccc23)C1=O ; Cl] |

TABLE 12-continued

| Example | Name | Structure |
|---|---|---|
| 160 | (S)-N-((S)-1-((5-bromo-2-methoxynaphthalen-1-yl)methyl)-7-cyano-5-(2-(methylsulfonyl)acetyl)-2-oxo-2,3,4,5-tetrahydro-1H-benzo[b][1,4]diazepin-3-yl)-2-(methylamino)propanamide hydrochloride | 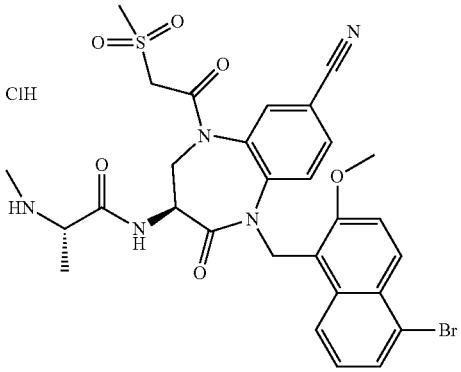 |
| 161 | (2S)-N-[(3S)-7-cyano-1-[[1-(2-cyanophenyl)indazol-3-yl]methyl]-5-(2-methylsulfonylacetyl)-2-oxo-3,4-dihydro-1,5-benzodiazepin-3-yl]-2-(methylamino)propanamide;2,2,2-trifluoroacetic acid | 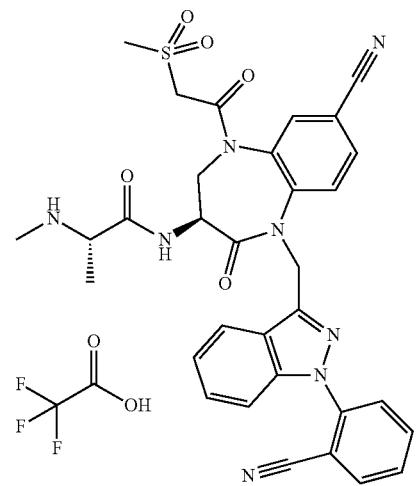 |
| 162 | (S)-N-((S)-5-(4-acetylbenzoyl)-7-cyano-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide hydrochloride | 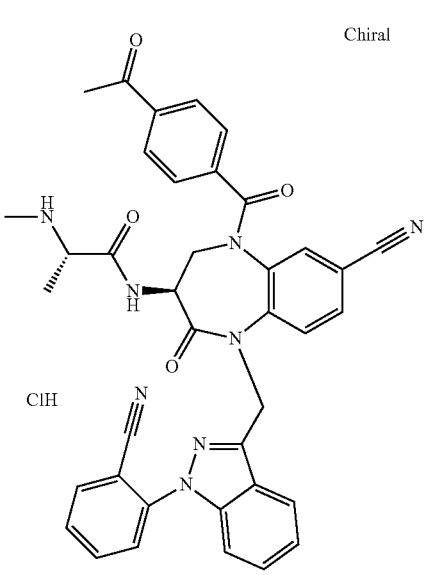 [SMILES: CN[C@@H](C)C(=O)N[C@H]1CN(C(=O)c2ccc(C(C)=O)cc2)c2cc(C#N)ccc2N(Cc2nn(-c3ccccc3C#N)c3ccccc23)C1=O ; Cl] |

TABLE 12-continued

| Example | Name | Structure |
|---|---|---|
| 163 | (S)-N-((S)-7-cyano-1-((1-(2-cyanophenyl)-1H-indazol-3-yl)methyl)-5-(4-fluorobenzoyl)-2-oxo-2,3,4,5-tetrahydro-1H-benzo[b][1,4]diazepin-3-yl)-2-(methylamino)propanamide hydrochloride | Chiral 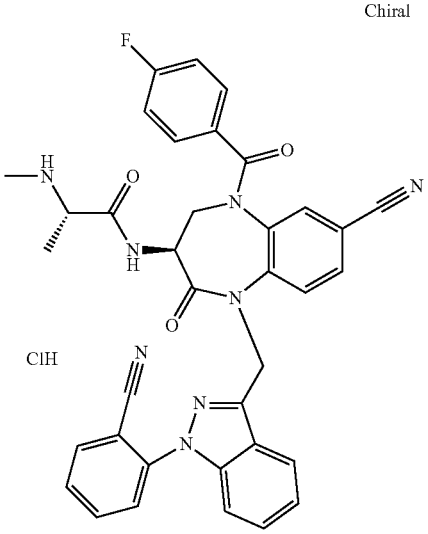 [SMILES: CN[C@@H](C)C(=O)N[C@H]1CN(C(=O)c2ccc(F)cc2)c2cc(C#N)ccc2N(Cc2nn(-c3ccccc3C#N)c3ccccc23)C1=O ; Cl] |
| 164 | (S)-N-((S)-7-cyano-1-((1-methyl-1H-indazol-3-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride | 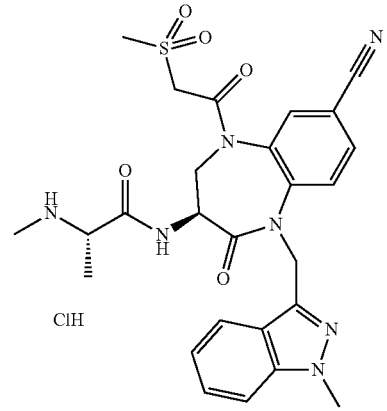 [SMILES: CN[C@@H](C)C(=O)N[C@H]1CN(C(=O)CS(C)(=O)=O)c2cc(C#N)ccc2N(Cc2nn(C)c3ccccc23)C1=O ; Cl] |
| 165 | (S)-N-((S)-7-cyano-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride | 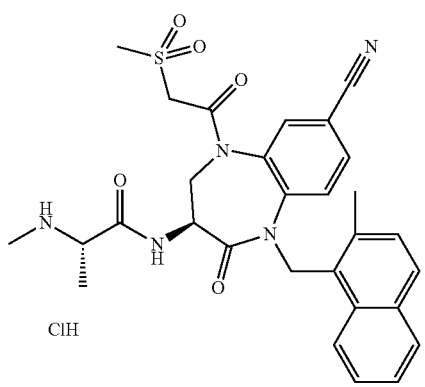 [SMILES: CN[C@@H](C)C(=O)N[C@H]1CN(C(=O)CS(C)(=O)=O)c2cc(C#N)ccc2N(Cc2c(C)ccc3ccccc23)C1=O ; Cl] |

TABLE 12-continued

| Example | Name | Structure |
|---|---|---|
| 166 | (S)-N-((S)-7-cyano-1-((2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride | 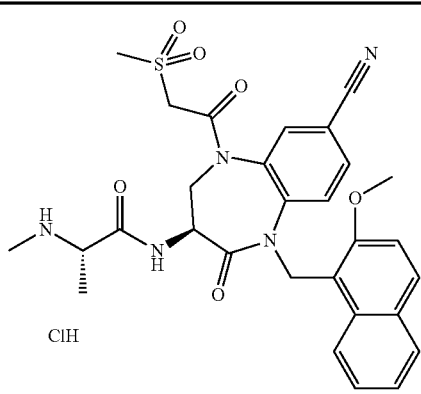 |
| 167 | (S)-N-((S)-8-cyano-1-((1-(2-cyanophenyl)-1H-indazol-3-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride | 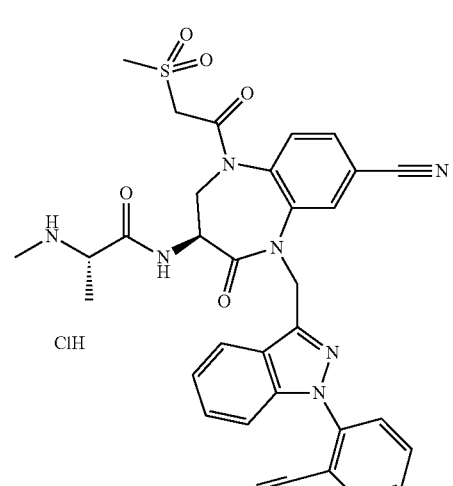 |
| 168 | (S)-N-((S)-7-cyano-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide dihydrochloride | Chiral<br>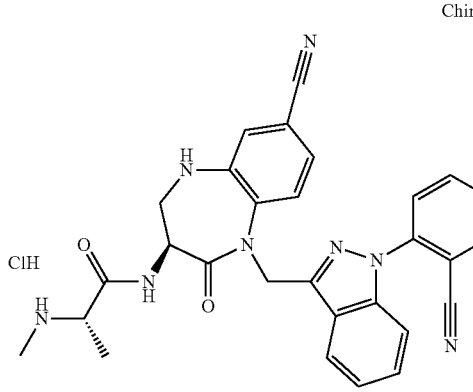 |

TABLE 12-continued

| Example | Name | Structure |
|---|---|---|
| 169 | (S)-N-((S)-5-acetyl-7-cyano-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide hydrochloride | 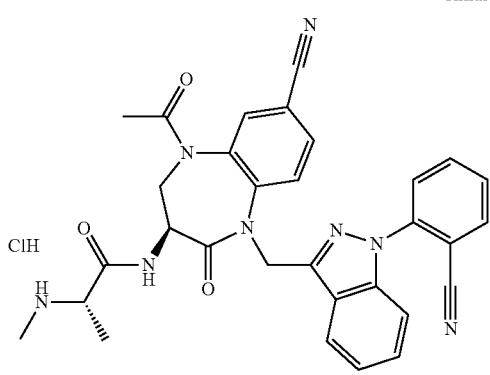 Chiral |
| 170 | (S)-N-((S)-7-cyano-1-((1-(2-cyanophenyl)-1H-indazol-3-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride | 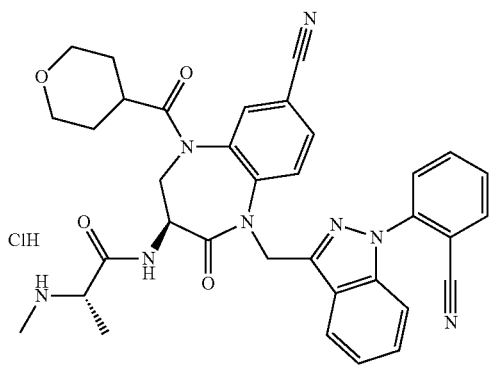 Chiral |
| 171 | (S)-N-((S)-8-cyano-1-((2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride | 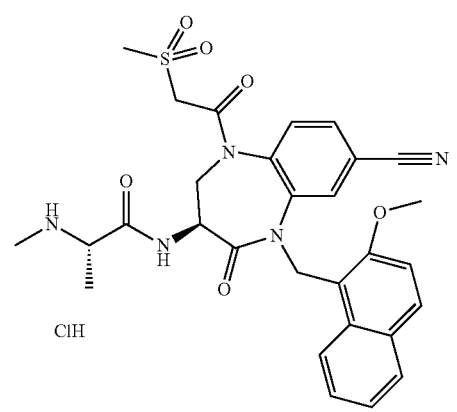 [SMILES: CN[C@@H](C)C(=O)N[C@H]1CN(C(=O)CS(C)(=O)=O)c2ccc(C#N)cc2N(Cc2c(OC)ccc3ccccc23)C1=O ; Cl] |
| 172 | (S)-N-((S)-8-cyano-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride | 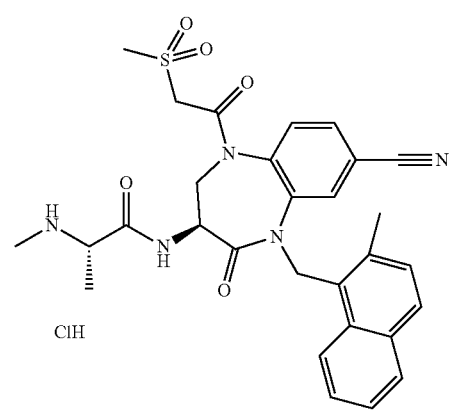 [SMILES: CN[C@@H](C)C(=O)N[C@H]1CN(C(=O)CS(C)(=O)=O)c2ccc(C#N)cc2N(Cc2c(C)ccc3ccccc23)C1=O ; Cl] |

TABLE 12-continued

| Example | Name | Structure |
|---|---|---|
| 173 | (S)-N-((S)-7-cyano-1-((1-(2-cyanophenyl)-1H-indazol-3-yl)methyl)-5-(3-methoxypropanoyl)-2-oxo-2,3,4,5-tetrahydro-1H-benzo[b][1,4]diazepin-3-yl)-2-(methylamino)propanamide hydrochloride | 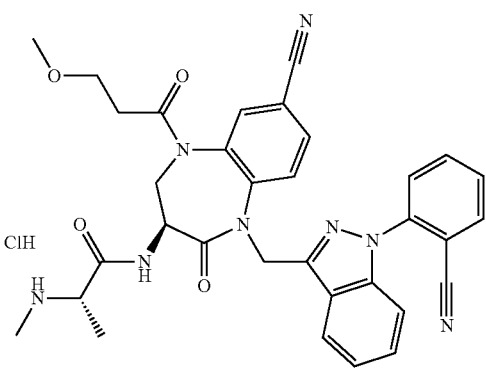 Chiral |
| 174 | (S)-N-((S)-7-cyano-1-((1-(2-cyanophenyl)-1H-indazol-3-yl)methyl)-5-isonicotinoyl-2-oxo-2,3,4,5-tetrahydro-1H-benzo[b][1,4]diazepin-3-yl)-2-(methylamino)propanamide dihydrochloride | 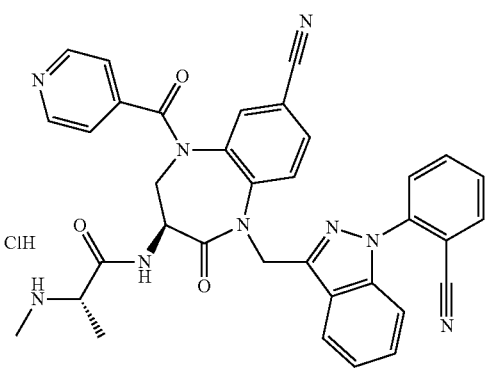 Chiral |
| 175 | (S)-N-((S)-1-((5-bromo-2-methoxynaphthalen-1-yl)methyl)-8-cyano-5-(2-(methylsulfonyl)acetyl)-2-oxo-2,3,4,5-tetrahydro-1H-benzo[b][1,4]diazepin-3-yl)-2-(methylamino)propanamide hydrochloride | 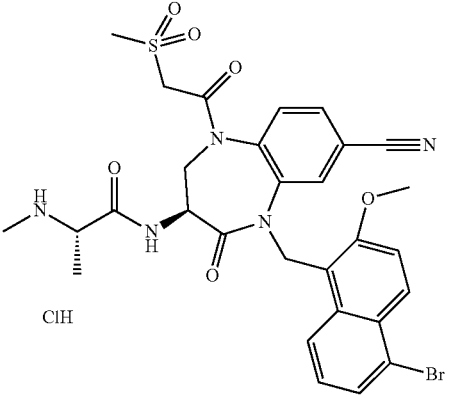 [SMILES: CN[C@@H](C)C(=O)N[C@H]1CN(C(=O)CS(C)(=O)=O)c2ccc(C#N)cc2N(Cc2c(OC)ccc3c(Br)cccc23)C1=O ; Cl] |

TABLE 12-continued

| Example | Name | Structure |
|---|---|---|
| 176 | (S)-N-((S)-5-acetyl-7-cyano-1-((5-cyano-2-cyclopropylnaphthalen-1-yl)methyl)-2-oxo-2,3,4,5-tetrahydro-1H-benzo[b][1,4]diazepin-3-yl)-2-(methylamino)propanamide hydrochloride | Chiral 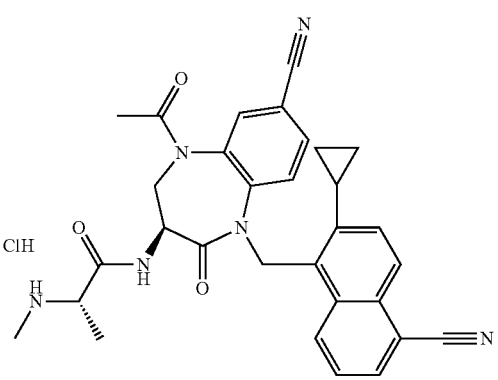 |
| 177 | (S)-N-((S)-5-acetyl-1-((1-(2-cyanophenyl)-1H-indazol-3-yl)methyl)-2-oxo-7-(trifluoromethyl)-2,3,4,5-tetrahydro-1H-benzo[b][1,4]diazepin-3-yl)-2-(methylamino)propanamide hydrochloride | Chiral 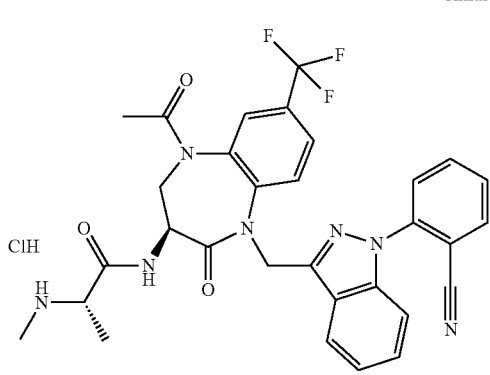 |
| 178 | (2S)-N-[(3S)-1-(4-aminobenzoyl)-5-[[2-(2-fluoroethoxy)naphthalen-1-yl]methyl]-4-oxo-2,3-dihydro-1,5-benzodiazepin-3-yl]-2-(methylamino)propanamide;hydrochloride | Chiral 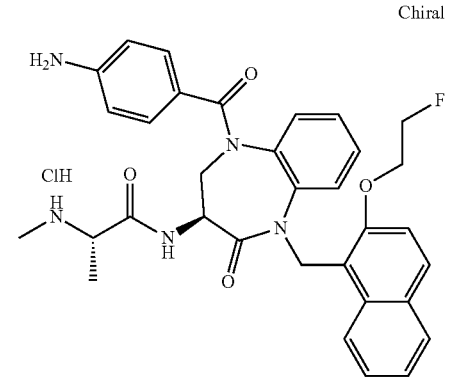 [SMILES: CN[C@@H](C)C(=O)N[C@H]1CN(C(=O)c2ccc(N)cc2)c2ccccc2N(Cc2c(OCCF)ccc3ccccc23)C1=O ; Cl] |
| 179 | (S)-N-((S)-5-acetyl-1-((5-bromo-2-methoxynaphthalen-1-yl)methyl)-7-cyano-2-oxo-2,3,4,5-tetrahydro-1H-benzo[b][1,4]diazepin-3-yl)-2-(methylamino)propanamide | Chiral 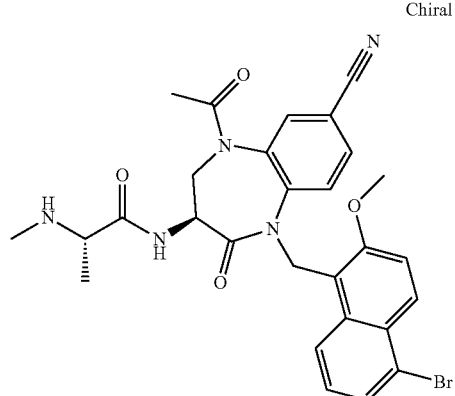 |

TABLE 12-continued

| Example | Name | Structure |
|---|---|---|
| 180 | (S)-N-((S)-7-cyano-1-((3-cyclopropylquinolin-4-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide | 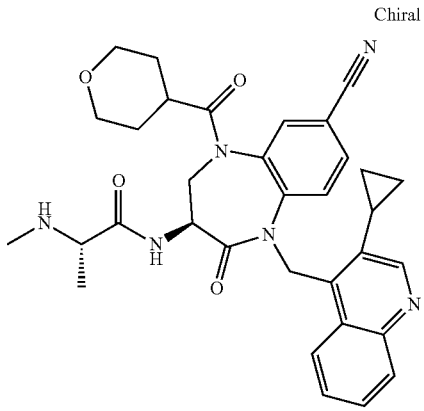 [SMILES: CN[C@@H](C)C(=O)N[C@H]1CN(C(=O)C2CCOCC2)c2cc(C#N)ccc2N(Cc2c(C3CC3)cnc3ccccc23)C1=O] Chiral |
| 181 | (S)-N-((S)-7-cyano-1-((3-cyclopropylquinolin-4-yl)methyl)-5-isonicotinoyl-2-oxo-2,3,4,5-tetrahydro-1H-benzo[b][1,4]diazepin-3-yl)-2-(methylamino)propanamide | 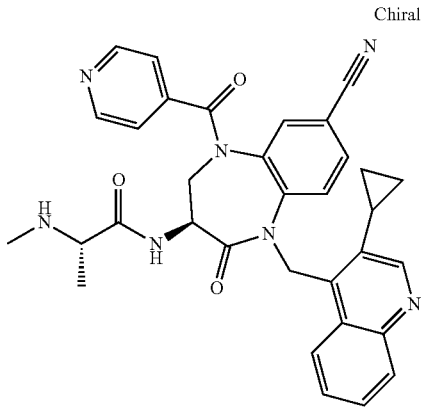 [SMILES: CN[C@@H](C)C(=O)N[C@H]1CN(C(=O)c2ccncc2)c2cc(C#N)ccc2N(Cc2c(C3CC3)cnc3ccccc23)C1=O] Chiral |
| 182 | (S)-N-((S)-5-acetyl-7-cyano-1-((5-cyano-2-methoxynaphthalen-1-yl)methyl)-2-oxo-2,3,4,5-tetrahydro-1H-benzo[b][1,4]diazepin-3-yl)-2-(methylamino)propanamide | 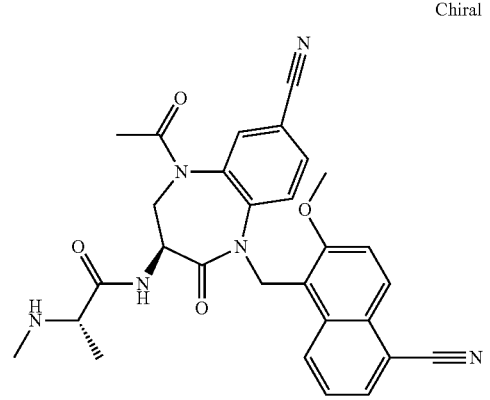 [SMILES: CN[C@@H](C)C(=O)N[C@H]1CN(C(C)=O)c2cc(C#N)ccc2N(Cc2c(OC)ccc3c(C#N)cccc23)C1=O] Chiral |

TABLE 12-continued

| Example | Name | Structure | |
|---|---|---|---|
| 183 | (S)-N-((S)-5-acetyl-1-((3-cyclopropylquinolin-4-yl)methyl)-2-oxo-7-(trifluoromethyl)-2,3,4,5-tetrahydro-1H-benzo[b][1,4]diazepin-3-yl)-2-(methylamino)propanamide | 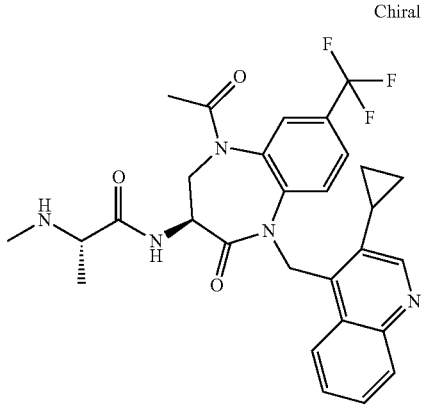 [SMILES: CN[C@@H](C)C(=O)N[C@H]1CN(C(C)=O)c2cc(C(F)(F)F)ccc2N(Cc2c(C3CC3)cnc3ccccc23)C1=O] | Chiral |
| 184 | (S)-N-((S)-1-((3-cyclopropylquinolin-4-yl)methyl)-2-oxo-5-(tetrahydro-2H-pyran-4-carbonyl)-7-(trifluoromethyr)-2,3,4,5-tetrahydro-1H-benzo[b][1,4]diazepin-3-yl)-2-(methylamino)propanamide | 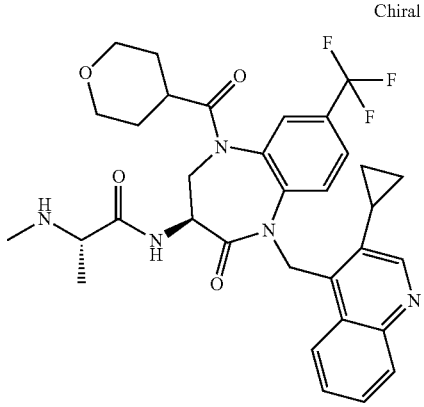 [SMILES: CN[C@@H](C)C(=O)N[C@H]1CN(C(=O)C2CCOCC2)c2cc(C(F)(F)F)ccc2N(Cc2c(C3CC3)cnc3ccccc23)C1=O] | Chiral |
| 185 | (S)-N-((S)-1-((3-cyclopropylquinolin-4-yl)methyl)-5-(3-methoxypropanoyl)-2-oxo-7-(trifluoromcthyl)-2,3,4,5-tetrahydro-1H-benzo[b][1,4]diazepin-3-yl)-2-(methylamino)propanamide | 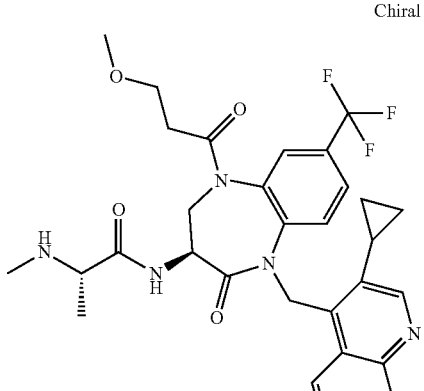 | Chiral |

TABLE 12-continued

| Example | Name | Structure |
|---|---|---|
| 186 | (S)-N-((S)-1-((3-cyclopropylquinolin-4-yl)methyl)-5-isonicolinoyl-2-oxo-7-(trifluoromethyl)-2,3,4,5-tetrahydro-1H-benzo[b][1,4]diazepin-3-yl)-2-(methylamino)propanamide | Chiral |
| 187 | (S)-N-((S)-1-((3-cyclopropylquinolin-4-yl)methyl)-5-(2-(methylsulfonyl)acetyl)-2-oxo-7-(trifluoromethyl)-2,3,4,5-tetrahydro-1H-benzo[b][1,4]diazepin-3-yl)-2-(methylamino)propanamide | Chiral |
| 188 | (S)-N-((S)-1-((3-cyclopropylquinolin-4-yl)methyl)-5-(3-(methylsulfonyl)propanoyl)-2-oxo-7-(trifluoromethyl)-2,3,4,5-tetrahydro-1H-benzo[b][1,4]diazepin-3-yl)-2-(methylamino)propanamide | Chiral |

TABLE 12-continued

| Example | Name | Structure |
|---|---|---|
| 189 | (S)-N-((S)-5-acetyl-1-((5-cyano-2-cyclopropylnaphthalen-1-yl)methyl)-2-oxo-7-(trifluoromethyl)-2,3,4,5-tetrahydro-1H-benzo[b][1,4]diazepin-3-yl)-2-(methylamino)propanamide | Chiral 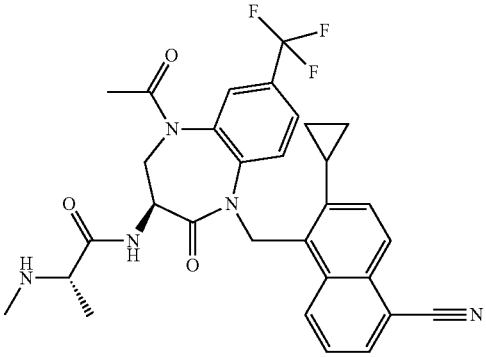 |
| 190 | (S)-N-((2S,3S)-1-acetyl-5-(2-(2,6-difluorophenylamino)-2-oxoethyl)-2-methyl-4-oxo-2,3,4,5-tetrahydro-1H-benzo[b][1,4]diazepin-3-yl)-2-(methylamino)propanamide hydrochloride | 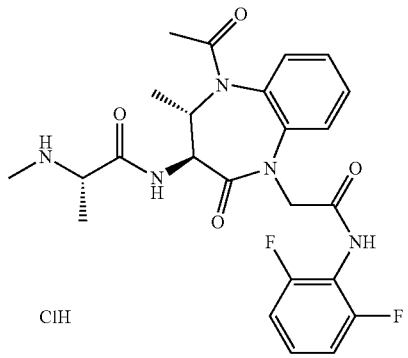 [SMILES: CN[C@@H](C)C(=O)N[C@@H]1C(=O)N(CC(=O)Nc2c(F)cccc2F)c2ccccc2N(C(C)=O)[C@H]1C ; Cl]<br>ClH |
| 191 | (S)-N-((2S,3S)-1-acetyl-2-methyl-4-oxo-5-(2-oxo-2-(phenylamino)ethyl)-2,3,4,5-tetrahydro-1H-benzo[b][1,4]diazepin-3-yl)-2-(methylamino)propanamide hydrochloride | 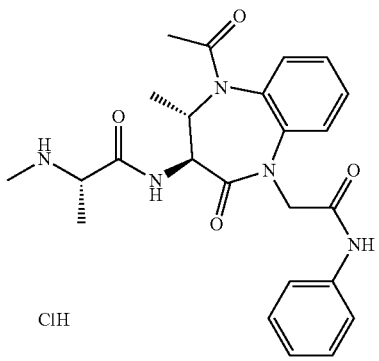 [SMILES: CN[C@@H](C)C(=O)N[C@@H]1C(=O)N(CC(=O)Nc2ccccc2)c2ccccc2N(C(C)=O)[C@H]1C ; Cl]<br>ClH |
| 192 | (2S)-N-((2S,3S)-1-acetyl-5-(2-(2,6-difluorophenylamino)-2-oxo-1-phenylethyl)-2-methyl-4-oxo-2,3,4,5-tetrahydro-1H-benzo[b][1,4]diazepin-3-yl)-2-(methylamino)propanamide hydrochloride | 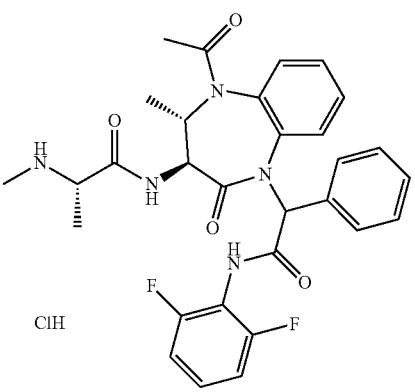 [SMILES: CN[C@@H](C)C(=O)N[C@@H]1C(=O)N(C(C(=O)Nc2c(F)cccc2F)c2ccccc2)c2ccccc2N(C(C)=O)[C@H]1C ; Cl]<br>ClH |

Example 193

Biochemical Assays

TR-FRET Assay for BIR2 and BIR3

The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK-(c-biotin)-OH 1:2 TFA ("Peptide A") was identified as a substrate for the TR-FRET assay by screening the 6× Histidine-tagged BIR2 domain and BIR3 domain of XIAP against a set of 29 peptides synthesized based on sequences reported by Sweeny et al. (*Biochemistry*, 2006, 45, 14740 14748). The peptides were labeled with the fluorescent tags FITC or TAMRA and Kd values were determined by fluorescence polarization assay. The sequence AVPIAQKSEK was identified as optimal for using in an assay. The peptide sequence was derivatized with biotin to provide AVPIAQKSEK-(c-biotin)-OH 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is MRHHHH-HHRDHFALDRPSETHADYLLRTGQVVDISDTIYPRN-PAMYSEEARLKSFQNW PDYAHLTPRELASAGLYYT-GIGDQVQCFACGGKLKNWEPGDRAWSEHRRHFPN CFFVL GRNLNIRSE. The sequence of the BIR3 domain used for the TR-FRET assay is MRHHHHHHRSDAVSS-DRNFPNSTNLPRNPSMADYEARIFTFGTWIYS-VNKEQLARAGF YALGEGDKVKCFHCGGGLTD-WKPSEDPWEQHAKWYPGCKYLLEQKGQEYINNIH LTH SLEECLVRTT.

Ten nanomolar of 6× Histidine-tagged BIR2 domain, corresponding to amino acids 124-240 of XIAP, or BIR3 domain, corresponding to amino acids 241-356 of XIAP, was mixed with 20 nM of the peptide AVPIAQKSEK-(c-biotin)-OH 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 min. incubation at 37° C., Europium-Streptavidin and Allophycocyanin conjugated anti-Histidine antibody were added to a final concentration of 1.5 nM and 15 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an $IC_{50}$ value for each test compound.

These values are listed below in Table 12.

TABLE 12

| Ex. | $IC_{50}$ BIR2 (μM) | $IC_{50}$ BIR3 (μM) | Ex. | $IC_{50}$ BIR2 (μM) | $IC_{50}$ BIR3 (μM) |
| --- | --- | --- | --- | --- | --- |
| 1 | 4.388 | >54.8 | 96g | 0.065 | 44.82 |
| 2 | 0.928 | >54.8 | 96h | 0.023 | 13.57 |
| 3 | 0.611 | >54.8 | 96i | 0.030 | 47.95 |
| 4 | 0.409 | >54.0 | 96j | 0.029 | 24.57 |
| 5 | 4.363 | >54.0 | 96k | 0.038 | 32.25 |
| 6 | 2.618 | >54.0 | 96l | 0.037 | >54.8 |
| 7 | 1.555 | >54.0 | 98b | 0.188 | >54.8 |
| 8 | 0.383 | >54.8 | 98c | 0.204 | 29.8 |
| 9 | 0.520 | >54.8 | 98d | 0.182 | 28.97 |
| 10 | 0.364 | >54.8 | 98e | 0.133 | 31.6 |
| 11 | 0.426 | >54.8 | 98f | 0.177 | >50.0 |
| 12 | 0.820 | >54.8 | 103 | 0.00914 | 41.06 |
| 13 | 0.234 | >54.8 | 104 | 0.012 | 47.42 |
| 14 | 0.244 | >54.8 | 105 | 0.503 | 46.08 |
| 15 | 0.076 | >54.8 | 106 | 0.238 | >51.5 |
| 16 | 0.126 | >54.8 | 107 | 0.146 | >54.8 |
| 17 | 1.434 | >54.8 | 108 | 0.0172 | >54.8 |
| 18 | 0.590 | >54.8 | 109 | 0.121 | 42.34 |
| 19 | 0.620 | >54.8 | 110 | 0.278 | >54.8 |
| 20 | 0.588 | >54.8 | 111 | 0.295 | >54.8 |
| 21 | 2.773 | >54.8 | 112 | 0.248 | 41.22 |
| 22 | 3.165 | >54.8 | 113 | 0.324 | >54.8 |
| 23 | 6.752 | >54.8 | 114 | 0.53 | >54.8 |
| 24 | 0.150 | >54.8 | 115 | 0.0687 | >54.8 |
| 25 | 2.226 | >54.8 | 116 | 0.0398 | >54.8 |
| 26 | 0.077 | >54.8 | 117 | 0.168 | >54.8 |
| 27 | 0.033 | >54.8 | 118 | 0.0519 | 23.69 |
| 28 | 0.039 | >54.8 | 119 | 0.0575 | 21.71 |
| 29 | 0.028 | 51.375 | 120 | 0.00628 | >54.8 |
| 30 | 0.033 | 52.745 | 121 | 0.0148 | 46.42 |
| 31 | 0.041 | >54.8 | 122 | 0.0132 | 26.39 |
| 32 | 0.025 | 41.535 | 123 | 0.00671 | 18.74 |
| 33 | 0.018 | 34.38 | 124 | 0.00568 | 13.11 |
| 34 | 0.033 | 15.89 | 125 | 0.00792 | 25.6 |
| 35 | 0.006 | 22.09 | 126 | 0.0172 | 21.48 |
| 36 | 5.000 | >54.8 | 127 | 0.00922 | 26.73 |
| 37 | 0.271 | >54.8 | 128 | 0.00499 | 44.82 |
| 38 | 1.073 | >54.8 | 129 | 0.00968 | >54.8 |
| 39 | 0.019 | 31.93 | 130 | 0.0356 | 16.43 |
| 40 | 0.173 | 7.423 | 131 | 0.0112 | 29.83 |
| 41 | 0.006 | 24.52 | 132 | 0.0379 | >54.8 |
| 42 | 0.037 | >54.8 | 133 | 0.0271 | >54.8 |
| 43 | 0.057 | 44.08 | 134 | 0.0325 | >54.8 |
| 44 | 0.016 | 17.365 | 135 | 0.032 | 36.21 |
| 45 | 0.016 | 29.915 | 136 | 0.186 | 41.9 |
| 46 | 0.062 | >54.8 | 137 | 0.0298 | >54.8 |
| 47 | 0.020 | 44.645 | 138 | 0.0694 | >54.8 |
| 48 | 0.023 | 33.16 | 139 | 0.0347 | 36.9 |
| 49 | 0.127 | >54.8 | 140 | 0.0497 | 48.75 |
| 50 | 0.013 | 18.51 | 141 | 0.0393 | 48.27 |
| 51 | 0.058 | 42.8 | 142 | 0.0324 | 47.23 |
| 52 | 0.047 | >54.8 | 143 | 0.00511 | 16.26 |
| 53 | 0.007 | 18.62 | 144 | 0.00615 | 23.76 |
| 54 | 0.018 | 16.02 | 145 | 0.0265 | >54.8 |
| 55 | 0.022 | >54.8 | 146 | 0.0167 | >54.8 |
| 56 | 0.010 | 38.12 | 147 | 0.0551 | >54.8 |
| 57 | 0.007 | 20.79 | 148 | 0.04005 | >54.8 |
| 58 | 0.358 | 19 | 149 | 0.183 | >54.8 |
| 59 | 3.782 | 31.43 | 150 | 0.00906 | 12.33 |
| 60 | 0.166 | >54.8 | 151 | 0.0284 | 48.96 |
| 61 | 0.072 | >54.8 | 152 | 0.0326 | 51.66 |
| 62 | 0.017 | 41.27 | 153 | 0.0524 | >54.8 |
| 63 | 0.019 | 42.95 | 154 | 0.0115 | 19.15 |
| 64 | 0.026 | >54.8 | 155 | 0.0186 | >54.8 |
| 65 | 0.007 | 23.57 | 156 | 0.0429 | >54.8 |
| 66 | 0.038 | 48.3 | 157 | 0.0194 | >54.8 |
| 67 | 0.022 | >54.8 | 158 | 0.0182 | >54.8 |
| 68 | 1.479 | >54.8 | 159 | 0.0413 | >54.8 |
| 69a | 0.032 | 47 | 160 | 0.0161 | >54.8 |
| 70 | 0.041 | 52.94 | 161 | 0.0539 | >54.8 |
| 71 | 0.064 | >54.8 | 162 | 0.0183 | >54.8 |
| 72 | 0.044 | >54.8 | 163 | 0.0172 | >54.8 |
| 73 | 0.006 | 28.25 | 164 | 0.103 | >54.8 |
| 74 | 0.049 | >54.8 | 165 | 0.0592 | >54.8 |
| 75a | 0.008 | 27 | 166 | 0.02 | 43.56 |
| 76a | 0.007 | 42.7 | 167 | 0.0995 | >54.8 |
| 77 | 0.047 | 47.52 | 168 | 0.0957 | >54.8 |
| 78 | 0.030 | 17.08 | 169 | 0.0332 | >54.8 |
| 79 | 0.001 | 3.479 | 170 | 0.0255 | >54.8 |
| 80 | 0.014 | >54.8 | 171 | 0.0303 | 41.24 |
| 81 | 0.024 | >54.8 | 172 | 0.0947 | >54.8 |
| 82 | 0.029 | >54.8 | 173 | 0.0376 | >54.8 |
| 83 | 0.121 | >54.8 | 174 | 0.0224 | >54.8 |
| 84 | 0.010 | 32.75 | 175 | 0.0183 | 17.59 |
| 85 | 0.012 | 33.91 | 176 | 0.0382 | 25.59 |
| 86 | 0.013 | 49.62 | 177 | 0.0353 | >54.8 |

TABLE 12-continued

| Ex. | IC$_{50}$ BIR2 (μM) | IC$_{50}$ BIR3 (μM) | Ex. | IC$_{50}$ BIR2 (μM) | IC$_{50}$ BIR3 (μM) | Ex. | IC$_{50}$ BIR2 (μM) | IC$_{50}$ BIR3 (μM) | Ex. | IC$_{50}$ BIR2 (μM) | IC$_{50}$ BIR3 (μM) |
|---|---|---|---|---|---|---|---|---|---|---|---|
| 87 | 0.019 | 54.42 | 178 | 0.0142 | 16.09 | 69e | 0.049 | 50.3 | | | |
| 88 | 0.014 | 39.89 | 179 | 0.0167 | 33.12 | 69f | 0.007 | 30.65 | | | |
| 89a | 0.006 | 44.49 | 180 | 0.018 | 16.51 | 69g | 0.011 | 42.52 | | | |
| 90a | 0.011 | 24.31 | 181 | 0.0169 | 16.28 | 69h | 0.020 | 30.31 | | | |
| 91a | 0.006 | 24.77 | 182 | 0.0235 | 32.39 | 69i | 0.039 | 51.97 | | | |
| 92 | 0.009 | 13.75 | 183 | 0.0448 | 27.49 | 69j | 0.213 | >54.8 | | | |
| 93 | 0.018 | 47.57 | 184 | 0.0183 | 15.24 | 69k | 0.027 | >54.8 | | | |
| 94 | 0.009 | 46.63 | 185 | 0.0601 | 33.19 | 69l | 0.009 | 41.51 | | | |
| 95 | 0.007 | 36.28 | 186 | 0.0256 | 25.94 | 69m | 0.007 | 49.4 | | | |
| 96a | 0.099 | >54.8 | 187 | 0.0493 | 34.43 | 69n | 0.011 | 25.85 | | | |
| 97 | 0.100 | >54.8 | 188 | 0.0225 | 25.41 | 75b | 0.006 | 30.29 | | | |
| 98a | 0.211 | >54.8 | 189 | 0.0304 | 29.28 | 75c | 0.005 | 30.43 | | | |
| 99 | 0.041 | 33.1 | 190 | 0.0853 | >54.8 | 75d | 0.006 | 18.19 | | | |
| 100 | 0.249 | >54.8 | 191 | 0.434 | >54.8 | 76b | 0.009 | >54.8 | | | |
| 101 | 0.036 | 53.43 | 192 | 0.24 | >54.8 | 76c | 0.009 | 45.89 | | | |
| 102 | 0.057 | >54.8 | | | | 76d | 0.005 | 33.25 | | | |
| 13b | 0.371 | >54.8 | | | | 76e | 0.010 | 33.72 | | | |
| 13c | 0.119 | >54.8 | | | | 89b | 0.005 | 17.01 | | | |
| 13d | 0.175 | >54.8 | | | | 89c | 0.010 | 49.9 | | | |
| 13e | 0.308 | >54.8 | | | | 89d | 0.006 | 24.77 | | | |
| 13f | 0.054 | >54.8 | | | | 89e | 0.011 | 32.45 | | | |
| 13g | 0.481 | >54.8 | | | | 90b | 0.011 | 26.96 | | | |
| 13h | 0.022 | 39.30 | | | | 90c | 0.006 | 21.85 | | | |
| 13i | 0.078 | >54.8 | | | | 90d | 0.006 | 25.66 | | | |
| 13j | 0.037 | >54.8 | | | | 90e | 0.010 | 48.56 | | | |
| 13k | 0.025 | >54.8 | | | | 90f | 0.020 | >54.8 | | | |
| 13l | 0.067 | >54.8 | | | | 91b | 0.015 | >54.8 | | | |
| 13m | 0.035 | >54.8 | | | | 91c | 0.006 | 30.57 | | | |
| 13n | 0.091 | >54.8 | | | | 91d | 0.018 | >54.8 | | | |
| 13o | 0.028 | 22.04 | | | | 96b | 0.071 | 38.81 | | | |
| 13p | 0.022 | 42.78 | | | | 96c | 0.106 | 28.12 | | | |
| 13q | 0.092 | >54.8 | | | | 96d | 0.046 | >54.8 | | | |
| 13r | 0.017 | 46.73 | | | | 96e | 0.685 | >54.8 | | | |
| 69b | 0.026 | 46.57 | | | | 96f | 0.020 | 32.79 | | | |
| 69c | 0.341 | >54.8 | | | | | | | | | |
| 69d | 0.012 | >54.8 | | | | | | | | | |

The invention claimed is:

1. A compound, selected from the group consisting of: Cyclic-5-[(S)-5-(2-Amino-ethyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride; Cyclic-5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride; Cyclic-5-[(S)-5-(3-amino-propyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride; Cyclic-5-[(S)-5-(4-Amino-butyryl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride; and Cyclic-5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, or a pharmaceutically acceptable salt thereof.

2. A compound, selected from the group consisting of:
(S)-2-Methylamino-N—((S)-1-naphthalen-1-ylmethyl-2-oxo-2,3,4,5-tetrahydro-1H-benzo[b][1,4]diazepin-3-yl)-propionamide hydrochloride, (S)—N—((S)-5-Acetyl-1-naphthalen-1-ylmethyl-2-oxo-2,3,4,5-tetrahydro-1H-benzo[b][1,4]diazepin-3-yl)-2-methylamino-propionamide hydrochloride, (S)-2-Methylamino-N—[(S)-5-(3-methyl-butyryl)-1-naphthalen-1-ylmethyl-2-oxo-2,3,4,5-tetrahydro-1H-benzo[b][1,4]diazepin-3-yl]-propionamide hydrochloride, (S)-2-Methylamino-N—((S)-1-naphthalen-1-ylmethyl-2-oxo-5-phenylacetyl-2,3,4,5-tetrahydro-1H-benzo[b][1,4]diazepin-3-yl)-propionamide hydrochloride, (S)-2-Methylamino-N—((S)-5-methyl-1-naphthalen-1-ylmethyl-2-oxo-2,3,4,5-tetrahydro-1H-benzo[b][1,4]diazepin-3-yl)-propionamide hydrochloride, (S)-2-Methylamino-N—[(S)-5-(3-methyl-butyl)-1-naphthalen-1-ylmethyl-2-oxo-2,3,4,5-tetrahydro-1H-benzo[b][1,4]diazepin-3-yl]-propionamide hydrochloride, (S)-2-Methylamino-N—((S)-1-naphthalen-1-ylmethyl-2-oxo-5-phenethyl-2,3,4,5-tetrahydro-1H-benzo[b][1,4]diazepin-3-yl)-propionamide trifluoroacetate, (S)-2-Methylamino-N—[(S)-5-(3-methyl-butyryl)-1-(2-methyl-naphthalen-1-ylmethyl)-2oxo-2,3,4,5-tetrahydro-1H-benzo[b][1,4]diazepin-3-yl]-propionamide hydrochloride, (S)-2-Methylamino-N—[(S)-1-(2-methyl-naphthalen-1-naphthalen-1ylmethyl)-2-oxo-5-(pyridine-4-carbonyl)-

2,3,4,5-tetrahydro-1H-benzo[b][1,4]diazepin-3-yl]-propionamide hydrochloride, (S)—N—[(S)-5-[2-(2-methoxy-ethoxy)-acetyl]-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-(2-Carbamoyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)-2-methylamino-N—{(S)-1-(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-yl}-propionamide hydrochloride, (S)—N—[(S)-5-{2-[2-(2-Methoxy-ethoxy)-ethoxy]-acetyl}-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)-2-Methylamino-N—[(S)-1-(2-methyl-naphthalen-1-ylmethyl)-2-oxo-5-(2-pyridin-4-yl-acetyl)-2,3,4,5-tetrahydro-1H-benzo[b][1,4]diazepin-3-yl]-propionamide dihydrochloride, (S)—N—[(S)-5-(4-Methanesulfonyl-benzoyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)-2-Methylamino-N—[(S)-1-(2-methyl-naphthalen-1-ylmethyl)-2-oxo-5-(5-oxo-hexanoyl)-2,3,4,5-tetrahydro-1H-benzo[b][1,4]diazepin-3-yl]-propionamide hydrochloride, methyl 6-((S)-3-((S)-2-(methylamino)propanamido)-5-((2-methylnaphthalen-1-yl)methyl)-4-oxo-2,3,4,5-tetrahydro-1H-benzo[b][1,4]diazepin-1-yl)-6-oxo-hexanoate hydrochloride, (S)—N—[(S)-5-(4-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)-2-Methylamino-N—[(S)-1-(2-methyl-naphthalen-1-ylmethyl)-2-oxo-5-(3,4,5-trimethoxy-benzoyl)-2,3,4,5-tetrahydro-1H-benzo[b][1,4]diazepin-3-yl]-propionamide hydrochloride, (S)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-cyclohexylacetyl)-2-oxo-2,3,4,5-tetrahydro-1H-benzo[b][1,4]diazepin-3-yl)-2-(methylamino)propanamide hydrochloride, (S)—N—{(S)-1-(6-Bromo-2-methoxy-naphthalen-1-ylmethyl)-5-[4-(2,2-dimethyl-propionyl)-benzoyl]-2-oxo-2,3,4,5-tetrahydro-1H-benzo[b][1,4]diazepin-3-yl}-2-methylamino-propionamide hydrochloride, (S)—N—{(S)-1-(6-Bromo-2-methoxy-naphthalen-1-ylmethyl)-2-oxo-5-[4-(2,2,2-trifluoro-1,1-dihydroxy-ethyl)-benzoyl]-2,3,4,5-tetrahydro-1H-benzo[b][1,4]diazepin-3-yl}-2-methylamino-propionamide trifluoroacetate, (S)—N—[(S)-5-(3-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(4-nitro-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(4-nitro-butyryl)-2-oxo-2,3,4,5-tetrahydro-1H-benzo[b][1,4]diazepin-3-yl]-2-methylamino-propionamide hydrochloride, (S)—N—[(S)-5-[2-(4-Acetyl-phenyl)-acetyl]-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—((S)-1-((6-bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—[(S)-5-(2-Adamantan-1-yl-acetyl)-1-(6-bromo-2-methoxy-naphthalen-1-ylmethyl)-2-oxo-2,3,4,5-tetrahydro-1H-benzo[b][1,4]diazepin-3-yl]-2-methyl-amino-propionamide hydrochloride, methyl 5-[[(3S)-1-[3-(9H-fluoren-9-ylmethoxycarbonylamino)propanoyl]-3-[[(2S)-2-(methylamino)propanoyl]amino]-4-oxo-2,3-dihydro-1,5-benzodiazepin-5-yl]methyl]-6-methoxy-naphthalene-2-carboxylate hydrochloride, (S)—N—[(S)-5-acetyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, 5-[(S)-3-((S)-2-methylamino-propionylamino)-5-(2-methyl-naphthalen-1-ymethyl)-4-oxo-2,3,4,5-tetrahydro-benzo[b][1,4]diazepin-1yl]-5-oxo-pentanoic acid hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-yl]-4-oxo-butyric acid hydrochloride, (S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methylamide hydrochloride, (S)—N—[(S)-5-methanesulfonylmethanesulfonyl-1-(2-methyl-naphthalen-1-ylmethyl)-2-oxo-2,3,4,5-tetrahydro-1H-benzo[b][1,4]diazepin-3-yl]-2-methyl-amino-propionamide trifluoroacetate, (S)—N—[(S)-5-methanesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methyl ester hydrochloride, (S)—N—[(S)-1-benzyl-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-1-(2-methoxy-benzyl)-5-(3-methyl-butyryl)-2-oxo-2,3,4,5-tetrahydro-1H-benzo[b[1,4]diazepin-3-yl]-2-methylamino-propionamide hydrochloride, (S)-2-Methylamino-N—[(S)-5-(3-methyl-butyryl)-2-oxo-1-phenethyl-2,3,4,5-tetrahydro-1H-benzo[b[1,4]diazepin-3-yl]-propionamide hydrochloride, (S)—N—[(S)-1-(2-Methoxy-naphthalen-1-ylmethyl)-5-(3-methyl-butyryl)-2-oxo-2,3,4,5-tetrahydro-1H-benzo[b[1,4]diazepin-3-yl]-2-methylamino-propionamide hydrochloride, (S)-2-Methylamino-N—[(S)-5-(3-methyl-butyryl)-1-(1-naphthalen-1-yl-ethyl)-2-oxo-2,3,4,5-tetrahydro-1H-benzo[b][1,4]diazepin-3-yl]-propionamide hydrochloride, (S)—N—[(S)-1-(6-bromo-2-methoxy-naphthalen-1-ylm-ethyl)-5-(3-methyl-butyryl)-2-oxo-2,3,4,5-tetrahydro-1H-benzo[b[1,4]diazepin-3-yl]-2-methylamino-pro-pionamide hydrochloride, (S)—N—[(S)-1-(6-bromo-2-methoxy-naphthalen-1-ylm-ethyl)-2-oxo-5-(5-oxo-hexanoyl)-2,3,4,5-tetrahydro-1H-benzo[b][1,4]diazepin-3-yl]-2-methylamino-pro-pionamide hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid methyl ester hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benz-amide hydrochloride, 4-[(S)-5-(6-bromo-2-methoxy-naphthalen-1-ylmethyl)-3-((S)-2-methylamino-propionylamino)-4-oxo-2,3,4,5-tetrabydro-benzo[b][1,4]diazepin-1-carbonyl]-N-cy-clohexylmethyl-benzamide hydrochloride, (S)—N—{(S)-1-(6-bromo-2-methoxy-naphthalen-1-yl-methyl)-2-oxo-5-[4-(2,2,2-trifluoro-1-hydroxy-ethyl)-benzoyl]-2,3,4,5-tetrahydro-1H-benzo[b][1,4]diaz-epin-3-yl}-2-methylamino-propionamide hydrochloride, (S)—N—{(S)-1-(6-bromo-2-methoxy-naphthalen-1-yl-methyl)-5-(4-(1-hydroxy-ethyl)-benzoyl)-2-oxo-2,3,4,5-tetrahydro-1H-benzo[b][1,4]diazepin-3-yl}-2-meth-ylamino-propionamide hydrochloride, (S)—N—[(S)-5-(Adamantan-1-carbonyl)-1-(6-bromo-2-methoxy-naphthalen-1-ylmethyl)-2-oxo-2,3,4,5-tetra-hydro-1H-benzo[b][1,4]diazepin-3-yl]-2-methyl-amino-propionamide hydrochloride, (S)—N—[(S)-5-(4-Amino-benzoyl)-1-(6-bromo-2-methoxy-naphthalen-1-ylmethyl)-2-oxo-2,3,4,5-tetra-hydro-1H-benzo[b][1,4]diazepin-3-yl]-2-methyl-amino-propionamide hydrochloride, (S)-Azetidine-2-carbonxylic acid[(S)-5-(4-acetyl-ben-zoyl)-1-(6-bromo-2-methoxy-naphthalen-1-ylmethyl)-2-oxo-2,3,4,5-tetrahydro-1H-benzo[[b][1,4]diazepin-3-yl]-amide hydrochloride, (R)—N—[(S)-5-(4-acetyl-benzoyl)-1-(6-bromo-2-methoxyl-napthalen-1-ylmethyl)-2-oxo-2,3,4,5-tetra-hydro-1H-benzo[b][1,4]diazepin-3-yl]-2-methyl-amino-propionamide hydrochloride, (S)—N—[(S)-5-(4-Acetyl-benzoyl)-1-(6-bromo-2-methoxy-naphthalen-1-ylmethyl)-2-oxo-2,3,4,5-tetra-hydro-1H-benzo[b][1,4]diazepin-3-yl]-2-dimethyl-amino-propionamide, (S)—N—[(S)-5-(4-acetyl-benzoyl)-1-(6-bromo-2-methoxy-naphthalen-1-ylmethyl)-2-oxo-2,3,4,5-tetra-hydro-1H-benzo[b][1,4]diazepin-3-yl]-2-amino-pro-pionamide, (S)—N—[(S)-5-(4-Acetyl-benzoyl)-1-(2-naphthalen-1-yl-ethyl)-2-oxo-2,3,4,5-tetrahydro-1H-benzo[b][1,4]diazepin-3-yl]-2-methylamino-propionamide hydro-chloride, (S)—N—[(S)-5-(4-amino-benzoyl)-1-(2-methoxy-naph-thalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-acetylamino-benzoyl)-1-(2-methoxy-naphthalen-1-ylmethyl)-2-oxo-2,3,4,5-tetrahydro-1H-benzo[b][1,4]diazepin-3-yl]-2-methylamino-propiona-mide hydrochloride, 5-[(S)-5-(4-Acetyl-benzoyl)-3-((S)-2-methylamino-pro-pionylamino)-2-oxo-2,3,4,5-tetrahydro-benzo[b][1,4]diazepin-1-ylmethyl]-6-methoxy-naphthalen-2-car-boxylic acid methyl ester hydrochloride, 5-[(S)-5-(4-acetyl-benzoy)-3-((S)-2-methylamino-pro-pionylamino)-2-oxo-2,3,4,5-tetrahydro-benzo[b][1,4]diazepin-1-ylmethyl]-6-methoxy-naphthalen-2-car-boxylic acid hydrochloride, 5-[(S)-5-(4-acetyl-benzoy)-3-((S)-2-methylamino-pro-pionylamino)-2-oxo-2,3,4,5-tetrahydro-benzo[b][1,4]diazepin-1-ylmethyl]-6-methoxy-naphthalen-2-car-boxylic acid hydroxyamide trifluoroacetate, 6-Methoxy-5-[(S)-3((S)-2-methylamino-propio-nylamino)-2-oxo-5-(5-oxo-hexanoyl)-2,3,4,5-tetra-hydro-benzo[b][1,4]diazepin-1-ylmethyl]-naphtha-lene-2-carboxylic acid methyl ester hydrochloride, 6-Methoxy-5-[(S)-3((S)-2-methylamino-propio-nylamino)-2-oxo-5-(5-oxo-hexanoyl)-2,3,4,5-tetra-hydro-benzo[b][1,4]diazepin-1-ylmethyl]-naphtha-lene-2-carboxylic acid hydrochloride, 5-[(S)-5-[4-(9H-Fluoren-9-ylmethoxycarbonylamino)-butyryl]-3-((S)-2-methylamino-propionylamino)-2-oxo-2,3,4,5-tetrahydro-benzo[b][1,4]diazepin-1-ylm-ethyl]-6-methoxy-naphthalene-2-carboxylic acid methyl ester hydrochloride, 5-[(S)-5-(4-Amino-butyryl)-3-((S)-2-methylamino-pro-pionylamino)-2-oxo-2,3,4,5-tetrahydro-benzo[b][1,4]diazepin-1-ylmethyl]-6-methoxy-naphthalene-2-car-boxylic acid methyl ester hydrochloride, 5-[(S)-5-(4-Amino-butyryl)-3-((S)-2-methylamino-pro-pionylamino)-2-oxo-2,3,4,5-tetrahydro-benzo[b][1,4]diazepin-1-ylmethyl]-6-methoxy-naphthalene-2-car-boxylic acid hydrochloride, Cyclic-5-[(S)-5-(4-Amino-butyryl)-3-((S)-2-methyl-amino-propionylamino)-2-oxo-2,3,4,5-tetrahydro-benzo[b][1,4]diazepin-1-ylmethyl]-6-methoxy-naph-thalene-2-carboxylic amide hydrochloride, 5-[(S)-5-(5-amino-pentanoyl)-3-((S)-2-methylamino-pro-pionylamino)-2-oxo-2,3,4,5-tetrahydro-benzo[b][[1,4]diazepin-1-ylmethyl]-6-methoxy-naphthalene-2-car-boxylic acid methyl ester hydrochloride, 5-[(S)-5-(5-amino-pentanoyl)-3-((S)-2-methylamino-pro-pionylamino)-2-oxo-2,3,4,5-tetrahydro-benzo[b][1,4]diazepin-1-ylmethyl]-6-methoxy-naphthalene-2-car-boxylic acid hydrochloride, Cyclic-5-[(S)-5-(5-amino-pentanoyl)-3-((S)-2-methyl-amino-propionylamino)-2-oxo-2,3,4,5-tetrahydro-benzo[b][1,4]diazepin-1-ylmethyl]-6-methoxy-naph-thalene-2-carboxylic amide hydrochloride, 5-[(S)-5-[4-(9H-Fluoren-9-ylmethoxycarbonylamino)-benzoyl]-3-((S)-2-methylamino-propionylamino)-2-oxo-2,3,4,5-tetrahydro-benzo[b][1,4]diazepin-1-ylm-ethyl]-6-methoxy-naphthalene-2-carboxylic acid methyl ester hydrochloride, 5-[(S)-5-(4-Amino-benzoyl)-3-((S)-2-methylamino-pro-pionylamino)-2-oxo-2,3,4,5-tetrahydro-benzo[b][1,4]diazepin-1-ylmethyl]-6-methoxy-naphthalene-2-car-boxylic acid methyl ester hydrochloride, 5-[(S)-5-(4-Amino-benzoyl)-3-((S)-2-methylamino-pro-pionylamino)-2-oxo-2,3,4,5-tetrahydro-benzo[b][1,4]diazepin-1-ylmethyl]-6-methoxy-naphthalene-2-car-boxylic acid hydrochloride, Cyclic-5-[(S)-5-(3-amino-propyl)-3-((S)-2-methylamino-propionylamino)-2-oxo-2,3,4,5-tetrahydro-benzo[b][[1,4]diazepin-1-ylmethyl]-6-methoxy-naphthalene-2-carboxylic amide hydrochloride, Cyclic-5-[(S)-5-(2-Amino-ethyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, 6-[(S)-3-((S)-2-Methylamino-propionylamino)-5-(2-methyl-naphthalen-1-ylmethyl)-4-oxo-2,3,4,5-tetrahydro-benzo[b][1,4]diazepin-1-yl]-6-oxo-hexanoic acid hydrochloride, 5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, Cyclic-5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride, (S)—N—((S)-5-(4-Acetylbenzoyl)-1-((2-methylnaphthalen-1-yl)methyl)-2-oxo-2,3,4,5-tetrahydro-1H-benzo[b][1,4]diazepin-3-yl)-2-aminopropanamide hydrochloride, (S)-2-Amino-N—((S)-5-(4-aminobenzoyl)-1-((2-methoxynaphthalen-1-yl)methyl)-2-oxo-2,3,4,5-tetrahydro-1H-benzo[b][1,4]diazepin-3-yl)propanamide hydrochloride, (S)-2-(Methylamino)-N—((S)-1-((2-methylnaphthalen-1-yl)methyl)-5-(4-nitrobenzoyl)-2-oxo-2,3,4,5-tetrahydro-1H-benzo[b][1,4]diazepin-3-yl)propanamide hydrochloride, (S)—N—((S)-5-(4-Aminobenzoyl)-1-((2-methylnaphthalen-1-yl)methyl)-2-oxo-2,3,4,5-tetrahydro-1H-benzo[b][1,4]diazepin-3-yl)-N-methyl-2-(methylamino)propanamide hydrochloride, (R)—N—((S)-5-(4-Acetylbenzoyl)-1-((2-methylnaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-Acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((7-methoxy-2-oxo-2H-chromen-4-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((6-bromobenzo[d]isoxazol-3-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-aminopropanamide hydrochloride, (S)—N—((S)-5-(4-acetylbenzoyl)-1-((2-(difluoromethoxy)naphthalen-1-yl)methyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-((7-methoxy-2-oxo-2H-chromen-4-yl)methyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-(benzo[d]isoxazol-3-ylmethyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, 4-(((S)-5-(4-Acetylbenzoyl)-3-((S)-2-(methylamino)propanamido)-2-oxo-2,3,4,5-tetrahydro-1H-benzo[b][1,4]diazepin-1-yl)methyl)-3-(2,2,2-trifluoroethoxy)quinoline 1-oxide hydrochloride, (S)—N—((S)-5-(4-Aminobenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, Methyl 4-((S)-5-(benzo[d]isoxazol-3-ylmethyl)-3-((S)-2-(methylamino)propanamido)-4-oxo-2,3,4,5-tetrahydro-1H-benzo[b][1,4]diazepine-1-carbonyl)benzoate hydrochloride, (S)—N—((S)-1-((5-Bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-5-(4-Cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide, (S)—N—((S)-1-((6-Bromo-2-methoxynaphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-methylbenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(isoxazole-5-carbonyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(tetrahydro-2H-pyran-4-carbonyl)-2, 3,4,5-tetrahydro-1H-benzo[b][1,4]diazepin-3-yl)-2-(methylamino)propanamide hydrochloride, (S)—N—((S)-1-((6-Bromo-2-methoxynaphthalen-1-yl)methyl)-2-oxo-5-(2-(pyridin-3-yl)acetyl)-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-(methylsulfonyl)acetyl)-2-oxo-2,3,4,5-tetrahydro-1H-benzo[b][1,4]di azepin-3-yl)-2-(methylamino)propanamide hydrochloride, (S)—N—((S)-1-((6-bromo-2-methoxynaphthalen-1-yl)methyl)-2-oxo-5-(pyrazine-2-carbonyl)-2,3,4,5-tetrahydro-1H-benzo[b][1,4]diazepin-3-yl)-2-(methylamino)propanamide hydrochloride, (S)—N—((S)-5-(4-acetamidobenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—((S)-1-((6-bromo-2-methoxynaphthalen-1-yl)methyl)-5-(1-methyl-1H-pyrazole-3-carbonyl)-2-oxo-2,3,4,5-tetrahydro-1H-benzo[b][1,4]diazepin-3-yl)-2-(methylamino)propanamide trifluoroacetate, (S)—N—((S)-5-Benzyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—((S)-1-((6-Bromo-2-methoxynaphthalen-1-yl)methyl)-5-(4-cyanobenzyl)-2-oxo-2,3,4,5-tetrahydro-1H-benzo[b][1,4]diazepin-3-yl)-2-(methylamino)propanamide trifluoroacetate, (S)—N—((S)-5-(4-Acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)butanamide hydrochloride, (S)—N—((S)-5-(4-Acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(ethylamino)propanamide hydrochloride, (S)—N—((S)-1-((5-Bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((2-(Difluoromethoxy)naphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—[(S)-1-(6-Bromo-2-(d3-methoxy)-naphthalen-1-ylmethyl)-5-(4-cyano-benzoyl)-2-oxo-2,3,4,5-tetrahydro-1H-benzo[b][1,4]diazepin-3-yl]-2-methyl-amino-propionamide hydrochloride, (S)—N—[(S)-1-(6-Bromo-2-(d3-methoxy)-naphthalen-1-ylmethyl)-2-oxo-5-(2-pyridin-3-yl-acetyl)-2,3,4,5-tetrahydro-1H-benzo[b][1,4]diazepin-3-yl]-2-methyl-amino-propionamide hydrochloride, (S)—N—[(S)-1-(6-Bromo-2-methoxy-naphthalen-1-yl-methyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-yl-methyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-yl-methyl)-2-oxo-5-(2-pyridin-3-yl-acetyl)-2,3,4,5-tetrahydro-1H-benzo[b][1,4]diazepin-3-yl]-2-methyl-amino-propionamide hydrochloride, (S)—N—[(S)-1-(6-Bromo-2-methoxy-naphthalen-1-yl-methyl)-2-oxo-5-(pyridine-2-carbonyl)-2,3,4,5-tetrahydro-1H-benzo[b][1,4]diazepin-3-yl]-2-methyl-amino-propionamide hydrochloride, (S)—N—((S)-1-((6-bromo-2-methoxynaphthalen-1-yl)methyl)-5-nicotinoyl-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(2-(pyridin-2-yl)acetyl)-2,3,4,5-tetrahydro-1H-benzo[b][1,4]diazepin-3-yl-2-(methylamino)propanamide hydrochloride, (S)—N—((S)-5-benzoyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(1-methyl-1H-pyrazole-4-carbonyl)-2-oxo-2,3,4,5-tetrahydro-1H-benzo[b][1,4]diazepin-3-yl)-2-(methylamino)propanamide hydrochloride, (S)—N—[(S)-1-(6-Bromo-2-methoxy-naphthalen-1-yl-methyl)-5-(2-fluoro-benzoyl)-2-oxo-2,3,4,5-tetrahydro-1H-benzo[b][1,4]diazepin-3-yl]-2-methyl-amino-propionamide hydrochloride, (S)—N—((S)-1-((6-bromo-2-methoxynaphthalen-1-yl)methyl)-5-(3-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-(methylsulfonyl)benzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-methoxypropanoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-cyanobenzoyl)-2-oxo-2,3,4,5-tetrahydro-1H-benzo[b][1,4]diazepin-3-yl)-2-(methylamino)propanamide hydrochloride, (S)—N—[(S)-5-Benzoyl-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—((S)-5-acetyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(5-methylfuran-2-carbonyl)-2-oxo-2,3,4,5-tetrahydro-1H-benzo[b][[1,4]diazepin-3-yl)-2-(methylamino)propanamide hydrochloride, (S)—N—((S)-1-((6-bromo-2-methoxynaphthalen-1-yl)methyl)-2-oxo-5-(4-(trifluoromethyl)benzoyl)-2,3,4,5-tetrahydro-1H-benzo[b][1,4]diazepin-3-yl)-2-(methylamino)propanamide hydrochloride, (S)—N—[(S)-1-(5-Bromo-2-methoxy-naphthalen-1-yl-methyl)-5-4fluoro-benzoyl)-2-oxo-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-yl-methyl)-5-(4-methyl-benzoyl)-2-oxo-2,3,4,5-tetrahydro-1H-benzo[b][1,4]diazepin-3-yl]-2-methyl-amino-propionamide hydrochloride, (S)—N—{(S)-1-(5-Bromo-2-methoxy-naphthalen-1-yl-methyl)-5-[4-(1-hydroxy-ethyl)-benzoyl]-2-oxo-2,3,4,5-tetrahydro-1H-benzo[b][1,4]diazepin-3-yl}-2-methylamino-propionamide, (S)—N—{(S)-1-(6-Bromo-2-methoxy-naphthalen-1-yl-methyl)-5-[4-(1-hydroxy-1-methyl-ethyl)-benzoyl]-2-oxo-2,3,4,5-tetrahydro-1H-benzo[b][1,4]diazepin-3-yl}-2-methylamino-propionamide trifluoroacetate, 4[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzoic acid methyl ester hydrochloride, (S)-2-Methylamino-N—[(S)-1-(2-methyl-naphthalen-1-ylmethyl)-2-oxo-5-(2-1H-tetrazol-5-yl-acetyl)-2,3,4,5-tetrahydro-1H-benzo[b][1,4]diazepin-3-yl]-propionamide hydrochloride, (S)-2-Methylamino-N—[(S)-1-(2-methyl-naphthalen-1-ylmethyl)-2-oxo-5-(2-tetrahydro-pyran-4-yl-acetyl)-2,3,4,5-tetrahydro-1H-benzo[b][1,4]diazepin-3-yl]-propionamide hydrochloride, (S)—N—[(S)-5-(4-Cyano-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(2-Cyclohexyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Chloro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)-2-Methylamino-N—[(S)-1-(2-methyl-naphthalen-1-ylmethyl)-2-oxo-5-(2-pyridin-3-yl-acetyl)-2,3,4,5-tetrahydro-1H-benzo[b][1,4]diazepin-3-yl]-propionamide, (S)—N—[(S)-5-(4-Fluoro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Amino-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)-2-Methylamino-N—[(S)-5-(4-methyl-benzoyl)-1-(2-methyl-naphthalen-1-ylmethyl)-2-oxo-2,3,4,5-tetrahydro-1H-benzo[b][1,4]diazepin-3-yl]-propionamide hydrochloride, (S)—N—[(S)-5-(4-Methoxy-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochoride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-carbonyl]-benzoic acid hydrochloride, (S)—N—[(S)-5-(4-Acetylamino-benzenesulfonyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)-2-Methylamino-N—[(S)-1-(2-methyl-naphthalen-1-ylmethyl)-5-methylsulfamoyl-2-oxo-2,3,4,5-tetrahydro-1H-benzo[b][1,4]diazepin-3-yl]-propionamide hydrochloride, (S)—N—[(S)-5-(4-Acetyl-benzenesulfonyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)-2-Methylamino-N—[(S)-1-(2-methyl-naphthalen-1-ylmethyl)-5-(4-nitro-benzenesulfonyl)-2-oxo-2,3,4,5-tetrahydro-1H-benzo[b][1,4]diazepin-3-yl]-propionamide hydrochloride, (S)—N—[(S)-5-Benzenesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Methoxy-benzenesulfonyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, 3-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzamide hydrochloride, (S)—N—[(S)-5-Dimethylsulfamoyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(2-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Hydroxymethyl-benzoyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (2 S)—N-((3 S)-1-((6-bromo-2-methoxynaphthalen-1-yl)methyl)-5-(4-(1-hydroxyethyl)benzoyl)-2-oxo-2,3,4,5-tetrahydro-1H-benzo[b][1,4]diazepin-3-yl)-2-(methylamino)propanamide, (2S)—N-((3S)-1-((6-bromo-2-methoxynaphthalen-1-yl)methyl)-5-(4-(1-hydroxyethyl)benzoyl)-2-oxo-2,3,4,5-tetrahydro-1H-benzo[b][1,4]diazepin-3-yl)-2-(methylamino)propanamide, (2S)—N-[(3 S)-1-(4-acetylbenzoyl)-5-[2-(naphthalen-1-ylamino)-2-oxoethyl]-4-oxo-2,3-dihydro-1,5-benzodiazepin-3-yl]-2-(methylamino)propanamide; 2,2,2-trifluoroacetic acid, (2S)—N-[(3S)-1-(4-acetylbenzoyl)-4-oxo-5-[2-oxo-2-(1,3-thiazol-2-ylamino)ethyl]-2,3-dihydro-1,5-benzodiazepin-3-yl]-2-(methylamino)propanamide; 2,2,2-trifluoroacetic acid, (S)—N—((S)-1-((6-bromo-2-methoxynaphthalen-1-yl)methyl)-5-(4-nitrobenzoyl)-2-oxo-2,3,4,5-tetrahydro-1H-benzo[b][1,4]diazepin-3-yl)-N-methyl-2-(methylamino)propanamide hydrochloride, (2S)—N-[(3S)-1-(4-acetylbenzoyl)-5-[2-(1,3-benzothiazol-2-ylamino)-2-oxoethyl]-4-oxo-2,3-dihydro-1,5-benzodiazepin-3-yl]-2-(methylamino)propanamide; 2,2,2-trifluoroacetic acid, (2S)—N-[5-(1-adamantylmethyl)-1-[(2-methoxynaphthalen-1-yl)methyl]-2,4-dioxo-1,5-benzodiazepin-3-yl]-2-(methylamino)propanamide, (2S)—N-[5-(1-adamantylmethyl)-1-[(2-methoxynaphthalen-1-yl)methyl]-2,4-dioxo-1,5-benzodiazepin-3-yl]-2-aminopropanamide, (2S)—N-[5-(1-adamantylmethyl)-1-[(2-methoxynaph-thalen-1-yl)methyl]-2,4-dioxo-1,5-benzodiazepin-3-yl]-2-(methylamino)butanamide, (2S)—N-(1-methyl-5-((2-methylnaphthalen-1-yl)methyl)-2,4-dioxo-2,3,4,5-tetrahydro-1H-benzo[b][1,4]diazepin-3-yl)-2-(methylamino)butanamide, (2S)-2-(methylamino)-N-(1-((2-methylnaphthalen-1-yl)methyl)-2,4-dioxo-5-phenyl-2,3,4,5-tetrahydro-1H-benzo[b][1,4]diazepin-3-yl)butanamide, (2S)-2-(methylamino)-N-(1-((2-methylnaphthalen-1-yl)methyl)-2,4-dioxo-5-phenyl-2,3,4,5-tetrahydro-1H-benzo[b][1,4]diazepin-3-yl)propanamide, (2S)—N-[(3S)-1-(4-aminophenyl)sulfonyl-5-[(2-methylnaphthalen-1-yl)methyl]-4-oxo-2,3-dihydro-1,5-benzodiazepin-3-yl]-2-(methylamino)propanamide; hydrochloride, (2S)—N-[(3S)-1-[3-(1-hydroxyethyl)benzoyl]-5-[(2-methylnaphthalen-1-yl)methyl]-4-oxo-2,3-dihydro-1,5-benzodiazepin-3-yl]-2-(methylamino)propanamide; hydrochloride, (2S)—N-[(3S)-1-[3-(1-hydroxyethyl)benzoyl]-5-[(2-methylnaphthalen-1-yl)methyl]-4-oxo-2,3-dihydro-1,5-benzodiazepin-3-yl]-2-(methylamino)propanamide; hydrochloride, (S)—N—((S)-5-(4-acetylbenzoyl)-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide 2,2,2-trifluoroacetate, (S)—N—((S)-5-(4-aminobenzoyl)-7-chloro-1-((2-methylnaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-aminobenzoyl)-7-chloro-1-((2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-aminobenzoyl)-1-((5-bromo-2-methoxynaphthalen-1-yl)methyl)-7-chloro-2-oxo-2,3,4,5-tetrahydro-1H-benzo[b][1,4]diazepin-3-yl)-2-(methylamino)propanamide hydrochloride, (S)—N—((S)-5-(4-aminobenzoyl)-1-((6-bromo-2-methoxynaphthalen-1-yl)methyl)-7-chloro-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-7-chloro-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-7-chloro-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-7-chloro-5-(4-cyanobenzoyl)-2-oxo-2,3,4,5-tetrahydro-1H-benzo[b][1,4]diazepin-3-yl)-2-(methylamino)propanamide hydrochloride, (2S)—N-(1-((6-bromo-2-methoxynaphthalen-1-yl)methyl)-2,4'-dioxo-5-phenyl-2,3,4,5-tetrahydro-1H-benzo[b][1,4]diazepin-3-yl)-2-(methylamino)propanamide, (2S)—N-(1-((5-bromo-2-methoxynaphthalen-1-yl)methyl)-2,4-dioxo-5-phenyl-2,3,4,5-tetrahydro-1H-benzo[b][1,4]diazepin-3-yl)-2-(methylamino)propanamide, (S)—N—((S)-1-((6-bromo-2-methoxynaphthalen-1-yl)methyl)-7-chloro-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-7-chloro-5-(4-cyanobenzoyl)-2-oxo-2,3,4,5-tetrahydro-1H-benzo[b][1,4]diazepin-3-yl)-2-(methylamino)propanamide hydrochloride, (2S)—N-(1-((6-bromo-2-methoxynaphthalen-1-yl)methyl)-2,4-dioxo-5-phenyl-2,3,4,5-tetrahydro-1H-benzo[b][1,4]diazepin-3-yl)-2-(ethylamino)butanamide, (2S)-2-amino-N-(1-((6-bromo-2-methoxynaphthalen-1-yl)methyl)-2,4-dioxo-5-phenyl-2,3,4,5-tetrahydro-1H-benzo[b][1,4]diazepin-3-yl)butanamide, (2S)—N-(1-((5-bromo-2-methoxynaphthalen-1-yl)methyl)-2,4-dioxo-5-phenyl-2,3,4,5-tetrahydro-1H-benzo[b][1,4]diazepin-3-yl)-2-(ethylamino)butanamide, (S)—N—((S)-1-((6-bromo-2-(2,2,2-trifluoroethoxy)naphthalen-1-yl)methyl)-7-chloro-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-(2,2,2-trifluoroethoxy)naphthalen-1-yl)methyl)-7-chloro-5-(4-fluorobenzoyl)-2-oxo-2,3,4,5-tetrahydro-1H-benzo[b][1,4]diazepin-3-yl)-2-(methylamino)propanamide hydrochloride, (2S)-2-amino-N-(1-((5-bromo-2-methoxynaphthalen-1-yl)methyl)-2,4-dioxo-5-phenyl-2,3,4,5-tetrahydro-1H-benzo[b][1,4]diazepin-3-yl)butanamide, (2S)—N-(1-((5-bromo-2-methoxynaphthalen-1-yl)methyl)-2,4-dioxo-5-phenyl-2,3,4,5-tetrahydro-1H-benzo[b][1,4]diazepin-3-yl)-2-(2-hydroxyethylamino)butanamide, (S)—N—((S)-7-chloro-5-(4-cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, (S)—N—((S)-7-chloro-1-((2-(difluoromethoxy)naphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (2S)—N-[(3S)-1-(1H-indazole-5-carbonyl)-5-[(2-methylnaphthalen-1-yl)methyl]-4-oxo-2,3-dihydro-1,5-benzodiazepin-3-yl]-2-(methylamino)propanamide, (S)—N—((S)-7-cyano-5-(4-cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-7-cyano-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-7-cyano-5-(4-cyanobenzoyl)-2-oxo-2,3,4,5-tetrahydro-1H-benzo[b][1,4]diazepin-3-yl)-2-(methylamino)propanamide hydrochloride, (2S)—N-[(3S)-1-(1H-indole-5-carbonyl)-5-[(2-methylnaphthalen-1-yl)methyl]-4-oxo-2,3-dihydro-1,5-benzodiazepin-3-yl]-2-(methylamino)propanamide, (2S)—N-[(3S)-1-(1H-indole-4-carbonyl)-5-[(2-methylnaphthalen-1-yl)methyl]-4-oxo-2,3-dihydro-1,5-benzodiazepin-3-yl]-2-(methylamino)propanamide, (2S)—N-[(3S)-1-(1H-indazole-4-carbonyl)-5-[(2-methylnaphthalen-1-yl)methyl]-4-oxo-2,3-dihydro-1,5-benzodiazepin-3-yl]-2-(methylamino)propanamide, (2S)—N-[(3S)-1-[2-[(1S)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide;

(2S)—N-[(3S)-1-[2-[(1R)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide, (S)—N—((S)-1-((6-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)propanamide, (S)—N—((S)-1-((5-bromo-2-methoxynaphthalen-1-yl)methyl)-7-cyano-5-(4-fluorobenzoyl)-2-oxo-2,3,4,5-tetrahydro-1H-benzo[b][1,4]diazepin-3-yl-2-(methylamino)propanamide hydrochloride, (S)—N—((S)-7-cyano-1-((2-(difluoromethoxy)naphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (2S)—N-[(3S)-1-(1H-indole-6-carbonyl)-5-[(2-methylnaphthalen-1-yl)methyl]-4-oxo-2,3-dihydro-1,5-benzodiazepin-3-yl]-2-(methylamino)propanamide, (2S)—N-[(3S)-1-[2-[(1S)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide;

(2S)—N-[(3S)-1-[2-[(1R)-1-hydroxyethyl]benzoyl]-5-[(2-methylnaphthalen-1-yl)methyl]-4-oxo-2,3-dihydro-1,5-benzodiazepin-3-yl]-2-(methylamino)propanamide, (S)—N—((S)-1-((6-bromo-2-methoxynaphthalen-1-yl)methyl)-7-cyano-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride, (S)—N—((S)-1-((5-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)propanamide hydrochloride, (S)—N—((S)-1-((6-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(ethylamino)butanamide hydrochloride, (2S)—N-[(3S)-1-(1H-indazole-6-carbonyl)-5-[(2-methylnaphthalen-1-yl)methyl]-4-oxo-2,3-dihydro-1,5-benzodiazepin-3-yl]-2-(methylamino)propanamide, (S)—N—((S)-1-((1-(2-cyanophenyl)-1H-indazol-3-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((5-bromo-2-methoxynaphthalen-1-yl)methyl)-7-cyano-5-(2-(methylsulfonyl)acetyl)-2-oxo-2,3,4,5-tetrahydro-1H-benzo[b][1,4]diazepin-3-yl)-2-(methylamino)propanamide hydrochloride, (2S)—N-[(3S)-7-cyano-1-[[1-(2-cyanophenyl)indazol-3-yl]methyl]-5-(2-methylsulfinylacetyl)-2-oxo-3,4-dihydro-1,5-benzodiazepin-3-yl]-2-(methylamino)propanamide; 2,2,2-trifluoroacetic acid, (S)—N—((S)-5-(4-acetylbenzoyl)-7-cyano-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-7-cyano-1-((1-methyl-1H-indazol-3-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-7-cyano-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-7-cyano-1-((2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-8-cyano-1-((1-(2-cyanophenyl)-1H-indazol-3-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide dihydrochloride, (S)—N—((S)-5-acetyl-7-cyano-1-((1-(2-cyanophenyl)-1H-indazol-3-yl)methyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide hydrochloride, (S)—N—((S)-8-cyano-1-((2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-8-cyano-1-((2-methylnaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-5-(3-methoxypropanoyl)-2-oxo-2,3,4,5-tetrahydro-1H-benzo[b][1,4]diazepin-3-yl)-2-(methylamino)propanamide hydrochloride, (S)—N—((S)-7-cyano-1-((1-(2-cyanophenyl)-1H-indazol-3-yl)methyl)-5-isonicotinoyl-2-oxo-2,3,4,5-tetrahydro-1H-benzo[b][1,4]diazepin-3-yl)-2-(methylamino)propanamide dihydrochloride, (S)—N—((S)-1-((5-bromo-2-methoxynaphthalen-1-yl)methyl)-8-cyano-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-5-acetyl-7-cyano-1-((5-cyano-2-cyclopropylnaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-acetyl-1-((1-(2-cyanophenyl)-1H-indazol-3-yl)methyl)-2-oxo-7-(trifluoromethyl)-2,3,4,5-tetrahydro-1H-benzo[b][1,4]diazepin-3-yl)-2-(methylamino)propanamide hydrochloride, (2S)—N-[(3S)-1-(4-aminobenzoyl)-5-[[2-(2-fluoroethoxy)naphthalen-1-yl]methyl]-4-oxo-2,3-dihydro-1,5-benzodiazepin-3-yl]-2-(methylamino)propananiide; hydrochloride, (S)—N—((S)-5-acetyl-1-((5-bromo-2-methoxynaphthalen-1-yl)methyl)-7-cyano-2-oxo-2,3,4,5-tetrahydro-1H-benzo[b][1,4]diazepin-3-yl)-2-(methylamino)propanamide,
(S)—N—((S)-7-cyano-1-((3-cyclopropylquinolin-4-yl)methyl)-2-oxo-5-(tetrahydro-2H-pyran-4-carbonyl)-2,3,4,5-tetrahydro-1H-benzo[b][1,4]diazepin-3-yl)-2-(methylamino)propanamide,
(S)—N—((S)-7-cyano-1-((3-cyclopropylquinolin-4-yl)methyl)-5-isonicotinoyl-2-oxo-2,3,4,5-tetrahydro-1H-benzo[b][1,4]diazepin-3-yl)-2-(methylamino)propanamide,
(S)—N—((S)-5-acetyl-7-cyano-1-((5-cyano-2-methoxynaphthalen-1-yl)methyl)-2-oxo-2,3,4,5-tetrahydro-1H-benzo[b][1,4]diazepin-3-yl)-2-(methylamino)propanamide,
(S)—N—((S)-5-acetyl-1-((3-cyclopropylquinolin-4-yl)methyl)-2-oxo-7-(trifluoromethyl)-2,3,4,5-tetrahydro-1H-benzo[b][1,4]diazepin-3-yl)-2-(methylamino)propanamide,
(S)—N—((S)-1-((3-cyclopropylquinolin-4-yl)methyl)-2-oxo-5-(tetrahydro-2H-pyran-4-carbonyl)-7-(trifluoromethyl)-2,3,4,5-tetrahydro-1H-benzo[b][1,4]diazepin-3-yl)-2-(methylamino)propanamide,
(S)—N—((S)-1-((3-cyclopropylquinolin-4-yl)methyl)-5-(3-methoxypropanoyl)-2-oxo-7-(trifluoromethyl)-2,3,4,5-tetrahydro-1H-benzo[b][1,4]diazepin-3-yl)-2-(methylamino)propanamide,
(S)—N—((S)-1-((3-cyclopropylquinolin-4-yl)methyl)-5-isonicotinoyl-2-oxo-7-(trifluoromethyl)-2,3,4,5-tetrahydro-1H-benzo[b][1,4]diazepin-3-yl)-2-(methylamino)propanamide,
(S)—N—((S)-1-((3-cyclopropylquinolin-4-yl)methyl)-5-(2-(methylsulfonyl)acetyl)-2-oxo-7-(trifluoromethyl)-2,3,4,5-tetrahydro-1H-benzo[b][1,4]diazepin-3-yl)-2-(methylamino)propanamide,
(S)—N—((S)-1-((3-cyclopropylquinolin-4-yl)methyl)-5-(3-(methylsulfonyl)propanoyl)-2-oxo-7-(trifluoromethyl)-2,3,4,5-tetrahydro-1H-benzo[b][1,4]diazepin-3-yl)-2-(methylamino)propanamide,
(S)—N—((S)-5-acetyl-1-((5-cyano-2-cyclopropylnaphthalen-1-yl)methyl)-2-oxo-7-(trifluoromethyl)-2,3,4,5-tetrahydro-1H-benzo[b][1,4]diazepin-3-yl)-2-(methylamino)propanamide,
(S)—N-((2S,3S)-1-acetyl-5-(2-(2,6-difluorophenylamino)-2-oxoethyl)-2-methyl-4-oxo-2,3,4,5-tetrahydro-1H-benzo[b][1,4]diazepin-3-yl)-2-(methylamino)propanamide hydrochloride,
(S)—N-((2S,3S)-1-acetyl-2-methyl-4-oxo-5-(2-oxo-2-(phenylamino)ethyl)-2,3,4,5-tetrahydro-1H-benzo[b][1,4]diazepin-3-yl)-2-(methylamino)propanamide hydrochloride,
Cyclic-5-[(S)-5-(3-Amino-acetyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide,
Cyclic-5-[(S)-5-(3-Amino-pentanoyl)-3-((S)-2-methyl-amino-propionylamino)-2-oxo-2,3,45-tetrahydro-benzo[b][1,4]diazepin-1-ylmethyl]-6-methoxy-naphthalene-2-carboxylic amide hydrochloride and
(2S)—N-((2S,3S)-1-acetyl-5-(2-(2,6-difluorophenylamino)-2-oxo-1-phenylethyl)-2-methyl-4-oxo-2,3,4,5-tetrahydro-1H-benzo[b][1,4]diazepin-3-yl)-2-(methylamino)propanamide hydrochloride,
or a pharmaceutically acceptable salt thereof.
3. A compound, selected from the group consisting of:

(R)—N—((S)-5-(4-Acetylbenzoyl)-1-((2-methylnaphthalen-1-yl)methyl)-2-oxo-2,3,4,5-tetrahydr 1H-benzo[b][1,4]diazepin-3-yl)-2-(methylamino)propanamide hydrochloride,
(R)—N—[(S)-5-(4-acetyl-benzoyl)-1-(6-bromo-2-methoxyl-naphthalen-1-ylmethyl)-2-oxo-2,3,4,5-tetrahydro-1H-benzo[b][1,4]diazepin-3-yl]-2-methyl-amino-propionamide hydrochloride,
(S)-2-(Methylamino)-N—((S)-1-((2-methylnaphthalen-1-yl)methyl)-5-(4-nitrobenzoyl)-2-oxo-2,3,4,5-tetrahydro-1H-benzo[b][1,4]diazepin-3-yl)propanamide hydrochloride,
(S)-2-Amino-N—((S)-5-(4-aminobenzoyl)-1-((2-methoxynaphthalen-1-yl)methyl)-2-oxo-2,3,4,5-tetrahydro-1H-benzo[b][1,4]diazepin-3-yl)propanamide hydrochloride,
(S)-2-Methylamino-N—((S)-1-naphthalen-1-ylmethyl-2-oxo-2,3,4,5-tetrahydro-1H-benzo[b][1,4]diazepin-3-yl)-propionamide hydrochloride,
(S)-2-Methylamino-N—((S)-1-naphthalen-1-ylmethyl-2-oxo-5-phenethyl-2,3,4,5-tetrahydro-1H-benzo[b][1,4]diazepin-3-yl)-propionamide trifluoroacetate,
(S)-2-methylamino-N—((S)-1-naphthalen-1-ylmethyl-2-oxo-5-phenylacetyl-2,3,4,5-tetrahydro-1H-benzo[b][1,4]diazepin-3-yl)-propionamide hydrochloride,
(S)-2-Methylamino-N—((S)-5-methyl-1-naphthalen-1-ylmethyl-2-oxo-2,3,4,5-tetrahydro-1H-benzo[b][1,4]diazepin-3-yl)-propionamide hydrochloride,
(S)-2-Methylamino-N—[(S)-1-(2-methyl-naphthalen-1-naphthalen-I ylmethyl)-2-oxo-5-(pyridine-4-carbonyl)-2,3,4,5-tetrahydro-1H-benzo[b][1,4]diazepin-3-yl]-propionamide hydrochloride,
(S)-2-Methylamino-N—[(S)-1-(2-methyl-naphthalen-1-ylmethyl)-2-oxo-5-(2-pyridin-4-yl-acetyl)-2,3,4,5-tetrahydro-1H-benzo[b][1,4]diazepin-3-yl]-propionamide dihydrochloride,
(S)-2-Methylamino-N—[(S)-1-(2-methyl-naphthalen-1-ylmethyl)-2-oxo-5-(5-oxo-hexanoyl)-2,3,4,5-tetrahydro-1H-benzo[b][1,4]diazepin-3-yl]-propionamide hydrochloride,
(S)-2-Methylamino-N—[(S)-1-(2-methyl-naphthalen-1-ylmethyl)-2-oxo-5-(3,4,5-trimethoxy-benzoyl)-2,3,4,5-tetrahydro-1H-benzo[b][1,4]diazepin-3-yl]-propionamide hydrochloride,
(S)-2-Methylamino-N—[(S)-1-(2-methyl-naphthalen-1-ylmethyl)-2-oxo-5-(2-1H-tetrazol-5-yl-acetyl)-2,3,4,5-tetrahydro-1H-benzo[b][1,4]diazepin-3-yl]-propionamide hydrochloride,
(S)-2-Methylamino-N—[(S)-1-(2-methyl-naphthalen-1-ylmethyl)-2-oxo-5-(2-tetrahydro-pyran-4-yl-acetyl)-2,3,4,5-tetrahydro-1H-benzo[b][1,4]diazepin-3-yl]-propionamide hydrochloride,
(S)-2-Methylamino-N—[(S)-1-(2-methyl-naphthalen-1-ylmethyl)-2-oxo-5-(2-pyridin-3-yl-acetyl)-2,3,4,5-tetrahydro-1H-benzo[b][1,4]diazepin-3-yl]-propionamide,
(S)-2-Methylamino-N—[(S)-1-(2-methyl-naphthalen-1-ylmethyl)-5-(4-nitro-benzenesulfonyl)-2-oxo-2,3,4,5-tetrahydro-1H-benzo[b][1,4]diazepin-3-yl]-propionamide hydrochloride,
(S)-2-Methylamino-N—[(S)-1-(2-methyl-naphthalen-1-ylmethyl)-5-methylsulfamoyl-2-oxo-2,3,4,5-tetrahydro-1H-benzo[b][1,4]diazepin-3-yl]-propionamide hydrochloride,
(S)-2-Methylamino-N—[(S)-5-(3-methyl-butyl)-1-naphthalen-1-ylmethyl-2-oxo-2,3,4,5-tetrahydro-1H-benzo[b][1,4]diazepin-3-yl]-propionamide hydrochloride, (S)-2-Methylamino-N—[(S)-5-(3-methyl-butyryl)-1-(1-naphthalen-1-yl-ethyl)-2-oxo-2,3,4,5-tetrahydro-1H-benzo[b][1,4]diazepin-3-yl]-propionamide hydrochloride, (S)-2-Methylamino-N—[(S)-5-(3-methyl-butyryl)-1-(2-methyl-naphthalen-1-ylmethyl)-2-oxo-2,3,4,5-tetrahydro-1H-benzo[b][1,4]diazepin-3-yl]-propionamide hydrochloride, (S)-2-Methylamino-N—[(S)-5-(3-methyl-butyryl)-1-naphthalen-1-ylmethyl-2-oxo-2,3,4,5-tetrahydro-1H-benzo[b][1,4]diazepin-3-yl]-propionamide hydrochloride, (S)-2-Methylamino-N—[(S)-5-(3-methyl-butyryl)-2-oxo-1-phenethyl-2,3,4,5-tetrahydro-1H-benzo[b[1,4]diazepin-3-yl]-propionamide hydrochloride, (S)-2-Methylamino-N—[(S)-5-(4-methyl-benzoyl)-1-(2-methyl-naphthalen-1-ylmethyl)-2-oxo-2,3,4,5-tetrahydro-1H-benzo[b][1,4]diazepin-3-yl]-propionamide hydrochloride, (S)-2-methylamino-N—((S)-1(2-methyl-naphthalen-1-ylmethyl)-5-[2-(4-methyl-piperazin-1-yl)-acetyl]-2-oxo-2,3,4,5-tetrahydro-1H-benzo[b][1,4]diazepin-3-yl) -propionamide hydrochloride, (S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methylamide hydrochloride, (S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methyl ester hydrochloride, (S)-Azetidine-2-carbonxylic acid[(S)-5-(4-acetyl-benzoyl)-1-(6-bromo-2-methoxy-naphthalen-1-ylmethyl)-2-oxo-2,3,4,5-tetrahydro-1H-benzo[[b][1,4]diazepin-3-yl]-amide hydrochloride, (S)—N—((S)-1-((2-(Difluoromethoxy)naphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((2-Methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((5-Bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((5-Bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(tetrahydro-21-pyran-4-carbonyl)-2,3,4,5-tetrahydro-1H-benzo[b][1,4]diazepin-3-yl)-2-(methylamino)propanamide hydrochloride, (S)—N—((S)-1-((6-Bromo-2-methoxynaphthalen-1-yl)methyl)-2-oxo-5-(2-(pyridin-3-yl)acetyl)-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(pyrazine-2-carbonyl)-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(2-(pyridin-2-yl)acetyl)-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-2-oxo-5-(4-(trifluoromethyl)benzoyl)-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(isoxazole-5-carbonyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(1-methyl-1H-pyrazole-3-carbonyl)-2-oxo-2,3,4,5-tetrahydro-1H-benzo[b][1,4]diazepin-3-yl)-2-(methylamino)propanamide trifluoroacetate, (S)—N—((S)-1-((6-bromo-2-methoxynaphthalen-1-yl)methyl)-5-(1-methyl-1H-pyrazole-4-carbonyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-(methylsulfonyl)acetyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(2-cyclohexylacetyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(3-methoxypropanoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-(methylsulfonyl)benzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-cyanobenzoyl)-2-oxo-2,3,4,5-tetrahydro-1H-benzo[b][1,4]diazepin-3-yl)-2-(methylamino)propanamide hydrochloride, (S)—N—((S)-1-((6-Bromo-2-methoxynaphthalen-1-yl)methyl)-5-(4-cyanobenzyl)-2-oxo-2,3,4,5-tetrahydro-1H-benzo[b][1,4]diazepin-3-yl)-2-(methylamino)propanamide trifluoroacetate, (S)—N—((S)-1-((6-Bromo-2-methoxynaphthalen-1-yl)methyl)-5-(4-fluorobenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(4-methylbenzoyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-(5-methylfuran-2-carbonyl)-2-oxo-2,3,4,5-tetrahydro-1H-benzo[b][1,4]diazepin-3-yl)-2-(methylamino)propanamide hydrochloride, (S)—N—((S)-1-((6-bromo-2-methoxynaphthalen-1-yl)methyl)-5-nicotinoyl-2-oxo-2,3,4,5-tetrahydro-1H-benzo[b][1,4]diazepin-3-yl)-2-(methylamino)propanamide hydrochloride, (S)—N—((S)-5-(4-acetamidobenzoyl)-1((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—((S)-5-(4-acetylbenzoyl)-1-((2-(difluoromethoxy)naphthalen-1l-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-(difluoromethoxy)naphthalen-1-yl)methyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-Acetylbenzoyl)-1-((2-methylnaphthalen-1-yl)methyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((5-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-(4-Acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(methylamino)butanamide hydrochloride, (S)—N—((S)-5-(4-Acetylbenzoyl)-1-((6-bromo-2-methoxynaphthalen-1-yl)methyl)-2-oxo-2,3,4,5-tetrahydro-1H-benzo[b][1,4]diazepin-3-yl)-2-(ethylamino)propanamide hydrochloride, (S)—N—((S)-5-(4-acetylbenzoyl)-1-((6-bromobenzo[d]isoxazol-3-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((7-methoxy-2-oxo-2H-chromen-4-yl)methyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-((7-methoxy-2-oxo-2H-chromen-4-yl)methyl)-2-oxo-2,3,4,5-tetrahydro-1H-benzo[b][1,4]diazepin-3-yl)-2-aminopropanamide hydrochloride, (S)—N—((S)-5-(4-acetylbenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, (S)—N—((S)-5-(4-acetylbenzoyl)-1-(benzo[d]isoxazol-3-ylmethyl)-2-oxo-2,3,4,5-tetrahydro-1H-benzo[b][1,4]diazepin-3-yl)-2-aminopropanamide hydrochloride, (S)—N—((S)-5-(4-Acetylbenzoyl)-2-oxo-1-((2-(2,2,2-trifluoroethoxy)naphthalen-1-yl)methyl)-2,3,4,5-tetrahydro-1H-benzo[b][1,4]diazepin-3-yl)-2-(methylamino)propanamide hydrochloride, (S)—N—((S)-5-(4-acetylbenzoyl)-2-oxo-14-(2-(2,2,2-trifluoroethoxy)naphthalen-1-yl)methyl)-2,3,4,5-tetrahydro-1H-benzo[b][1,4]diazepin-3-yl)-2-aminopropanamide hydrochloride, (S)—N—((S)-5-(4-Aminobenzoyl)-1-((2-methylnaphthalen-1-yl)methyl)-2-oxo-2,3,4,5-tetrahydro-1H-benzo[b][1,4]diazepin-3-yl)-N-methyl-2-(methylamino)propanamide hydrochloride, (S)—N—((S)-5-(4-Aminobenzoyl)-1-(benzo[d]isoxazol-3-ylmethyl)-2-oxo-2,3,4,5-tetrahydro-1H-benzo[b][1,4]diazepin-3-yl)-2-(methylamino)propanamide hydrochloride, (S)—N—((S)-5-(4-Cyanobenzoyl)-1-((2-(difluoromethoxy)naphthalen-1-yl)methyl)-2-oxo-2,3,4,5-tetrahydro-1H-benzo[b][1,4]diazepin-3-yl)-2-(methylamino)propanamide, (S)—N—((S)-5-acetyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-Acetyl-1-naphthalen-1-ylmethyl-2-oxo-2,3,4,5-tetrahydro-1H-benzo[b][1,4]diazepin-3-yl)-2-methylamino-propionamide hydrochloride, (S)—N—((S)-5-benzoyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide hydrochloride, (S)—N—((S)-5-Benzyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate, (S)—N—[(S)-1-(2-methoxy-benzyl)-5-(3-methyl-butyryl)-2-oxo-2,3,4,5-tetrahydro-1H-benzo[b[1,4]diazepin-3-yl]-2-methylamino-propionamide hydrochloride, (S)—N—[(S)-1-(2-Methoxy-naphthalen-1-ylmethyl)-5-(3-methyl-butyryl)-2-oxo-2,3,4,5-tetrahydro-1H-benzo[b[1,4]diazepin-3-yl]-2-methylamino-propionamide hydrochloride, (S)—N—[(S)-1-(5-Bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-2-oxo-5-(2-pyridin-3-yl-acetyl)-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-5-(4-fluoro-benzoyl)-2-oxo-2,3,4,5-tetrahydro-1H-benzo[b][1,4]diazepin-3-yl]-2-methylamino-propionamide hydrochloride, (S)—N—[(S)-1-(5-Bromo-2-methoxy-naphthalen-1-ylmethyl)-5-(4-methyl-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-(d3-methoxy)-naphthalen-1-ylmethyl)-2-oxo-5-(2-pyridin-3-yl-acetyl)-2,3,4,5-tetrahydro-1H-benzo[b][1,4]diazepin-3-yl]-2-methyl-amino-propionamide hydrochloride, (S)—N—[(S)-1-(6-Bromo-2-(d3-methoxy)-naphthalen-1-ylmethyl)-5-(4-cyano-benzoyl)-2-oxo-2,3,4,5-tetrahydro-1H-benzo[b][1,4]diazepin-3-yl]-2-methyl-amino-propionamide hydrochloride, (S)—N—[(S)-1-(6-Bromo-2-methoxy-naphthalen-1-ylmethyl)-2-oxo-5-(2-tetrahydro-pyran-4-yl-acetyl)-2,3,4,5-tetrahydro-1H-benzo[b][1,4]diazepin-3-yl]-2-methylamino-propionamide hydrochloride, (S)—N—[(S)-1-(6-bromo-2-methoxy-naphthalen-1-ylmethyl)-2-oxo-5-(5-oxo-hexanoyl)-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-2-oxo-5-(pyridine-2-carbonyl)-2,3,4,5-tetrahydro-1H-benzo[b][1,4]diazepin-3-yl]-2-methyl-amino-propionamide hydrochloride, (S)—N—[(S)-1-(6-Bromo-2-methoxy-naphthalen-1-ylmethyl)-5-(2-fluoro-benzoyl)-2-oxo-2,3,4,5-tetrahydro-1H-benzo[b][1,4]diazepin-3-yl]-2-methyl-amino-propionamide hydrochloride, (S)—N—[(S)-1-(6-bromo-2-methoxy-naphthalen-1-ylmethyl)-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(4-nitro-benzoyl)-2-oxo-2,3,4,5-tetrahydro-1H-benzo[b][1,4]diazepin-3-yl]-2-methylamino-propionamide hydrochloride, (S)—N—[(S)-1-(6-Bromo-2-methoxy-naphthalen-1-ylmethyl)-5-(4-nitro-butyryl)-2-oxo-2,3,4,5-tetrahydro-1H-benzo[b][1,4]diazepin-3-yl]-2-methylamino-propionamide hydrochloride, (S)—N—[(S)-1-benzyl-5-(3-methyl-butyryl)-2-oxo-2,3,4,5-tetrahydro-1H-benzo[b][1,4]diazepin-3-yl]-2-methylamino-propionamide hydrochloride, (S)—N—[(S)-5-(2-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(2-Adamantan-1-yl-acetyl)-1-(6-bromo-2-methoxy-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-(2-Carbamoyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(2-Cyclohexyl-acetyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(3-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(3-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-(3-Amino-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Acetylamino-benzenesulfonyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-(4-acetylamino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzenesulfonyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-(4-Acetyl-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(2-naphthalen-1-yl-ethyl)-2-oxo-2,3,4,5-tetrahydro-1H-benzo[b][1,4]diazepin-3-yl]-2-methylamino-propionamide hydrochloride, (S)—N—[(S)-5-(4-Acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-dimethyl-amino-propionamide, (S)—N—[(S)-5-(4-acetyl-benzoyl)-1-(6-bromo-2-methoxy-naphthalen-1-ylmethyl)-2-oxo-2,3,4,5-tetrahydro-1H-benzo[b][1,4]diazepin-3-yl]-2-amino-propionamide, (S)—N—[(S)-5-(4-amino-benzoyl)-1-(2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-(4-Amino-benzoyl)-1-(6-bromo-2-methoxy-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-(4-Chloro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Cyano-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Fluoro-benzoyl)-1-(2-methyl-naphthalen-1-ylmethyl)-2-oxo-2,3,4,5-tetrahydro-1H-benzo[b][1,4]diazepin-3-yl]-2-methylamino-propionamide, (S)—N—[(S)-5-(4-Hydroxymethyl-benzoyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-(4-Methanesulfonyl-benzoyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-(4-Methoxy-benzenesulfonyl)-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-(4-Methoxy-benzoyl)-1-(2-methyl-naphthalen-1-ylmethyl)-2-oxo-2,3,4,5-tetrahydro-1H-benzo[b][1,4]diazepin-3-yl]-2-methylamino-propionamide hydrochoride, (S)—N—[(S)-5-(Adamantan-1-carbonyl)-1-(6-bromo-2-methoxy-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-[2-(2-methoxy-ethoxy)-acetyl]-1-(2-methyl-naphthalen-1-ylmethyl)-2-oxo-2,3,4,5-tetrahydro-1H-benzo[b][1,4]diazepin-3-yl]-2-methyl-amino-propionamide hydrochloride, (S)—N—[(S)-5-[2-(4-Acetyl-phenyl)-acetyl]-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-{2-[2-(2-Methoxy-ethoxy)-ethoxy]-acetyl}-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-acetyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Benzenesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Benzoyl-1-(6-bromo-2-methoxy-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-Dimethylsulfamoyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-methanesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride, (S)—N—[(S)-5-methanesulfonylmethanesulfonyl-1-(2-methyl-naphthalen-1-ylmethyl)-2-oxo-2,3,4,5-tetrahydro-1H-benzo[b][1,4]diazepin-3-yl]-2-methylamino-propionamide trifluoroacetate, (S)—N—{(S)-1-(5-Bromo-2-methoxy-naphthalen-1-ylmethyl)-5-[4-(1-hydroxy-ethyl)-benizoyl]-2-oxo-2,3,4,5-tetrahydro-1H-benzo[b][1,4]diazepin-3-yl}-2-methylamino-propionamide, (S)—N—{(S)-1-(6-Bromo-2-methoxy-naphthalen-1-ylmethyl)-2-oxo-5-[4-(2,2,2-trifluoro-1,1-dihydroxy-ethyl)-benzoyl]-2,3,4,5-tetrahydro-1H-benzo[b][1,4]diazepin-3-yl}-2-methylamino-propionamide trifluoroacetate, (S)—N—{(S)-1-(6-bromo-2-methoxy-naphthalen-1-ylmethyl)-2-oxo-5-[4-(2,2,2-trifluoro-1-hydroxy-ethyl)-benzoyl]-2,3,4,5-tetrahydro-1H-benzo[b][1,4]diazepin-3-yl}-2-methylamino-propionamide hydrochloride, (S)—N—{(S)-1-(6-bromo-2-methoxy-naphthalen-1-ylmethyl)-5-(4-(1-hydroxy-ethyl)-benzoyl]-2-oxo-2,3,4,5-tetrahydro-1H-benzo[b][1,4]diazepin-3-yl}-2-methylamino-propionamide hydrochloride, (S)—N—((S)-1-(6-Bromo-2-methoxy-naphthalen-1-ylmethyl)-5-[4-(1-hydroxy-1-methyl-ethyl)-benzoyl]-2-oxo-2,3,4,5-tetrahydro-1H-benzo[b][1,4]diazepin-3-yl)-2-methylamino-propionamide trifluoroacetate, (S)—N—{(S)-1-(6-Bromo-2-methoxy-naphthalen-1-ylmethyl)-5-[4-(2,2-dimethyl-propionyl)-benzoyl]-2-oxo-2,3,4,5-tetrahydro-1H-benzo[b][1,4]diazepin-3-yl}-2-methylamino-propionamide hydrochloride, 3-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzamide hydrochloride, 4-(((S)-5-(4-Acetylbenzoyl)-3-((S)-2-(methylamino)propanamido)-2-oxo-2,3,4,5-tetrahydro-1H-benzo[b][1,4]diazepin-1-yl)methyl)-3-(2,2,2-trifluoroethoxy)quinoline 1-oxide hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-yl]-4-oxo-butyric acid hydrochloride, 4-[(S)-3-((S)-2-Methylamino-propionylamino)-5-(2-methyl-naphthalen-1-ylmethyl)-4-oxo-2,3,4,5-tetrahydro-benzo[b][1,4]diazepine-1-carbonyl]-benzoic acid methyl ester hydrochloride, 4-[(S)-3-((S)-2-methylamino-propionylamino)-5-(2-methyl-naphthalen-1-ylmethyl)-4-oxo-2,3,4,5-tetrahydro-benzo[b][1,4]diazepine-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid methyl ester hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzoic acid hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-benzamide hydrochloride, 4-[(S)-5-(6-bromo-2-methoxy-naphthalen-1-ylmethyl)-3-((S)-2-methylamino-propionylamino)-4-oxo-2,3,4,5-tetrahydro-benzo[b][1,4]diazepin-1-carbonyl]-N-cyclohexylmethyl-benzamide hydrochloride, 5-[(S)-3-((S)-2-methylamino-propionylamino)-5-(2-methyl-naphthalen-1-ymethyl)-4-oxo-2,3,4,5-tetrahydro-benzo[b][1,4]diazepin-1 yl]-5-oxo-pentanoic acid hydrochloride, 5-[(S)-5-(3-Amino-propionyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(3-Amino-propionyl)-3-((S)-2-methylamino-propionylamino)-2-oxo-2,3,4,5-tetrahydro-benzo[b][[1,4]diazepin-1-ylmethyl]-6-methoxy-naphthalene-2-carboxylic acid hydrochloride, 5-[(S)-5-(4-acetyl-benzoy)-3-((S)-2-methylamino-propionylamino)-2-oxo-2,3,4,5-tetrahydro-benzo[b](1,4]diazepin-1-ylmethyl]-6-methoxy-naphthalen-2-carboxylic acid hydrochloride, 5-[(S)-5-(4-acetyl-benzoy)-3-((S)-2-methylamino-propionylamino)-2-oxo-2,3,4,5-tetrahydro-benzo[b][[1,4]diazepin-1-ylmethyl]-6-methoxy-naphthalen-2-carboxylic acid hydroxyamide trifluoroacetate, 5-[(S)-5-(4-Acetyl-benzoyl)-3-((S)-2-methylamino-propionylamino)-2-oxo-2,3,4,5-tetrahydro-benzo[b][[1,4]diazepin-1-ylmethyl]-6-methoxy-naphthalen-2-carboxylic acid methyl ester hydrochloride, 5-[(S)-5-(4-Amino-benzoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride, 5-[(S)-5-(4-Amino-benzoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride, 5-[(S)-5-(4-Amino-butyryl)-3-((S)-2-methylamino-propionylamino)-2-oxo-2,3,4,5-tetrahydro-benzo[b][[1,4]diazepin-1-ylmethyl]-6-methoxy-naphthalene-2-carboxylic acid methyl ester hydrochloride, 5-[(S)-5-(4-Amino-butyryl)-3-((S)-2-methylamino-propionylamino)-2-oxo-2,3,4,5-tetrahydro-benzo[b][1,4]

diazepin-1-ylmethyl]-6-methoxy-naphthalene-2-carboxylic acid hydrochloride,
5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride,
5-[(S)-5-(5-amino-pentanoyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic acid hydrochloride,
5-[(S)-5-[4-(9H-Fluoren-9-ylmethoxycarbonylamino)-benzoyl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride,
5-[(S)-5-[4-(9H-Fluoren-9-ylmethoxycarbonylamino)-butyryl]-3-((S)-2-methylamino-propionylamino)-2-oxo-2,3,4,5-tetrahydro-benzo[b][1,4]diazepin-1-ylmethyl]-6-methoxy-naphthalene-2-carboxylic acid methyl ester hydrochloride,
6-[(S)-3-((S)-2-Methylamino-propionylamino)-5-(2-methyl-naphthalen-1-ylmethyl)-4-oxo-2,3,4,5-tetrahydro-benzo[b][1,4]diazepin-1-yl]-6-oxo-hexanoic acid hydrochloride,
6-Methoxy-5-[(S)-3-((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid methyl ester hydrochloride,
6-Methoxy-5-[(S)-3-((S)-2-methylamino-propionylamino)-2-oxo-5-(5-oxo-hexanoyl)-2,3,4,5-tetrahydro-benzo[b][1,4]diazepin-1-ylmethyl]-naphthalene-2-carboxylic acid hydrochloride,
Cyclic-5-[(S)-5-(2-Amino-ethyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride,
Cyclic-5-[(S)-5-(3-Amino-propionyl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride,
Cyclic-5-[(S)-5-(3-amino-propyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride,
Cyclic-5-[(S)-5-(4-Amino-butyryl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride,
Cyclic-5-[(S)-5-(5-amino-pentanoyl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride,
Methyl 4-((S)-5-(benzo[d]isoxazol-3-ylmethyl)-3-((S)-2-(methylamino)propanamido)-4-oxo-2,3,4,5-tetrahydro-1H-benzo[b][1,4]diazepine-1-carbonyl)benzoate hydrochloride,
methyl 5-(((S)-5-(3-(((9H-fluoren-9-yl)methoxy)carbonylamino)propanoyl)-3-((S)-2-(methylamino)propanamido)-2-oxo-2,3,4,5-tetrahydro-1H-benzo[b][1,4]diazepin-1-yl)methyl)-6-methoxy-2-naphthoate hydrochloride, and
methyl 6-((S)-3-((S)-2-(methylamino)propanamido)-5-((2-methylnaphthalen-1-yl)methyl)-4-oxo-2,3,4,5-tetrahydro-1H-benzo[b][1,4]diazepin-1-yl)-6-oxo-hexanoate hydrochloride,
or a pharmaceutically acceptable salt thereof.

4. A compound, selected from the group consisting of:
(S)-2-Methylamino-N—((S)-1-naphthalen-1-ylmethyl-2-oxo-5-phenethyl-2,3,4,5-tetrahydro-1H-benzo[b][1,4]diazepin-3-yl)-propionamide trifluoroacetate,
(S)-2-Methylamino-N—[(S)-1-(2-methyl-naphthalen-1-ylmethyl)-5-(4-nitro-benzenesulfonyl)-2-oxo-2,3,4,5-tetrahydro-1H-benzo[b][1,4]diazepin-3-yl]-propionamide hydrochloride,
(S)-2-Methylamino-N—[(S)-1-(2-methyl-naphthalen-1-ylmethyl)-5-methylsulfamoyl-2-oxo-2,3,4,5-tetrahydro-1H-benzo[b][1,4]diazepin-3-yl]-propionamide hydrochloride,
(S)-3-((S)-2-methylamino-propionylamino)-5-(2-methyl-naphthalen-1-ylmethyl)-4-oxo-2,3,4,5-tetrahydro-benzo[b][1,4]diazepin-1-carboxylic acid methyl ester hydrochloride,
(S)—N—((S)-1-((6-Bromo-2-methoxynaphthalen-1-yl)methyl)-5-(4-cyanobenzyl)-2-oxo-2,3,4,5-tetrahydro-1H-benzo[b][1,4]diazepin-3-yl)-2-(methylamino)propanamide trifluoroacetate,
(S)—N—((S)-5-Benzyl-1-((6-bromo-2-methoxynaphthalen-1-yl)methyl)-2-oxo-2,3,4,5-tetrahydro-1H-benzo[b][1,4]diazepin-3-yl)-2-(methylamino)propanamide trifluoroacetate,
(S)—N—[(S)-5-(4-Acetylamino-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
(S)—N—[(S)-5-(4-Acetyl-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
(S)—N—[(S)-5-(4-Methoxy-benzenesulfonyl)-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
(S)—N—[(S)-5-Benzenesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
(S)—N—[(S)-5-Dimethylsulfamoyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
(S)—N—[(S)-5-methanesulfonyl-1-(2-methyl-naphthalen-1-ylmethyl)-2-oxo-2,3,4,5-tetrahydro-1H-benzo[b][1,4]diazepin-3-yl]-2-methylamino-propionamide hydrochloride,
(S)—N—[(S)-5-methanesulfonylmethanesulfonyl-1-(2-methyl-naphthalen-1-ylmethyl)-2-oxo-2,3,4,5-tetrahydro-1H-benzo[b][1,4]diazepin-3-yl]-2-methylamino-propionamide trifluoroacetate,
Cyclic-5-[(S)-5-(2-Amino-ethyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride,
Cyclic-5-[(S)-5-(3-Amino-propionyl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride,
Cyclic-5-[(S)-5-(3-amino-propyl)-3-((S)-2-methylamino-propionylamino)-2-oxo-2,3,4,5-tetrahydro-benzo[b][1,4]diazepin-1-ylmethyl]-6-methoxy-naphthalene-2-carboxylic amide hydrochloride,
Cyclic-5-[(S)-5-(4-Amino-butyryl)-3-((S)-2-methyl-amino-propionylamino)-2-oxo-2,3,4,5-tetrahydrobenzo[b][1,4]diazepin-1-ylmethyl]-6-methoxy-naphthalene-2-carboxylic amide hydrochloride, and Cyclic-5-[(S)-5-(5-amino-pentanoyl)-3-((S)-2-methyl-amino-propionylamino)-2-oxo-2,3,4,5-tetrahydro-benzo[b][1,4]diazepin-1-ylmethyl]-6-methoxy-naphthalene-2-carboxylic amide hydrochloride, or a pharmaceutically acceptable salt thereof.

\* \* \* \* \*